(12) United States Patent
Lee et al.

(10) Patent No.: US 12,089,847 B2
(45) Date of Patent: Sep. 17, 2024

(54) END TOOL OF SURGICAL INSTRUMENT, AND SURGICAL INSTRUMENT COMPRISING SAME

(71) Applicant: LIVSMED INC., Seongnam-si (KR)

(72) Inventors: Jaeyeong Lee, Seongnam-si (KR); Junghwan Kim, Seongnam-si (KR); Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/414,162

(22) Filed: Jan. 16, 2024

(65) Prior Publication Data

US 2024/0225644 A1   Jul. 11, 2024

Related U.S. Application Data

(63) Continuation of application No. 18/579,795, filed as application No. PCT/KR2022/010382 on Jul. 15, 2022.

(30) Foreign Application Priority Data

Jul. 16, 2021   (KR) ........................ 10-2021-0093833

(51) Int. Cl.
*A61B 17/072*   (2006.01)
*A61B 34/00*   (2016.01)

(52) U.S. Cl.
CPC ........ *A61B 17/07207* (2013.01); *A61B 34/71* (2016.02); *A61B 2017/07271* (2013.01); *A61B 2017/07285* (2013.01)

(58) Field of Classification Search
CPC ............ A61B 17/07207; A61B 17/068; A61B 17/072; A61B 2017/07278; A61B 2017/07285; A61B 2017/07271; A61B 2017/07214; A61B 2017/07221;
(Continued)

(56) References Cited

U.S. PATENT DOCUMENTS 5,762,256 A  *  6/1998  Mastri ................. A61B 17/072
                                                          227/176.1
2004/0199147 A1* 10/2004 Nishizawa ........... A61B 17/062
                                                          606/1
(Continued)

FOREIGN PATENT DOCUMENTS

CN        111419310 A     7/2020
EP          3205274 A1    8/2017
(Continued)

*Primary Examiner* — Stephen F. Gerrity
*Assistant Examiner* — Linda J Hodge
(74) *Attorney, Agent, or Firm* — Bridgeway IP Law Group, PLLC; Sang Ho Lee; Hyun Woo Shin

(57) ABSTRACT

The present disclosure relates to an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation portion, and a surgical instrument including the same.

20 Claims, 94 Drawing Sheets

(58) Field of Classification Search
CPC .......... A61B 2017/07228; A61B 2017/07257;
A61B 2017/07264
See application file for complete search history.

(56) References Cited

U.S. PATENT DOCUMENTS

| | | | | |
|---|---|---|---|---|
| 2012/0181322 A1* | 7/2012 | Whitman | ............. | A61B 17/068 |
| | | | | 227/176.1 |
| 2016/0166249 A1* | 6/2016 | Knodel | ............ | A61B 17/07207 |
| | | | | 227/177.1 |
| 2017/0265954 A1* | 9/2017 | Burbank | ................ | A61B 34/37 |

FOREIGN PATENT DOCUMENTS

| | | | | |
|---|---|---|---|---|
| JP | 2016-198492 A | 12/2016 | | |
| KR | 10-2122508 B1 | 6/2020 | | |
| WO | WO-2004112618 A2 * | 12/2004 | ......... | A61B 17/0644 |
| WO | 2020/055705 A1 | 3/2020 | | |

\* cited by examiner

FIG. 45
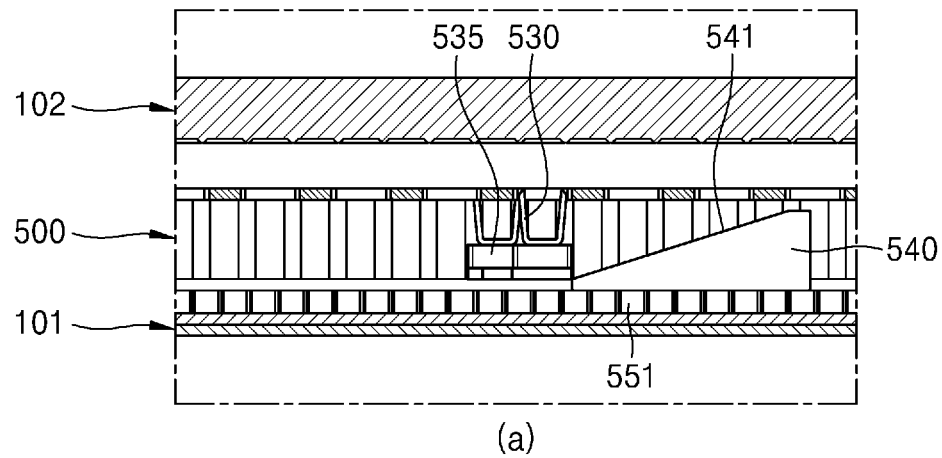
(a)
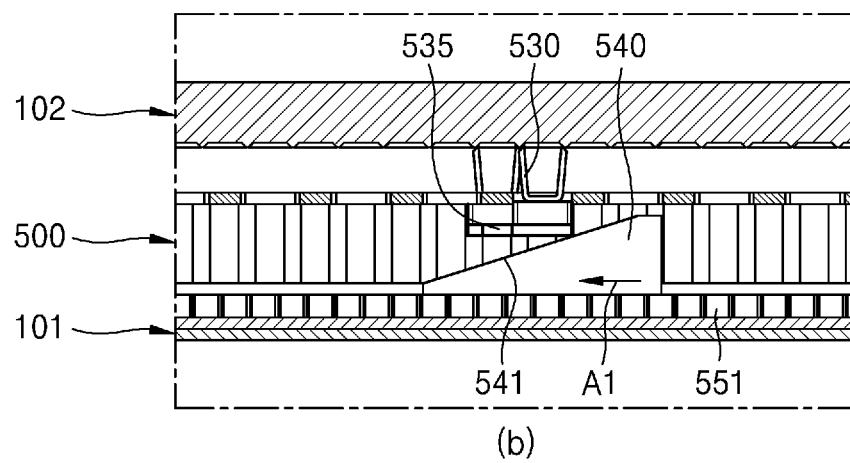
(b)
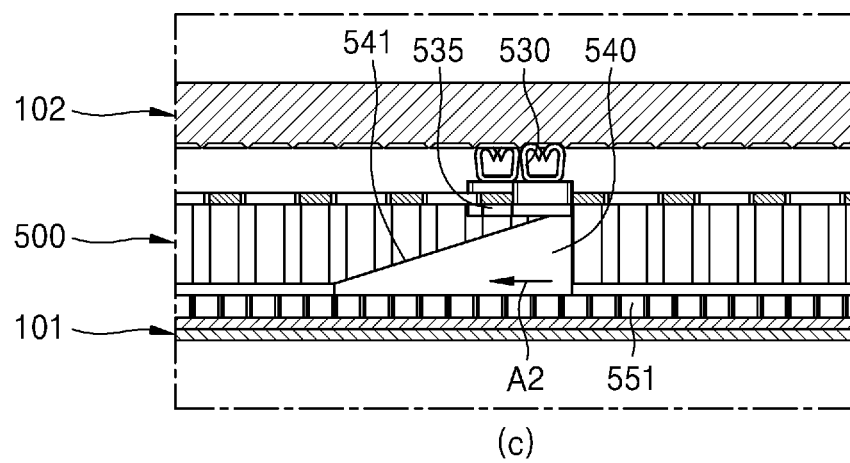
(c)

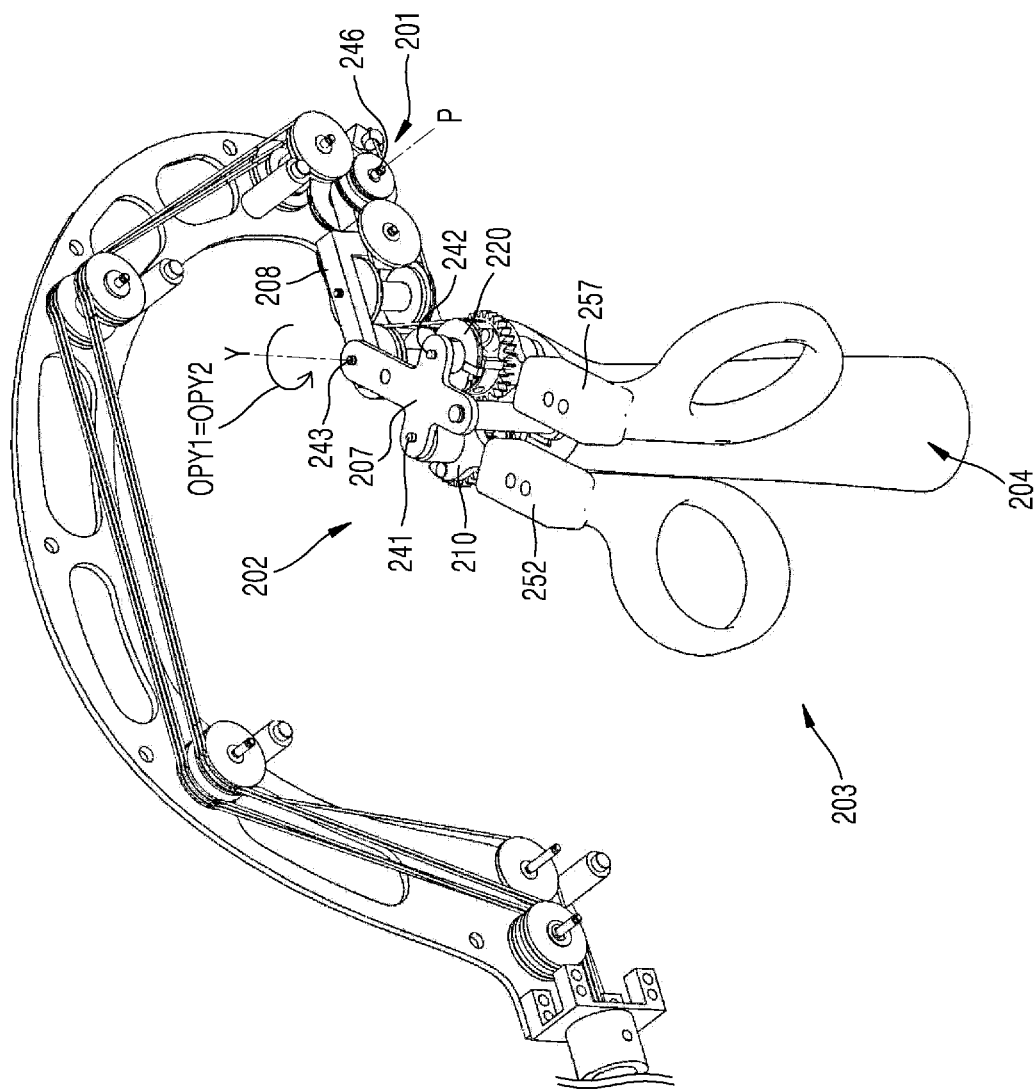
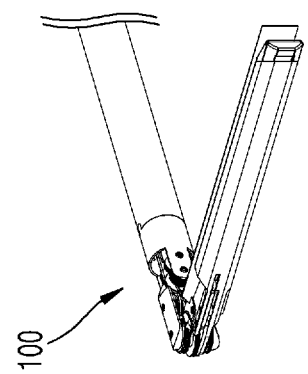
FIG. 50

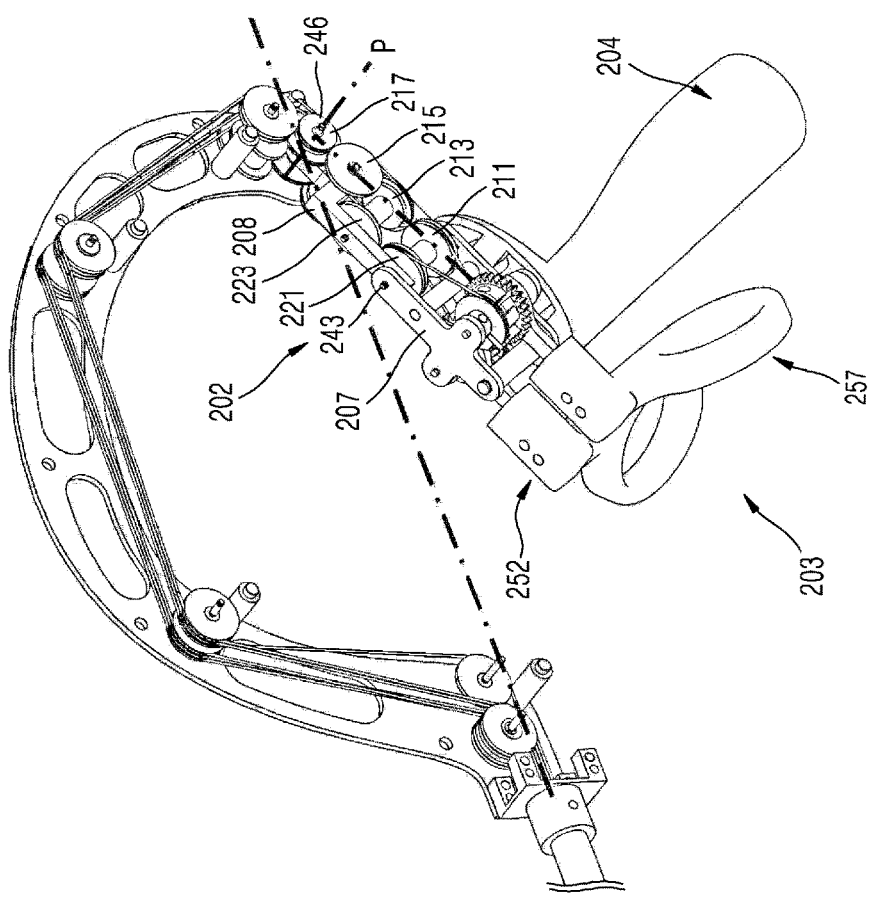
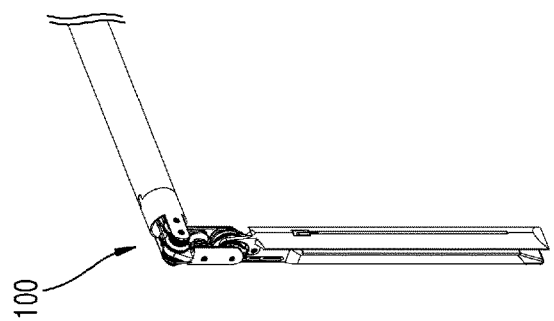
FIG. 56

END TOOL OF SURGICAL INSTRUMENT, AND SURGICAL INSTRUMENT COMPRISING SAME

CROSS-REFERENCE TO RELATED APPLICATION

This application is a continuation application of U.S. Ser. No. 18/579,795 filed on Jan. 16, 2024, which is a national-stage entry of international application No. PCT/KR2022/010382, filed on Jul. 15, 2022, which claims priority to Korean Patent Application No. 10-2021-0093833, filed on Jul. 16, 2021, the entire disclosures of which are incorporated herein by reference.

TECHNICAL FIELD

The present disclosure relates to an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation portion, and a surgical instrument including the same.

BACKGROUND ART

In recent years, laparoscopic surgery has been actively utilized to reduce postoperative recovery time and complications through small incisions. The laparoscopic surgery is a surgical method in which a plurality of small holes are drilled in the abdomen of a patient and the inside of the abdominal cavity is observed through these holes, and is widely used in general surgery and the like.

In performing the laparoscopic surgery, a suturing instrument inserted into the body is used to suture a surgical site in the abdominal cavity, and a surgical stapler for suturing the surgical site by using medical staples is used as the suturing instrument.

In general, a surgical stapler is a medical instrument that is often used for cutting and anastomosis of an organ in abdominal and thoracic surgery. The surgical stapler includes an open stapler used in thoracotomy and laparotomy and an endo stapler used in thoracoscopic surgery and celioscopic surgery.

The surgical stapler has advantages of not only shortening operation time because cutting of a surgical site and anastomosis of an organ are simultaneously performed, but also accurately stapling the surgical site. In addition, the surgical stapler has advantages of a faster recovery and a smaller scar than those when tissue is cut and stapled by using a surgical stapling thread, and thus has been widely used in modern surgical operations. In particular, the surgical stapler has been widely used in cancer surgery to cut cancer tissue and suture a cut site.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

DESCRIPTION OF EMBODIMENTS

Technical Problem

The present disclosure is directed to providing a surgical instrument, which may be mounted on a robotic arm or operable manually to be used in laparoscopic surgery or other various surgeries and includes an end tool rotatable in two or more directions and moved in a way that intuitively matches a motion of a manipulation portion, and a surgical instrument including the same.

Solution to Problem

The present disclosure provides a surgical instrument including: an end tool including: a first jaw; a second jaw formed to face the first jaw; a first jaw pulley coupled to the first jaw and formed to be rotatable around a first shaft; a second jaw pulley coupled to the second jaw, formed to be rotatable around a shaft that is substantially the same as or parallel to the first shaft, and formed to be spaced apart from the first jaw pulley by a certain extent; and a staple drive assembly including a first staple pulley and a second staple pulley formed adjacent to the first jaw pulley or the second jaw pulley; and a cartridge including: a reciprocating assembly that is connected to the staple drive assembly, and is linearly moved when the first staple pulley and the second staple pulley is rotationally moved; and an operation member that is brought into contact with the reciprocating assembly, and is moved in one direction by the reciprocating assembly when the reciprocating assembly is moved in the one direction.

ADVANTAGEOUS EFFECTS OF DISCLOSURE

According to the present disclosure, a manipulation direction of a manipulation portion by an operator and an operating direction of an end tool are intuitively identical to each other, so that the operator's convenience may be improved, and the accuracy, reliability and speed of surgery may be improved.

BRIEF DESCRIPTION OF DRAWINGS (a) of FIG. 1 is a conceptual diagram of a pitch motion of a conventional surgical instrument, and (b) of FIG. 1 is a conceptual diagram of a yaw motion.

(c) of FIG. 1 is a conceptual diagram of a pitch motion of another conventional surgical instrument, and (d) of FIG. 1 is a conceptual diagram of a yaw motion.

(e) of FIG. 1 is a conceptual diagram of a pitch motion of a surgical instrument according to the present disclosure, and (f) of FIG. 1 is a conceptual diagram of a yaw motion.

Figure 2:
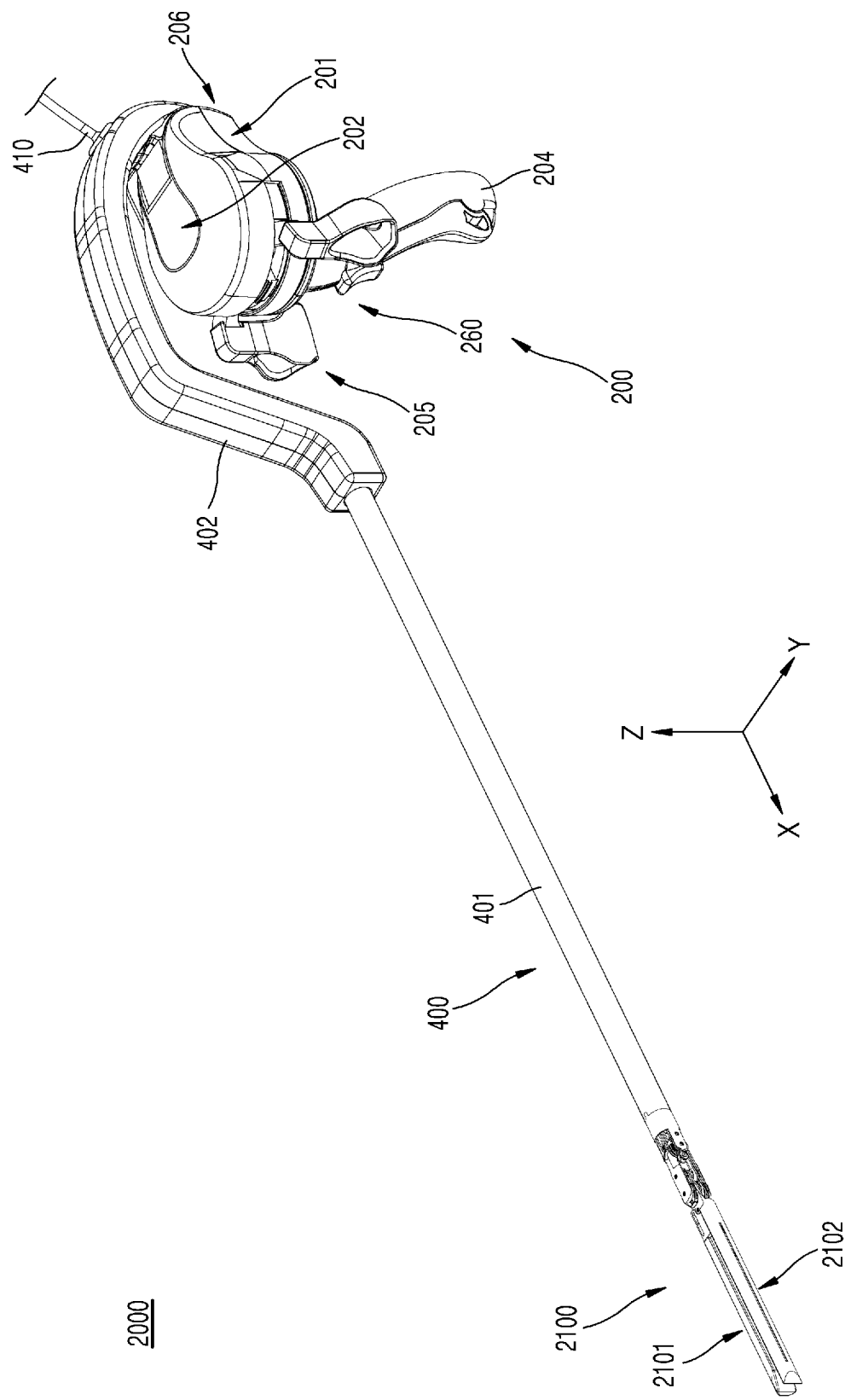
FIG. 2 is a perspective view illustrating a surgical instrument according to a first embodiment of the present disclosure.

FIGS. 21, 22, 23, and 24 are plan views illustrating opening and closing motions of the first jaw and the second jaw of the surgical instrument of FIG. 2.

Figure 25:
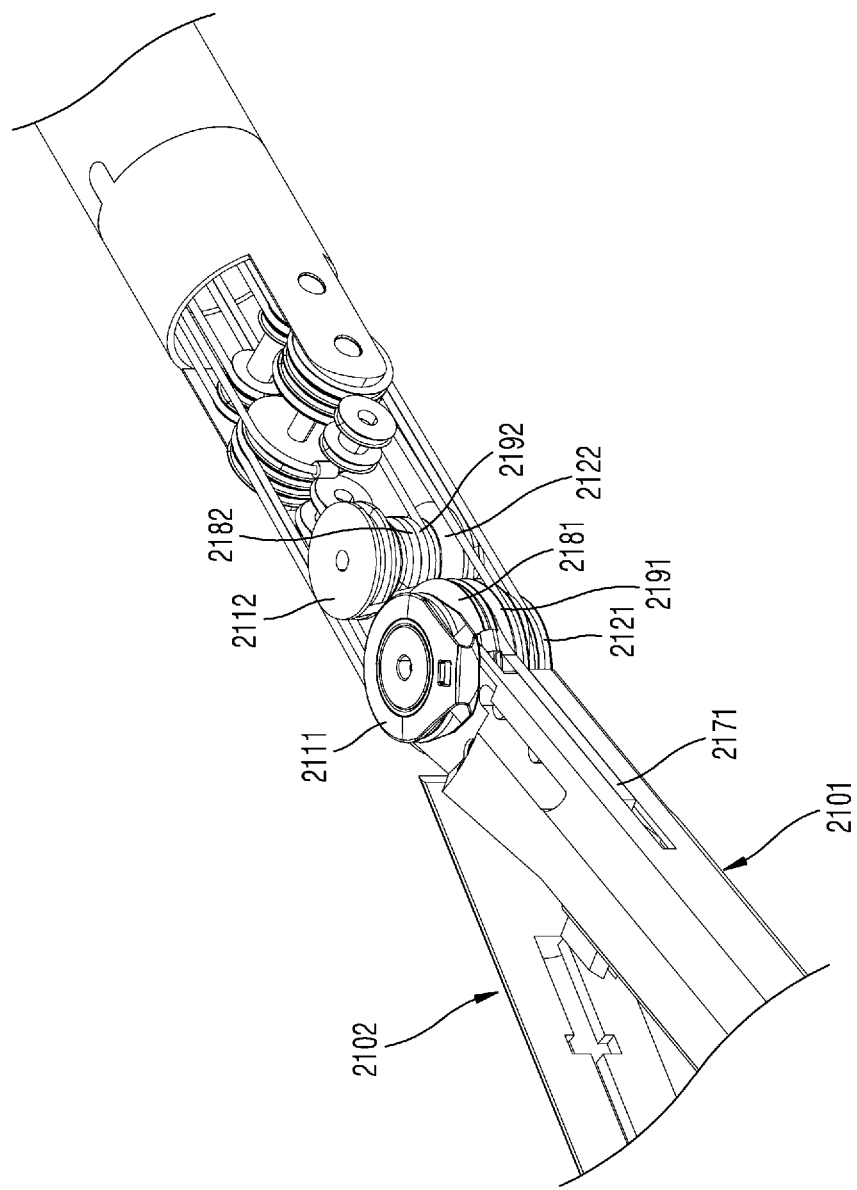
Figure 26:
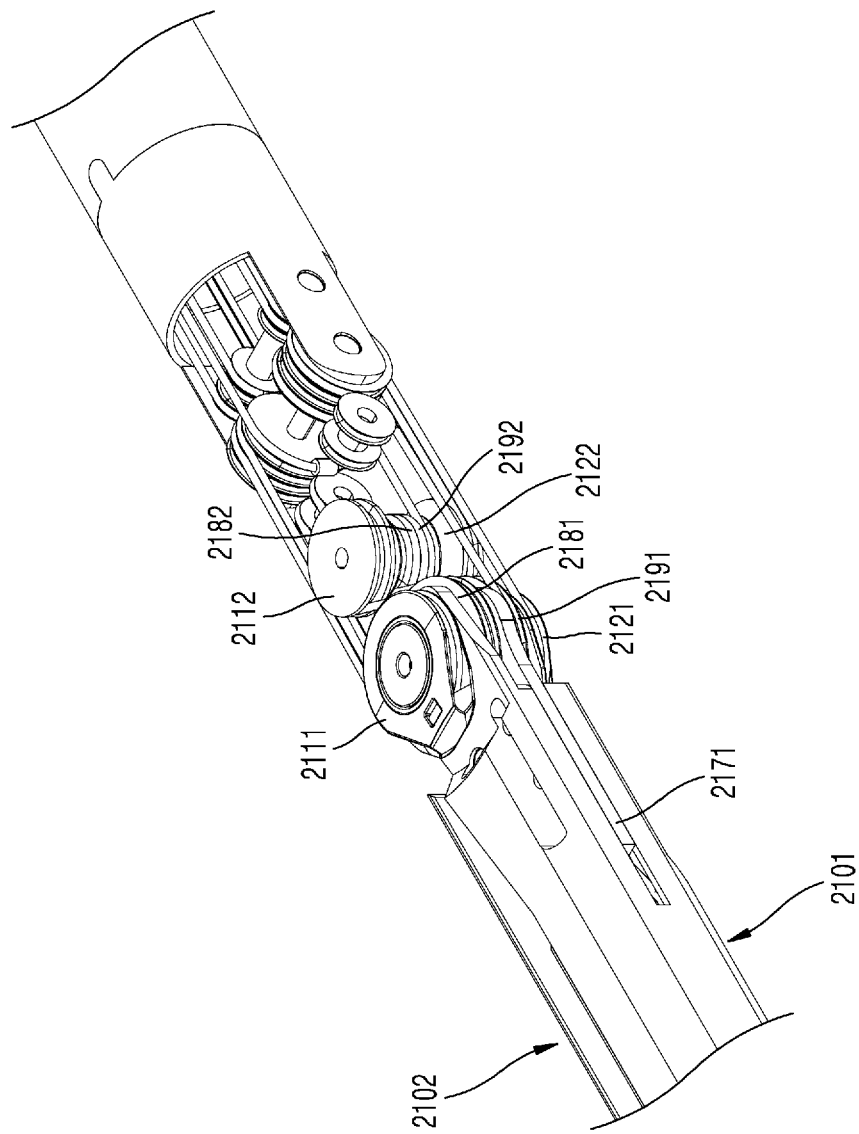

FIGS. 25 and 26 are perspective views illustrating opening and closing motions of the end tool of the surgical instrument of FIG. 2.

Figure 27:
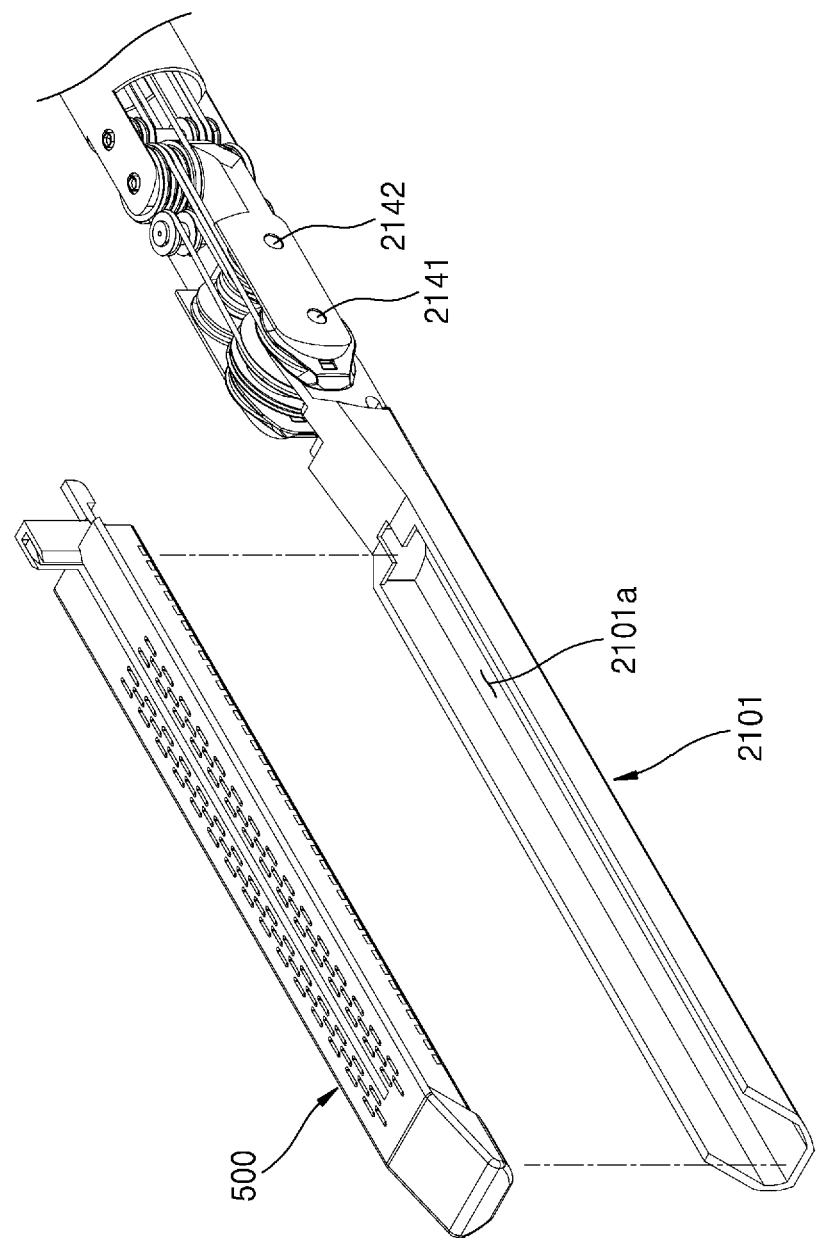

FIG. 27 is a perspective view illustrating the first jaw and a cartridge of the surgical instrument of FIG. 2.

Figure 28:
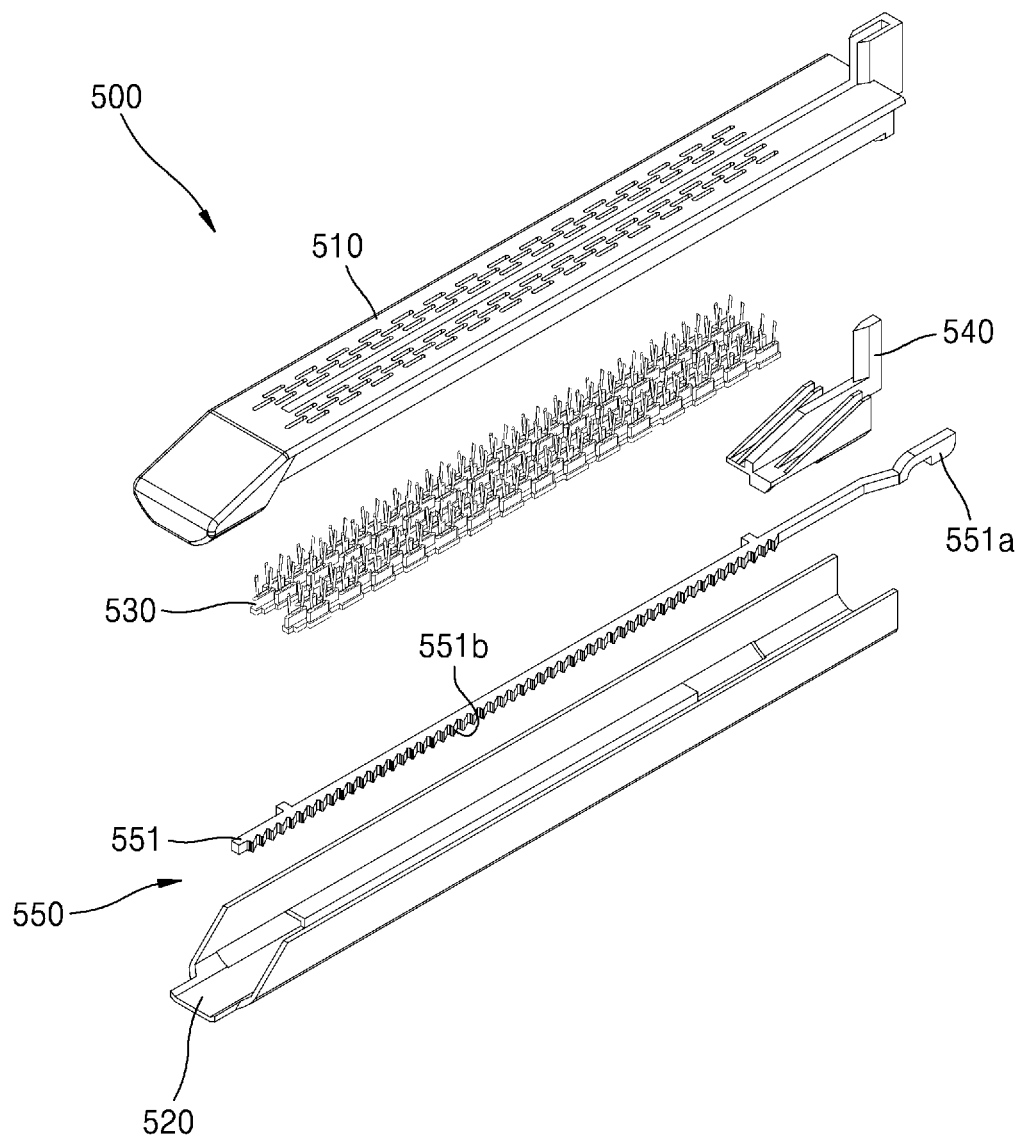

FIG. 28 is an exploded perspective view illustrating the cartridge of FIG. 27.

Figure 29:
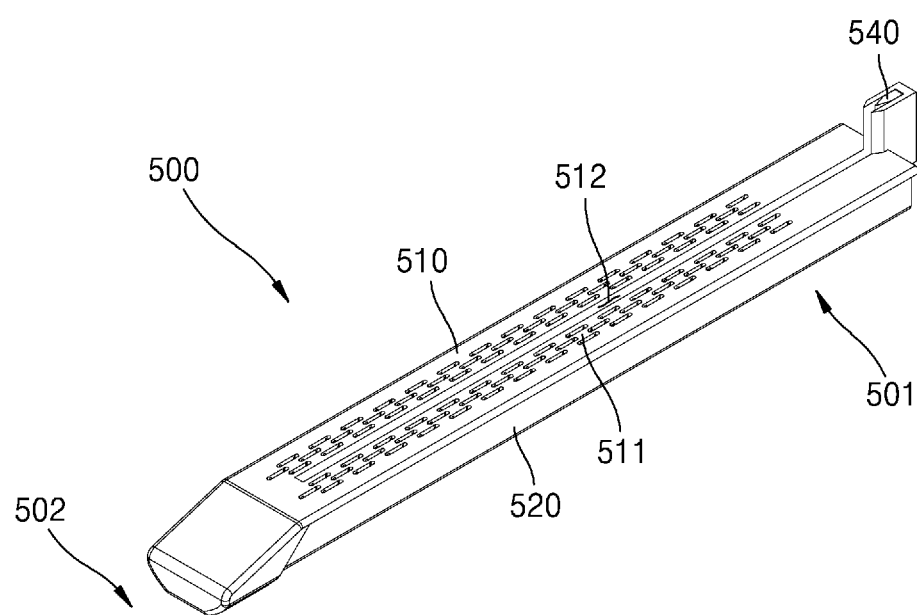

FIG. 29 is a combined perspective view illustrating the cartridge of FIG. 27.

Figure 30:
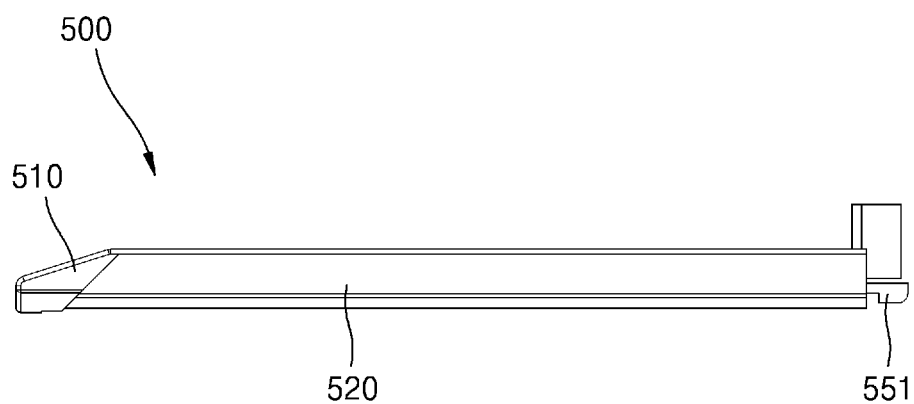

FIG. 30 is a side view illustrating the cartridge of FIG. 27.

Figure 31:
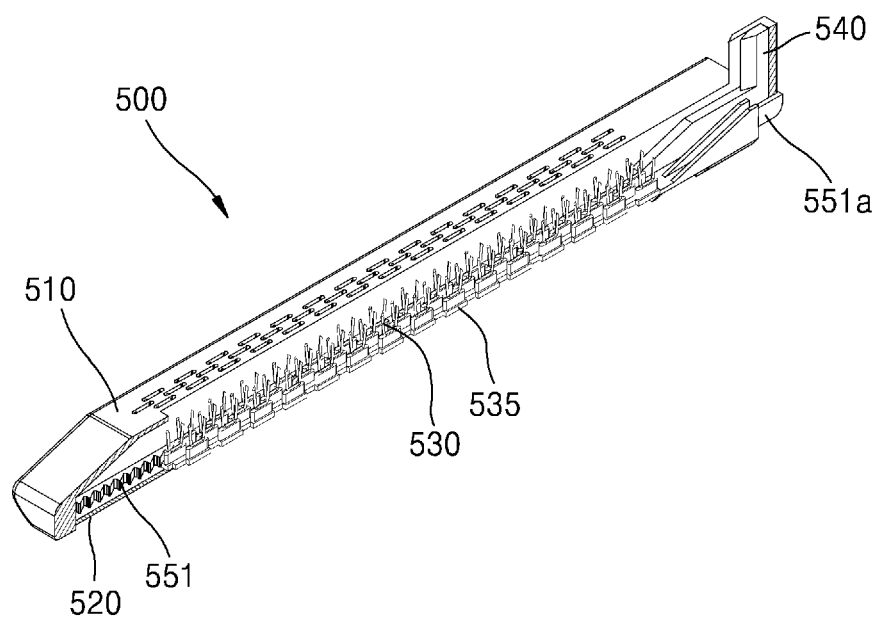

FIG. 31 is a perspective cross-sectional view illustrating the cartridge of FIG. 27.

Figure 32:
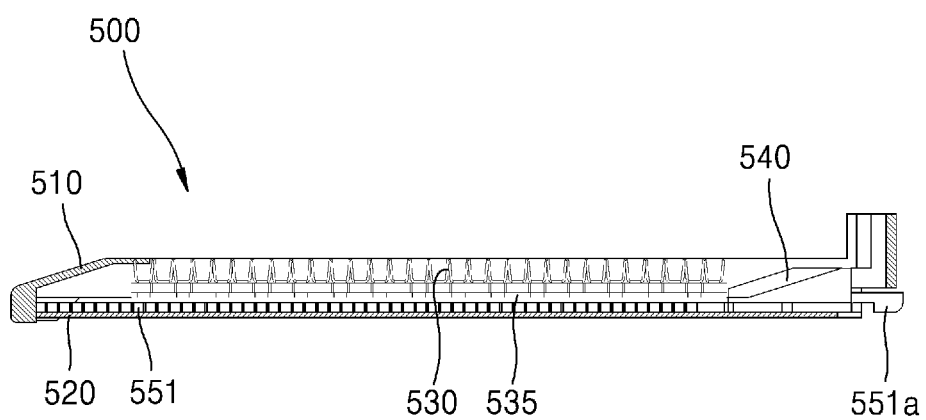

FIG. 32 is a side cross-sectional view illustrating the cartridge of FIG. 27.

Figure 33:
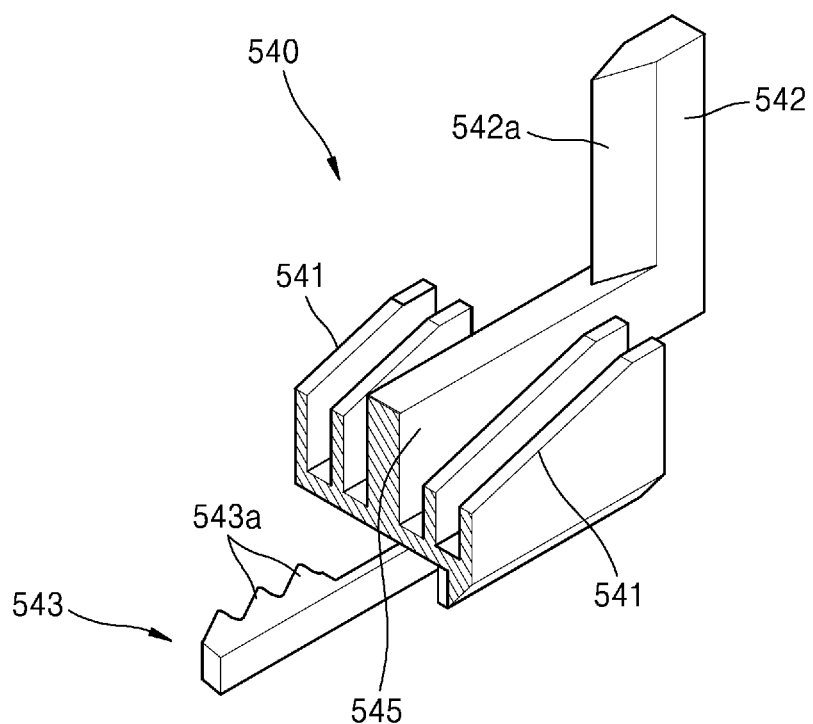
Figure 34:
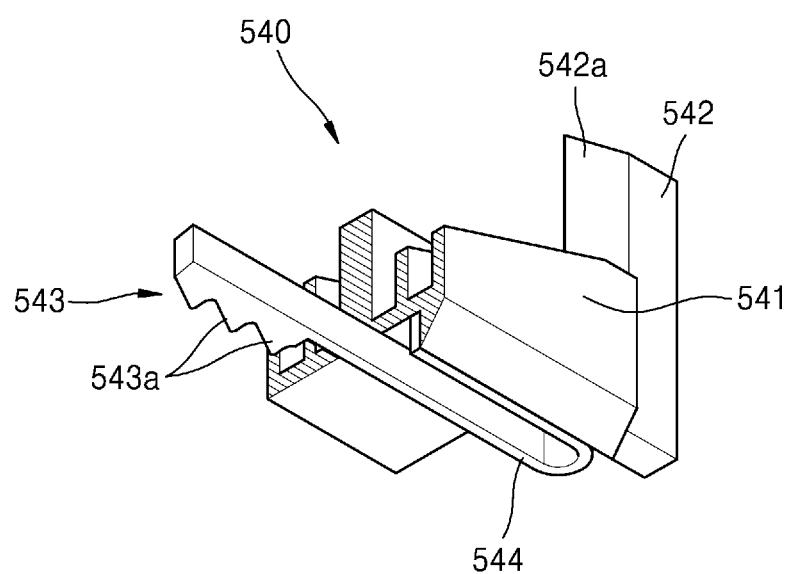

FIGS. 33 and 34 are perspective views illustrating an operation member of the cartridge of FIG. 27.

Figure 35:
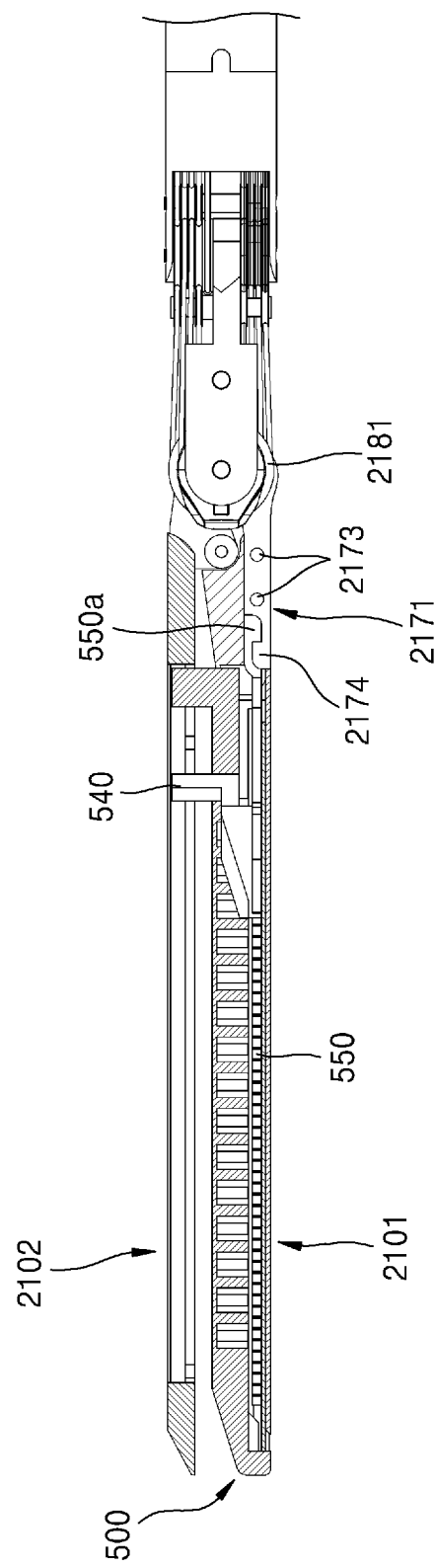

FIG. 35 is a side cross-sectional view illustrating a stapling-related structure of the end tool of the surgical instrument of FIG. 2.

Figure 36:
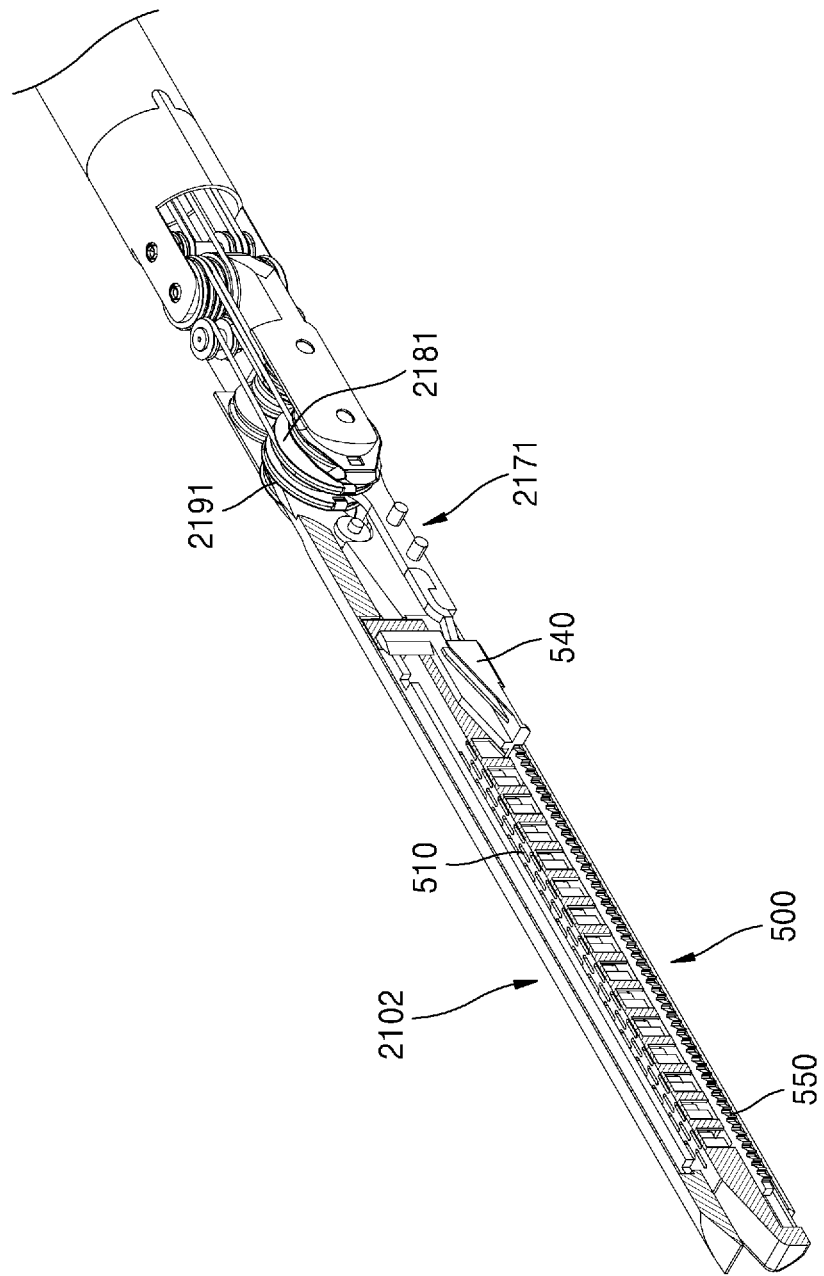
Figure 37:
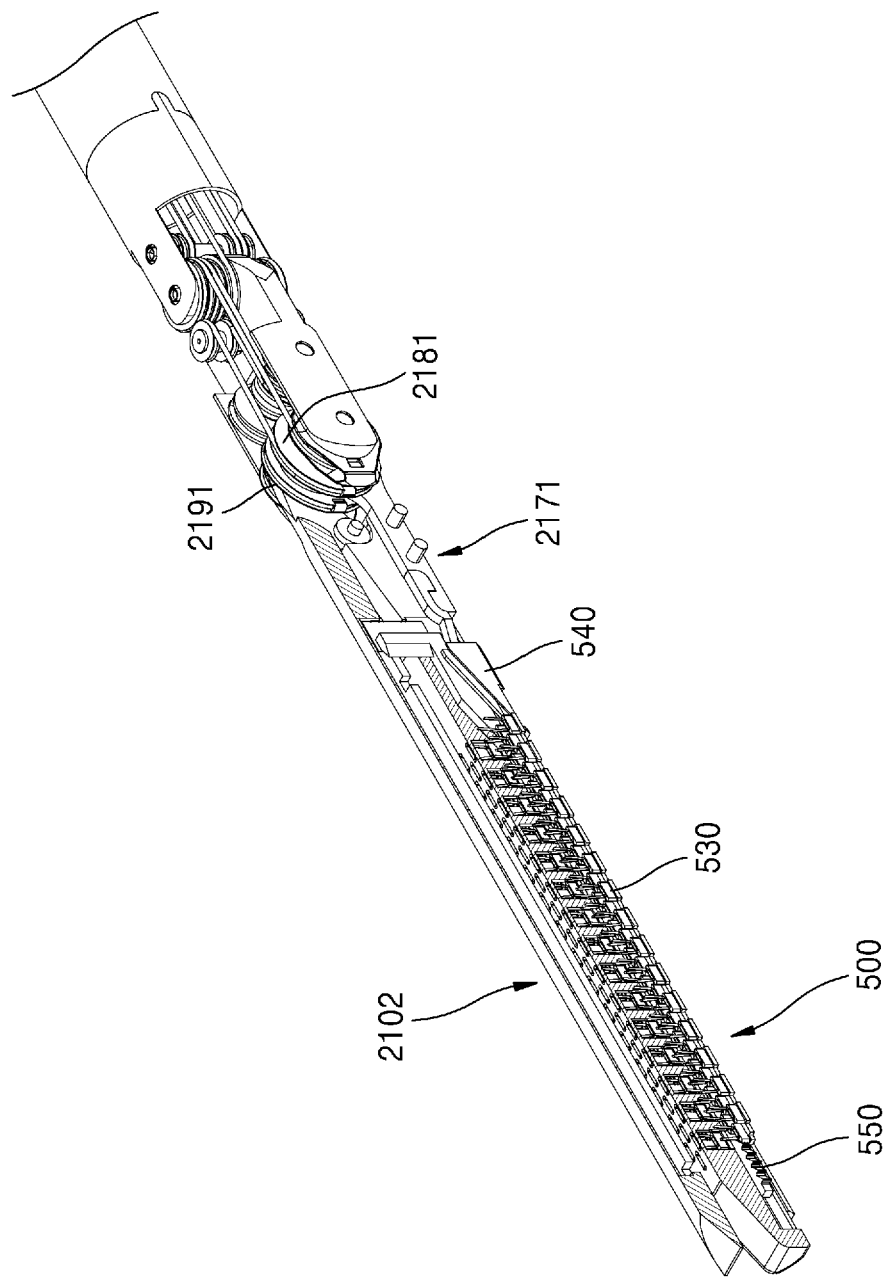
Figure 38:
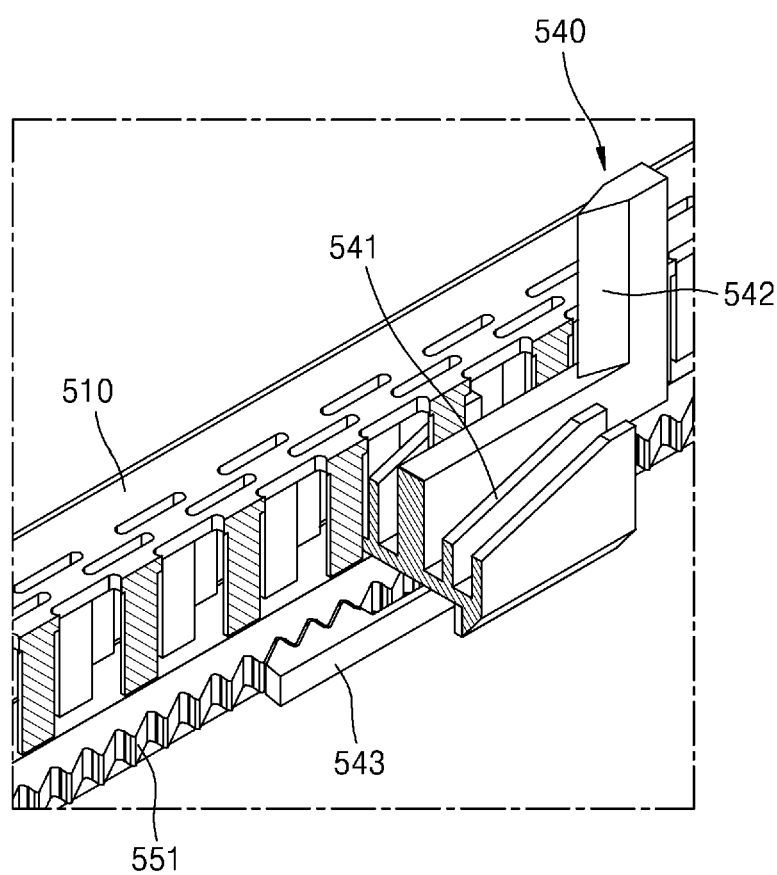
Figure 39:
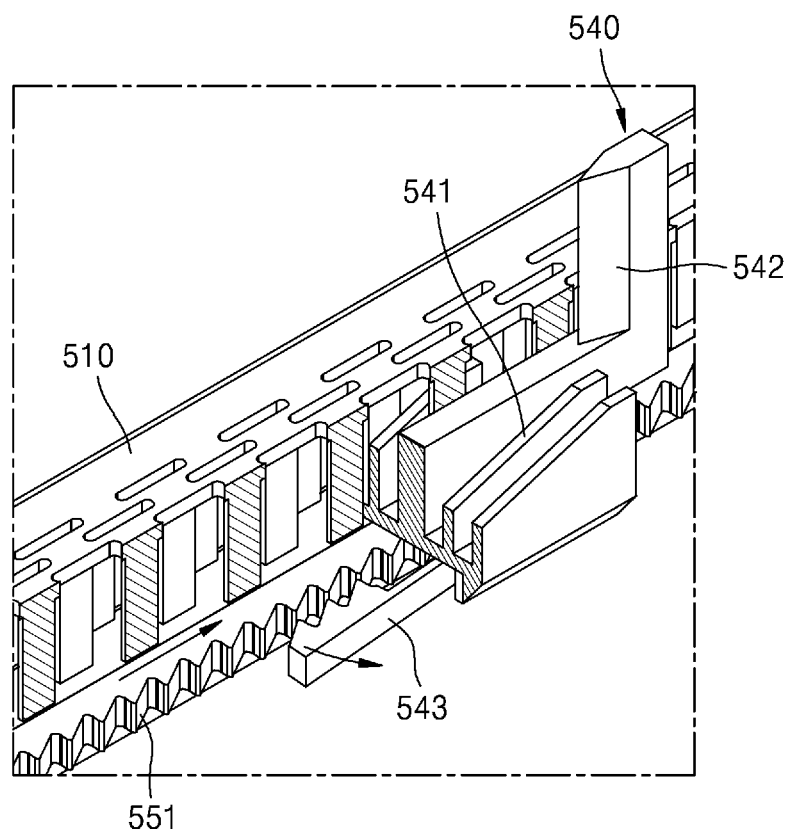

FIGS. 36 and 37 are perspective cross-sectional views illustrating a stapling structure of the end tool of the surgical instrument of FIG. 2.

FIGS. 38 to 41 are perspective views illustrating a ratchet drive operation of the end tool of FIG. 30.

Figure 42:
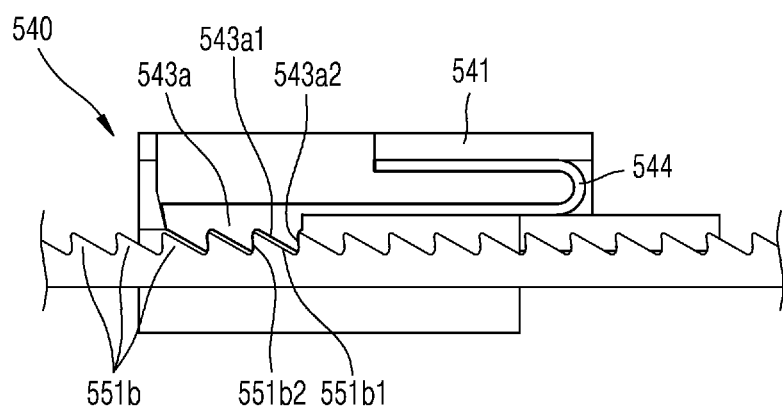
Figure 43:
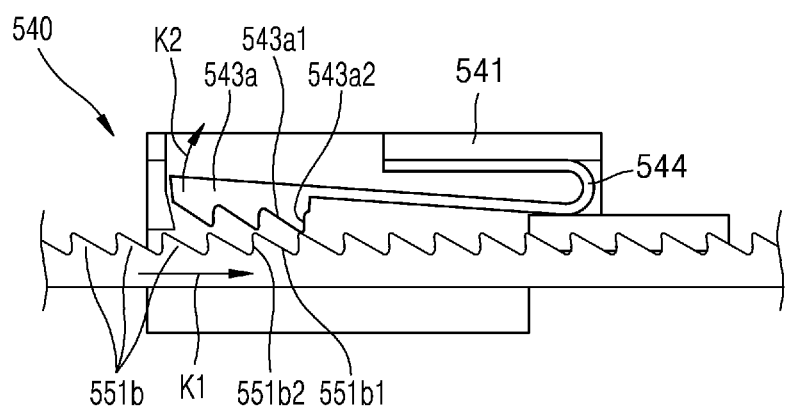

FIGS. 42 and 43 are plan views illustrating a ratchet drive operation of the end tool of FIG. 36.

Figure 44:
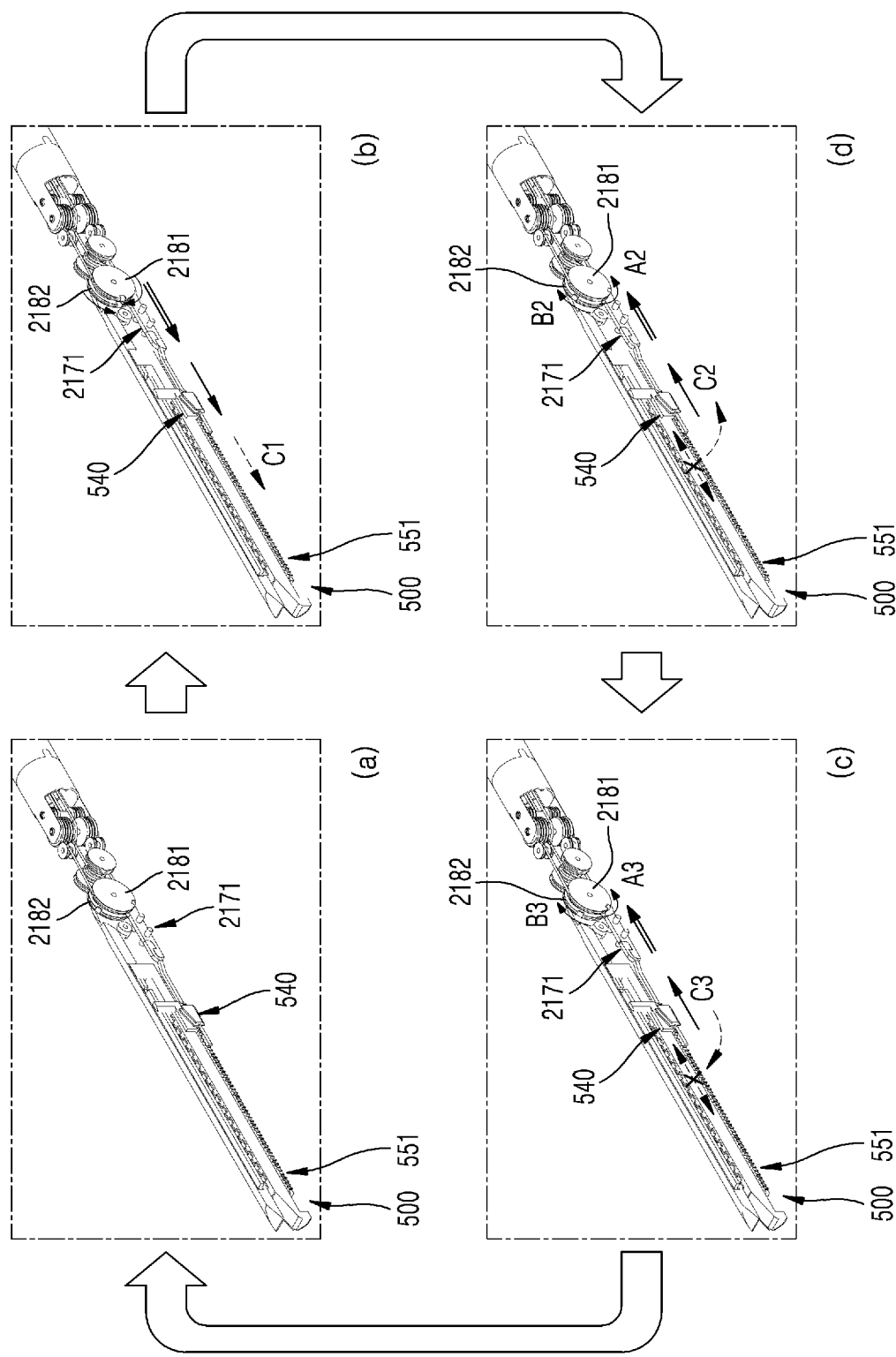

FIG. 44 is a perspective view illustrating an entire ratchet drive operation of the end tool of FIG. 36.

Figure 46:
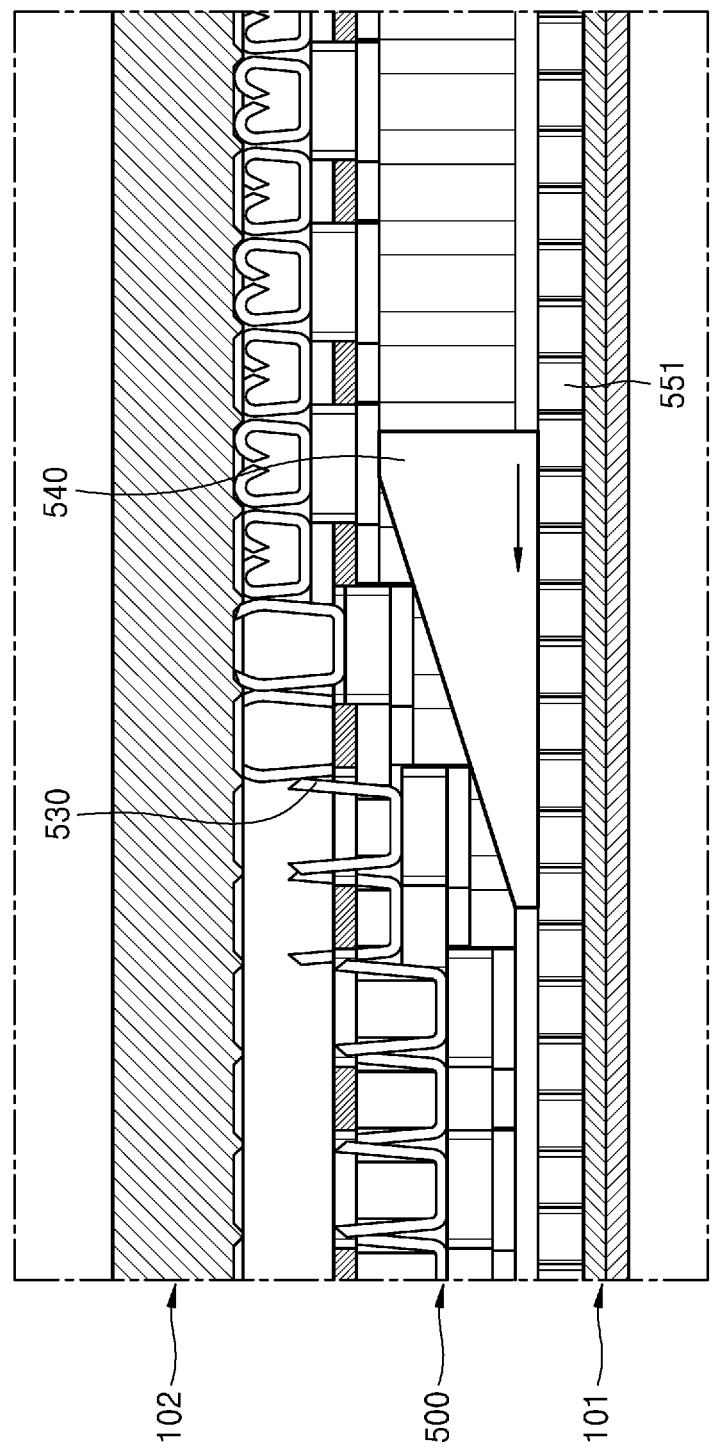

FIGS. 45 and 46 are perspective views illustrating an entire stapling motion of the end tool of FIG. 36.

Figure 47:
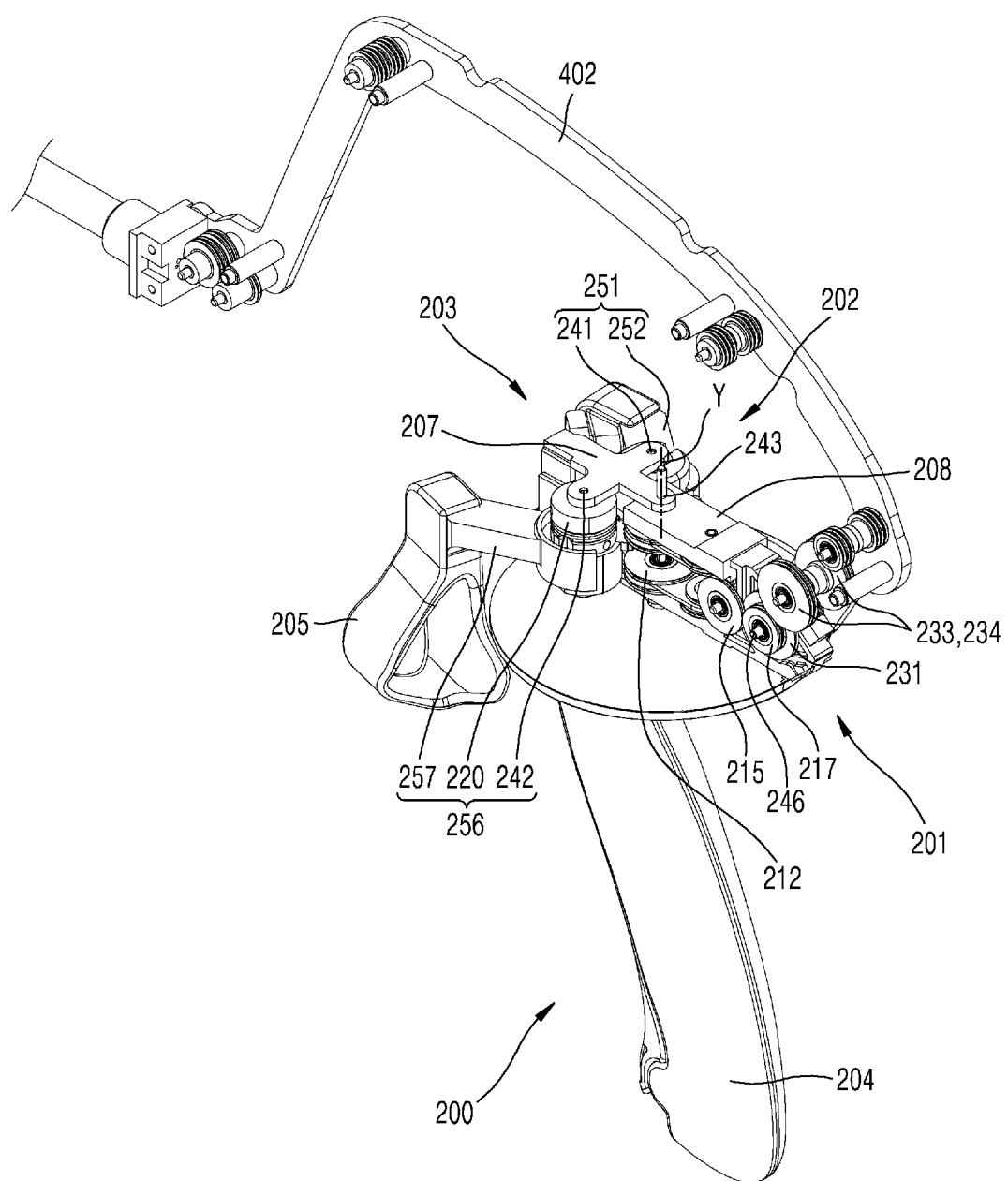
Figure 48:
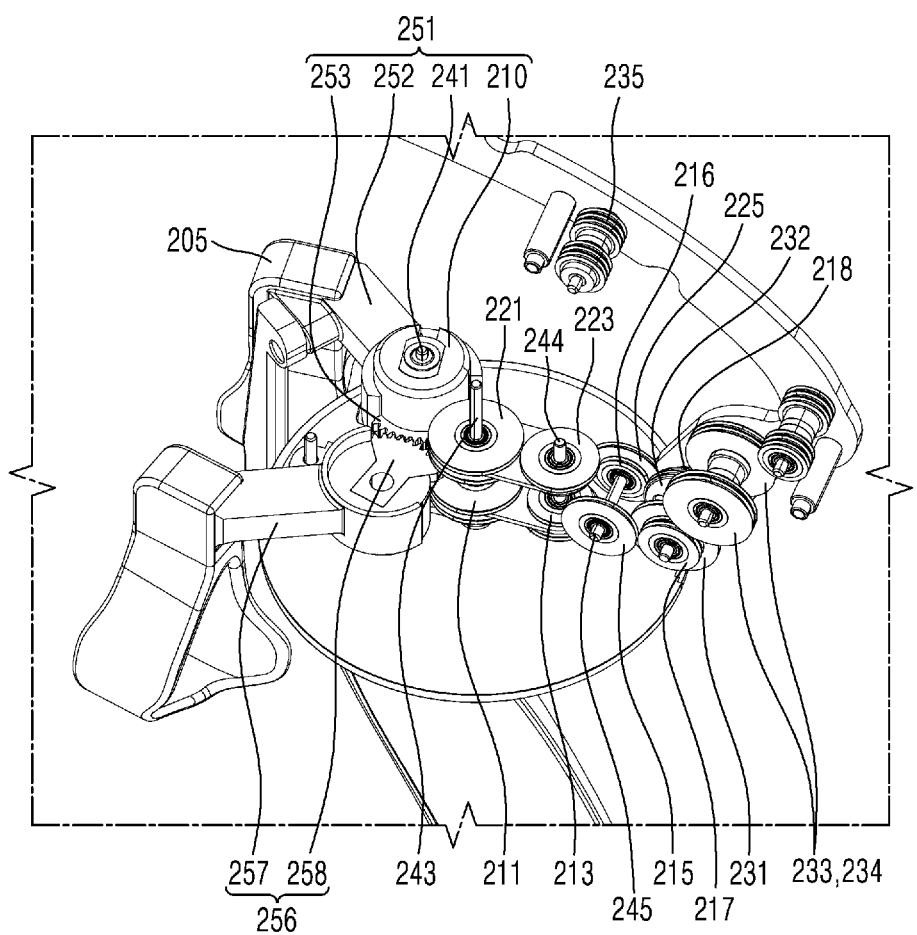

FIGS. 47 and 48 are perspective views illustrating a manipulation portion of the surgical instrument of FIG. 2.

Figure 49:
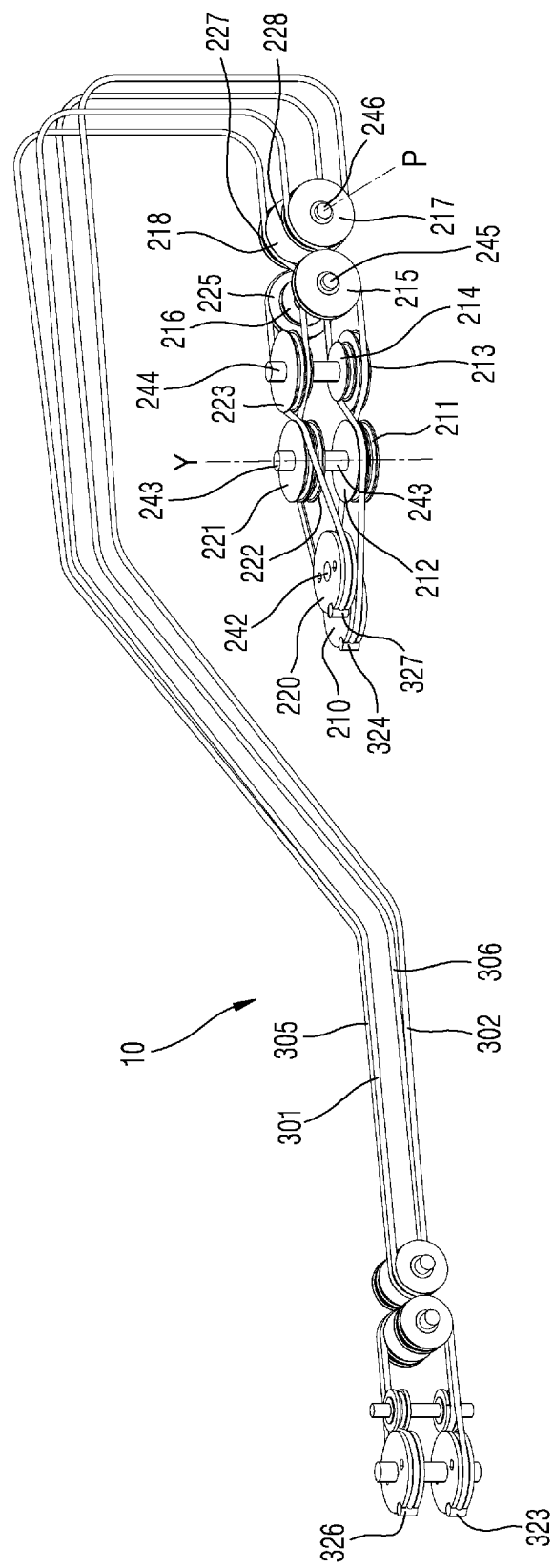

FIG. 49 is a diagram schematically illustrating only a configuration of pulleys and wires constituting joints of the surgical instrument illustrated in FIG. 2.

FIG. 50 is a perspective view illustrating a yaw motion of the surgical instrument of FIG. 2.

Figure 51:
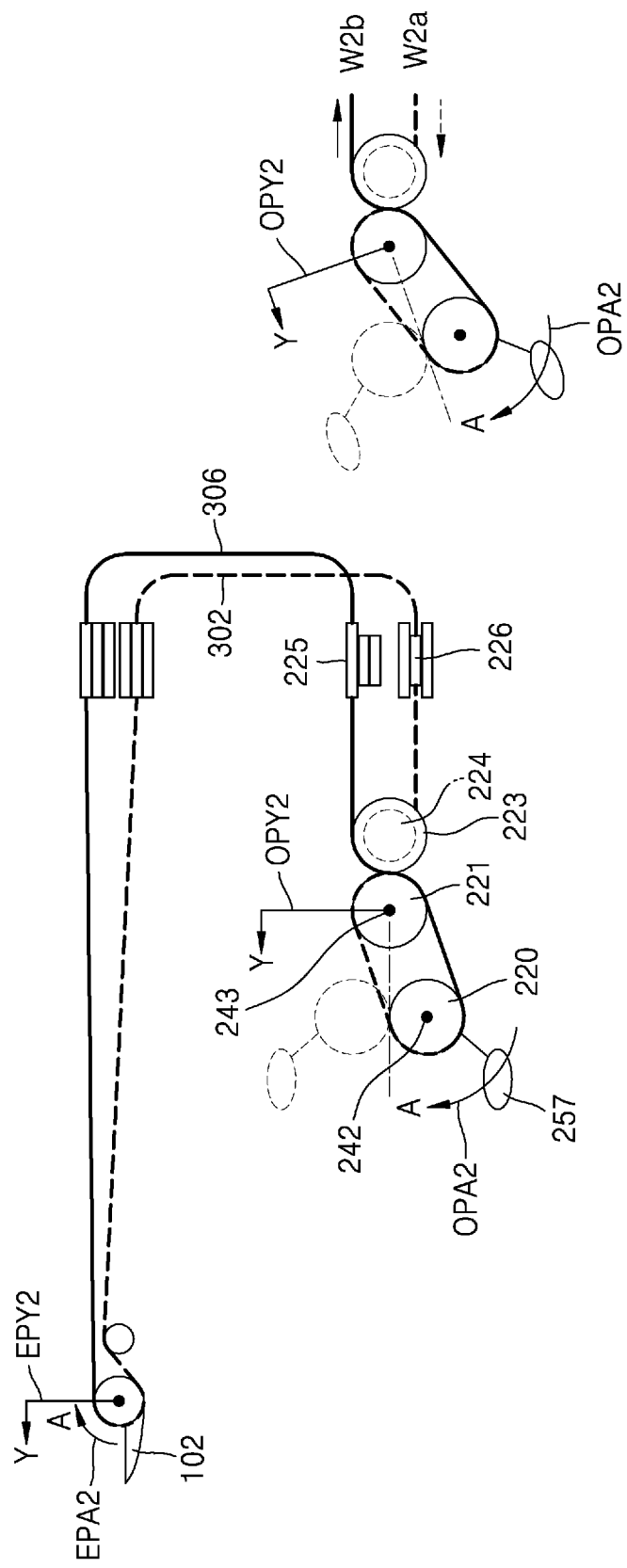
Figure 52:
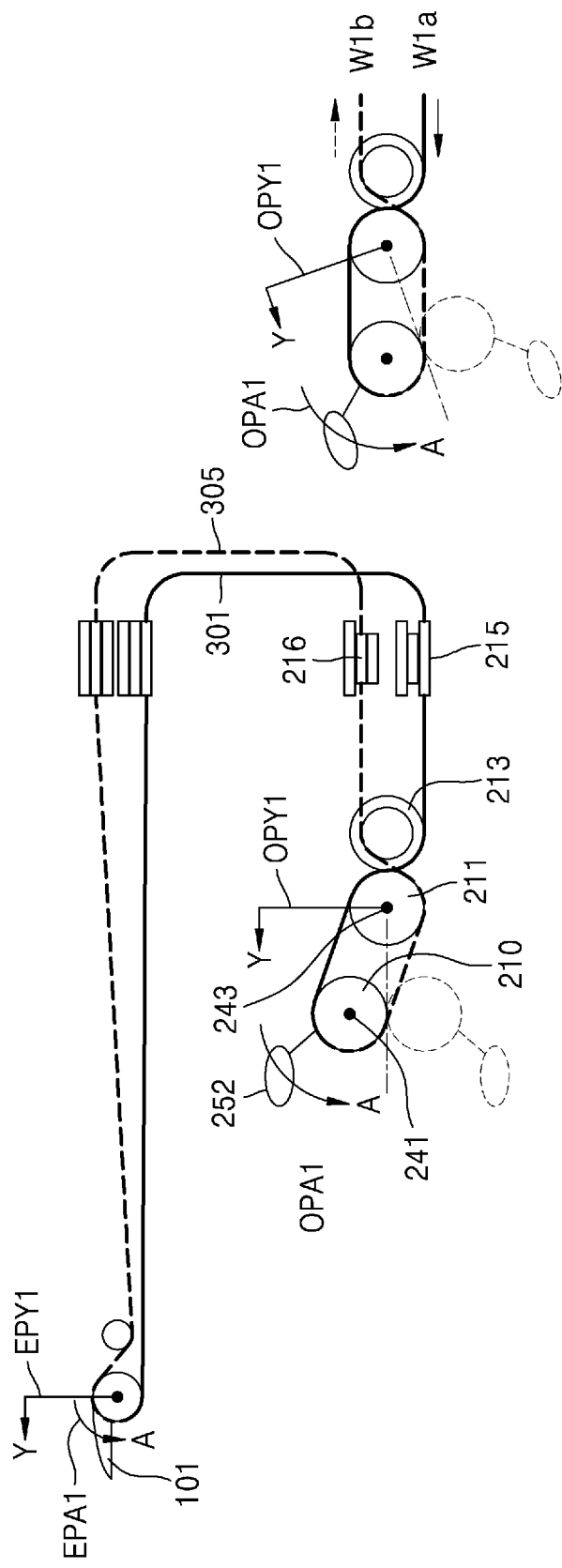

FIGS. 51 and 52 are diagrams illustrating a configuration of pulleys and wires, which are related to an actuation motion and a yaw motion of the surgical instrument illustrated in FIG. 2, in detail for each of the first jaw and the second jaw.

FIGS. 53, 54, 55A, and 55B are diagrams illustrating a configuration of pulleys and wires, which are related to stapling and cutting motions of the surgical instrument illustrated in FIG. 2, in detail for each of the first jaw and the second jaw.

FIG. 56 is a perspective view illustrating a pitch motion of the surgical instrument of FIG. 2.

Figure 57:
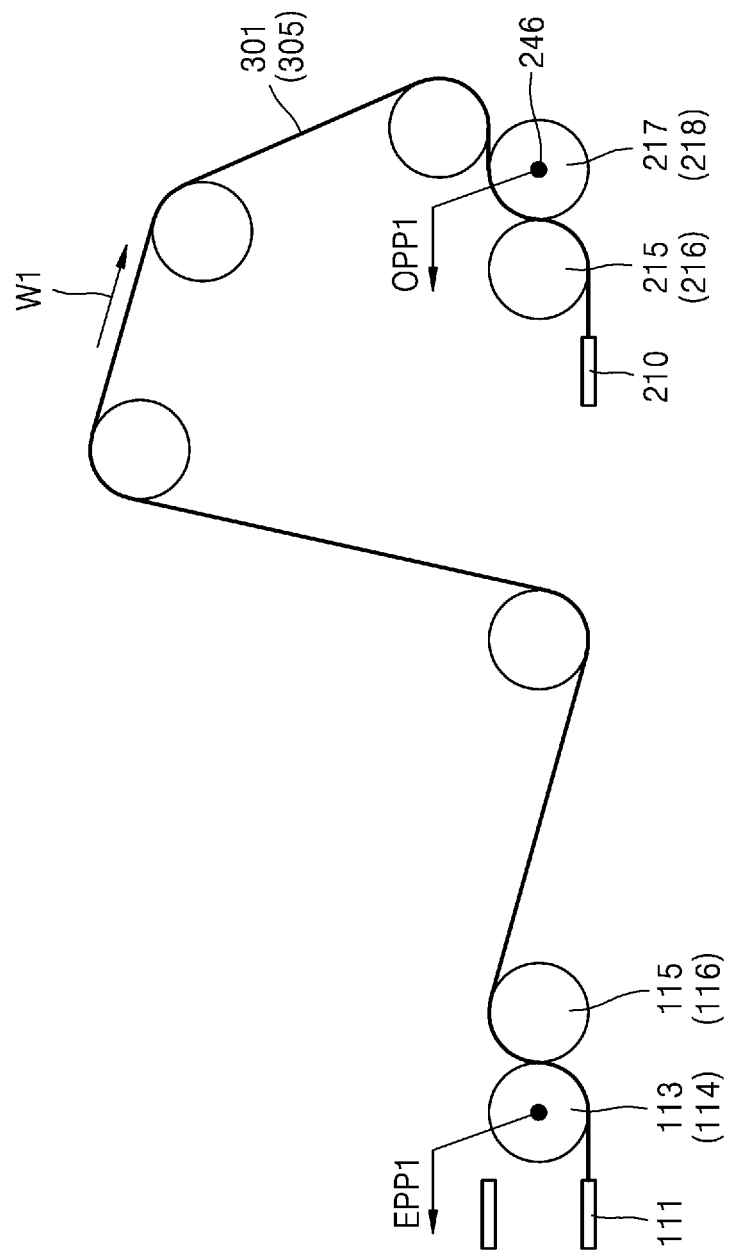
Figure 58:
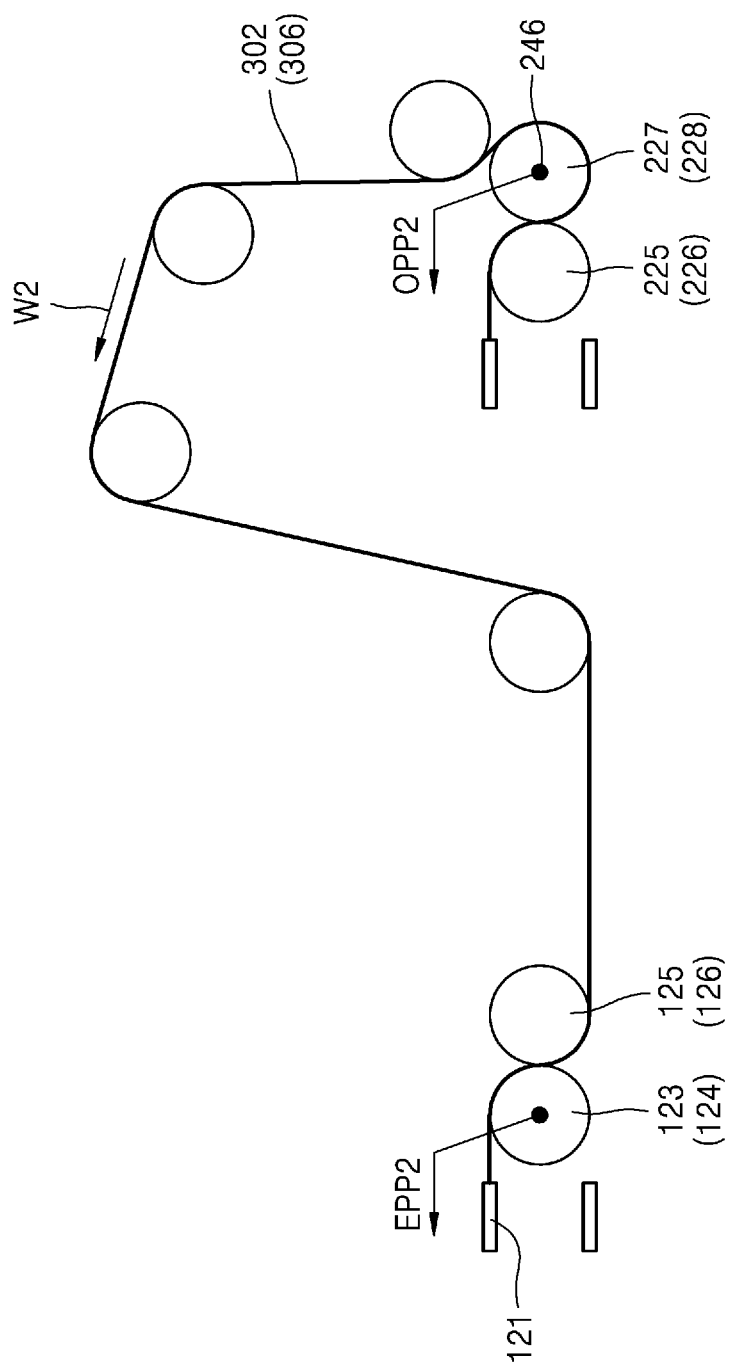
Figure 59:
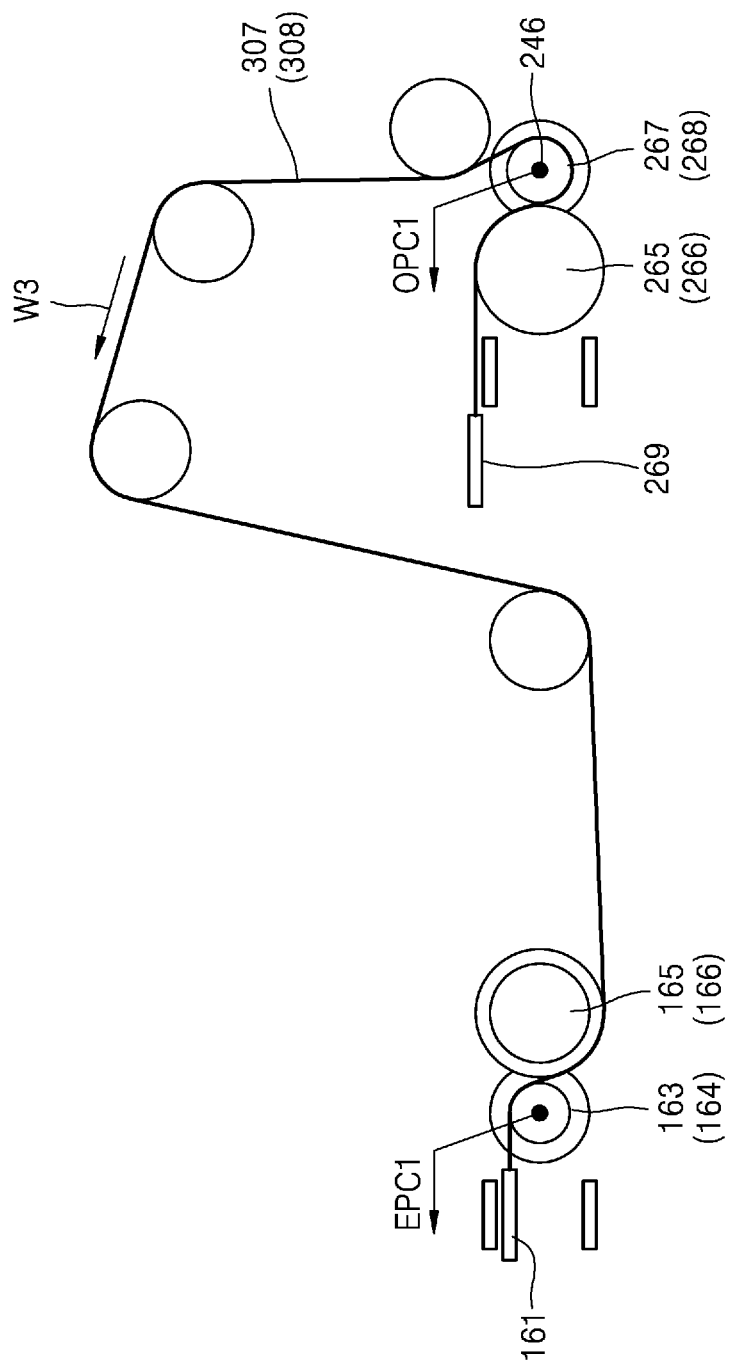

FIGS. 57, 58, and 59 are diagrams illustrating a configuration of pulleys and wires, which are related to a pitch motion of the surgical instrument illustrated in FIG. 2, in detail for each of the first jaw and the second jaw.

FIGS. 60, 61, 62, and 63 are plan views illustrating an actuation motion of the end tool of the surgical instrument of FIG. 2, and are diagrams illustrating a process of performing an actuation motion in a state in which the jaws are yaw-rotated by −90°.

FIGS. 64, 65, 66, and 67 are plan views illustrating an actuation motion of the end tool of the surgical instrument of FIG. 2, and are diagrams illustrating a process of performing an actuation motion in a state in which the jaws are yaw-rotated by +90°.

Figure 68:
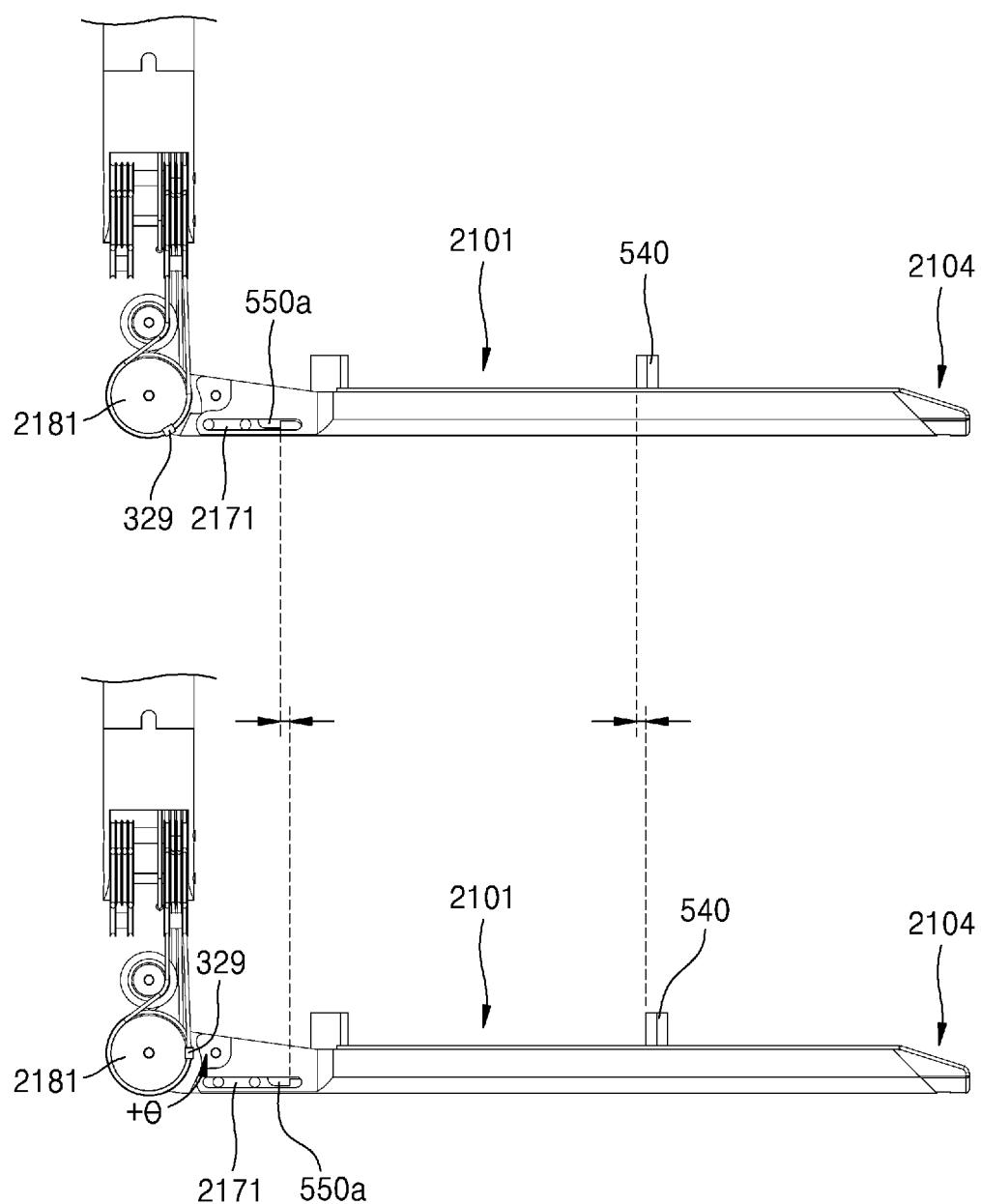
Figure 69:
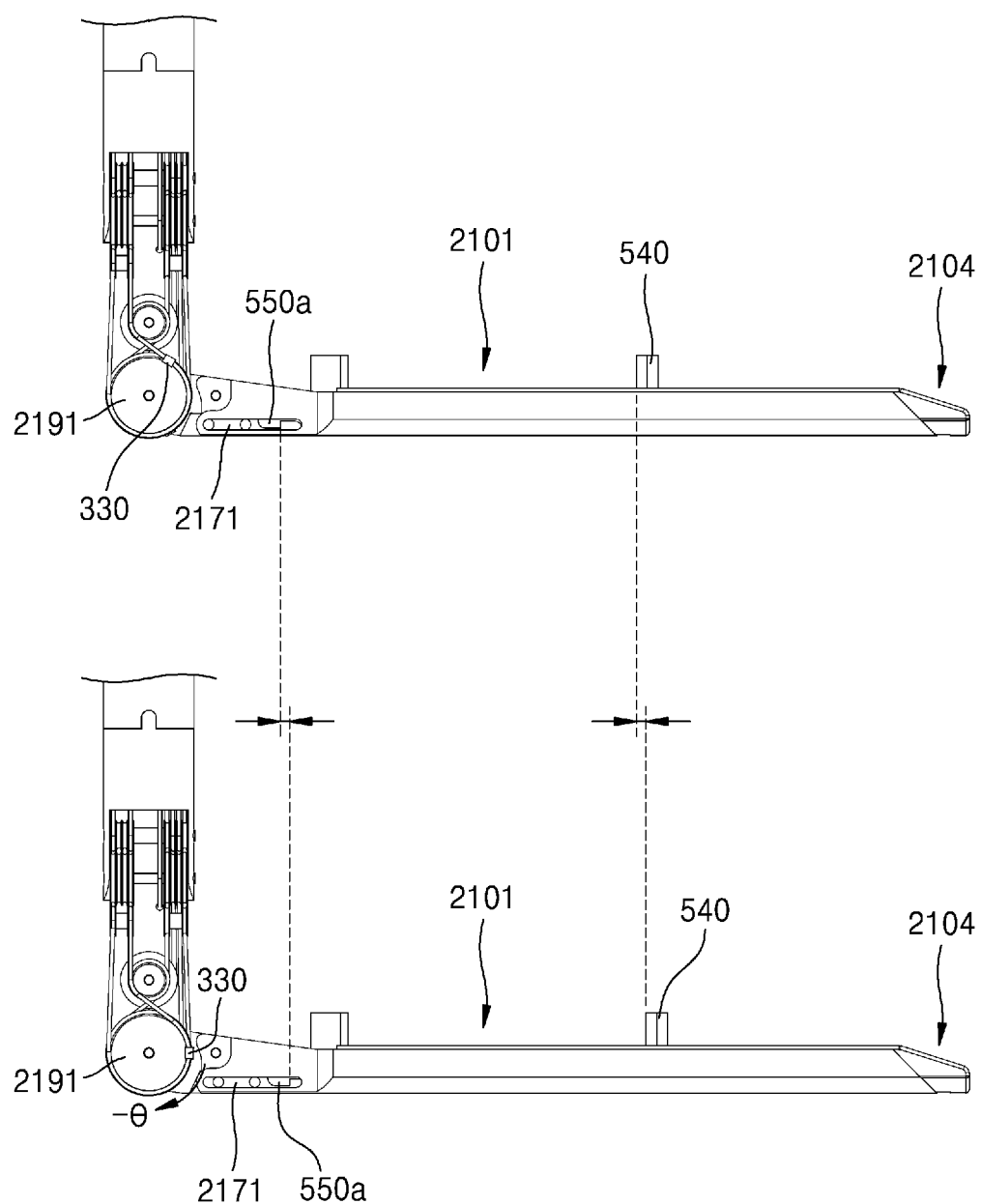

FIGS. 68 and 69 are plan views illustrating a stapling motion of the end tool of the surgical instrument of FIG. 2, and is a diagram illustrating a process of performing a stapling motion in a state in which jaws are yaw-rotated by +90°.

Figure 70:
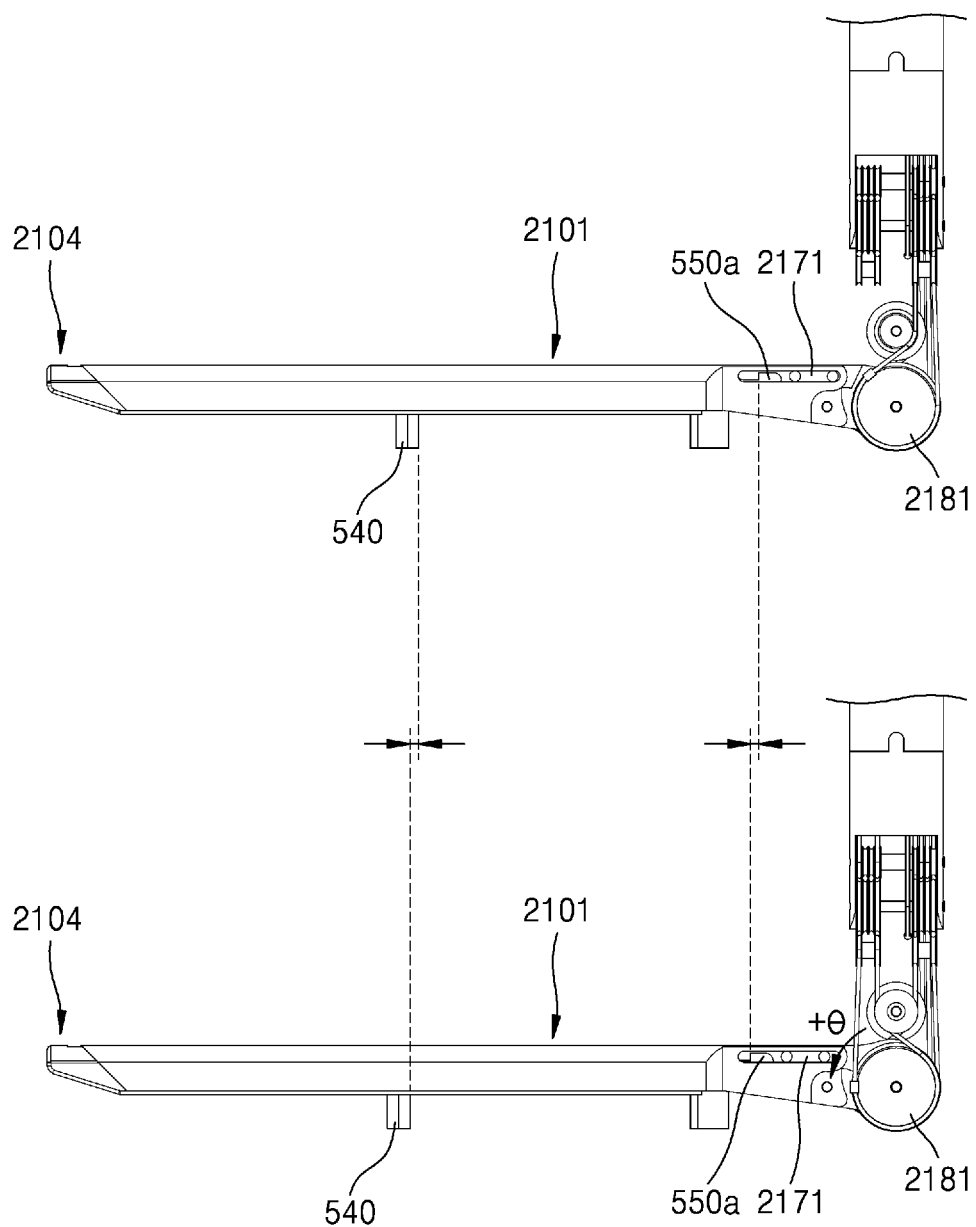
Figure 71:
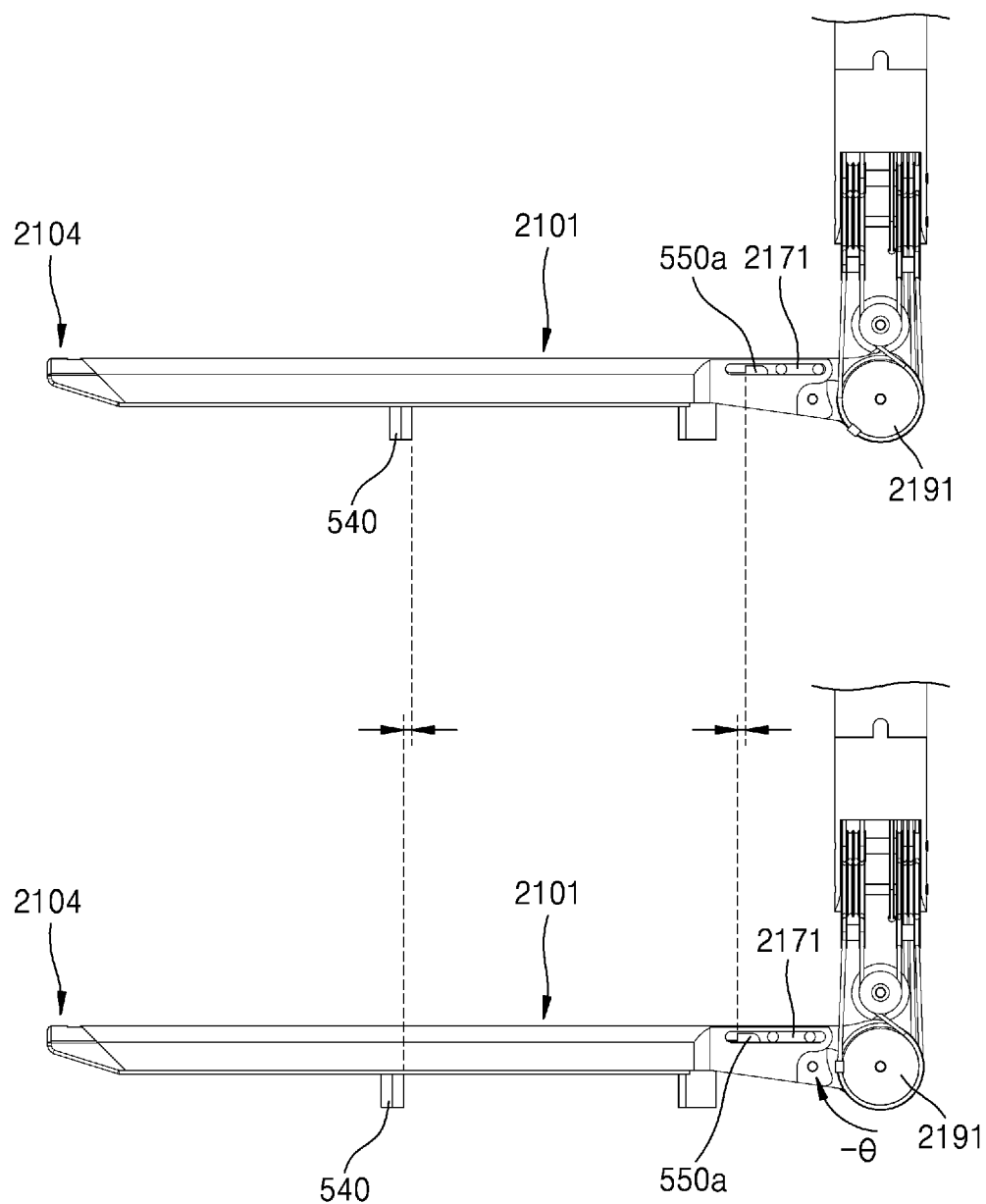

FIGS. 70 and 71 are plan views illustrating a stapling motion of the end tool of the surgical instrument of FIG. 2, and are diagrams illustrating a process of performing a stapling motion in a state in which jaws are yaw-rotated by −90°.

FIGS. 72, 73, 74, and 75 are perspective views illustrating a pitch motion of the surgical instrument of FIG. 2.

FIGS. 76, 77, 78, and 79 are perspective views illustrating a yaw motion of the surgical instrument of FIG. 2.

FIGS. 80, 81, 82, and 83 are plan views illustrating a state in which the end tool of the surgical instrument of FIG. 2 is pitch-rotated and yaw-rotated.

Figure 84:
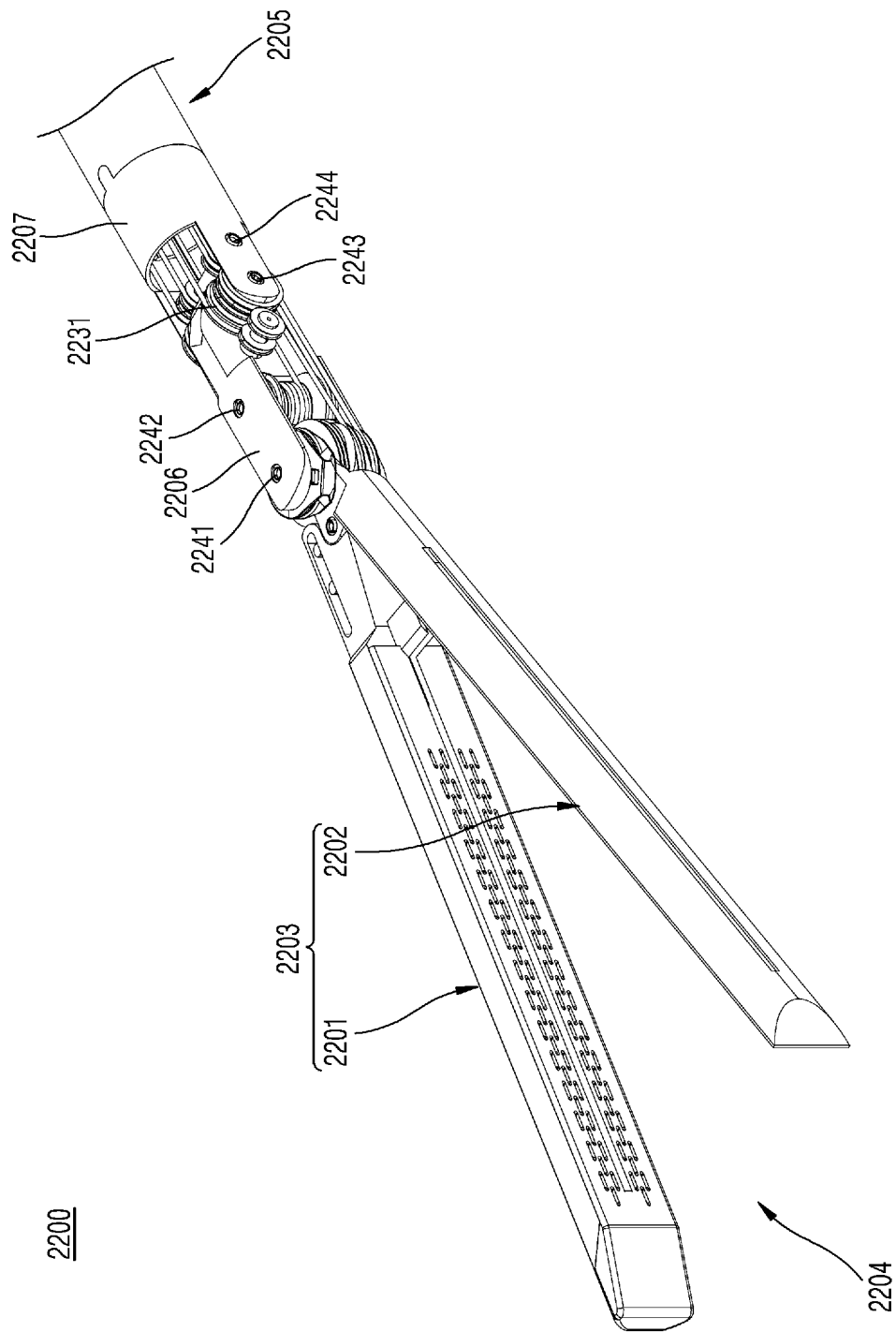
Figure 85:
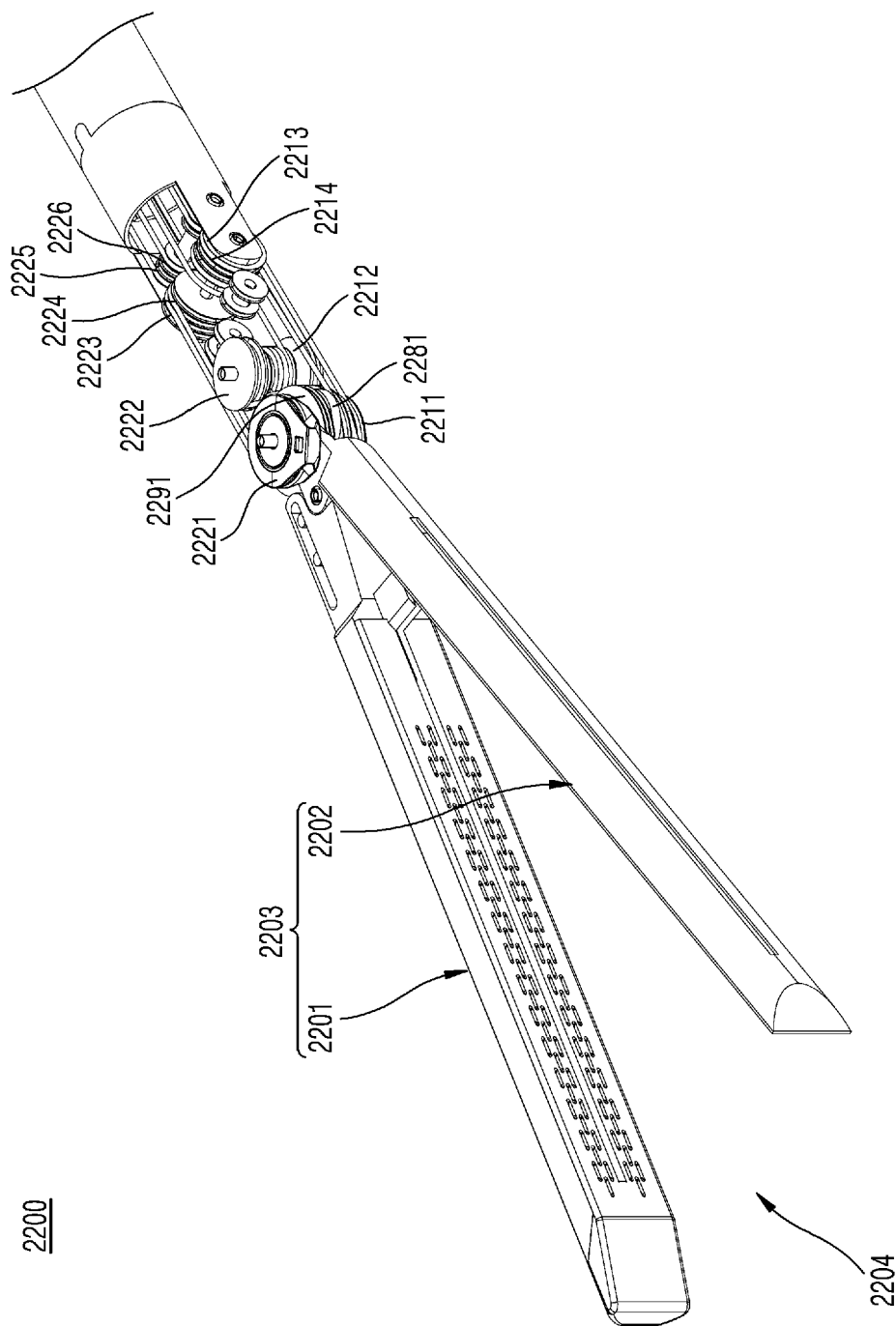

FIGS. 84 and 85 are perspective views illustrating an end tool of a surgical instrument according to a modified example of the present disclosure.

Figure 86:
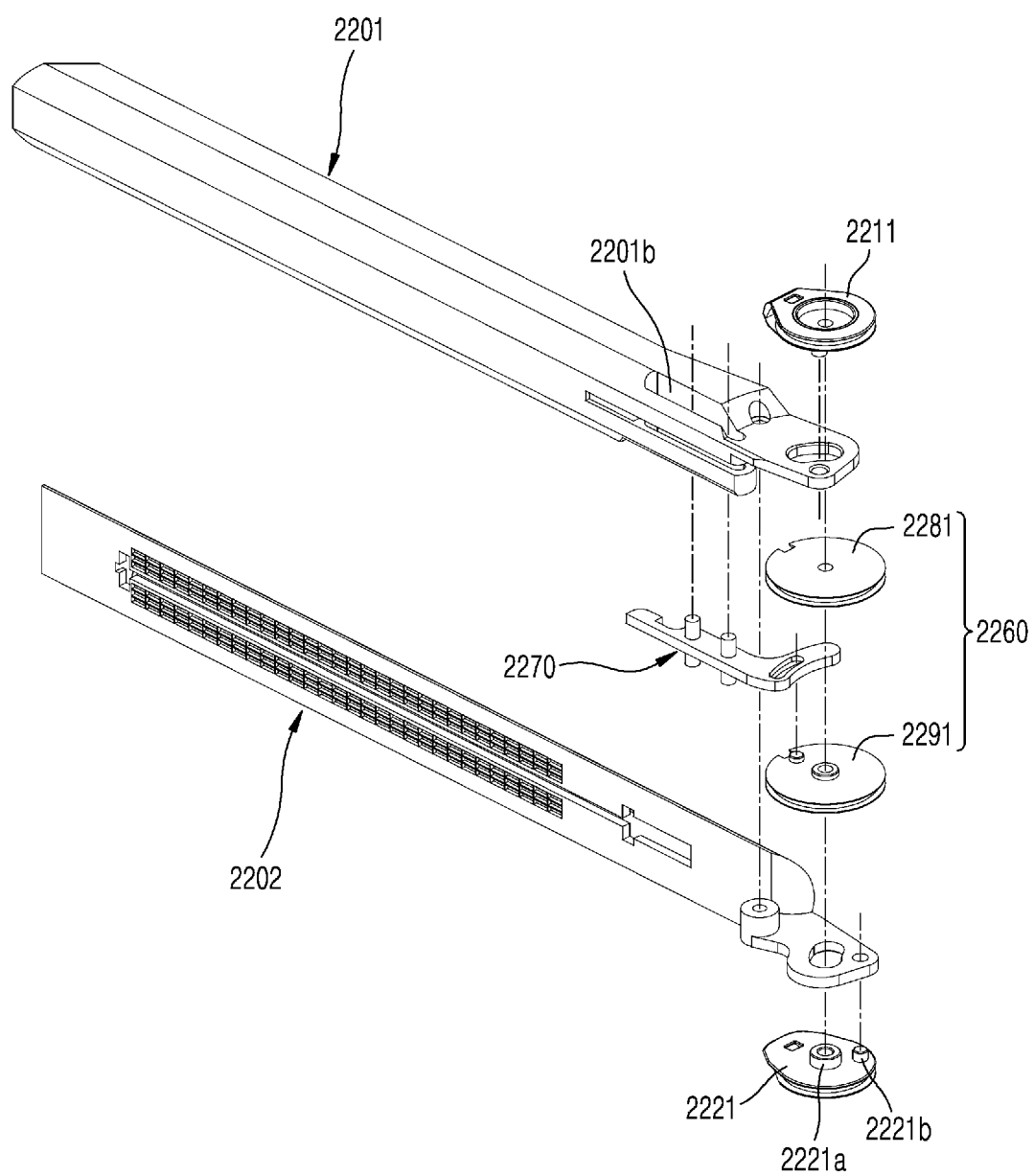
Figure 87:
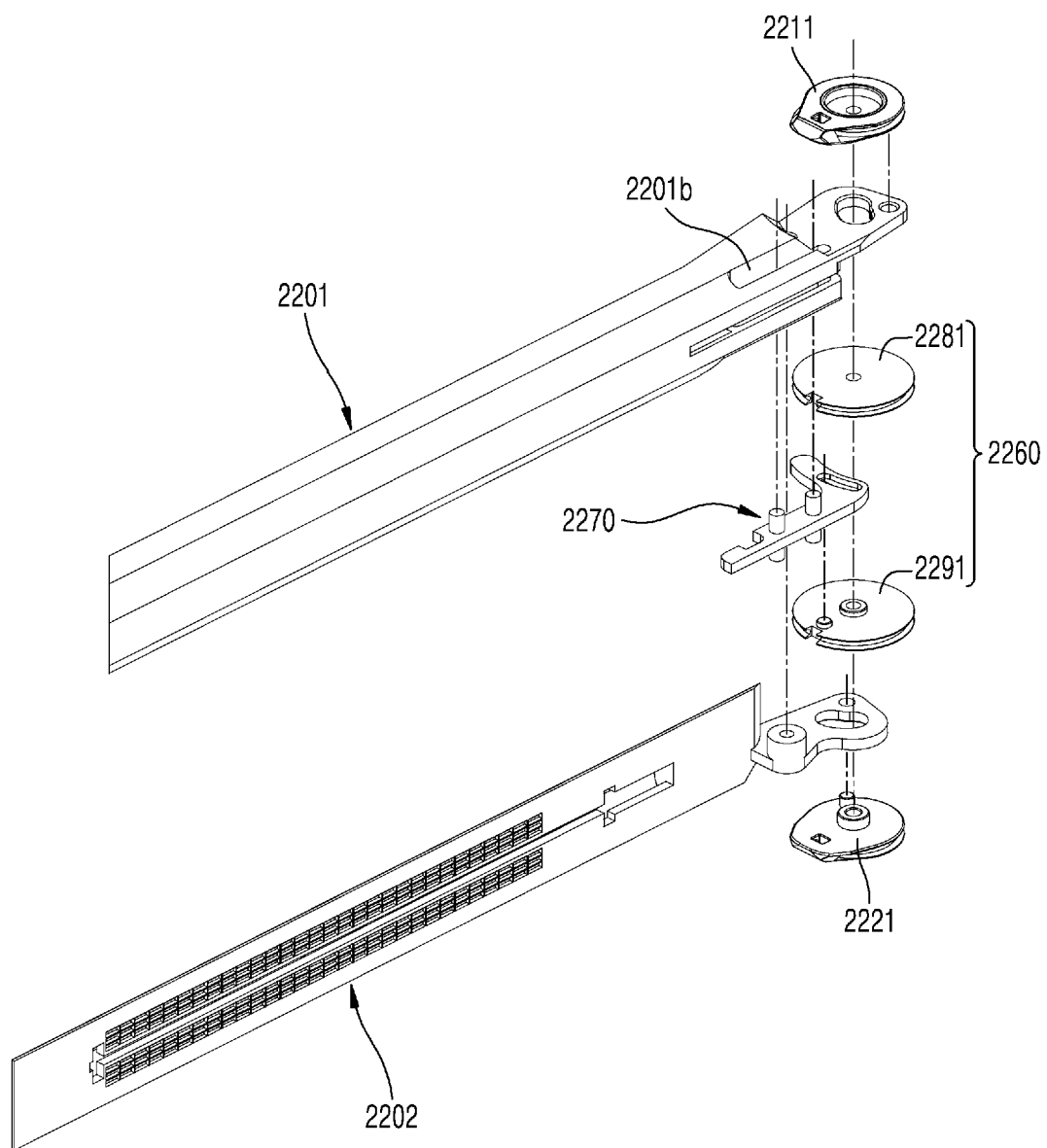

FIGS. 86 and 87 are exploded perspective views of the tool end of the surgical instrument of FIG. 84.

Figure 88:
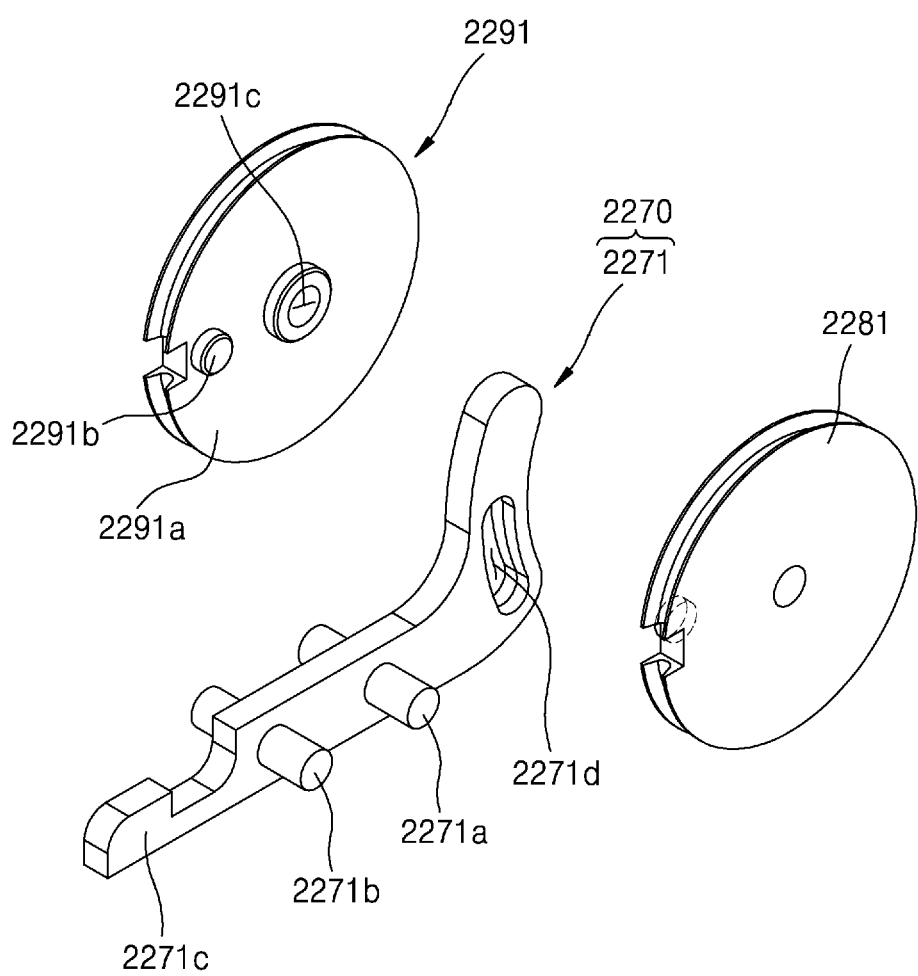
Figure 89:
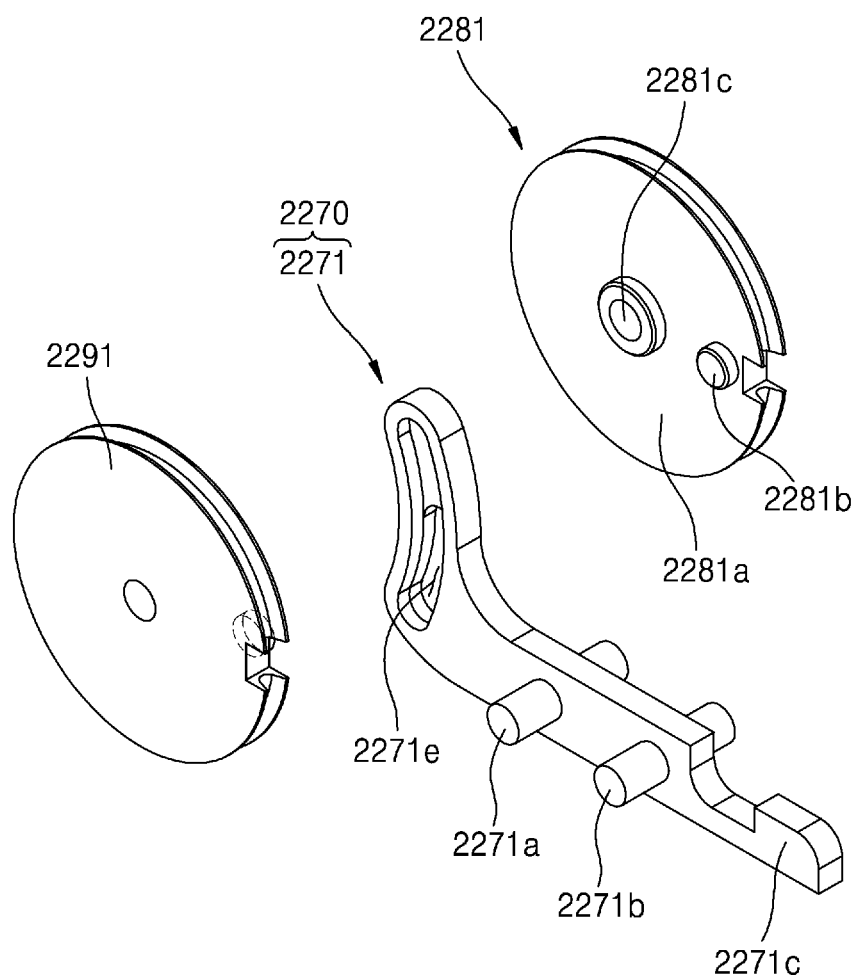

FIGS. 88 and 89 are exploded perspective views illustrating a staple pulley assembly and a staple link assembly of the surgical instrument of FIG. 84.

Figure 90:
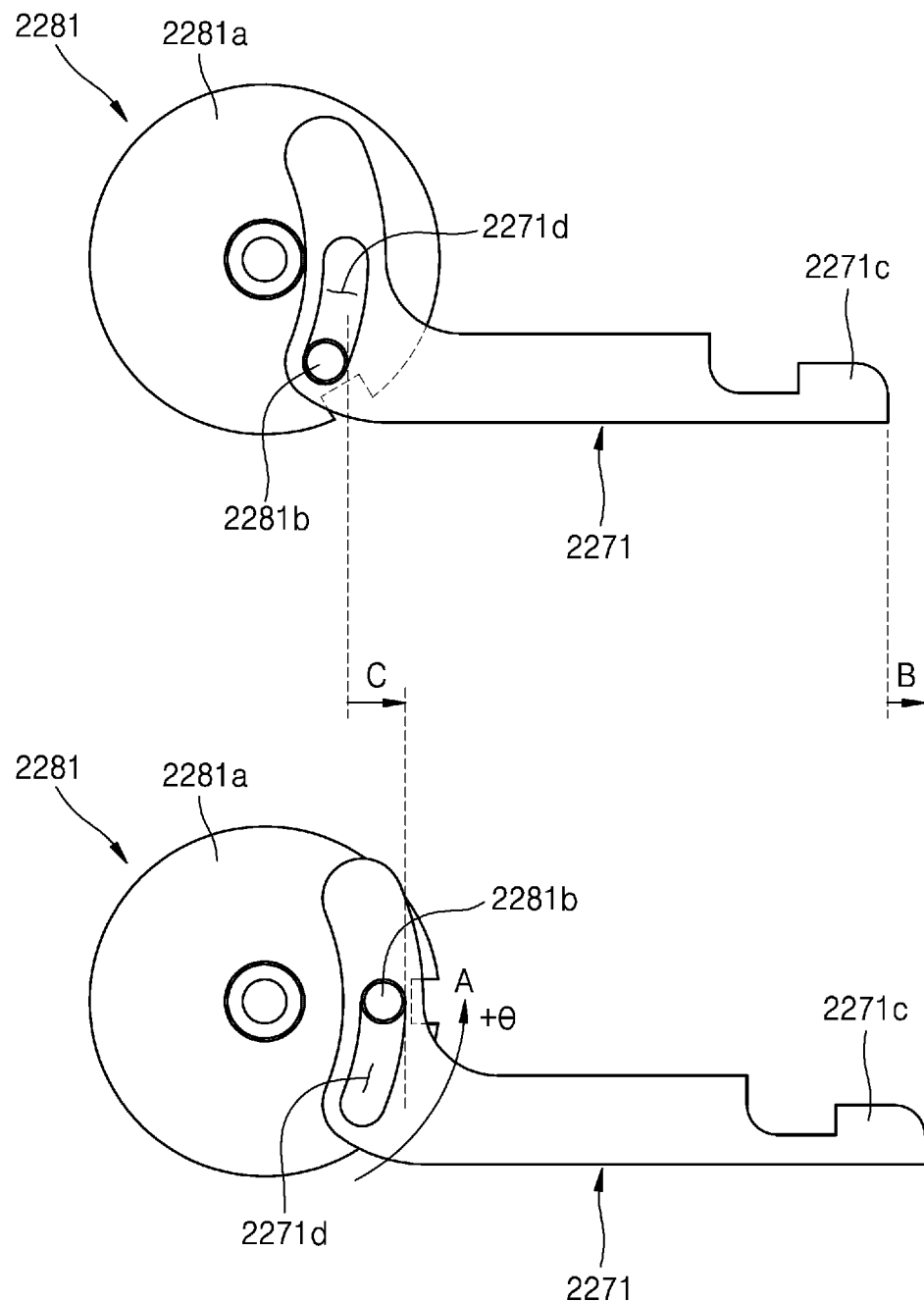
Figure 91:
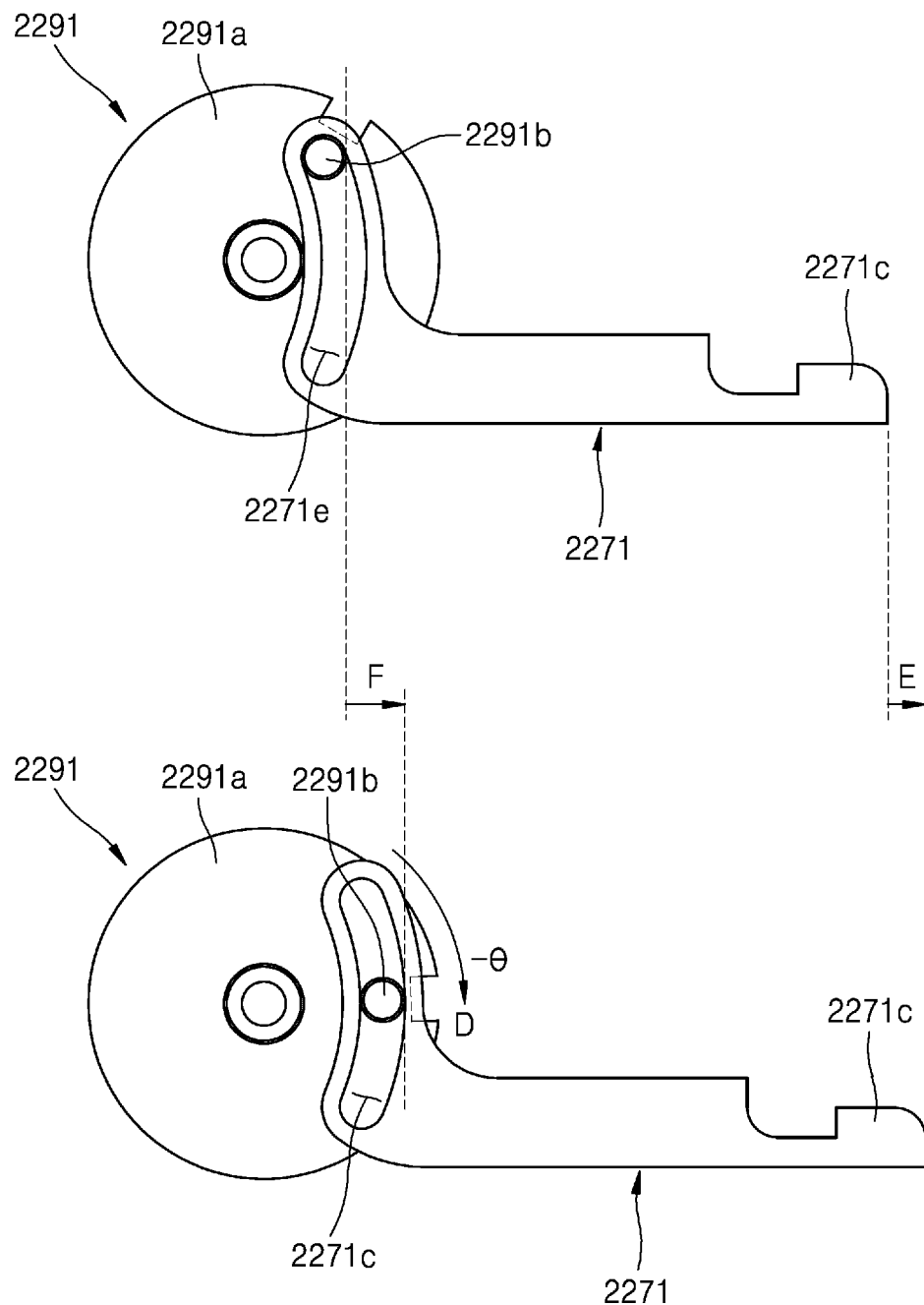

FIGS. 90 and 91 are side views illustrating operating states of a staple pulley in the end tool of the surgical instrument of FIG. 84.

Figure 92:
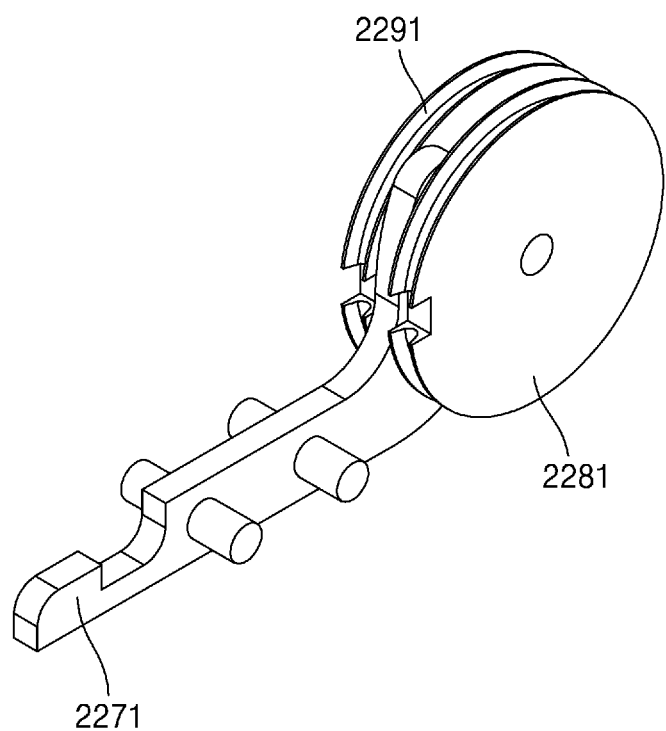
Figure 93:
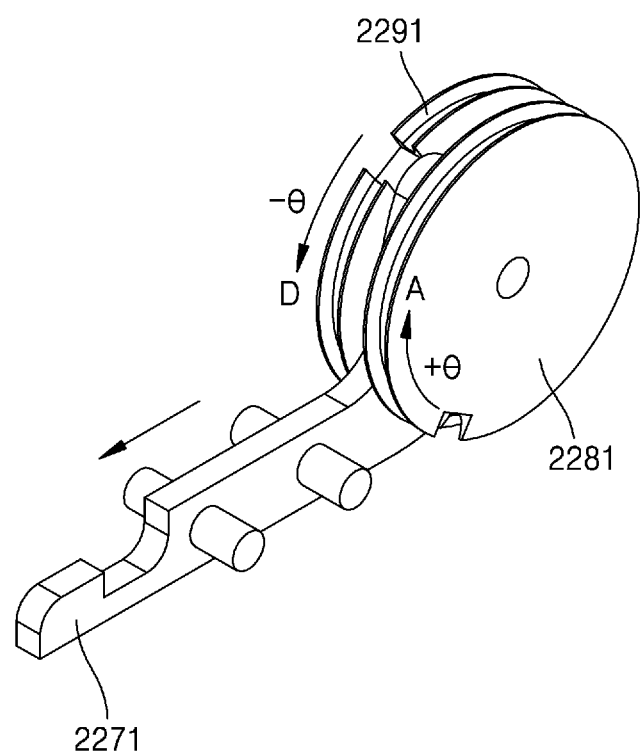

FIGS. 92 and 93 are perspective views illustrating operating states of the staple pulley in the end tool of the surgical instrument of FIG. 84.

BEST MODE

One aspect of the present disclosure provides a surgical instrument comprising: an end tool comprising: a first jaw; a second jaw formed to face the first jaw; a first jaw pulley coupled to the first jaw and formed to be rotatable around a first shaft; a second jaw pulley coupled to the second jaw, formed to be rotatable around a shaft that is substantially the same as or parallel to the first shaft, and formed to be spaced apart from the first jaw pulley by a certain extent; and a staple drive assembly comprising a first staple pulley and a second staple pulley formed adjacent to the first jaw pulley or the second jaw pulley; and a cartridge comprising: a reciprocating assembly that is connected to the staple drive assembly, and is linearly moved when the first staple pulley and the second staple pulley is rotationally moved; and an operation member that is brought into contact with the reciprocating assembly, and is moved in one direction by the reciprocating assembly when the reciprocating assembly is moved in the one direction.

In the present disclosure, when the first staple pulley or the second staple pulley is rotated, the reciprocating assembly connected to the staple drive assembly is moved toward a distal end or a proximal end of the cartridge.

In the present disclosure, when the first staple pulley or the second staple pulley is rotated alternately in a clockwise direction and a counterclockwise direction, the reciprocating assembly connected to the staple drive assembly is moved alternately toward the distal end and the proximal end of the cartridge.

In the present disclosure, when the reciprocating assembly is moved toward the distal end of the cartridge, the operation member is moved toward the distal end of the cartridge by the reciprocating assembly.

In the present disclosure, a bidirectional rotational motion of the first staple pulley or the second staple pulley is converted, by the staple drive assembly, into a reciprocating linear motion of the reciprocating assembly connected to the staple drive assembly.

In the present disclosure, as the operation member is moved in the one direction, a wedge of the operation member sequentially pushes and raises a plurality of staples in the cartridge to perform a stapling motion, and simultaneously a blade formed on one side of the wedge of the operation member is moved in the one direction to perform a cutting motion.

In the present disclosure, the staple drive assembly further comprises a link member connecting the first staple pulley and the second staple pulley to the reciprocating assembly.

In the present disclosure, the operation member comprises a ratchet member having a ratchet formed on at least one surface thereof, and the ratchet of the ratchet member is formed to be able to be in contact with the reciprocating assembly.

In the present disclosure, the operation member is moved toward a distal end of the cartridge together with the reciprocating assembly only when the reciprocating assembly is moved toward the distal end of the cartridge.

In the present disclosure, when the first staple pulley is rotated in a first direction among a clockwise direction and a counterclockwise direction, and the second staple pulley is rotated in a direction opposite to the first direction among the clockwise direction and the counterclockwise direction, the link member connected to the first staple pulley and the second staple pulley, the reciprocating assembly connected to the link member, and the operation member in contact with the reciprocating assembly are moved toward a distal end of the cartridge.

In the present disclosure, when the first staple pulley is rotated in the direction opposite to the first direction among the clockwise direction and the counterclockwise direction, and the second staple pulley is rotated in the first direction among the clockwise direction and the counterclockwise direction, the link member connected to the staple pulleys, and the reciprocating assembly connected to the link member are moved toward a proximal end of the end tool, and the operation member remains stationary with respect to the one direction.

In the present disclosure, a first protruding member is formed in the first staple pulley, a second protruding member is formed in the second staple pulley, a first slot is formed on a surface of the link member facing the first staple pulley, and a second slot is formed on one surface of the link member facing the second staple pulley.

In the present disclosure, the first protruding member and the second protruding member are formed in a form of a cam, and the link member is moved, as the first protruding member presses the first slot of the link member while rotating, and the second protruding member presses the second slot of the link member while rotating.

In the present disclosure, a center of the first protruding member does not coincide with a center of the first staple pulley, the first protruding member is formed to be eccentric to a certain extent with respect to the first staple pulley, a center of the second protruding member does not coincide with a center of the second staple pulley, and the second protruding member is formed to be eccentric to a certain extent with respect to the second staple pulley.

In the present disclosure, when the first staple pulley and the second staple pulley are rotated in directions opposite to each other, the link member is moved in one direction, and when the first staple pulley and the second staple pulley are rotated in the same direction, the link member remains stationary with respect to the one direction.

In the present disclosure, the surgical instrument may further comprise a first staple wire coupled to the first staple pulley to rotate the first staple pulley; and a second staple wire coupled to the second staple pulley to rotate the second staple pulley.

In the present disclosure, the surgical instrument may further comprise a pair of end tool first jaw pitch main pulleys formed on one side of the first jaw pulley, and formed to be rotatable around a second shaft forming a predetermined angle with the first shaft; and a pair of end tool second jaw pitch main pulleys formed on one side of the second jaw pulley, and formed to be rotatable around a shaft that is substantially the same as or parallel to the second shaft.

In the present disclosure, the end tool is formed to be yaw-rotatable around the first shaft and simultaneously pitch-rotatable around the second shaft.

In the present disclosure, the first jaw pulley, the first staple pulley, the second staple pulley, and the second jaw pulley are sequentially stacked.

In the present disclosure, the staple drive assembly is formed between the first jaw pulley and the second jaw pulley.

Another aspect of the present disclosure provides An end tool of a surgical instrument, the end tool comprising: a first jaw capable of accommodating a cartridge; a second jaw formed to face the first jaw; a first jaw pulley coupled to the first jaw and formed to be rotatable around a first shaft; a second jaw pulley coupled to the second jaw, formed to be rotatable around a shaft that is substantially the same as or parallel to the first shaft, and formed to be spaced apart from the first jaw pulley by a certain extent; a staple drive assembly comprising a first staple pulley and a second staple pulley formed adjacent to the first jaw pulley or the second jaw pulley; a first staple wire at least partially in contact with the first staple pulley and configured to transmit, to the first staple pulley, a driving force necessary for rotating the first staple pulley; and a second staple wire at least partially in contact with the second staple pulley and configured to transmit, to the second staple pulley, a driving force necessary for rotating the second staple pulley, wherein the staple drive assembly is connected to a reciprocating assembly of the cartridge and configured to convert a rotational motion of the staple pulley into a linear motion of the reciprocating assembly.

In the present disclosure, the end tool may further comprise an end tool hub comprising a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion to each other, wherein the first jaw pulley is arranged adjacent to the first jaw pulley coupling portion of the end tool hub, the second jaw pulley is arranged adjacent to the second jaw pulley coupling portion of the end tool hub, and at least a portion of the staple drive assembly is formed between the first jaw pulley and the second jaw pulley.

In the present disclosure, the first shaft is sequentially inserted through the first jaw pulley coupling portion, the first jaw pulley, the first staple pulley, the second staple pulley, the second jaw pulley, and the second jaw pulley coupling portion.

In the present disclosure, the first jaw pulley, the first staple pulley, the second staple pulley, the second jaw pulley are sequentially stacked inside the end tool hub.

In the present disclosure, the first jaw pulley, the first staple pulley, the second staple pulley, and the second jaw pulley are formed to be rotatable independently of each other.

In the present disclosure, the end tool may further comprise a first staple auxiliary pulley arranged between the first staple pulley and the guide portion.

In the present disclosure, the first staple wire is located on a common internal tangent of the first staple pulley and the first staple auxiliary pulley, and a rotation angle of the first staple pulley is increased by the first staple auxiliary pulley.

In the present disclosure, the staple drive assembly further comprises a staple link assembly connecting the first staple pulley and the second staple pulley to the reciprocating assembly.

In the present disclosure, the staple link assembly comprises a link member coupled to each of the first staple pulley, the second staple pulley, and the reciprocating assembly.

In the present disclosure, a first protruding member is formed in the first staple pulley, a second protruding member is formed in the second staple pulley, a first slot to which the first protruding member is coupled and a second slot to which the second protruding member is coupled are formed in the link member, when the first staple pulley is rotated, the first protruding member is moved in the first slot while in contact with the first slot, and when the second staple pulley is rotated, the second protruding member is moved in the second slot while in contact with the second slot.

In the present disclosure, the first slot and the second slot are formed symmetrically to each other on the link member, when the first staple pulley and the second staple pulley are rotated in directions opposite to each other, the link member is moved in one direction, and when the first staple pulley and the second staple pulley are rotated in the same direction, the link member remains stationary with respect to the one direction.

In the present disclosure, when the first staple pulley or the second staple pulley is rotated alternately in a clockwise direction and a counterclockwise direction, the staple link assembly connected to the first staple pulley or the second staple pulley is moved alternately toward a distal end and a proximal end of the end tool.

In the present disclosure, a bidirectional rotational motion of the first staple pulley or the second staple pulley is converted, by the staple link assembly, into a reciprocating linear motion of the reciprocating assembly connected to the staple link assembly.

In the present disclosure, a guide groove is formed on the first jaw in a length direction of the first jaw, and the staple link assembly is moved along the guide groove.

In the present disclosure, the end tool may further comprise a jaw rotation shaft inserted through the first jaw and the second jaw to be a center of rotation of the first jaw and the second jaw, wherein the first shaft is a jaw pulley rotation shaft, which is inserted through the first jaw pulley and the second jaw pulley to be a center of rotation of the first jaw pulley and the second jaw pulley, and when the first jaw pulley and the second jaw pulley are rotated around the jaw pulley rotation shaft, the jaw rotation shaft is moved relative to the jaw pulley rotation shaft.

In the present disclosure, when the first jaw and the second jaw are closed, the jaw rotation shaft is moved toward a distal end of the end tool, and when the first jaw and the second jaw are opened, the jaw rotation shaft is moved toward a proximal end of the end tool.

In the present disclosure, the end tool may further comprise a pair of end tool first jaw pitch main pulleys formed on one side of the first jaw pulley, and formed to be rotatable around a second shaft forming a predetermined angle with the first shaft; and a pair of end tool second jaw pitch main pulleys formed on one side of the second jaw pulley, and formed to be rotatable around a shaft that is substantially the same as or parallel to the second shaft.

In the present disclosure, the end tool is formed to be yaw-rotatable around the first shaft and simultaneously pitch-rotatable around the second shaft.

In the present disclosure, the end tool may further comprise a first jaw wire of which at least a portion is wound around the first jaw pulley and the pair of end tool first jaw pitch main pulleys; and a second jaw wire of which at least a portion is wound around the second jaw pulley and the pair of end tool second jaw pitch main pulleys.

Another aspect of the present disclosure provides an end tool of a surgical instrument, the end tool comprising: a first jaw and a second jaw that are rotatable independently of each other; a first jaw pulley coupled to the first jaw and formed to be rotatable around a first shaft; a second jaw pulley coupled to the second jaw and formed to be rotatable around a shaft that is substantially the same as or parallel to the first shaft; a first staple pulley formed to be rotatable around a shaft that is substantially the same as or parallel to the first shaft, and arranged adjacent to the first jaw pulley; a second staple pulley formed to be rotatable around a shaft that is substantially the same as or parallel to the first shaft, and arranged adjacent to the second jaw pulley; and a staple link assembly connected to each of the first staple pulley and the second staple pulley and reciprocating according to bidirectional rotation of the first staple pulley or the second staple pulley.

In the present disclosure, the staple link assembly is coupled to a reciprocating assembly of a cartridge accommodated in the first jaw, and configured to reciprocate the reciprocating assembly.

In the present disclosure, the staple link assembly is moved toward a distal end or a proximal end of the end tool according to a rotation direction of the first staple pulley or the second staple pulley.

In the present disclosure, a first protruding member is formed in the first staple pulley, a second protruding member is formed in the second staple pulley, a first slot is formed on a surface of the staple link assembly facing the first staple pulley, and a second slot is formed on a surface of the staple link assembly facing the second staple pulley.

In the present disclosure, when the first staple pulley is rotated, the first protruding member is moved in the first slot while in contact with the first slot, and when the second staple pulley is rotated, the second protruding member is moved in the second slot while in contact with the second slot.

In the present disclosure, the staple link assembly comprises a single link.

In the present disclosure, the first protruding member and the second protruding member are formed in a form of a cam, and the staple link assembly is moved, as the first protruding member presses the first slot of the staple link assembly while rotating, and the second protruding member presses the second slot of the staple link assembly while rotating.

In the present disclosure, a center of the first protruding member does not coincide with a center of the first staple pulley, the first protruding member is formed to be eccentric to a certain extent with respect to the first staple pulley, a center of the second protruding member does not coincide with a center of the second staple pulley, and the second protruding member is formed to be eccentric to a certain extent with respect to the second staple pulley.

In the present disclosure, the first slot and the second slot are formed to be vertically symmetrical with each other on the staple link assembly.

In the present disclosure, when the first staple pulley and the second staple pulley are rotated in directions opposite to each other, the staple link assembly is moved in one direction, and when the first staple pulley and the second staple pulley are rotated in the same direction, the staple link assembly remains stationary with respect to the one direction.

In the present disclosure, a guide groove is formed on the first jaw in a length direction of the first jaw, and the staple link assembly is moved along the guide groove.

In the present disclosure, the end tool may further comprise a pair of end tool first jaw pitch main pulleys formed on one side of the first jaw pulley, and formed to be rotatable around a second shaft forming a predetermined angle with the first shaft; and a pair of end tool second jaw pitch main pulleys formed on one side of the second jaw pulley, and formed to be rotatable around a shaft that is substantially the same as or parallel to the second shaft.

In the present disclosure, when the first jaw pulley and the second jaw pulley are rotated in the same direction around the second shaft, the first staple pulley and the second staple pulley are rotated together with the first jaw pulley and the second jaw pulley.

In the present disclosure, when the first jaw pulley and the second jaw pulley are rotated in the same direction around the first shaft, the first staple pulley and the second staple pulley are rotated together with the first jaw pulley and the second jaw pulley.

In the present disclosure, when the first jaw pulley and the second jaw pulley are rotated in directions opposite to each other around the first shaft, the first staple pulley and the second staple pulley are rotated together with any one of the first jaw pulley or the second jaw pulley.

In the present disclosure, there is a case in which the first jaw pulley and the second jaw pulley are not rotated while the first staple pulley and the second staple pulley are rotated around the first shaft by a staple wire.

In the present disclosure, a cartridge accommodation portion in which a cartridge is able to be accommodated is formed in the first jaw, and an anvil with which a staple of the cartridge is able to be in contact is formed in the second jaw.

In the present disclosure, the end tool may further comprise a first jaw wire of which at least a portion is wound around the first jaw pulley; a second jaw wire of which at least a portion is wound around the second jaw pulley; a first staple wire of which at least a portion is wound around the first staple pulley; and a second staple wire of which at least a portion is wound around the second staple pulley.

Another aspect of the present disclosure provides an end tool of a surgical instrument, the end tool comprising: a first jaw and a second jaw that are rotatable independently of each other; a first jaw pulley coupled to the first jaw and formed to be rotatable around a first shaft; a first jaw wire of which at least a portion is wound around the first jaw pulley; a second jaw pulley coupled to the second jaw and formed to be rotatable around the first shaft; a second jaw wire of which at least a portion is wound around the second jaw pulley; a pair of end tool first jaw pitch main pulleys formed on one side of the first jaw pulley, and formed to be rotatable around a second shaft forming a predetermined angle with the first shaft; a pair of end tool second jaw pitch main pulleys formed on one side of the second jaw pulley, and formed to be rotatable around a shaft that is substantially the same as or parallel to the second shaft; a first staple pulley and a second staple pulley formed to be rotatable around the first shaft and arranged between the first jaw pulley and the second jaw pulley; a staple link assembly connected to the first staple pulley and the second staple pulley and reciprocating according to bidirectional rotation of the first staple pulley or the second staple pulley; a first staple wire at least partially in contact with the first staple pulley and configured to transmit, to the first staple pulley, a driving force necessary for rotating the first staple pulley; and a second staple wire at least partially in contact with the second staple pulley and configured to transmit, to the second staple pulley, a driving force necessary for rotating the second staple pulley.

In the present disclosure, a bidirectional rotational motion of the first staple pulley or the second staple pulley is converted into a reciprocating linear motion of the staple link assembly.

In the present disclosure, the staple link assembly is coupled to a reciprocating assembly of a cartridge accommodated in the first jaw, and a rotational motion of the first staple pulley or the second staple pulley is transmitted to an operation member of the cartridge via the staple link assembly and the reciprocating assembly.

In the present disclosure, a bidirectional rotational motion of the first staple pulley or the second staple pulley is converted, by the staple link assembly, into a reciprocating linear motion of the reciprocating assembly connected to the staple link assembly.

In the present disclosure, the end tool may further comprise a jaw rotation shaft inserted through the first jaw and the second jaw to be a center of rotation of the first jaw and the second jaw, wherein the first shaft is a jaw pulley rotation shaft, which is inserted through the first jaw pulley and the second jaw pulley to be a center of rotation of the first jaw pulley and the second jaw pulley, and when the first jaw pulley and the second jaw pulley are rotated around the jaw pulley rotation shaft, the jaw rotation shaft is moved relative to the jaw pulley rotation shaft.

In the present disclosure, when the first jaw and the second jaw are closed, the jaw rotation shaft is moved toward a distal end of the end tool, and when the first jaw and the second jaw are opened, the jaw rotation shaft is moved toward a proximal end of the end tool.

In the present disclosure, a movable-coupling hole is formed in the first jaw or the second jaw, a shaft coupling portion is formed in the first jaw pulley or the second jaw pulley, and the shaft coupling portion is formed to be movable to a certain extent in the movable-coupling hole in a state in which the shaft coupling portion is fitted into the movable-coupling hole.

In the present disclosure, when the first staple pulley or the second staple pulley is rotated alternately in a clockwise direction and a counterclockwise direction, the staple link assembly connected to the first staple pulley or the second staple pulley is moved alternately toward a distal end and a proximal end of the end tool.

In the present disclosure, a guide groove is formed on the first jaw in a length direction of the first jaw, and the staple link assembly is moved along the guide groove.

In the present disclosure, the staple link assembly comprises a link member coupled to each of the first staple pulley and the second staple pulley.

In the present disclosure, a first protruding member is formed in the first staple pulley, a second protruding member is formed in the second staple pulley, a first slot is formed on a surface of the link member facing the first staple pulley, and a second slot is formed on one surface of the link member facing the second staple pulley.

In the present disclosure, the first protruding member and the second protruding member are formed in a form of a cam, and the link member is moved, as the first protruding member presses the first slot of the link member while rotating, and the second protruding member presses the second slot of the link member while rotating.

In the present disclosure, a center of the first protruding member does not coincide with a center of the first staple pulley, the first protruding member is formed to be eccentric to a certain extent with respect to the first staple pulley, a center of the second protruding member does not coincide with a center of the second staple pulley, and the second protruding member is formed to be eccentric to a certain extent with respect to the second staple pulley.

In the present disclosure, each of a thickness of the first slot and a thickness of the second slot is less than a thickness of the link member.

In the present disclosure, a sum of a thickness of the first slot and a thickness of the second slot is substantially equal to a thickness of the link member.

In the present disclosure, when the first staple pulley is rotated, the first protruding member is moved in the first slot while in contact with the first slot, and when the second staple pulley is rotated, the second protruding member is moved in the second slot while in contact with the second slot.

In the present disclosure, the first slot and the second slot are formed symmetrically to each other on the link member, when the first staple pulley and the second staple pulley are rotated in directions opposite to each other, the link member is moved in one direction, and when the first staple pulley and the second staple pulley are rotated in the same direction, the link member remains stationary with respect to the one direction.

In the present disclosure, the protruding member is formed in the form of a pin, and the link member is moved as the protruding member presses the slot of the link while rotating.

In the present disclosure, the slot is formed obliquely without being concentric with the staple pulley, and the pin is moved along the slot.

In the present disclosure, the link member is formed as a single member.

In the present disclosure, the end tool may further comprise a pair of end tool first jaw pitch main pulleys formed on one side of the first jaw pulley, and formed to be rotatable around a second shaft forming a predetermined angle with the first shaft; and a pair of end tool second jaw pitch main pulleys formed on one side of the second jaw pulley, and formed to be rotatable around a shaft that is substantially the same as or parallel to the second shaft.

In the present disclosure, the end tool is formed to be yaw-rotatable around the first shaft and simultaneously pitch-rotatable around the second shaft.

In the present disclosure, the end tool may further comprise a first jaw wire of which at least a portion is wound around the first jaw pulley and the pair of end tool first jaw pitch main pulleys; and a second jaw wire of which at least a portion is wound around the second jaw pulley and the pair of end tool second jaw pitch main pulleys.

In the present disclosure, a pair of first staple pitch main pulleys formed on one side of the first staple pulley and formed to be rotatable around the second shaft forming the predetermined angle with the first shaft; and a pair of second staple pitch main pulleys formed on one side of the second staple pulley, and formed to be rotatable around a shaft that is substantially the same as or parallel to the second shaft.

In the present disclosure, the end tool may further comprise a staple wire separation prevention pulley arranged between the first staple pulley and the first staple pitch main pulley or between the second staple pulley and the second staple pitch main pulley, formed to be rotatable around a shaft that is substantially the same as or parallel to the second shaft, and configured to guide a path of the first staple wire or the second staple wire.

Another aspect of the present disclosure provides a method of driving a surgical instrument, the method comprising operations: (a) in which, when a first staple pulley of a staple drive assembly is rotated in a first direction around a first shaft and a second staple pulley is rotated in a second direction opposite to the first direction around the first shaft, a staple link assembly connected to the first staple pulley and the second staple pulley, and a reciprocating assembly of a cartridge connected to the staple link assembly are moved along a second shaft toward a distal end of the cartridge; (b) in which, when the reciprocating assembly is moved toward the distal end of the cartridge, an operation member in contact with the reciprocating assembly is moved toward the distal end of the cartridge together with the reciprocating assembly; (c) in which, as the operation member is moved toward the distal end of the cartridge, the operation member ejects staples in the cartridge to the outside of the cartridge, and simultaneously, a blade of the operation member is moved toward the distal end of the cartridge; and (d) in which, when the first staple pulley is rotated in the second direction around the first shaft and the second staple pulley is rotated in the first direction around the first shaft, the staple link assembly connected to the first staple pulley and the second staple pulley, and the reciprocating assembly of the cartridge connected to the staple link assembly are moved toward a proximal end of the cartridge.

In the present disclosure, when the first staple pulley or the second staple pulley is rotated in the first direction or the second direction, the reciprocating assembly is moved toward the distal end of the cartridge or toward the proximal end of the cartridge.

In the present disclosure, a bidirectional rotational motion of the first staple pulley or the second staple pulley around the first shaft is converted into a reciprocating linear motion of the reciprocating assembly connected to the first staple pulley and the second staple pulley along the second shaft.

In the present disclosure, the operation member is moved toward the distal end of the cartridge by the reciprocating linear motion of the reciprocating assembly.

In the present disclosure, a rack is formed on one surface of the reciprocating assembly, the operation member comprises a ratchet member having a ratchet formed thereon, and as the rack pushes the ratchet member while being in close contact with the ratchet member, the ratchet member is moved toward the distal end of the cartridge.

In the present disclosure, in operation (d), the operation member remains stationary with respect to a direction of the second shaft.

In the present disclosure, the operation member is moved toward the distal end of the cartridge together with the reciprocating assembly only when the reciprocating assembly is moved toward the distal end of the cartridge.

In the present disclosure, the end tool may further comprise a first staple wire coupled to the first staple pulley to rotate the first staple pulley, and a second staple wire coupled to the second staple pulley to rotate the second staple pulley, wherein bidirectional rotation of the first staple pulley or the first staple pulley by the first staple wire or the second staple wire is converted into a reciprocating linear motion of the reciprocating assembly.

In the present disclosure, as the operation member is moved toward the distal end of the cartridge, a wedge of the operation member sequentially pushes and raises a plurality of staples in the cartridge to perform a stapling motion, and simultaneously, the blade formed on one side of the wedge of the operation member is moved toward the distal end of the cartridge to perform a cutting motion.

In the present disclosure, operations (a) to (d) are repeatedly performed.

Other aspects, features, advantages other than those described above will become apparent from the following drawings, claims, and detailed description of the present disclosure.

MODE OF DISCLOSURE

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, detailed description of known related arts will be omitted when it is determined that the gist of the present disclosure may be unnecessarily obscured Although terms such as "first," "second," and the like may be used to describe various components, such components should not be limited to the above terms The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise," "comprising," "include," and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

In a surgical instrument according to the present disclosure, when a manipulation part is rotated in one direction for at least any one of pitch, yaw, and actuation motions, an end tool is rotated in intuitively the same direction as a direction in which the manipulation part is moved.

FIG. 1A is a conceptual diagram of a pitch motion of a conventional surgical instrument, and FIG. 1B is a conceptual diagram of a yaw motion thereof.

Referring to FIG. 1A, in performing a pitch motion of a conventional surgical instrument, in a state in which an end tool 120a is formed in front of a rotation center 121a of the end tool, and a manipulation part 110a is formed at the rear of a rotation center 111a of the manipulation part, when the manipulation part 110a is rotated in a clockwise direction, the end tool 120a is also rotated in the clockwise direction, and when the manipulation part 120a is rotated in a counterclockwise direction, the end tool 120a is also rotated in the counterclockwise direction. Referring to FIG. 1B, in performing a yaw motion of the conventional surgical instrument, in a state in which the end tool 120a is formed in front of the rotation center 121a of the end tool, and the manipulation part 110a is formed at the rear of the rotation center 111a of the manipulation part, when the manipulation part 110a is rotated in the clockwise direction, the end tool 120a is also rotated in the clockwise direction, and when the manipulation part 120a is rotated in the counterclockwise direction, the end tool 120a is also rotated in the counterclockwise direction. In this case, in view of left and right directions of a user, when the user moves the manipulation part 110a to the left, the end tool 120a is moved to the right, and when the user moves the manipulation part 110a to the right, the end tool 120a is moved to the left. As a result, a manipulation direction of the user and an operation direction of the end tool are opposite to each other, which may cause the user to make a mistake, and user's manipulation may not be easy.

FIG. 1C is a conceptual diagram of a pitch motion of another conventional surgical instrument, and FIG. 1D is a conceptual diagram of a yaw motion thereof.

Referring to FIG. 1C, in the conventional surgical instrument, which is partially formed in a mirror symmetrical shape, in performing a pitch motion, in a state in which an end tool 120b is formed in front of a rotation center 121b of the end tool, and a manipulation part 110b is formed at the rear of a rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of a joint is not intuitive, the user may make an error. Further, referring to FIG. 1D, in performing a yaw motion, in a state in which the end tool 120b is formed in front of the rotation center 121b of the end tool, and the manipulation part 110b is formed at the rear of the rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of the joint is not intuitive, the user may make an error. In the user's pitch or yaw manipulation of the conventional surgical instrument, the user's manipulation direction and the end tool's operation direction do not match each other in view of one of the rotation direction and the left and right directions. This is because the configurations of the end tool and the manipulation part are different from each other in the joint configuration of the conventional surgical instrument. That is, this is because the manipulation part is formed at the rear of the rotation center of the manipulation part, while the end tool is formed in front of the rotation center of the end tool. In order to address the above problems, in a surgical instrument according to an embodiment of the present disclosure, which is illustrated in FIGS. 1E and 1F, an end tool 120c is formed in front of a rotation center 121c of the end tool and a manipulation part 110c is also formed in front of a rotation center 111c of the manipulation part, so that the operations of the manipulation part 110c and the end tool 120c are intuitively matched with each other. In other words, unlike existing examples such as those shown in FIGS. 1A, 1B, 1C, and 1D, in which the manipulation part is close to a user with respect to the joint thereof (that is, away from the end tool), the surgical instrument according to an embodiment of the present disclosure, which is illustrated in FIGS. 1E and 1F, is formed such that at least a portion of the manipulation part is closer (than a joint thereof) to the end tool with respect to the joint thereof at any one moment or more in a manipulation process.

In other words, in the conventional surgical instrument as illustrated in FIGS. 1A, 1B, 1C, and 1D, the manipulation part is formed at the rear of the rotation center thereof, while the end tool is located in front of the rotation center thereof, and thus the end tool is moved at a front side thereof with a rear side fixed through a motion of the manipulation part that is moved at a rear side thereof with a front side thereof fixed, which is not an intuitively matching structure. Accordingly, a mismatch may occur between the manipulation of the manipulation part and the motion of the end tool in view of the left and right directions or in view of the rotation direction, which may cause confusion to the user, and the manipulation of the manipulation part may be difficult to perform intuitively and quickly and may cause mistakes. In contrast, in the surgical instrument according to an embodiment of the present disclosure, since both the end tool and the manipulation part are moved with respect to the rotation center formed at the rear side thereof, it may be said that the motions are intuitively matched with each other in terms of structure. In other words, moving portions of the manipulation part are moved with respect to the rotation center formed at the rear side thereof just as moving portions of the end tool are moved with respect to the rotation center formed at the rear side thereof, and thus it may be said that the motions are intuitively matched with each other in terms of structure. This allows the user to intuitively and quickly perform a control in a direction toward the end tool, and a possibility of making a mistake may be significantly reduced. Hereinafter, a detailed mechanism enabling the above-described function will be described below.

<First Embodiment of Surgical Instrument>

Figure 3:
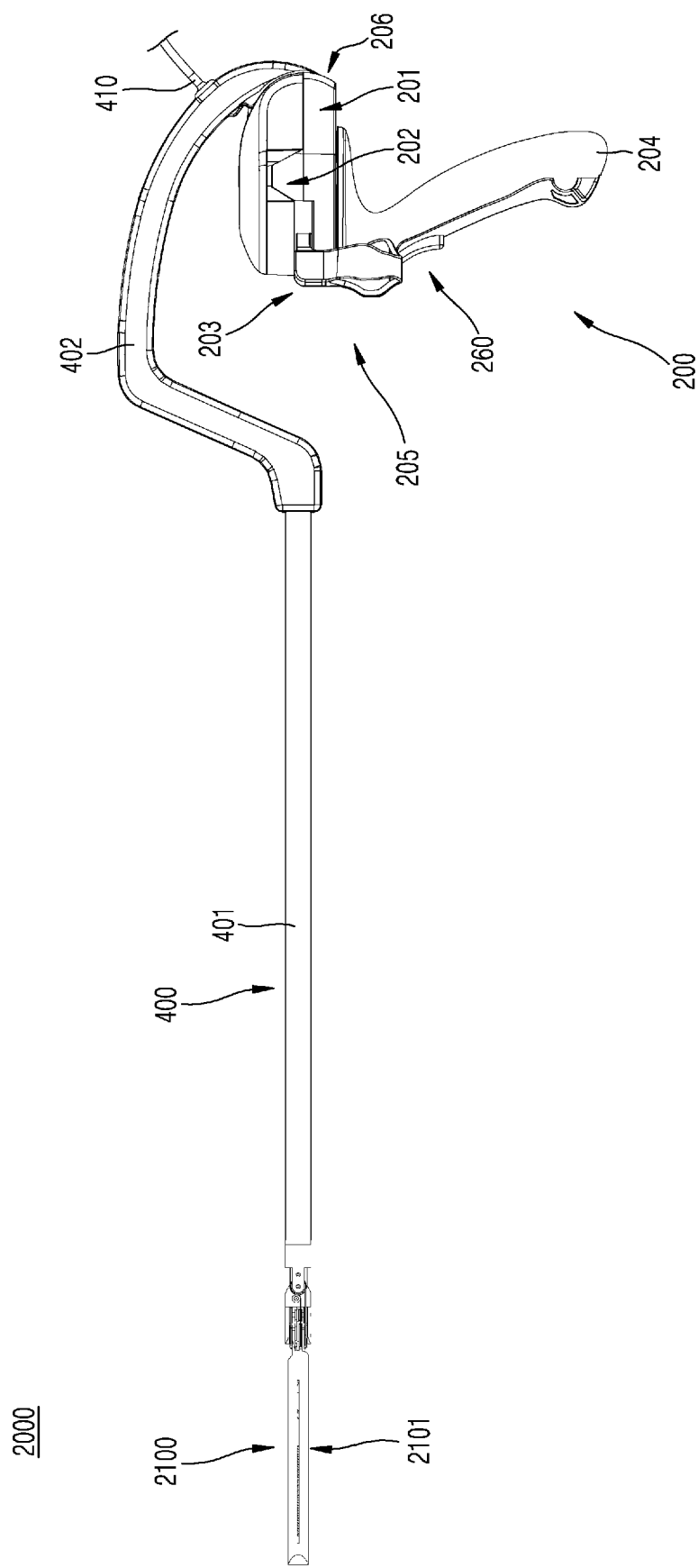
FIG. 3 is a side view of the surgical instrument of FIG. 2.
Figure 4:
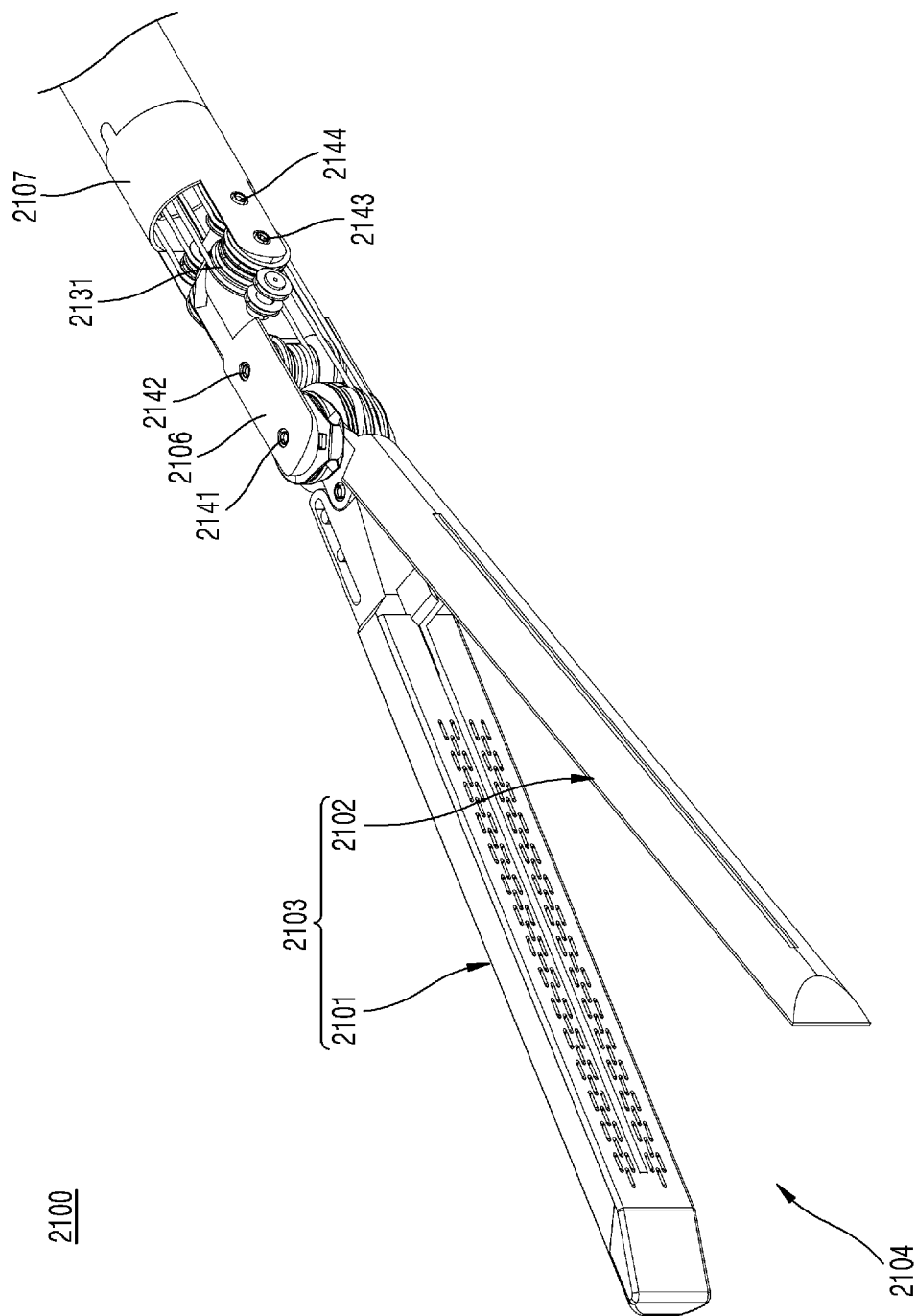
FIGS. 4 and 5 are perspective views illustrating an end tool of the surgical instrument of FIG. 2.
Figure 5:
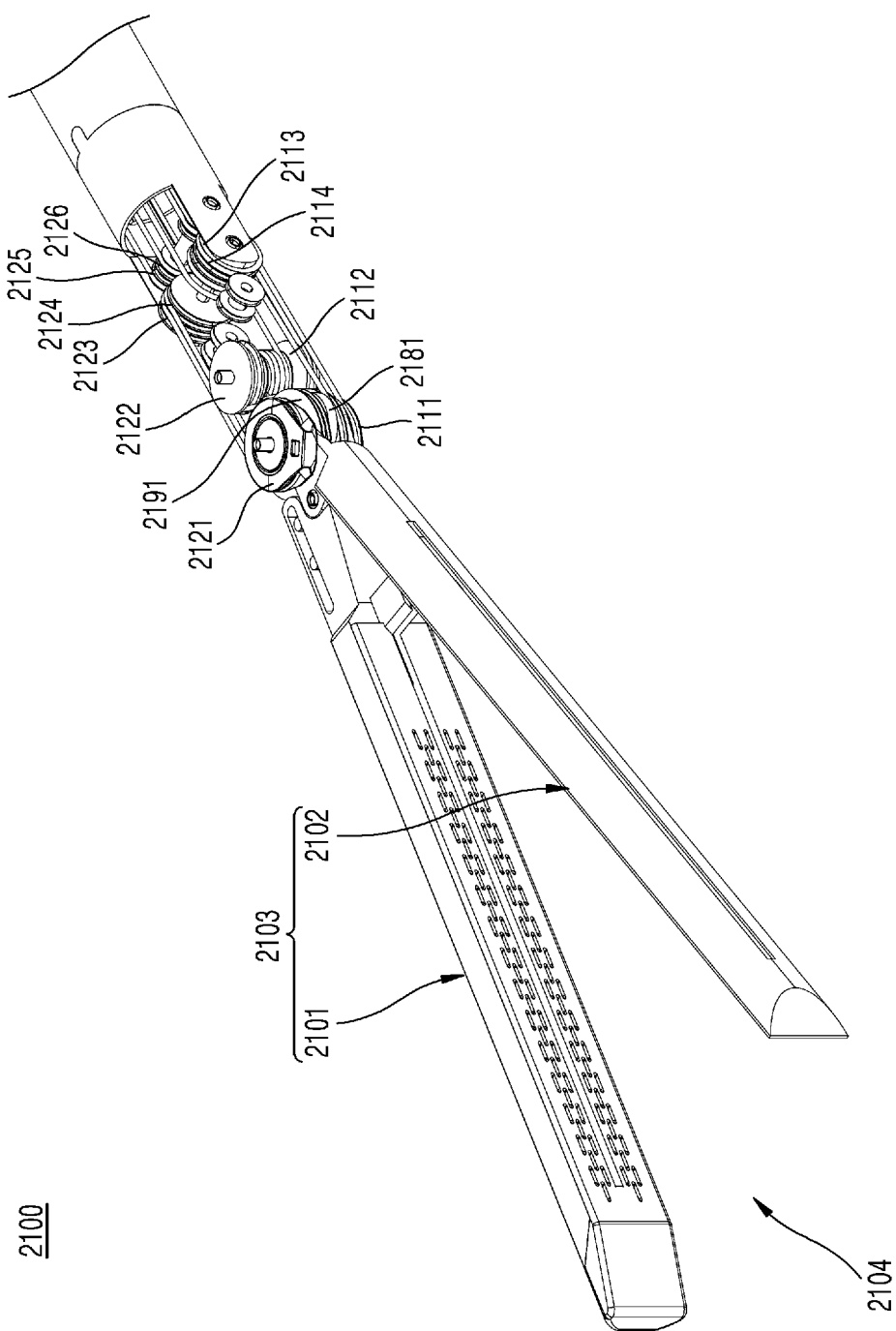
Figure 6:
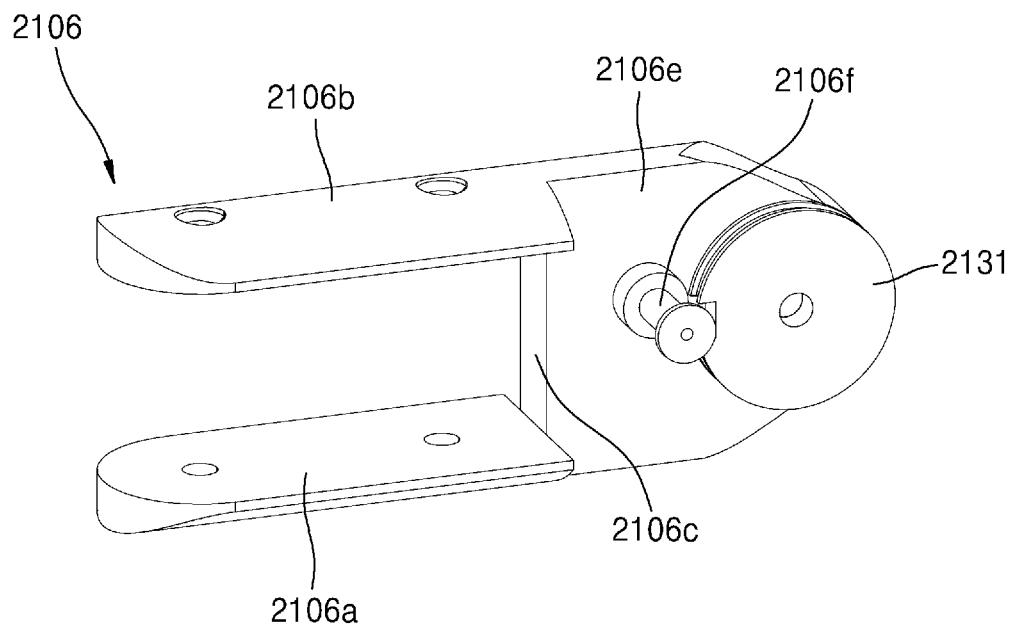
FIG. 6 is a perspective view illustrating an end tool hub of the end tool of the surgical instrument of FIG. 2.
Figure 7:
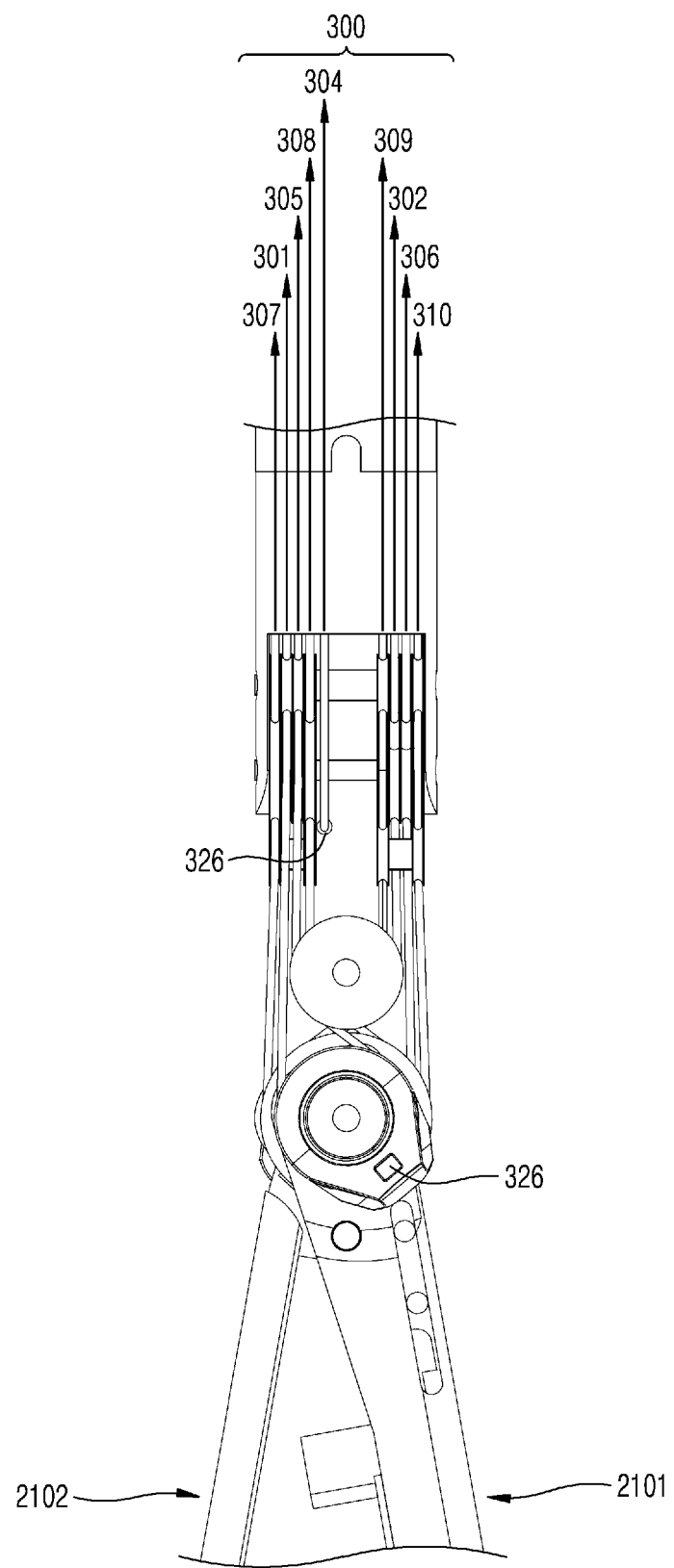
FIGS. 7 and 8 are plan views illustrating the end tool of the surgical instrument of FIG. 2.
Figure 8:
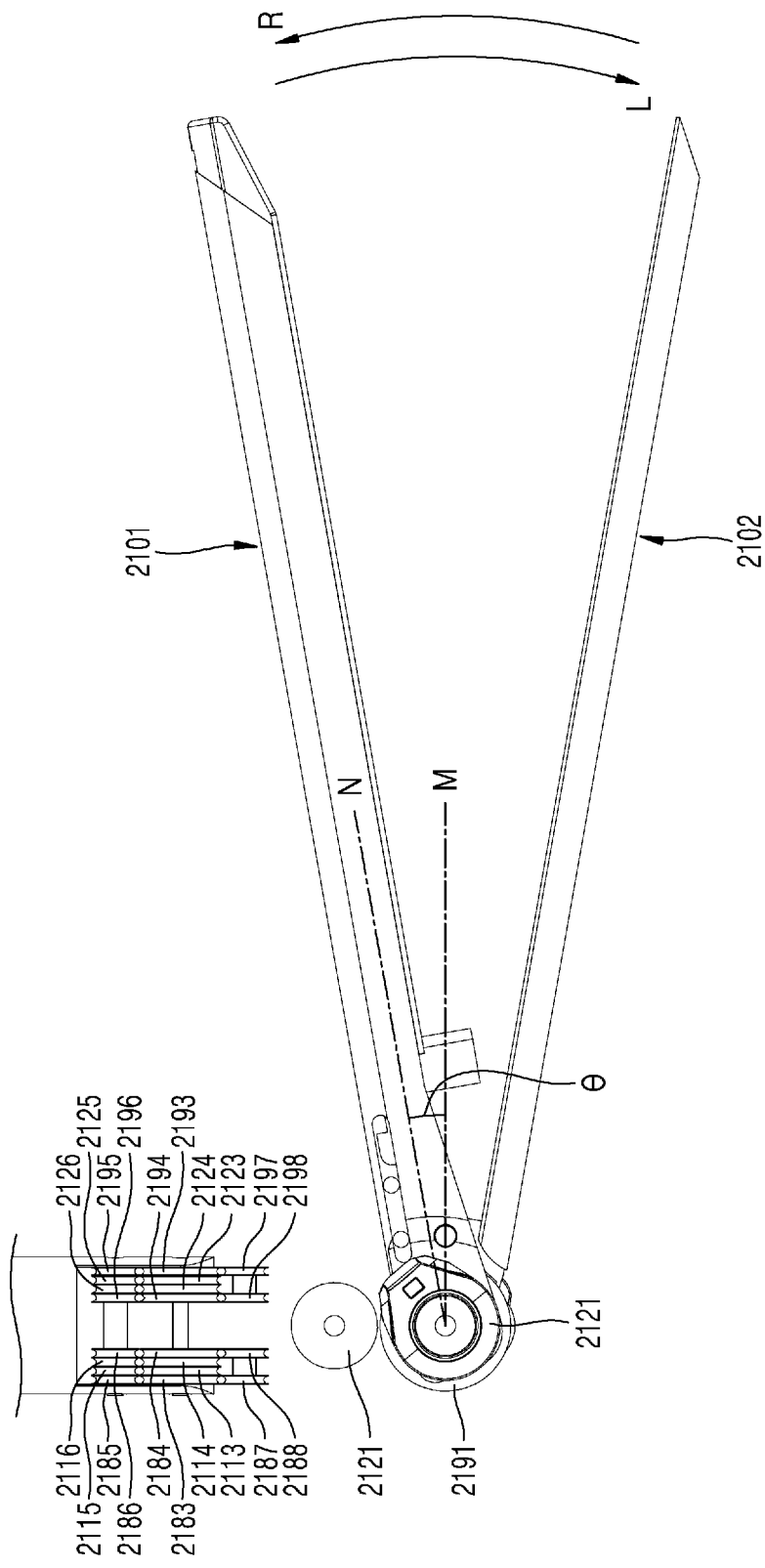
Figure 9:
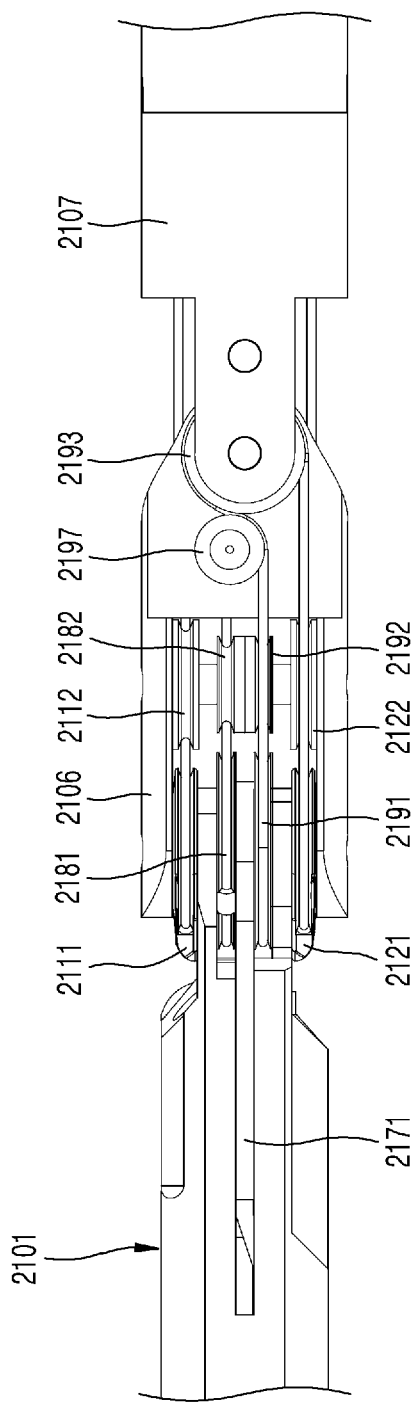
FIG. 9 is a side view illustrating the end tool of the surgical instrument of FIG. 2.
Figure 10:
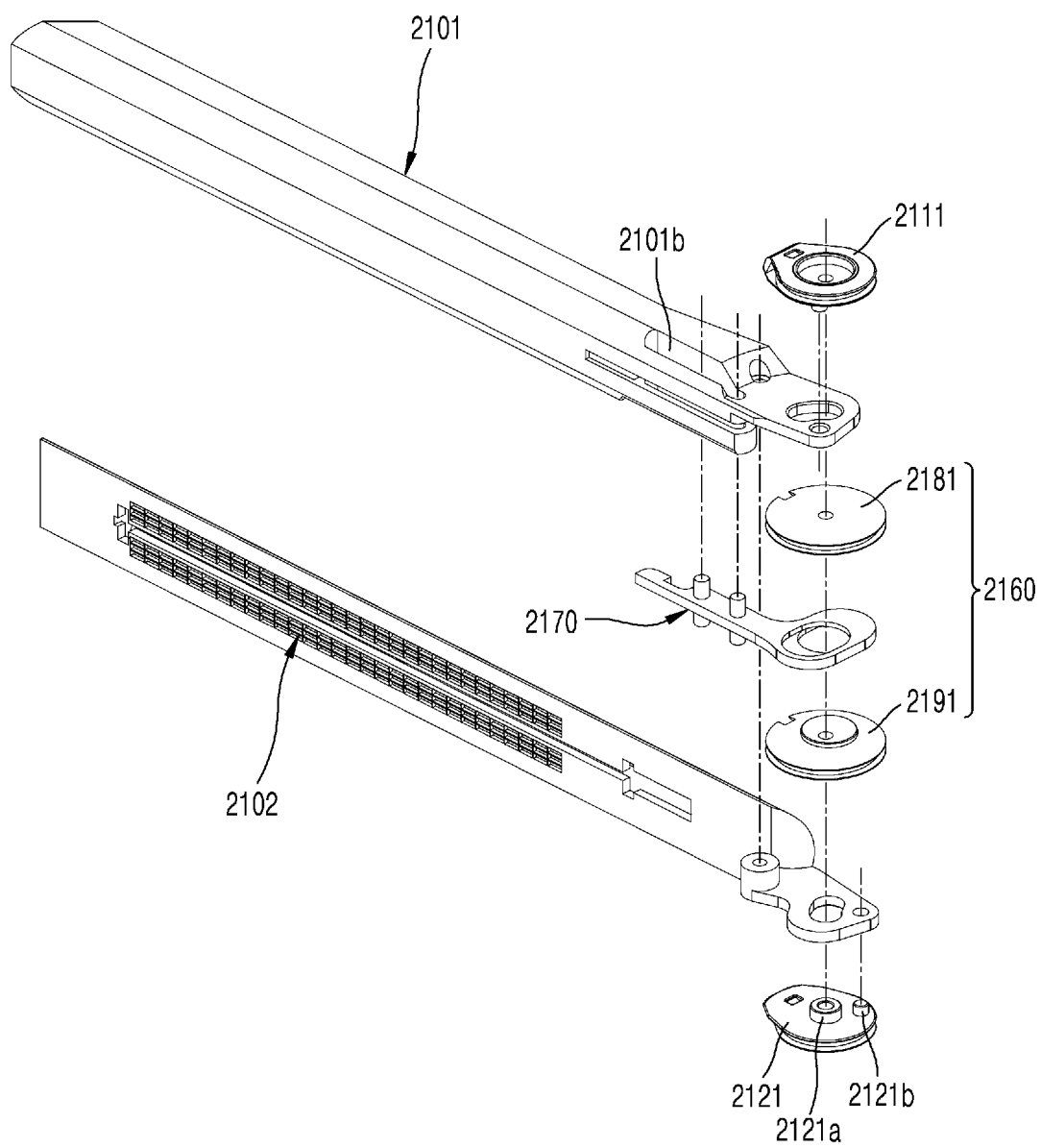
FIGS. 10 and 11 are exploded perspective views of the end tool of the surgical instrument of FIG. 2.
Figure 11:
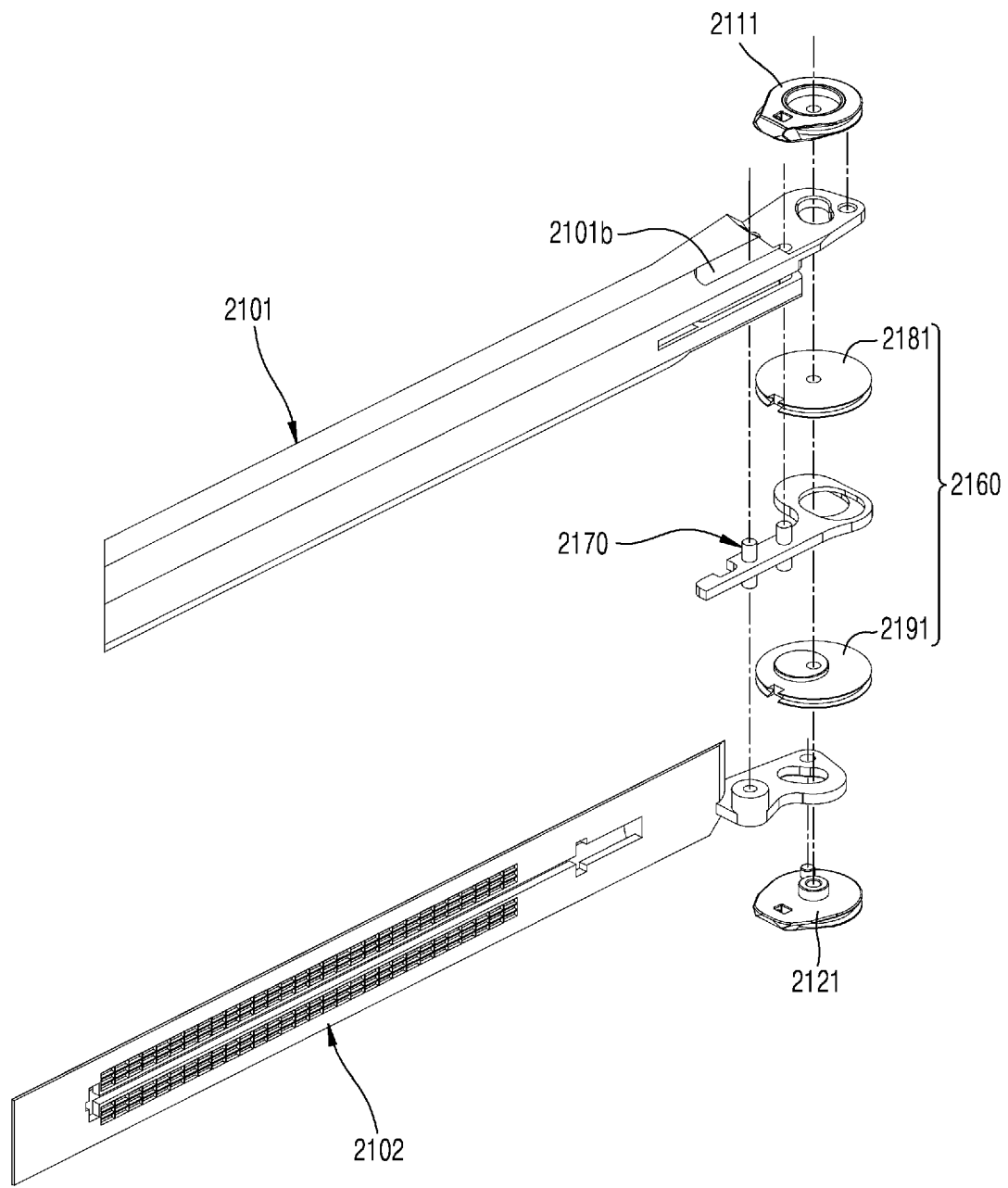
Figure 12:
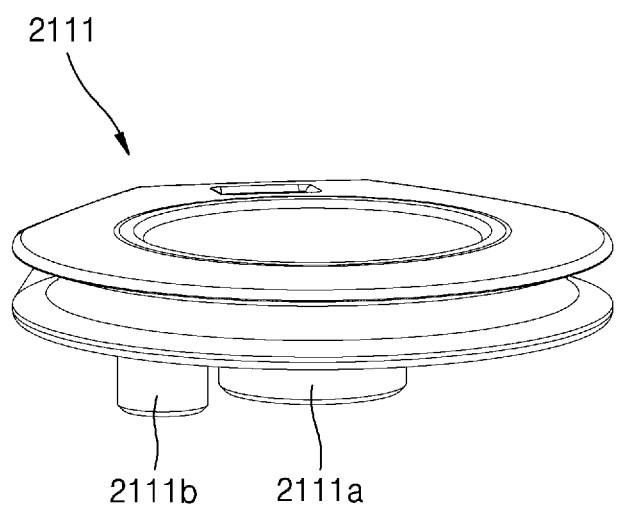
FIG. 12 is a perspective view illustrating a first jaw pulley of the surgical instrument of FIG. 2.
Figure 13:
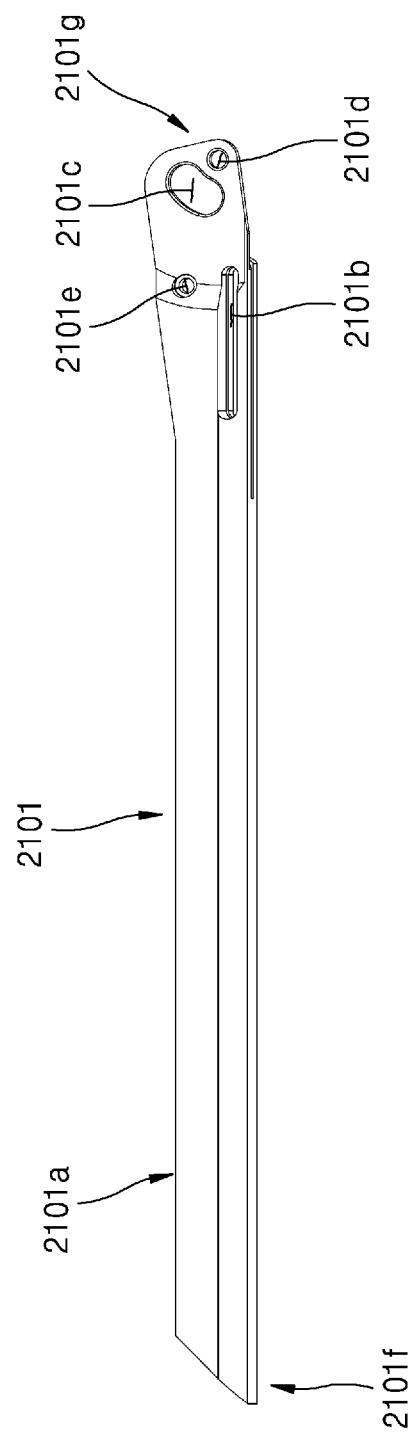
FIG. 13 is a plan view illustrating a first jaw of the surgical instrument of FIG. 2.
Figure 14:
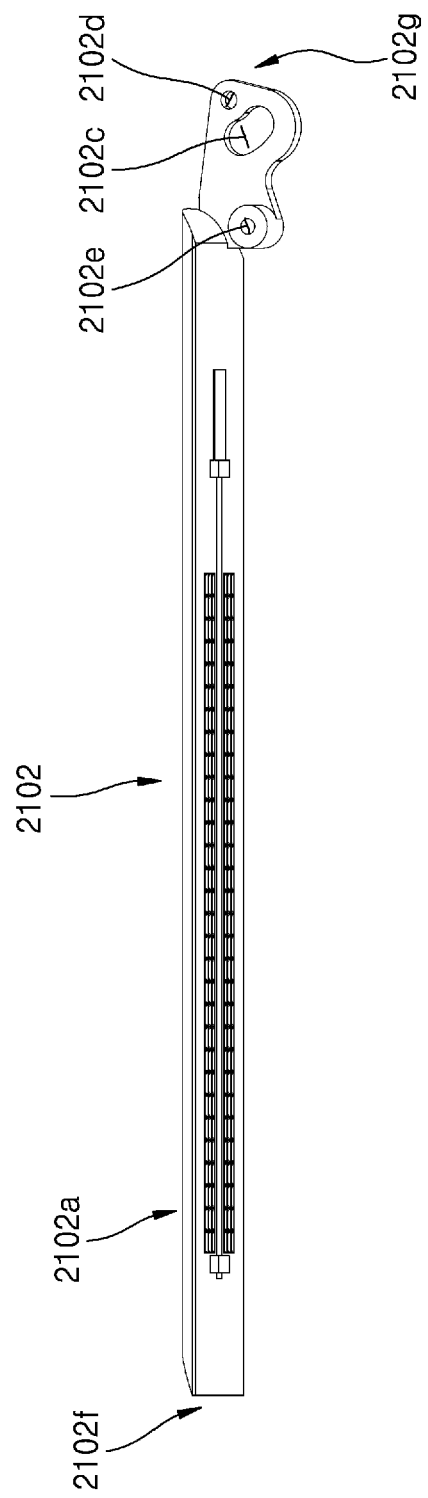
FIG. 14 is a plan view illustrating a second jaw of the surgical instrument of FIG. 2.
Figure 15:
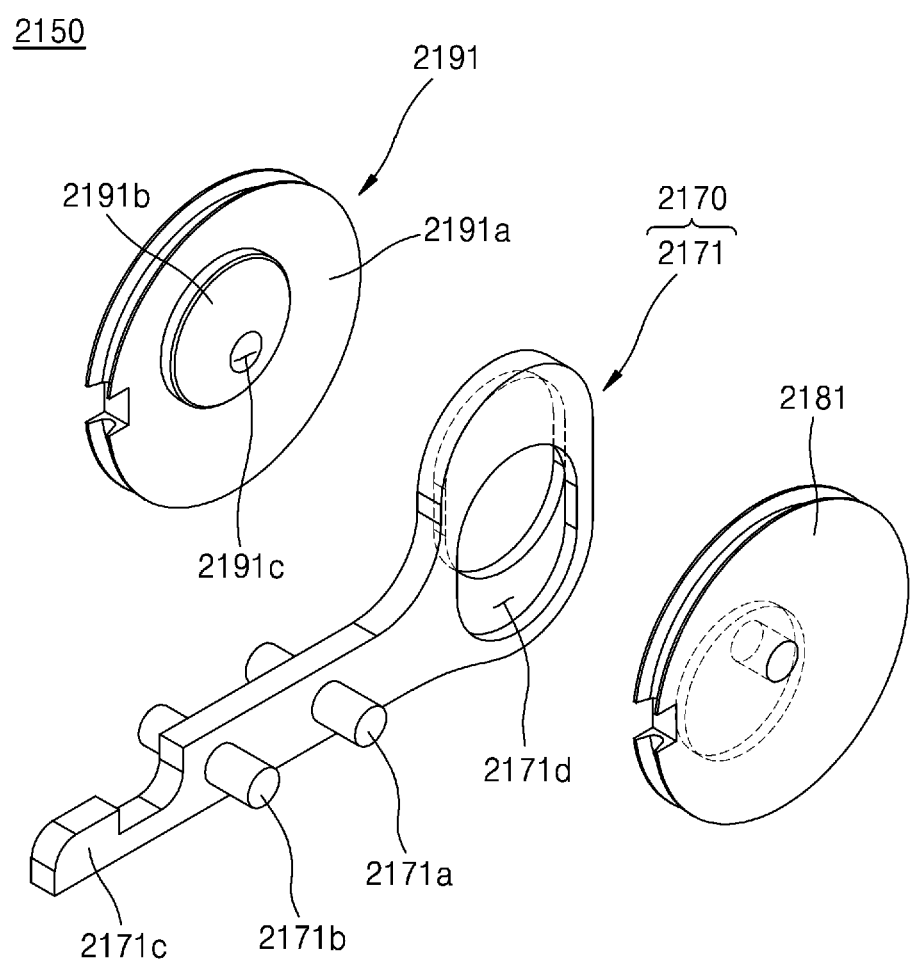
FIGS. 15 and 16 are exploded perspective views illustrating a staple pulley and a staple link of the surgical instrument of FIG. 2.
Figure 16:
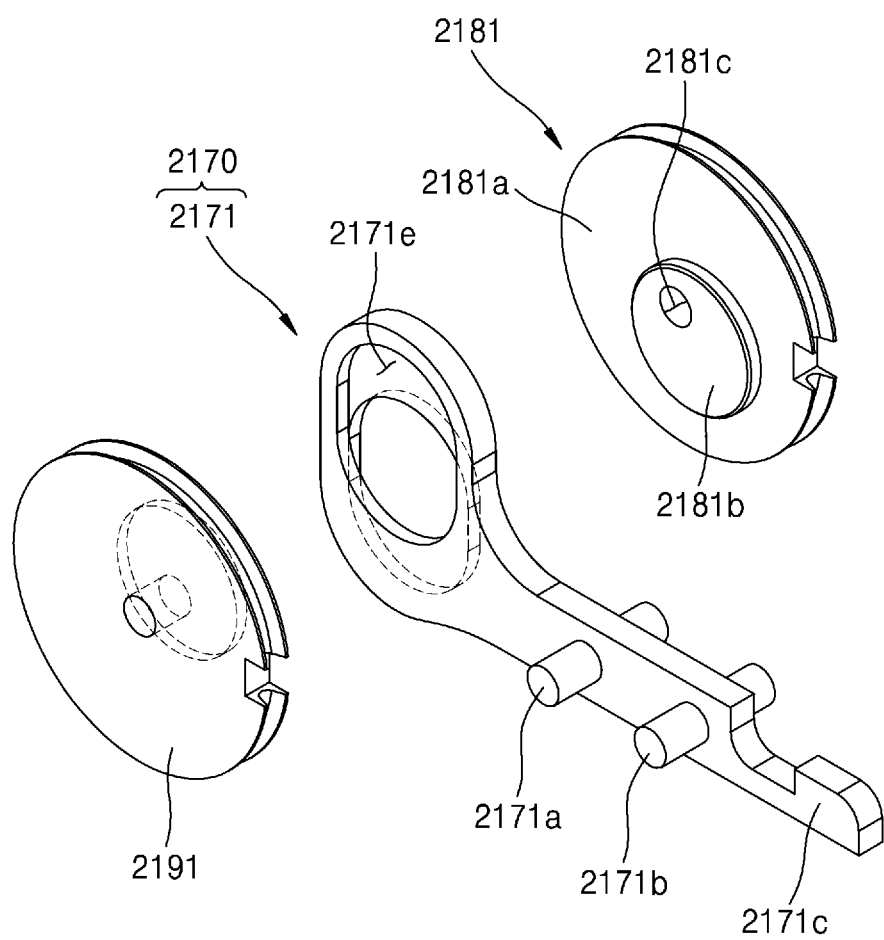
Figure 17:
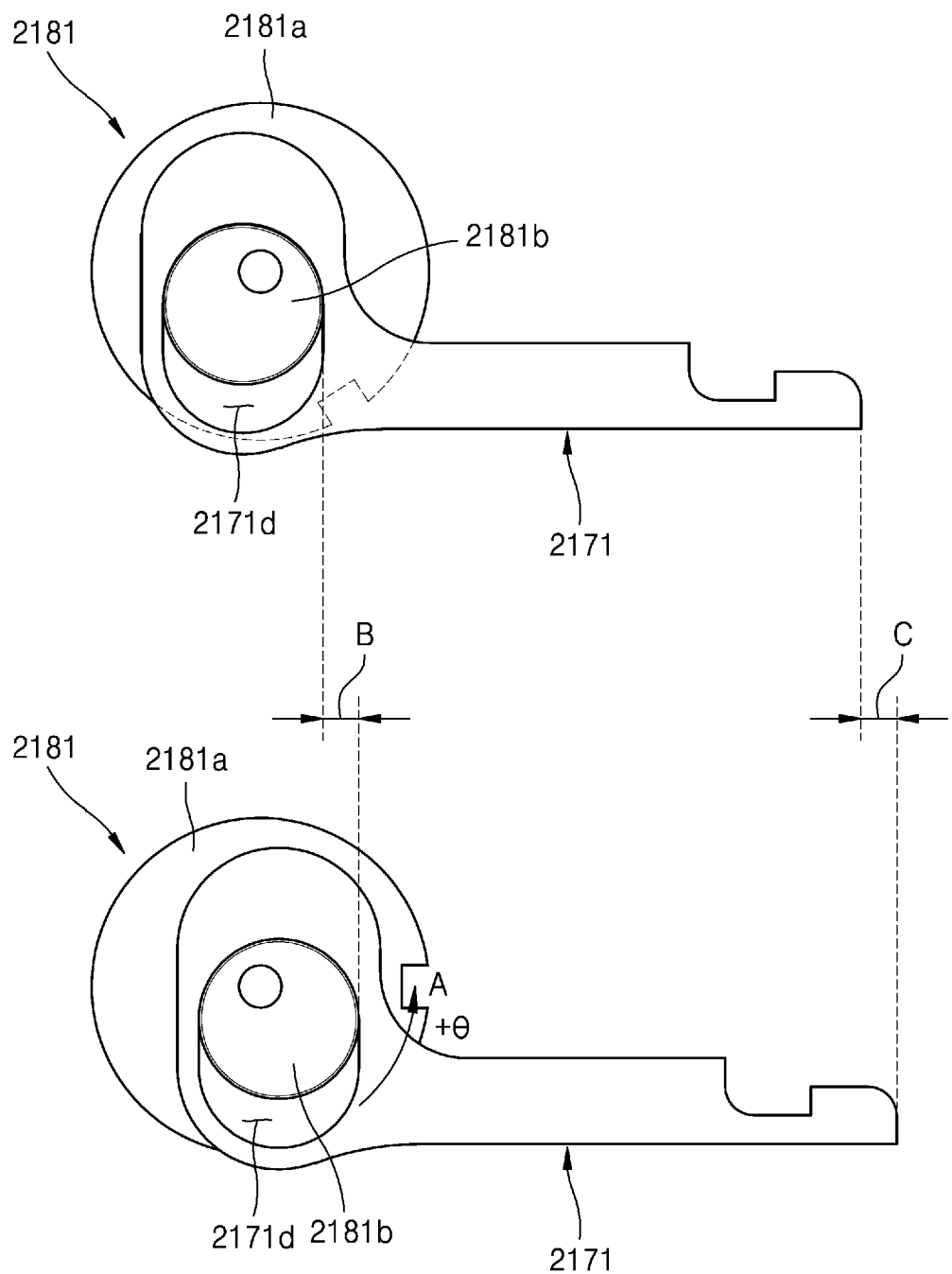
FIGS. 17 and 18 are side views illustrating operating states of a staple pulley in the end tool of the surgical instrument of FIG. 2.
Figure 18:
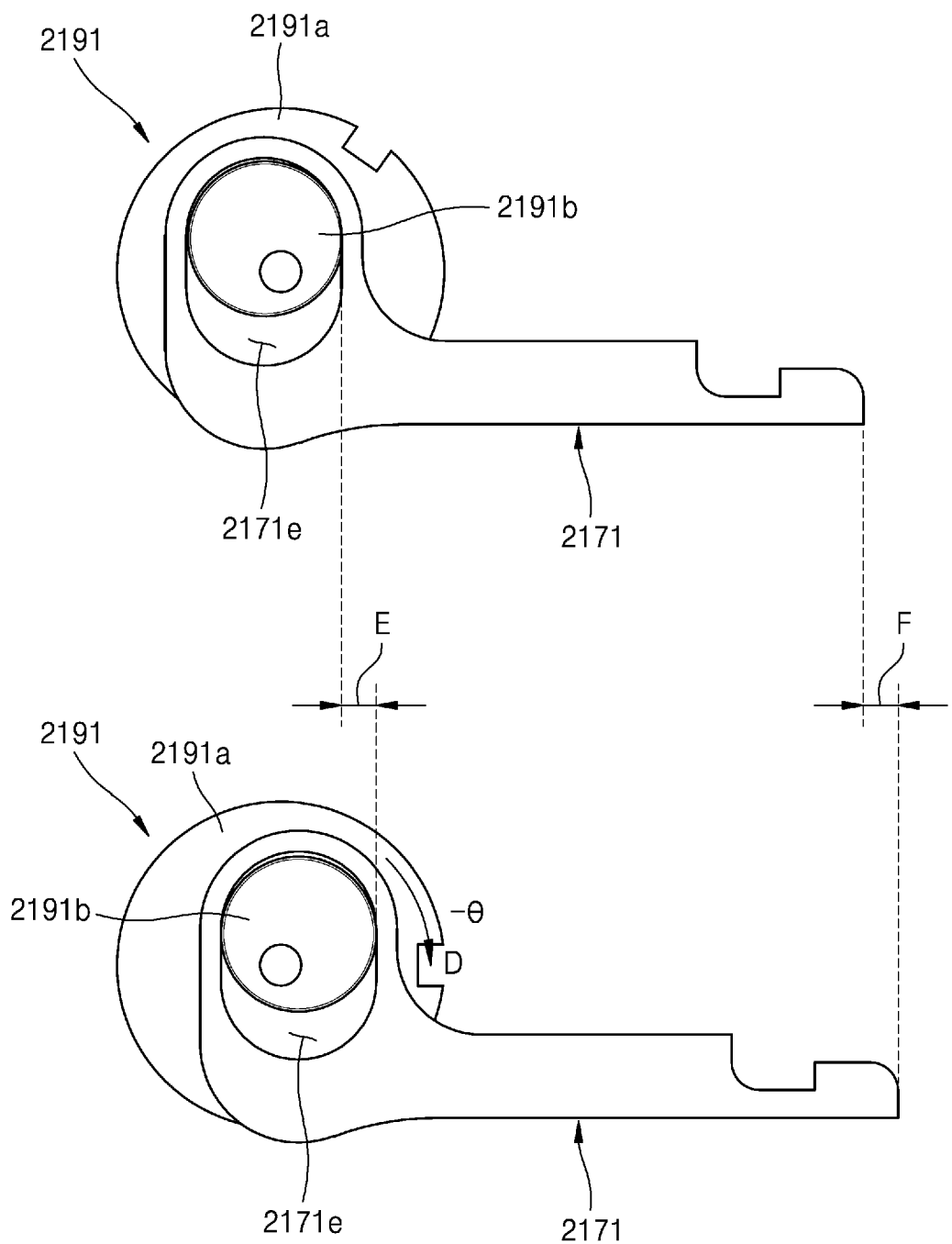
Figure 19:
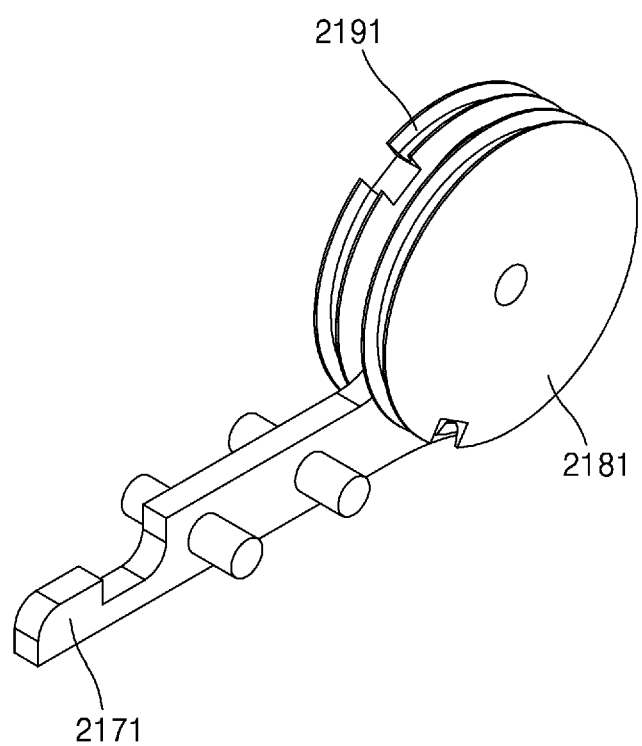
FIGS. 19 and 20 are perspective views illustrating operating states of the staple pulley in the end tool of the surgical instrument of FIG. 2.
Figure 20:
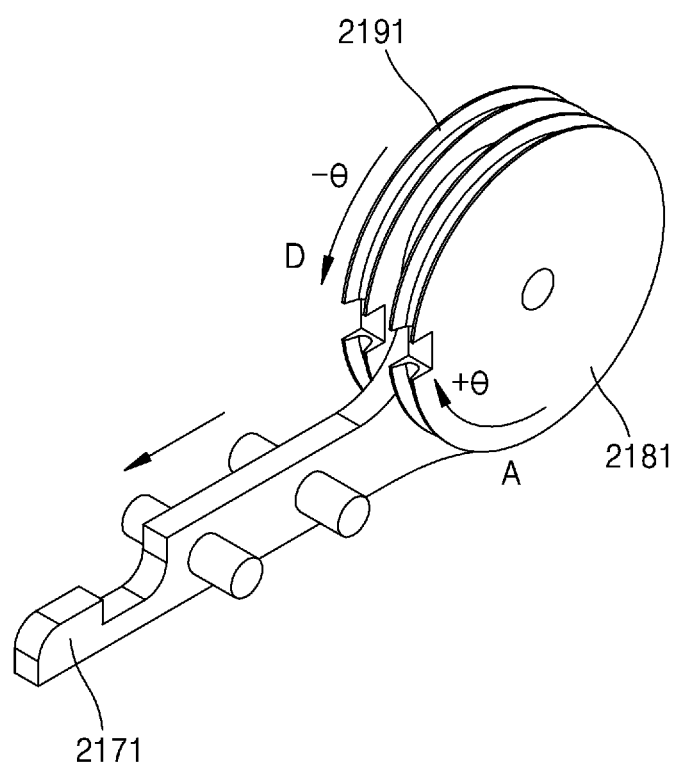

FIG. 2 is a perspective view illustrating a surgical instrument according to a first embodiment of the present disclosure. FIG. 3 is a side view of the surgical instrument of FIG. 2. FIGS. 4 and 5 are perspective views illustrating an end tool of the surgical instrument of FIG. 2. FIG. 6 is a perspective view illustrating an end tool hub of the end tool of the surgical instrument of FIG. 2. FIGS. 7 and 8 are plan views illustrating the end tool of the surgical instrument of FIG. 2. FIG. 9 is a side view illustrating the end tool of the surgical instrument of FIG. 2. FIGS. 10 and 11 are exploded perspective views of the end tool of the surgical instrument of FIG. 2. FIG. 12 is a perspective view illustrating a first jaw pulley of the surgical instrument of FIG. 2. FIG. 13 is a plan view illustrating a first jaw of the surgical instrument of FIG. 2. FIG. 14 is a plan view illustrating a second jaw of the surgical instrument of FIG. 2. FIGS. 15 and 16 are exploded perspective views illustrating a staple pulley and a staple link of the surgical instrument of FIG. 2. FIGS. 17 and 18 are side views illustrating operating states of a staple pulley in the end tool of the surgical instrument of FIG. 2. FIGS. 19 and 20 are perspective views illustrating operating states of the staple pulley in the end tool of the surgical instrument of FIG. 2. FIGS. 21, 22, 23, and 24 are plan views illustrating opening and closing motions of the first jaw and the second jaw of the surgical instrument of FIG. 2. FIGS. 25 and 26 are perspective views illustrating opening and closing motions of the end tool of the surgical instrument of FIG. 2.

First, referring to FIGS. 2 and 3, a surgical instrument 2000 according to a first embodiment of the present disclosure includes an end tool 2100, a manipulation part 200, a power transmission part 300, and a connection part 400.

Here, the connection part 400 is formed in the shape of a hollow shaft, and one or more wires and electric wires may be accommodated therein. The manipulation part 200 is coupled to one end portion of the connection part 400, the end tool 2100 is coupled to the other end portion thereof, and the connection part 400 may serve to connect the manipulation part 200 and the end tool 2100. Here, the connection part 400 of the surgical instrument 2000 according to the first embodiment of the present disclosure includes a straight part 401 and a bent part 402, wherein the straight part 401 is formed at a side coupled to the end tool 2100, and the bent part 402 is formed at a side to which the manipulation part 200 is coupled. As such, since the end portion of the connection part 400 at the side of the manipulation part 200 is formed to be bent, a pitch manipulation part 201, a yaw manipulation part 202, and an actuation manipulation part 203 may be formed along an extension line of the end tool 2100 or adjacent to the extension line. From another perspective, it may be said that the pitch manipulation part 201 and the yaw manipulation part 202 are at least partially accommodated in a concave portion formed by the bent part 402. Due to the above-described shape of the bent part 402, the shapes and motions of the manipulation part 200 and the end tool 2100 may be further intuitively matched with each other.

Meanwhile, a plane on which the bent part 402 is formed may be substantially the same plane as a pitch plane, that is, an XZ plane of FIG. 2. As such, as the bent part 402 is formed on substantially the same plane as the XZ plane, interference with the manipulation part may be reduced. Of course, for intuitive motions of the end tool and the manipulation part, any form other than the XZ plane may be possible.

Meanwhile, a connector 410 may be formed on the bent part 402. The connector 410 may be connected to an external power source (not shown), and the connector 410 may also be connected to the end tool 2100 via an electric wire, and may transmit, to the end tool 2100, electric energy supplied from the external power source (not shown). In addition, the electric energy transmitted to the end tool 2100 as described above may produce a driving force for rotating a staple pulley (see 161 of FIG. 5) to be described later in the clockwise or counterclockwise direction.

The manipulation part 200 is formed at the one end portion of the connection part 400 and provided as an interface to be directly controlled by a medical doctor, for example, a tongs shape, a stick shape, a lever shape, or the like, and when the medical doctor controls the manipulation part 200, the end tool 2100, which is connected to the interface and inserted into the body of a surgical patient, performs a certain motion, thereby performing surgery. Here, the manipulation part 200 is illustrated in FIG. 2 as being formed in a handle shape that is rotatable while the finger is inserted therein, the concept of the present disclosure is not limited thereto, and various types of manipulation parts that are connected to the end tool 2100 and manipulate the end tool 2100 may be possible.

The end tool 2100 is formed on the other end portion of the connection part 400, and performs necessary motions for surgery by being inserted into a surgical site. In an example of the end tool 2100, as illustrated in FIG. 2, a pair of jaws 103 for performing a grip motion may be used. However, the concept of the present disclosure is not limited thereto, and various devices for performing surgery may be used as the end tool 2100. For example, a configuration of a cantilever cautery may also be used as the end tool. The end tool 2100 is connected to the manipulation part 200 by the power transmission part 300, and receives a driving force of the manipulation part 200 through the power transmission part 300 to perform a motion necessary for surgery, such as gripping, cutting, suturing, or the like.

Here, the end tool 2100 of the surgical instrument 2000 according to the first embodiment of the present disclosure is formed to be rotatable in at least one direction, for example, the end tool 2100 may perform a pitch motion around a Y-axis of FIG. 2 and simultaneously perform a yaw motion and an actuation motion around a Z-axis of FIG. 2.

Here, each of the pitch, yaw, and actuation motions used in the present disclosure are defined as follows.

First, the pitch motion means a motion of the end tool 2100 rotating in a vertical direction with respect to an extension direction of the connection part 400 (an X-axis direction of FIG. 2), that is, a motion rotating around the Y-axis of FIG. 2. In other words, the pitch motion means a motion of the end tool 2100, which is formed to extend from the connection part 400 in the extension direction of the connection part 400 (the X-axis direction of FIG. 2), rotating vertically around the Y-axis with respect to the connection part 400.

Next, the yaw motion means a motion of the end tool 2100 rotating in the left and right directions, that is, a motion rotating around the Z-axis of FIG. 2, with respect to the extension direction of the connection part 400 (the X-axis direction of FIG. 2). In other words, the yaw motion means a motion of the end tool 2100, which extends from the connection part 400 in the extension direction of the connection part 400 (the X-axis direction of FIG. 2), rotating horizontally around the Z-axis with respect to the connection part 400. That is, the yaw motion means a motion of the two jaws 103, which are formed on the end tool 2100, rotating around the Z-axis in the same direction.

Meanwhile, the actuation motion may mean a motion of the end tool 2100 rotating around the same shaft of rotation as that of the yaw motion, while the two jaws 103 rotating in the opposite directions so as to be closed or opened. That is, the actuation motion means rotating motions of the two jaws 103, which are formed on the end tool 2100, in the opposite directions around the Z-axis.

The power transmission part 300 may connect the manipulation part 200 to the end tool 2100, transmit the driving force of the manipulation part 200 to the end tool 2100, and include a plurality of wires, pulleys, links, sections, gears, or the like.

The end tool 2100, the manipulation part 200, and the power transmission part 300 of the surgical instrument 2000 of FIG. 2 will be described in detail later.

(Intuitive Driving)

Hereinafter, intuitive driving of the surgical instrument 2000 of the present disclosure will be described.

First, while holding a first handle 204 with the palm of the hand, the user may rotate a first handle 204 around the Y-axis (i.e., a rotation shaft 246 of FIG. 25) to perform a pitch motion, and rotate the first handle 204 around the Z-axis (i.e., a rotation shaft 243 of FIG. 43) to perform a yaw motion. In addition, the user may perform an actuation motion by manipulating the actuation manipulation part 203 while inserting the thumb and the index finger into a first actuation extension part 252 and/or a second actuation extension part 257 in the form of a hand ring formed at one end portion of the actuation manipulation part 203.

Here, in the surgical instrument 2000 according to the first embodiment of the present disclosure, when the manipulation part 200 is rotated in one direction with respect to the connection part 400, the end tool 2100 is rotated in a direction that is intuitively the same as a manipulation direction of the manipulation part 200. In other words, when the first handle 204 of the manipulation part 200 is rotated in one direction, the end tool 2100 is also rotated in a direction intuitively the same as the one direction, so that a pitch motion or a yaw motion is performed. Here, the phrase "intuitively the same direction" may be further explained as meaning that a direction of movement of the user's finger gripping the manipulation part 200 and a direction of movement of a distal end of the end tool 2100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 2100 is moved to the left, and when the user's finger moves down, the end portion of the end tool 2100 is moved down.

In addition, to this end, in the surgical instrument 2000 according to the first embodiment of the present disclosure, the manipulation part 200 and the end tool 2100 are formed in the same direction with respect to a plane perpendicular to the extension axis (X-axis) of the connection part 400. That is, when viewed based on a YZ plane of FIG. 2, the manipulation part 200 is formed to extend in a positive (+) X-axis direction, and the end tool 2100 is also formed to extend in the positive (+) X-axis direction. In other words, it may be said that a formation direction of the end tool 2100 on one end portion of the connection part 400 is the same as a formation direction of the manipulation part 200 on the other end portion of the connection part 400 on the basis of the YZ plane. Further, in other words, it may be said that the manipulation part 200 may be formed in a direction away from the body of a user holding the manipulation part 200, that is, in a direction in which the end tool 2100 is formed. That is, in the parts such as the first handle 204, a first actuation manipulation part 251, a second actuation manipulation part 256, and the like, which are moved by the user's grip for actuation motion, yaw motion, and pitch motions, a corresponding portion that is moved for the motion is formed to extend in the positive (+) X-axis direction from the rotation center of a corresponding joint for the motion. In this manner, the manipulation part 200 may be configured in the same manner as the end tool 2100 in which each moving portion is formed to extend in the positive (+) X-axis direction from the rotation center of a corresponding joint for the motion, and as described with reference to FIG. 1, the manipulation direction of the user may be identical to the operation direction of the end tool from the viewpoint of the rotation directions and the left and right directions. As a result, intuitively the same manipulation may be achieved.

In detail, in the case of the conventional surgical instrument, a direction in which a user manipulates the manipulation part is different from a direction in which the end tool is actually operated, that is, intuitively different from the direction in which the end tool is actually operated, and thus, a surgical operator may not easily intuitively manipulate the surgical instrument and may spend a long time to learn a skill of operating the end tool in desired directions, and in some cases, malfunctions may occur, which may cause damage to patients.

In order to address such problems, the surgical instrument 2000 according to the first embodiment of the present disclosure is configured such that the manipulation direction of the manipulation part 200 and the operation direction of the end tool 2100 are intuitively identical to each other. To this end, the manipulation part 200 is configured like the end tool 2100, that is, in the manipulation part 200, portions that are actually moved for actuation, yaw, and pitch motions extend respectively from rotation centers of corresponding joints in the positive (+) X-axis direction.

Hereinafter, the end tool 2100, the manipulation part 200, the power transmission part 300, and the like of the surgical instrument 2000 of FIG. 2 will be described in more detail.

(Power Transmission Part)

Hereinafter, the power transmission part 300 of the surgical instrument 2000 of FIG. 2 will be described in more detail.

Referring to FIGS. 2 to 20, 49, and the like, the power transmission part 300 of the surgical instrument 2000 according to an embodiment of the present disclosure may include a wire 301, a wire 302, a wire 303, a wire 304, a wire 305, a wire 306, a wire 307, a wire 308, a wire 309, and a wire 310.

Here, the wire 301 and the wire 305 may form a pair to serve as a first jaw wire. The wire 302 and the wire 306 may form a pair to serve as a second jaw wire. Here, a component encompassing the wire 301 and the wire 305, which are the first jaw wire, and the wire 302 and the wire 306, which are the second jaw wire, may be referred to as a jaw wire. The wire 303 and the wire 304 may form a pair to serve as a pitch wire. In addition, the wire 307 and the wire 308 may form a pair to serve as a staple wire.

In addition, the power transmission part 300 of the surgical instrument 2000 according to an embodiment of the present disclosure may include a fastening member 321 a fastening member 323, a fastening member 324, a fastening member 326, a fastening member 327, a fastening member 329, and a fastening member 330 that are coupled to respective ends of the wires to respectively combine the wires with the pulleys. Here, each of the fastening members may have various shapes as necessary, such as a ball shape, a tube shape, and the like.

Here, on the side of the end tool 2100, the fastening member 321 may serve as a pitch wire-end tool fastening member, the fastening member 323 may serve as a first jaw wire-end tool fastening member, the fastening member 326 may serve as a second jaw wire-end tool fastening member, and the fastening member 329 may serve as a staple wire-end tool fastening member.

In addition, on the side of the manipulation portion 200, the fastening member 324 may serve as a first jaw wire-manipulation portion fastening member, and the fastening member 327 may serve as a second jaw wire-manipulation portion fastening member. In addition, although not illustrated in the drawings, a pitch wire-manipulation portion fastening member and a staple wire-manipulation portion fastening member may be further formed on the side of the manipulation portion 200.

The coupling relationship between the wires, the fastening members, and each pulley will be described as follows.

First, the wire 301 and the wire 305, which are the first jaw wire, may be a single wire. The fastening member 323, which is the first jaw wire-end tool fastening member, may be fit into a middle point of the first jaw wire and when the fastening member 323 is fixed through crimping, two strands of the first jaw wire on either side of the fastening member 323 may be referred to as the wire 301 and the wire 305, respectively.

Alternatively, the wire 301 and the wire 305, which are the first jaw wire, may be formed as separate wires, and the wire 301 and the wire 305 may be connected to each other by the fastening member 323.

In addition, as the fastening member 323 is coupled to a pulley 2111, the wire 301 and the wire 305 may be fixedly coupled to the pulley 2111. This allows the pulley 2111 to rotate as the wire 301 and the wire 305 are pulled and unwound.

In the wire 301 and the wire 305, the first jaw wire-manipulation portion fastening member (see 324 of FIG. 49) may be coupled to an end opposite to the end to which the fastening member 323 is coupled.

In addition, as the first jaw wire-manipulation portion fastening member (see 324 of FIG. 49) is coupled to a pulley 210, the wire 301 and the wire 305 may be fixedly coupled to the pulley 210. As a result, when the pulley 210 is rotated by a motor or human force, the pulley 2111 of the end tool 2100 may rotate as the wire 301 and the wire 305 are pulled and unwound.

In the same manner, the wire 302 and the wire 306, which are the second jaw wire, are coupled to the fastening member (see 326 of FIG. 49), which is the second jaw wire-end tool, and the second jaw wire-manipulation portion fastening member (see 327 of FIG. 49), respectively. In addition, the fastening member (see 326 of FIG. 49) is coupled to a pulley 2121, and the second jaw wire-manipulation portion fastening member (see 327 of FIG. 49) is coupled to a pulley 220. As a result, when the pulley 220 is rotated by a motor or human force, the pulley 2121 of the end tool 2100 may rotate as the wire 302 and the wire 306 are pulled and unwound.

In the same manner, the wire 303 and the wire 304, which are the pitch wire, are coupled to the fastening member 321, which is the pitch wire-end tool fastening member, and the pitch wire-manipulation portion fastening member (not shown), respectively. In addition, the fastening member 321 is coupled to a pulley 2131, and the pitch wire-manipulation portion fastening member (not shown) is coupled to a pulley 231. As a result, when the pulley 231 is rotated by a motor or a human force, the pulley 2131 of the end tool 2100 may be rotated as the wire 303 and the wire 304 are pulled and unwound.

In the same manner, the wire 307 and the wire 308, which are first staple wires, are coupled to the fastening member (see 329 of FIG. 68), which is the staple wire-end tool fastening member, and the staple wire-manipulation portion fastening member (not shown), respectively. In addition, the fastening member (see 329 of FIG. 68) is coupled to a first staple pulley 2181, and the staple wire-manipulation portion fastening member (not shown) is coupled to a pulley (see 269 of FIG. 47). As a result, when the pulley 269 is rotated by a motor or a human force, the first staple pulley 2181 of the end tool 2100 may be rotated as the wire 307 and the wire 308 are pulled and unwound.

In the same manner, the wire 309 and the wire 310, which are second staple wires, are coupled to the fastening member (see 330 of FIG. 68), which is the staple wire-end tool fastening member, and the staple wire-manipulation portion fastening member (not shown), respectively. In addition, the fastening member (see 330 of FIG. 68) is coupled to a second staple pulley 2191, and the staple wire-manipulation portion fastening member (not shown) is coupled to a pulley (see 270 of FIG. 53). As a result, when the pulley 270 is rotated by a motor or a human force, the second staple pulley 2191 of the end tool 2100 may be rotated as the wire 309 and the wire 310 are pulled and unwound.

(End Tool)

Hereinafter, the end tool 2100 of the surgical instrument 2000 of FIG. 2 will be described in more detail.

FIGS. 4 and 5 are perspective views illustrating the end tool of the surgical instrument of FIG. 2, FIG. 6 is a perspective view illustrating an end tool hub of the end tool of the surgical instrument of FIG. 2, and FIGS. 7 and 8 are plan views illustrating the end tool of the surgical instrument of FIG. 2.

Here, FIG. 4 illustrates a state in which an end tool hub 2106 and a pitch hub 2107 are coupled to each other, and FIG. 5 illustrates a state in which the end tool hub 2106 is removed. Meanwhile, FIG. 7 is a diagram mainly illustrating the wires, and FIG. 8 is a diagram mainly illustrating the pulleys.

Referring to FIGS. 4 to 8 and the like, the end tool 2100 of the first embodiment of the present disclosure includes a pair of jaws for performing a grip motion, that is, a first jaw 2101 and a second jaw 2102. Here, a component encompassing each of the first jaw 2101 and the second jaw 2102 or both the first jaw 2101 and the second jaw 2102 may be referred to as a jaw 2103.

In addition, the end tool 2100 may include the pulley 2111, a pulley 2112, a pulley 2113, a pulley 2114, a pulley 2115, and a pulley 2116, which are associated with the rotational motion of the first jaw 2101. In addition, the end tool 2100 may include the pulley 2121, a pulley 2122, a pulley 2123, a pulley 2124, a pulley 2125, and a pulley 2126, which are associated with the rotational motion of the second jaw 2102.

Here, although the drawings illustrate that the pulleys facing each other are arranged in parallel with each other, the technical concepts of the present disclosure are not limited thereto, and the pulleys may be formed in various positions and sizes suitable for the configuration of the end tool.

In addition, the end tool 2100 of the first embodiment of the present disclosure may include the end tool hub 2106 and the pitch hub 2107.

A rotation shaft 2141 and a rotation shaft 2142 to be described below may be inserted through the end tool hub 2106, and the end tool hub 2106 may accommodate therein at least portions of the pulley 2111 and the pulley 2121, which are axially coupled to the rotation shaft 2141. In addition, the end tool hub 2106 may accommodate therein at least portions of the pulley 2112 and the pulley 2122, which are axially coupled to the rotation shaft 2142.

In detail, referring to FIG. 6, the end tool hub 2106 includes a first jaw pulley coupling portion 2106a, a second jaw pulley coupling portion 2106b, a guide portion 2106c, a pitch pulley coupling portion 2106e, and a separation prevention pulley coupling portion 2106f.

In detail, the first jaw pulley coupling portion 2106a and the second jaw pulley coupling portion 2106b are formed to face each other, and the pulley 2111, the pulley 2121, the first staple pulley 2181, and the second staple pulley 2191 are accommodated inside the first jaw pulley coupling portion 2106a and the second jaw pulley coupling portion 2106b. In addition, a through hole is formed in each of the first jaw pulley coupling portion 2106a and the second jaw pulley coupling portion 2106b such that the rotation shaft 2141 passes through and axially couples the first jaw pulley coupling portion 2106a, the pulley 2111, the first staple pulley 2181, the second staple pulley 2191, the pulley 2121, and the second jaw pulley coupling portion 2106b.

The first jaw pulley coupling portion 2106a and the second jaw pulley coupling portion 2106b are connected to each other by the guide portion 2106c. That is, the first jaw pulley coupling portion 2106a and the second jaw pulley coupling portion 2106b, which are parallel to each other, are coupled to each other by the guide portion 2106c formed in a direction approximately perpendicular to the first jaw pulley coupling portion 2106a and the second jaw pulley coupling portion 2106b, such that the first jaw pulley coupling portion 2106a, the second jaw pulley coupling portion 2106b, and the guide portion 2106c form an approximately C-shape, and the pulley 2111, the pulley 2121, the first staple pulley 2181, and the second staple pulley 2191 are accommodated therein.

Here, the pulley 2111, which is a first jaw pulley, is arranged adjacent to the first jaw pulley coupling portion 2106a of the end tool hub 2106, and the pulley 2121, which is a second jaw pulley, is arranged adjacent to the second jaw pulley coupling portion 2106b of the end tool hub 2106, such that a staple assembly accommodation portion may be formed between the first jaw pulley coupling portion 2106a and the second jaw pulley coupling portion 2106b. In addition, at least portions of a staple pulley assembly (see 2160 of FIG. 13) and a staple link assembly (see 2170 of FIG. 13) to be described below may be formed in the staple assembly accommodation portion. In other words, it may be said that at least portions of the first staple pulley 2181, the second staple pulley 2191, and a link member 2171 are arranged between the first jaw pulley coupling portion 2106a and the second jaw pulley coupling portion 2106b. As such, according to the present disclosure, by arranging at least portions of the staple pulley assembly (see 2160 of FIG. 13) and the staple link assembly (see 2170 of FIG. 13) between the pulley 2111, which is a first jaw pulley, and the pulley 2121, which is a second jaw pulley, the end tool 2100 is allowed to perform pitch and yaw motions, as well as stapling and cutting motions using the first staple pulley 2181 and the second staple pulley 2191. This will be described below in more detail.

Meanwhile, the pulley 2131 serving as an end tool pitch pulley may be formed at one end of the end tool hub 2106. As illustrated in FIG. 6, the pulley 2131 may be integrally formed with the end tool hub 2106 as one body. That is, a disk-shaped pulley may be formed at one end of the end tool hub 2106, and a groove around which a wire may be wound may be formed on an outer circumferential surface of the end tool hub 2106. Alternatively, the pulley 2131 may be formed as a separate member from the end tool hub 2106 and coupled to the end tool hub 2106. The wire 303 and the wire 304 described above are coupled to the pulley 2131 serving as an end tool pitch pulley, and a pitch motion is performed as the pulley 2131 rotates around a rotation shaft 2143.

Meanwhile, the separation prevention pulley coupling portion 2106f may be further formed on one side of the pulley 2131. The separation prevention pulley coupling portion 2106f may be formed parallel to the rotation shaft 2143, which is an end tool pitch rotation shaft, such that a pulley 2187, a pulley 2188, a pulley 2197, and a pulley 2198 to be described below are coupled thereto. Here, the pulley 2187 and the pulley 2188 may function as first staple wire separation prevention pulleys, and the pulley 2197 and pulley 2198 may function as second staple wire separation prevention pulleys. This will be described below in more detail.

The rotation shaft 2143 and a rotation shaft 2144 to be described below may be inserted through the pitch hub 2107, and the pitch hub 2107 and the end tool hub 2106 may be axially coupled to the pitch hub 2107 by the rotation shaft 2143. Thus, the end tool hub 2106 and the pulley 2131 may be formed to be rotatable around the rotation shaft 2143 with respect to the pitch hub 2107.

In addition, the pitch hub 2107 may accommodate therein at least portions of the pulley 2113, the pulley 2114, the pulley 2123, and the pulley 2124 that are axially coupled to the rotation shaft 2143. In addition, the pitch hub 2107 may accommodate therein at least portions of the pulley 2115, the pulley 2116, the pulley 2125, and the pulley 2126 that are axially coupled to the rotation shaft 2144.

Meanwhile, the end tool 2100 of the first embodiment of the present disclosure may include the rotation shaft 2141, the rotation shaft 2142, the rotation shaft 2143, and the rotation shaft 2144. As described above, the rotation shaft 2141 and the rotation shaft 2142 may be inserted through the end tool hub 2106, and the rotation shaft 2143 and the rotation shaft 2144 may be inserted through the pitch hub 2107.

The rotation shaft 2141, the rotation shaft 2142, the rotation shaft 2143, and the rotation shaft 2144 may be arranged sequentially from a distal end 2104 of the end tool 2100 toward a proximal end 2105. Accordingly, in the direction from the distal end 2104, the rotation shaft 2141 may be referred to as a first pin, the rotation shaft 2142 may be referred to as a second pin, the rotation shaft 2143 may be referred to as a third pin, and the rotation shaft 2144 may be referred to as a fourth pin.

Here, the rotation shaft 2141 may function as an end tool jaw pulley rotation shaft, the rotation shaft 2142 may function as an end tool jaw auxiliary pulley rotation shaft, the rotation shaft 2143 may function as an end tool pitch rotation shaft, and the rotation shaft 2144 may function as an end tool pitch auxiliary rotation shaft of the end tool 2100.

One or more pulleys may be fit into each of the rotation shafts 2141, 2142, 2143, and 2144, which will be described below in detail.

Meanwhile, a rotation shaft 2145 may be further formed on one side of the rotation shaft 2141, specifically, on the side of the distal end 2104 of the rotation shaft 2141. The rotation shaft 2145 may be inserted through the first jaw 2101 and the second jaw 2102 to function as a jaw rotation shaft. This will be described in detail below.

The pulley 2111 functions as an end tool first jaw pulley, and the pulley 2121 functions as an end tool second jaw pulley. The pulley 2111 may be referred to as a first jaw pulley, the pulley 2121 may be referred to as a second jaw pulley, and the two components may be collectively referred to as an end tool jaw pulley or simply as a jaw pulley.

The pulley 2111 and the pulley 2121, which are end tool jaw pulleys, are formed to face each other, and are formed to be rotatable independently of each other around the rotation shaft 2141, which is an end tool jaw pulley rotation shaft. In this case, the pulley 2111 and the pulley 2121 are formed to be spaced apart from each other by a certain extent, and a staple assembly accommodation portion may be formed therebetween. In addition, at least portions of the staple pulley assembly 2160 and the staple link assembly 2170 to be described below may be arranged in the staple assembly accommodation portion.

Here, although the drawings illustrate that the pulley 2111 and the pulley 2121 are formed to rotate around one rotation shaft 2141, it is also possible that each end tool jaw pulley may be formed to be rotatable around a separate shaft. Here, the first jaw 2101 may be fixedly coupled to the pulley 2111 to rotate together with the pulley 2111, and the second jaw 2102 may be fixedly coupled to the pulley 2121 to rotate together with the pulley 2121. Yaw and actuation motions of the end tool 2100 are performed according to the rotation of the pulley 2111 and the pulley 2121. That is, when the pulley 2111 and the pulley 2121 rotate in the same direction around the rotation shaft 2141, the yaw motion is performed, and when the pulley 2111 and the pulley 2121 rotate in opposite directions around the rotation shaft 2141, the actuation motion is performed.

Here, the first jaw 2101 and the pulley 2111 may be formed as separate members and coupled to each other, or the first jaw 2101 and the pulley 2111 may be integrally formed as one body. Similarly, the second jaw 2102 and the pulley 2121 may be formed as separate members and coupled to each other, or the second jaw 2102 and the pulley 2121 may be integrally formed as one body.

The pulley 2112 functions as an end tool first jaw auxiliary pulley, the pulley 2122 functions as an end tool second jaw auxiliary pulley, and the two components may be collectively referred to as an end tool jaw auxiliary pulley or simply as an auxiliary pulley.

In detail, the pulley 2112 and the pulley 2122, which are the end tool jaw auxiliary pulley, may be additionally provided on one side of the pulley 2111 and the pulley 2121. In other words, the pulley 2112, which is an auxiliary pulley, may be arranged between the pulley 2111 and the pulley 2113/the pulley 2114. In addition, the pulley 2122, which is an auxiliary pulley, may be arranged between the pulley 2121 and the pulley 2123/the pulley 2124. The pulley 2112 and the pulley 2122 may be formed to be rotatable independently of each other around the rotation shaft 2142. Here, although the drawings illustrate that the pulley 2112 and the pulley 2122 are formed to rotate around one rotation shaft 2142, it is also possible that each of the pulley 2112 and the pulley 2122 may be formed to be rotatable around a separate shaft. Such an auxiliary pulley will be described below in more detail.

The pulley 2113 and the pulley 2114 function as end tool first jaw pitch main pulleys, the pulley 2123 and the pulley 2124 function as end tool second jaw pitch main pulleys, and the two components may collectively be referred to as an end tool jaw pitch main pulley.

The pulley 2115 and the pulley 2116 function as end tool first jaw pitch subsidiary pulleys, the pulley 2125 and the pulley 2126 function as end tool second jaw pitch subsidiary pulleys, and the two components may collectively be referred to as an end tool jaw pitch subsidiary pulley.

Hereinafter, components associated with the rotation of the pulley 2111 will be described.

The pulley 2113 and the pulley 2114 function as end tool first jaw pitch main pulleys. That is, the pulley 2113 and the pulley 2114 function as main rotation pulleys of the pitch motion of the first jaw 2101. Here, the wire 301, which is the first jaw wire, is wound around the pulley 2113, and the wire 305, which is the first jaw wire, is wound around the pulley 2114.

The pulley 2115 and the pulley 2116 function as end tool first jaw pitch subsidiary pulleys. That is, the pulley 2115 and the pulley 2116 function as subsidiary rotation pulleys of the pitch motion of the first jaw 2101. Here, the wire 301, which is the first jaw wire, is wound around the pulley 2115, and the wire 305, which is the first jaw wire, is wound around the pulley 2116.

Here, the pulley 2113 and the pulley 2114 are arranged on one side of the pulley 2111 and the pulley 2112 to face each other. Here, the pulley 2113 and the pulley 2114 are formed to be rotatable independently of each other around the rotation shaft 2143, which is an end tool pitch rotating shaft. In addition, the pulley 2115 and the pulley 2116 are arranged on one side of each of the pulley 2113 and the pulley 2114 to face each other. Here, the pulley 2115 and the pulley 2116 are formed to be rotatable independently of each other around the rotation shaft 2144, which is an end tool pitch auxiliary rotating shaft. Here, although the drawings illustrate that the pulley 2113, the pulley 2115, the pulley 2114, and the pulley 2116 are formed to be rotatable around a Y-axis direction, the technical concepts of the present disclosure are not limited thereto, and the rotation shafts of each pulley may be formed in various directions suitable for their respective configurations.

The wire 301, which is the first jaw wire, is wound sequentially such that at least a portion thereof is in contact with the pulley 2115, the pulley 2113, and the pulley 2111. In addition, the wire 305 connected to the wire 301 by the fastening member 323 is sequentially wound such that at least a portion thereof is in contact with the pulley 2111, the pulley 2112, the pulley 2114, and the pulley 2116.

In other words, the wire 301 and wire 305, which are the first jaw wire, are be sequentially wound such that at least portions thereof are in contact with the pulley 2115, the pulley 2113, the pulley 2111, the pulley 2112, the pulley 2114, and the pulley 2116, and the wire 301 and the wire 305 are formed to move along the pulleys while rotating the pulleys.

Accordingly, when the wire 301 is pulled toward an arrow 301 of FIG. 7, the fastening member 323 coupled to the wire 301 and the pulley 2111 coupled to the fastening member 323 rotate in the direction of an arrow L of FIG. 7. On the contrary, when the wire 305 is pulled toward the arrow 305 of FIG. 7, the fastening member 323 coupled to the wire 305 and the pulley 2111 coupled to the fastening member 323 rotate in the direction of the arrow R of FIG. 7.

Next, components associated with the rotation of the pulley 2121 will be described.

The pulley 2123 and the pulley 2124 function as end tool second jaw pitch main pulleys. That is, the pulley 2123 and the pulley 2124 function as main rotation pulleys of the pitch motion of the second jaw 2102. Here, the wire 306, which is the second jaw wire, is wound around the pulley 2123, and the wire 302, which is the second jaw wire, is wound around the pulley 2124.

The pulley 2125 and the pulley 2126 function as end tool second jaw pitch subsidiary pulleys. That is, the pulley 2125 and the pulley 2126 function as subsidiary rotation pulleys of the pitch motion of the second jaw 2102. Here, the wire 306, which is the second jaw wire, is wound around the pulley 2125, and the wire 302, which is the second jaw wire, is wound around the pulley 2126.

The pulley 2123 and the pulley 2124 are arranged on one side of the pulley 2121 to face each other. Here, the pulley 2123 and the pulley 2124 are formed to be rotatable independently of each other around the rotation shaft 2143, which is an end tool pitch rotating shaft. In addition, the pulley 2125 and the pulley 2126 may be arranged on one side of each of the pulley 2123 and the pulley 2124 to face each other. Here, the pulley 2125 and the J15 pulley 2123J25 are formed to be rotatable independently of each other around the rotation shaft 2144, which is an end tool pitch auxiliary rotating shaft. Here, although the drawings illustrate that the pulley 2123, the pulley 2125, the pulley 2124, and the pulley 2126 are formed to be rotatable around the Y-axis direction, the technical concepts of the present disclosure are not limited thereto, and the rotation shafts of each pulley may be formed in various directions suitable for their respective configurations.

The wire 306, which is the second jaw wire, is wound sequentially such that at least a portion thereof is in contact with the pulley 2125, the pulley 2123, and the pulley 2121. In addition, the wire 302 connected to the wire 306 by the fastening member 326 is sequentially wound such that at least a portion thereof is in contact with the pulley 2121, the pulley 2122, the pulley 2124, and the pulley 2126.

In other words, the wire 306 and wire 302, which are the second jaw wire, are sequentially wound such that at least portions thereof are in contact with the pulley 2125, the pulley 2123, the pulley 2121, the pulley 2122, the pulley 2124, and the pulley 2126, and the wire 306 and the wire 302 are formed to move along the pulleys while rotating the pulleys.

Accordingly, when the wire 306 is pulled in the direction of an arrow 306 of FIG. 7, the fastening member 322 to which the wire 306 is coupled, and the pulley 2121 coupled to the fastening member 322 rotate in the direction of the arrow R of FIG. 7. On the contrary, when the wire 302 is pulled in the direction of the arrow 302 of FIG. 7, the fastening member 326 to which the wire 302 is coupled, and the pulley 2121 coupled to the fastening member 326 rotate in the direction of the arrow L of FIG. 7.

Hereinafter, the pulley 2112 and the pulley 2122 serving as auxiliary pulleys will be described in more detail.

As the pulley 2112 and the pulley 2122 are in contact with the wire 305, which is the first jaw wire, and the wire 302, which is the second jaw wire, to change an arrangement path of the wire 305 and the wire 302 to a certain extent, the pulley 2112 and the pulley 2122 may serve to enlarge a rotation angle of each of the first jaw 2101 and the second jaw 2102.

That is, when no auxiliary pulley is arranged, each of first jaw and the second jaw may rotate up to the right angle, however, in an embodiment of the present disclosure, by additionally arranging the pulley 2112 and the pulley 2122, which are auxiliary pulleys, the maximum rotation angle may be increased by θ as illustrated in FIG. 8. This enables the opening motion of the two jaws of the end tool 2100 for the actuation motion when the two jaws are yaw-rotated by 90° in the L direction. This is because the second jaw 2102 may rotate by the additional angle θ as illustrated in FIG. 8. Similarly, the actuation motion may be performed even when the two jaws are yaw-rotated in the L direction. In other words, through the pulley 2112 and the pulley 2122, a range of yaw rotation allowing the actuation motion may be expanded.

This will be described in more detail as follows.

When no auxiliary pulley is arranged, as the first jaw wire is fixedly coupled to the end tool first jaw pulley, and the second jaw wire is fixedly coupled to the end tool second jaw pulley, each of the end tool first jaw pulley and the end tool second jaw pulley may rotate only up to 90°. In this case, when the actuation motion is performed in a state where the first jaw and the second jaw are placed on the 90° line, the first jaw may be opened, but the second jaw may not be able to rotate over 90°. Accordingly, in a state where the first jaw and the second jaw perform the yaw motion over a certain angle, the actuation motion may not be performed smoothly.

In order to address such a problem, in the surgical instrument 2000 of the present disclosure, the pulley 2112 and the pulley 2122, which are auxiliary pulleys, are additionally arranged at one sides of the pulley 2111 and the pulley 2121, respectively. By arranging the pulley 2112 and the pulley 2122, the arrangement path of the wire 305, which is the first jaw wire, and the wire 302, which is the second jaw wire, is changed to a certain extent, and a tangential direction of the wire 305 and the wire 302 are changed, which allows rotation of the fastening member 323 coupling the wire 302 to the pulley 2111 up to the N line of FIG. 8. That is, the fastening member 323, which is a coupling portion between the wire 301 and the pulley 2111, is rotatable until it is positioned on a common internal tangent of the pulley 2111 and the pulley 2112. Similarly, the fastening member 326, which is a coupling portion of the wire 302 and the pulley 2121, is rotatable until it is positioned on a common internal tangent of the pulley 2121 and the pulley 2122, which allows expansion of the rotation range in the R direction.

In other words, by the pulley 2112, the wire 301 and the wire 305, which are two strands of the first jaw wire wound around the pulley 2111, are arranged on one side with respect to a plane perpendicular to the Y-axis and passing through the X-axis. At the same time, by the pulley 2122, the wire 302 and the wire 306, which are two strands of the second jaw wire wound around the pulley 2121, are arranged on another side with respect to the plane perpendicular to the Y-axis and passing through the X-axis.

In other words, the pulley 2113 and the pulley 2114 are arranged on one side with respect to the plane perpendicular to the Y-axis and passing through the X-axis, and the pulley 2123 and the pulley 2124 are arranged on another side with respect to the plane perpendicular to the Y-axis and passing through the X-axis.

In other words, the wire 305 is arranged on an internal tangent of the pulley 2111 and the pulley 2112, and the rotation angle of the pulley 2111 may be expanded by the pulley 2112. In addition, the wire 302 is arranged on an internal tangent of the pulley 2121 and the pulley 2122, and the rotation angle of the pulley 2121 is expanded by the pulley 2122.

According to the present disclosure, as the rotational radius of the jaw 2101 and the jaw 2102 is widened, the range of yaw motion allowing a normal open-and-shut actuation motion may be expanded.

Hereinafter, the pitch motion of the present disclosure will be described in more detail.

Meanwhile, when the wire 301 is pulled in the direction of the arrow 301 of FIG. 7, and simultaneously the wire 305 is pulled in the direction of the arrow 305 of FIG. 7 (i.e., both strands of the first jaw wire are pulled), as the wire 301 and the wire 305 are wound downward around the pulley 2113 and the pulley 2114, which are rotatable around the rotation shaft 2143 which is the end tool pitch rotation shaft, as illustrated in FIG. 49, the pulley 2111 fixedly coupled to the wire 301 and the wire 305 and the end tool hub 2106 coupled to the pulley 2111 rotate in the counterclockwise direction around the rotation shaft 2143, and as a result, the end tool 2100 rotates downward to perform the pitch motion. In this case, as the second jaw 2102 and the wire 302 and the wire 306 fixedly coupled to the second jaw 2102 are wound upward around the pulley 2123 and the pulley 2124, which are rotatable around the rotation shaft 2143, the wire 302 and the wire 306 are unwound in directions opposite to the directions 302 and 306, respectively.

On the contrary, when the wire 302 is pulled in the direction of the arrow 302 of FIG. 7, and simultaneously the wire 306 is pulled in the direction of the arrow 306 of FIG. 7, as the wire 302 and the wire 306 are wound upward around the pulley 2123 and the pulley 2124, which are rotatable around the rotation shaft 2143, which is the end tool pitch rotation shaft, as illustrated in FIG. 49, the pulley 2121 fixedly coupled to the wire 302 and the wire 306 and the end tool hub 2106 coupled to the pulley 2121 rotate around the rotation shaft 2143 in the clockwise direction, and as a result, the end tool 2100 rotates upward to perform the pitch motion. In this case, as the first jaw 2101 and the wire 301 and the wire 305 fixedly coupled to the first jaw 2101 are wound downward around the pulley 2113 and the pulley 2114, which are rotatable around the rotation shaft 2143, the wire 302 and the wire 306 are moved in directions opposite to the directions 301 and 305, respectively.

Meanwhile, the end tool 2100 of the surgical instrument 2000 of the present disclosure may further include the pulley 2131, which is an end tool pitch pulley, the manipulation portion 200 may further include the pulley 231 and a pulley 232, which are manipulation portion pitch pulleys, and the power transmission part 300 may further include the wire 303 and the wire 304, which are pitch wires. In detail, the pulley 2131 of the end tool 2100 is rotatable around the rotation shaft 2143, which is an end tool pitch rotation shaft, and may be integrally formed with the end tool hub 2106 as one body (or to be fixedly coupled to the end tool hub 2106). In addition, the wire 303 and the wire 304 may serve to connect the pulley 2131 of the end tool 2100 to the pulley 231 and the pulley 232 of the manipulation portion 200.

Thus, when the pulley 231 and the pulley 232 of the manipulation portion 200 rotate, the rotation of the pulley 231 and the pulley 232 is transmitted to the pulley 2131 of the end tool 2100 through the wire 303 and the wire 304 such that the pulley 2131 rotates together therewith, and as a result, the end tool 2100 performs a pitch motion while rotating.

That is, in the surgical instrument 2000 according to the first embodiment of the present disclosure, by providing the pulley 2131 of the end tool 2100, the pulley 231 and the pulley 232 of the manipulation portion 200, and the wire 303 and the wire 304 of the power transmission part 300, the driving force for the pitch motion of the manipulation portion 200 may be perfectly transmitted to the end tool 2100, thereby improving operation reliability.

Here, a diameter of the pulley 2113, the pulley 2114, the pulley 2123, and the pulley 2124, which are end tool jaw pitch main pulleys, and a diameter of the pulley 2131, which is an end tool pitch pulley, may be equal to or different from each other. Here, a ratio of the diameter of the end tool jaw pitch main pulley to the diameter of the end tool pitch pulley may be equal to a ratio of a diameter of the manipulation portion pitch pulley of the manipulation portion 200 to a diameter of a manipulation portion pitch main pulley to be described below. This will be described in detail below.

(Components Associated with Staple Pulley)

Hereinafter, the first staple pulley 2181 and the second staple pulley 2191 of the staple pulley assembly 2160 of the end tool 2100 of the surgical instrument 2000 of FIG. 2 will be described in more detail.

FIG. 9 is a side view illustrating the end tool of the surgical instrument of FIG. 2, and FIGS. 10 and 11 are perspective views illustrating the first jaw of the surgical instrument of FIG. 2. FIG. 12 is a perspective view illustrating the first jaw pulley of the surgical instrument of FIG. 2, FIG. 13 is a plan view illustrating the first jaw of the surgical instrument of FIG. 2, FIG. 14 is a plan view illustrating the second jaw of the surgical instrument of FIG. 2, and FIGS. 15 and 16 are exploded perspective views illustrating the staple pulley and the staple link of the surgical instrument of FIG. 2.

Referring to FIGS. 4 to 16 and the like, the end tool 2100 of the first embodiment of the present disclosure may include the first staple pulley 2181, a first staple auxiliary pulley 2182, a pulley 2183, a pulley 2184, a pulley 2185, and a pulley 2186 that are associated with linear/rotational motions of respective pulleys and links for stapling and cutting. In addition, the end tool 2100 of the first embodiment of the present disclosure may further include the pulley 2187 and the pulley 2188.

In addition, the end tool 2100 of the first embodiment of the present disclosure may include the second staple pulley 2191, a second staple auxiliary pulley 2192, a pulley 2193, a pulley 2194, a pulley 2195, and a pulley 2196 that are associated with linear/rotational motions of respective pulleys and links for stapling and cutting. In addition, the end tool 2100 of the first embodiment of the present disclosure may further include the pulley 2197 and the pulley 2198.

The first staple pulley 2181 and the second staple pulley 2191 are formed to face the pulley 2111 and the pulley 2121, which are end tool jaw pulleys, and are formed to be rotatable independently of each other around the rotation shaft 2141, which is an end tool jaw pulley rotation shaft. Here, although the drawings illustrate that the first staple pulley 2181 and the second staple pulley 2191 are arranged between the pulley 2111 and the pulley 2121, the technical concepts of the present disclosure is not limited thereto, and the first staple pulley 2181 and the second staple pulley 2191 may be arranged at various positions adjacent to the pulley 2111 or the pulley 2121.

Here, according to the present disclosure, the first staple pulley 2181, the second staple pulley 2191, the pulley 2111, and the pulley 2121 are formed to rotate around substantially the same shaft. As such, as the first staple pulley 2181, the second staple pulley 2191, the pulley 2111, and the pulley 2121 are formed to rotate around the same shaft, it is possible to perform a pitch motion/yaw motion/actuation motion as well as stapling and cutting motions. This will be described below in more detail. However, although the drawings illustrate that the first staple pulley 2181, the second staple pulley 2191, the pulley 2111, and the pulley 2121 are formed to rotate around one rotation shaft 2141, the pulleys may also be formed to be rotatable around separate shafts that are concentric with each other.

In other words, it may also be described that the pulley 2111, which is the first jaw pulley, the first staple pulley 2181, the second staple pulley 2191, and the pulley 2121, which is the second jaw pulley, are sequentially stacked along the rotation shaft 2141. Alternatively, it may also be described that the first staple pulley 2181 and the second staple pulley 2191 are arranged between the pulley 2111 and the pulley 2121 facing each other. Here, the pulley 2111, which is the first jaw pulley, the first staple pulley 2181, the second staple pulley 2191, and the pulley 2121, which is the second jaw pulley, may be formed to rotate independently of each other.

The first staple auxiliary pulley 2182 may be additionally provided on one side of the first staple pulley 2181. In other words, the first staple auxiliary pulley 2182 may be arranged between the first staple pulley 2181 and the pulley 2183/the pulley 2184. The first staple auxiliary pulley 2182 may be formed to be rotatable independently of the pulley 2112 and the pulley 2122 around the rotation shaft 2142.

Meanwhile, the pulley 2187 and the pulley 2188 may be additionally arranged between the first staple auxiliary pulley 2182 and the pulley 2183/the pulley 2184. The pulley 2187 and the pulley 2188 may be formed to be rotatable around the separation prevention pulley coupling portion 2106f of the end tool hub 2106. Here, the separation prevention pulley coupling portion 2106f may be formed parallel to the rotation shaft 2143, which is the central axis of the pulley 2183 and the pulley 2184. Here, the pulley 2187 and the pulley 2188 may function as first staple wire separation prevention pulleys.

Meanwhile, the pulley 2183 and the pulley 2184 may function as staple pitch main pulleys, and the pulley 2185 and the pulley 2186 may function as staple pitch subsidiary pulleys.

The second staple auxiliary pulley 2192 may be additionally provided on one side of the second staple pulley 2191. In other words, the second staple auxiliary pulley 2192 may be arranged between the second staple pulley 2191 and the pulley 2193/the pulley 2194. The second staple auxiliary pulley 2192 may be formed to be rotatable independently of the pulley 2112 and the pulley 2122 around the rotation shaft 2142.

Here, although the drawings illustrate that the first staple auxiliary pulley 2182, the second staple auxiliary pulley 2192, the pulley 2112, and the pulley 2122 are formed to rotate around one rotation shaft 2142, the first staple auxiliary pulley 2182, the second staple auxiliary pulley 2192, the pulley 2112, and the pulley 2122 may also be formed to be rotatable around separate shafts. Such a staple auxiliary pulley will be described in more detail below.

Meanwhile, the pulley 2197 and the pulley 2198 may be additionally arranged between the second staple auxiliary pulley 2192 and the pulley 2193/the pulley 2194. The pulley 2197 and the pulley 2198 may be formed to be rotatable around the separation prevention pulley coupling portion 2106f of the end tool hub 2106. Here, the separation prevention pulley coupling portion 2106f may be formed parallel to the rotation shaft 2143, which is the central axis of the pulley 2183 and the pulley 2184. Here, the pulley 2197 and the pulley 2198 may function as second staple wire separation prevention pulleys.

Meanwhile, the pulley 2193 and the pulley 2194 may function as staple pitch main pulleys, and the pulley 2195 and the pulley 2196 may function as staple pitch subsidiary pulleys.

Hereinafter, the first staple auxiliary pulley 2182 will be described in more detail.

The first staple auxiliary pulley 2182 may serve to increase the rotation angle of the first staple pulley 2181 by coming into contact with the wire 308, which is a first staple wire, to change the arrangement path of the wire 308 to a certain extent.

That is, when no staple auxiliary pulley is arranged, the staple pulley is rotatable only up to a right angle, but in an embodiment of the present disclosure, by additionally providing the first staple auxiliary pulley 2182, which is an auxiliary pulley, the maximum rotation angle may be increased by 0. This allows the first staple pulley 2181 to rotate for the stapling and cutting motions while the two jaws of the end tool 2100 are yaw-rotated together by 90°, thus enabling a linear motion of an operation member 540 to be described below. In other words, a feature of increasing the range of yaw rotation in which stapling and cutting motions are possible may be obtained through the first staple auxiliary pulley 2182.

This will be described in more detail as follows.

In the surgical instrument 2000 of the present disclosure, the first staple auxiliary pulley 2182 is further arranged on one side of the first staple pulley 2181. As such, by arranging the first staple auxiliary pulley 2182 to change the arrangement path of the wire 308, which is the first staple wire, to a certain extent, the tangential direction of the wire 308 is changed, and thus the rotation angle of the fastening member (see 329 of FIG. 62) that couple the wire 308 to the first staple pulley 2181 is increased. That is, the fastening member (see 329 of FIG. 62), which is a coupling portion of the wire 308 and the first staple pulley 2181, is rotatable until the fastening member 329 is located on the common internal tangent of the first staple pulley 2181 and the staple auxiliary pulley 2122.

In other words, the wire 308 is located on the internal tangent of the first staple pulley 2181 and the first staple auxiliary pulley 2182, and the rotation angle of the first staple pulley 2181 is increased by the first staple auxiliary pulley 2182.

According to the present disclosure, as the rotation radius of the first staple pulley 2181 increases, a yaw motion range in which normal stapling and cutting motions may be performed may be increased.

Hereinafter, the pulley 2187 and the pulley 2188, which are first staple wire separation prevention pulleys, will be described in more detail.

The end tool 2100 of the surgical instrument according to the first embodiment of the present disclosure may further include the pulley 2187 and the pulley 2188, which are the first staple wire separation prevention pulleys, and thus may serve to prevent separation of the wire 307 and the wire 308, which are the first staple wires.

That is, the pulley 2187/the pulley 2188 are arranged between the first staple auxiliary pulley 2182 and the pulley 2183/the pulley 2184 so as to change the path of the wire 307 to the first staple pulley 2181 via the pulley 2183 and the path of the wire 308 to the first staple auxiliary pulley 2182 via the pulley 2184, to a certain extent. In more detail, the path of the wire 307/the wire 308 is changed to a certain extent such that the wire 307 toward the first staple pulley 2181 via the pulley 2183 and the wire 308 toward the first staple auxiliary pulley 2182 via the pulley 2184 are parallel to the X-axis.

In detail, the height of the wire 307 wound around the pulley 2183 in the Z-axis direction is different from the height of the wire 307 toward the first staple pulley 2181 in the Z-axis direction. Similarly, the height of the wire 308 wound around the pulley 2184 in the Z-axis direction is different from the height of the wire 308 toward the first staple auxiliary pulley 2182 in the Z-axis direction. Thus, when the pulley 2187/the pulley 2188, which are the first staple wire separation prevention pulleys, do not exist, the path of the wire 307/the wire 308 becomes oblique (i.e., the fleet angle of the wire relative to the pulley increases), and thus, there is a risk that the wire 307/the wire 308 are separated from the pulley, and there is also a risk that the wire 307/the wire 308 are damaged.

Thus, in the present embodiment, the pulley 2187/the pulley 2188, which are the first staple wire separation prevention pulleys, are arranged between the first staple auxiliary pulley 2182 and the pulley 2183/the pulley 2184, to serve to change the path of the wire 307/the wire 308 to a certain extent such that the wire 307/the wire 308 toward the distal end 2104 of the end tool 2100 after being wound around the pulley 2183/the pulley 2184 are parallel to the X-axis.

According to the present disclosure, the wire 307 and the wire 308, which are the first staple wires, are prevented from being separated from the pulleys, thereby more smoothly performing the cutting motion.

Hereinafter, components associated with the rotation of the first staple pulley 2181 will be described.

The pulley 2183 and the pulley 2184 function as staple pitch main pulleys. Here, the wire 307, which is a first staple wire, is wound around the pulley 2183, and the wire 308, which is a first staple wire, is wound around the pulley 2184.

The pulley 2185 and the pulley 2186 function as staple pitch subsidiary pulleys. Here, the wire 307, which is a first staple wire, is wound around the pulley 2185, and the wire 308, which is a first staple wire, is wound around the pulley 2186.

Here, the pulley 2183 and the pulley 2184 are arranged on one side of the first staple pulley 2181, the first staple auxiliary pulley 2182, and the pulley 2187/the pulley 2188, to face each other. Here, the pulley 2183 and the pulley 2184 are formed to be rotatable independently of each other around the rotation shaft 2143, which is an end tool pitch rotation shaft. In addition, the pulley 2185 and the pulley 2186 are arranged on one sides of the pulley 2183 and the pulley 2184, respectively, to face each other. Here, the pulley 2185 and the pulley 2186 are formed to be rotatable independently of each other around the rotation shaft 2144, which is an end tool pitch auxiliary rotating shaft. Although the drawings illustrate that the pulley 2183, the pulley 2185, the pulley 2184, and the pulley 2186 are formed to be rotatable around the Y-axis direction, the technical concepts of the present disclosure are not limited thereto, and the rotation shafts of each pulley may be formed in various directions suitable for their respective configurations.

As described above, the rotation shaft 2141, the rotation shaft 2142, the rotation shaft 2143, and the rotation shaft 2144 may be arranged sequentially from the distal end 2104 of the end tool 2100 toward the proximal end 2105. Accordingly, the first staple pulley 2181, the first staple auxiliary pulley 2182, the pulley 2187/the pulley 2188, the pulley 2183/the pulley 2184, and the pulley 2185/the pulley 2186 may be arranged sequentially from the distal end 2104 of the end tool 2100 to the proximal end 2105.

The wire 307, which is the first staple wire, is sequentially wound such that at least a portion thereof is in contact with the pulley 2185, the pulley 2183, the pulley 2187, and the first staple pulley 2181. In addition, the wire 308 connected to the wire 307 by the fastening member (see 329 of FIG. 62) is sequentially wound such that at least a portion thereof is in contact with the first staple pulley 2181, the first staple auxiliary pulley 2182, the pulley 2188, the pulley 2184, and the pulley 2186.

In other words, the wire 307 and the wire 308, which are first staple wires, are sequentially wound such that at least portions thereof are in contact with the pulley 2185, the pulley 2183, the first staple pulley 2181, the first staple auxiliary pulley 2182, the pulley 2188, the pulley 2184, and the pulley 2186, and the wire 307 and the wire 308 are formed to move along the pulleys while rotating above pulleys.

Accordingly, when the wire 307 is pulled, the fastening member (see 329 of FIG. 62) to which the wire 307 is coupled and the first staple pulley 2181 coupled to the fastening member 329 rotate in one direction. On the contrary, when the wire 308 is pulled, the fastening member (see 329 of FIG. 62) to which the wire 308 is coupled and the first staple pulley 2181 coupled to the fastening member 329 rotate in the opposite direction.

Meanwhile, the second staple pulley 2191, the second staple auxiliary pulley 2192, and the pulley 2193, the pulley 2194, the pulley 2195, the pulley 2196, the pulley 2197, the pulley 2198, the wire 309, the wire 310, and the like, which are associated with the second staple pulley 2191, the second staple auxiliary pulley 2192, may have the same or similar configurations as those of the components associated with the first staple pulley 2181 described above.

In detail, the pulley 2193 and the pulley 2194 function as staple pitch main pulleys. Here, the wire 310, which is a second staple wire, is wound around the pulley 2193, and the wire 309, which is a second staple wire, is wound around the pulley 2194.

The pulley 2195 and the pulley 2196 function as staple pitch subsidiary pulleys. Here, the wire 310, which is a second staple wire, is wound around the pulley 2195, and the wire 309, which is a second staple wire, is wound around the pulley 2196.

Here, the pulley 2193 and the pulley 2194 are arranged on one side of the second staple pulley 2191, the second staple auxiliary pulley 2192, and the pulley 2197/the pulley 2198, to face each other. Here, the pulley 2193 and the pulley 2194 are formed to be rotatable independently of each other around the rotation shaft 2143, which is an end tool pitch rotation shaft. In addition, the pulley 2195 and the pulley 2196 are arranged on one sides of the pulley 2193 and the pulley 2194, respectively, to face each other. Here, the pulley 2195 and the pulley 2196 are formed to be rotatable independently of each other around the rotation shaft 2144, which is an end tool pitch auxiliary rotating shaft. Although the drawings illustrate that the pulley 2193, the pulley 2195, the pulley 2194, and the pulley 2196 are formed to be rotatable around the Y-axis direction, the technical concepts of the present disclosure are not limited thereto, and the rotation shafts of each pulley may be formed in various directions suitable for their respective configurations.

As described above, the rotation shaft 2141, the rotation shaft 2142, the rotation shaft 2143, and the rotation shaft 2144 may be arranged sequentially from the distal end 2104 of the end tool 2100 toward the proximal end 2105. Accordingly, the second staple pulley 2191, the second staple auxiliary pulley 2192, the pulley 2197/the pulley 2198, the pulley 2193/the pulley 2194, and the pulley 2195/the pulley 2196 may be arranged sequentially from the distal end 2104 of the end tool 2100 to the proximal end 2105.

The wire 310, which is the second staple wire, is sequentially wound such that at least a portion thereof is in contact with the pulley 2195, the pulley 2193, the pulley 2197, and the first staple pulley 2191. In addition, the wire 309 connected to the wire 310 by the fastening member (see 330 of FIG. 62) is sequentially wound such that at least a portion thereof is in contact with the first staple pulley 2191, the first staple auxiliary pulley 2192, the pulley 2198, the pulley 2194, and the pulley 2196.

In other words, the wire 310 and the wire 309, which are second staple wires, are sequentially wound such that at least portions thereof are in contact with the pulley 2195, the pulley 2193, the first staple pulley 2191, the first staple auxiliary pulley 2192, the pulley 2198, the pulley 2194, and the pulley 2196, and the wire 310 and the wire 309 are formed to move along the pulleys while rotating above pulleys.

Accordingly, when the wire 310 is pulled, the fastening member (see 330 of FIG. 62) to which the wire 310 is coupled and the first staple pulley 2191 coupled to the fastening member 330 rotate in one direction. On the contrary, when the wire 309 is pulled, the fastening member (see 330 of FIG. 62) to which the wire 309 is coupled and the first staple pulley 2191 coupled to the fastening member 330 rotate in the opposite direction.

(Staple Drive Assembly)

Hereinafter, a staple drive assembly 2150 will be described in detail.

Referring to FIGS. 15 to 20 and the like, the staple drive assembly 2150 may include the staple pulley assembly 2160 and the staple link assembly 2170. Here, the staple drive assembly 2150 is connected to a reciprocating assembly 550 of a cartridge 500 to be described below, to convert a rotational motion of the staple pulley assembly 2160 into a linear motion of the reciprocating assembly 550. In other embodiments of the present disclosure to be described below, the staple drive assembly may be understood as a concept including the staple pulley assembly and the staple link assembly.

The staple pulley assembly 2160 may include one or more staple pulleys. The staple pulley assembly 2160 may be formed between the pulley 2111 and the pulley 2121 to be adjacent to the pulley 2111 and the pulley 2121. In the present embodiment, it is assumed that the staple pulley assembly 2160 includes two staple pulleys, which are the first staple pulley 2181 and the second staple pulley 2191.

The staple link assembly 2170 may include one or more link members 2171. In addition, the link member 2171 may include one or more links. In the first embodiment of the present disclosure, it is assumed that the staple link assembly 2170 includes one link member 2171 and the link member 2171 includes one link.

In the end tool 2100 of the surgical instrument according to the present disclosure, the staple pulley assembly 2160 and the staple link assembly 2170 form a cam/slot structure. In addition, with such a structure, a force for moving the reciprocating assembly 550 forward may be amplified.

In detail, the staple pulley assembly 2160 may include the first staple pulley 2181 and the second staple pulley 2191.

The first staple pulley 2181 may include a body 2181a, a protruding member 2181b, and a shaft pass-through part 2181c.

The body 2181a is formed in a disk shape.

The shaft pass-through part 2181c may be formed in a central portion of the body 2181a. The shaft pass-through part 2181c may be formed in the form of a hole, and the rotation shaft 2141, which is an end tool jaw pulley rotation shaft, may be inserted through the shaft pass-through part 2181c.

In addition, the protruding member 2181b may be formed on the body part 2181a of the first staple pulley 2181. The protruding member 2181b may be coupled to the link member 2171 of the staple link assembly 2170. Here, the center of the protruding member 2181b may not coincide with the center of the first staple pulley 2181, and the protruding member 2181b may be formed to be eccentric to a certain extent with respect to the first staple pulley 2181. The protruding member 2181b may be fitted into a first slot 2171d of the link member 2171 to be described below.

The second staple pulley 2191 may include a body 2191a, a protruding member 2191b, and a shaft pass-through part 2191c.

The body 2191a is formed in a disk shape.

the shaft pass-through part 2191c may be formed in a central portion of the body 2191a. The shaft pass-through part 2191c may be formed in the form of a hole, and the rotation shaft 2141, which is an end tool jaw pulley rotation shaft, may be inserted through the shaft pass-through part 2191c.

In addition, the protruding member 2191b may be formed on the body part 2191a of the second staple pulley 2191. The protruding member 2191b may be coupled to the link member 2171 of the staple link assembly 2170. Here, the center of the protruding member 2191b may not coincide with the center of the second staple pulley 2191, and the protruding member 2191b may be formed to be eccentric to a certain extent with respect to the first staple pulley 2191. The protruding member 2191b may be fitted into a second slot 2171e of the link member 2171 to be described below.

Meanwhile, the end tool 2100 of the present disclosure may further include the staple link assembly 2170 connected to the staple pulley assembly 2160, and the staple link assembly 2170 may include the link member 2171. Here, the staple link assembly 2170 may serve to connect the staple pulley assembly 2160 to a reciprocating assembly 2150 of a cartridge 2110 to be described below.

In the present embodiment, the staple link assembly 2170 includes one link member 2171, and the link member 2171 includes only one link. That is, by coupling the staple pulley assembly 2160 to the staple link assembly 2170 by a cam/slot structure, it is possible to convert a rotational motion of the staple pulley assembly 2160 into a linear motion of the staple link assembly 2170 even when the staple link assembly 2170 includes only one link.

In detail, the link member 2171 may be formed as a single link.

The link member 2171 is formed in a shape of a combination of an elongated bar with an elliptical flat plate, and may be formed in an approximately 'L' shape. Here, the link member 2171 may include a first protrusion 2171a, a second protrusion 2171b, a fastening portion 2171c, the first slot 2171d, and the second slot 2171e.

the first protrusion 2171a and the second protrusion 2171b may be formed in one region of a central portion of the link member 2171. The first protrusion 2171a and the second protrusion 2171b may be fitted into a guide groove 2101b of the first jaw 2101.

As such, as the first protrusion 2171a and the second protrusion 2171b are moved along the guide groove 2101b in a state in which the first protrusion 2171a and the second protrusion 2171b of the link member 2171 formed in a protruding shape are fitted into the groove-shaped guide groove 2101b, the link member 2171 is moved with respect to the first jaw 2101 (and the cartridge 500 therein). This will be described below in more detail.

Meanwhile, the fastening portion 2171c may be formed at one end of the link member 2171. The fastening portion 2171c may be coupled to a fastening portion 551a of a reciprocating member 551 of the cartridge 500.

Meanwhile, the first slot 2171d and the second slot 2171e may be formed at an end opposite to the end of the link member 2171 at which the fastening portion 2171c is formed.

In detail, the first slot 2171d may be formed on a surface of the link member 2171 facing the first staple pulley 2181. Here, the first slot 2171d may be formed in the shape of an elongated hole, and the protruding member 2181b of the first staple pulley 2181 may be inserted into the first slot 2171d. The first slot 2171d may be formed to have a predetermined curvature, and may be formed in an approximately elliptical shape. Here, the first slot 2171d may be formed to be greater than the protruding member 2181b by a certain extent. Accordingly, the protruding member 2181b is formed to be movable to a certain extent in the first slot 2171d in a state in which the protruding member 2181b of the first staple pulley 2181 is fitted into the first slot 2171d of the link member 2171.

As described above, the protruding member 2181b may be formed to be eccentric with respect to the center of the first staple pulley 2181 by a certain extent. Accordingly, when the first staple pulley 2181 rotates, the protruding member 2181b in contact with the first slot 2171d may push the first slot 2171d to move the link member 2171. That is, when the first staple pulley 2181 rotates, the protruding member 2181b may move while being in contact with the first slot 2171d within the first slot 2171d, and accordingly, the link member 2171 may linearly move along the guide groove 2101b of the first jaw 2101.

Here, the first slot 2171d may be formed not to pass through the entire thickness of the link member 2171, but to pass through about half of the entire thickness of the link member 2171. In other words, the first slot 2171d may be formed to have substantially the same thickness as the thickness of the protruding member 2181b of the first staple pulley 2181.

Meanwhile, the second slot 2171e may be formed in the link member 2171. In detail, the second slot 2171e may be formed on a surface of the link member 2171 facing the second staple pulley 2191. Here, the second slot 2171e may be formed in the shape of an elongated hole, and the protruding member 2191b of the second staple pulley 2191 may be inserted into the second slot 2171e. The second slot 2171e may be formed to have a predetermined curvature, and may be formed in an approximately elliptical shape. Here, the second slot 2171e may be formed to be greater than the protruding member 2191b by a certain extent. Accordingly, the protruding member 2191b is formed to be movable to a certain extent in the second slot 2171e in a state in which the protruding member 2191b of the second staple pulley 2191 is fitted into the second slot 2171e of the link member 2171.

As described above, the protruding member 2191b may be formed to be eccentric with respect to the center of the second staple pulley 2191 by a certain extent. Accordingly, when the second staple pulley 2191 rotates, the protruding member 2191b in contact with the second slot 2171e may push the second slot 2171e to move the link member 2171. That is, when the second staple pulley 2191 rotates, the protruding member 2191b may move while being in contact with the second slot 2171e within the second slot 2171e, and accordingly, the link member 2171 may linearly move along the guide groove 2101b of the first jaw 2101.

Here, the second slot 2171e may be formed not to pass through the entire thickness of the link member 2171, but to pass through about half of the entire thickness of the link member 2171. In other words, the second slot 2171e may be formed to have substantially the same thickness as the thickness of the protruding member 2191b of the second staple pulley 2191.

Here, the first slot 2171d and the second slot 2171e may be formed to at least partially overlap each other. In addition, the sum of the thicknesses of the first slot 2171d and the second slot 2171e in the Y-axis direction may be substantially equal to the thickness of the link member 2171 in the Y-axis direction.

Here, the first slot 2171d and the second slot 2171e may be formed to be vertically symmetrical with respect to the rotation shaft 2141. As such, as the first slot 2171d and the second slot 2171e are vertically symmetrical with respect to the rotation shaft 2141, the protruding member 2181b of the first staple pulley 2181 and the protruding member 2191b of the second staple pulley 2191, which are coupled to the link member 2171, may be arranged to be symmetrical with each other. This will be described below in more detail.

(Displacement and Operation of Staple Link Assembly According to Rotation of Staple Pulley)

Hereinafter, displacement of the staple link assembly 2170 according to rotation of the first staple pulley 2181 and the second staple pulley 2191 will be described.

Referring to FIG. 17, in the first embodiment of the present disclosure, the first staple pulley 2181 and the staple link assembly 2170 are coupled to each other in a cam/slot form. That is, the cam-shaped protruding member 2181b formed on the first staple pulley 2181 is coupled to the first slot 2171d formed in the link member 2171. Thus, when the first staple pulley 2181 rotates in the direction of an arrow A, the displacement of the protruding member 2181b of the first staple pulley 2181 in the X-axis direction becomes B. In addition, the displacement of the staple link assembly 2170 in the X-axis direction becomes C.

Similarly, referring to FIG. 18, in the first embodiment of the present disclosure, the second staple pulley 2191 and the staple link assembly 2170 are coupled to each other in a cam/slot form. That is, the cam-shaped protruding member 2191b formed on the second staple pulley 2191 is coupled to the second slot 2171e formed in the link member 2171. Thus, when the second staple pulley 2191 rotates in the direction of an arrow D, the displacement of the protruding member 2191b of the second staple pulley 2191 in the X-axis direction becomes E. In addition, the displacement of the staple link assembly 2170 in the X-axis direction becomes F.

In comparison with the above case, when a staple pulley and a staple link assembly are coupled to each other in a link-shaft manner rather than the cam/slot manner, the displacement of the staple link assembly in the X-axis direction becomes much longer than that in the first embodiment of the present disclosure.

In other words, compared to when the staple pulley and the staple link assembly are axially coupled to each other, when the staple pulley and the staple link assembly are coupled to each other in the cam/slot manner as in the present embodiment, the displacement of the staple link assembly displacement in the X-axis direction decreases even when the staple pulley rotates by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the first embodiment of the present disclosure, because the first staple pulley 2181 and the second staple pulley 2191 are each coupled to the staple link assembly 2170 in the cam/slot form, and the displacement of the staple link assembly 2170 in the X-axis direction due to the rotation of the first staple pulley 2181 and the second staple pulley 2191 is relatively reduced compared to other embodiments, the force received by the staple link assembly 2170 in the X-axis direction relatively increases compared to a simple link structure.

According to the first embodiment of the present disclosure described above, a force for moving forward the staple link assembly 2170 and the reciprocating assembly 550 connected thereto is amplified, and thus, a stapling motion may be performed more robustly.

In particular, in the first embodiment of the present disclosure, because two staple pulleys (i.e., the first staple pulley 2181 and the second staple pulley 2191) symmetrical to each other are provided, the force with which the staple pulley assembly 2160 pushes the staple link assembly 2170 may be amplified by approximately two times compared to a case in which only one staple pulley is provided.

In addition, because the first staple pulley 2181 and the second staple pulley 2191 are arranged to be horizontally symmetrical with each other with respect to an XZ plane, the horizontal balance is achieved in performing a stapling motion, such that the end tool 2100 may perform the motion stably with respect to the rotation shaft 2141, which a yaw rotation shaft, without shaking left and right. In addition, when the winding directions of the wire 307/the wire 308, which are first staple wires, and the wire 309/the wire 310, which are second staple wires, are changed to be opposite to each other with respect to the rotation shaft 2143, which is a pitch rotation shaft, shaking with respect to the rotation shaft 2143 may be mutually offset.

Hereinafter, rotation directions of the first staple pulley 2181 and the second staple pulley 2191 will be described.

Referring to FIGS. 17, 18, 19, 20, and the like, the first staple pulley 2181 moves forward the staple link assembly 2170 when rotating in the direction of an arrow A of FIG. 20 (i.e., the clockwise direction), and the second staple pulley 2191 moves forward the staple link assembly 2170 when rotating in the direction of an arrow D of FIG. 20 (i.e., the counterclockwise direction).

On the contrary, the first staple pulley 2181 moves backward the staple link assembly 2170 when rotating in the counterclockwise direction, and the second staple pulley 2191 moves backward the staple link assembly 2170 when rotating in the clockwise direction.

Accordingly, when the first staple pulley 2181 and the second staple pulley 2191 rotate in opposite directions, the staple link assembly 2170 is moved (forward or backward). On the contrary, when the first staple pulley 2181 and the second staple pulley 2191 rotate in the same direction, the rotation of the two pulleys is offset, and thus, the staple link assembly 2170 is not moved.

Accordingly, in a state illustrated in FIG. 19, when the first staple pulley 2181 rotates in the clockwise direction and the second staple pulley 2191 rotates in the counterclockwise direction at the same time, the link member 2171 connected to the first staple pulley 2181 and the second staple pulley 2191 may move toward a distal end (see 2101*f* of FIG. 13) of the first jaw 2101.

On the contrary, when the first staple pulley 2181 rotates in the counterclockwise direction and the second staple pulley 2191 rotates in the clockwise direction at the same time, the link member 2171 connected to the first staple pulley 2181 and the second staple pulley 2191 may move toward a proximal end (see 101*g* of FIG. 13) of the first jaw 2101.

Thus, a bidirectional rotational motion of the staple pulley assembly 2160 causes a reciprocating linear motion of the reciprocating assembly 550 of the cartridge 500 through the staple link assembly 2170. This will be described below in more detail.

(First and Second Jaws and Actuation Motion)

Hereinafter, the coupling structure of the first jaw 2101 and the second jaw 2102 of the end tool 2100 of the surgical instrument 2000 of FIG. 2 will be described in more detail.

Figure 21:
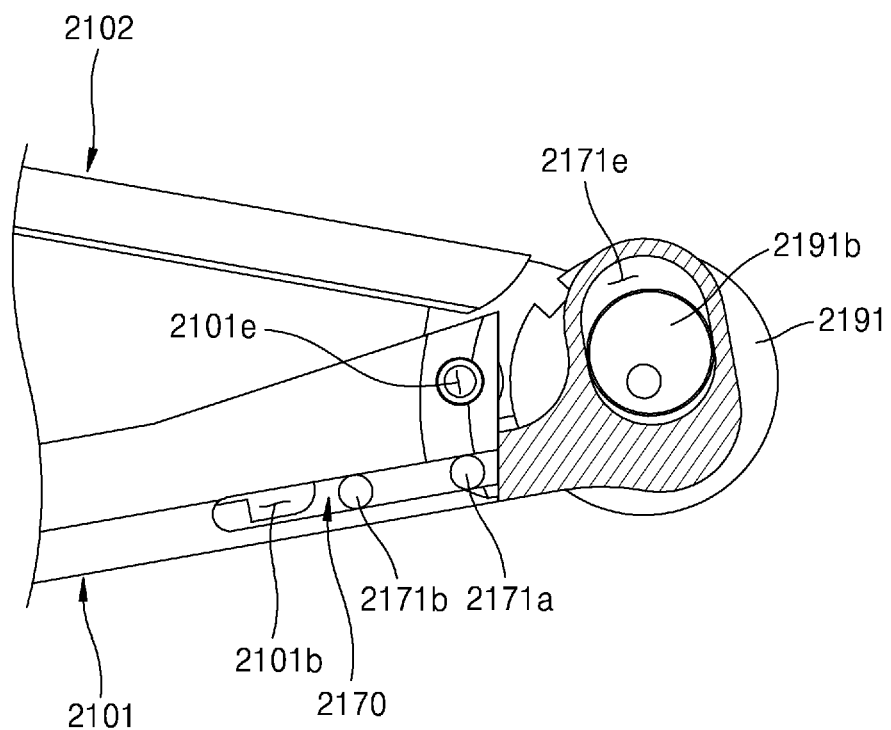
Figure 22:
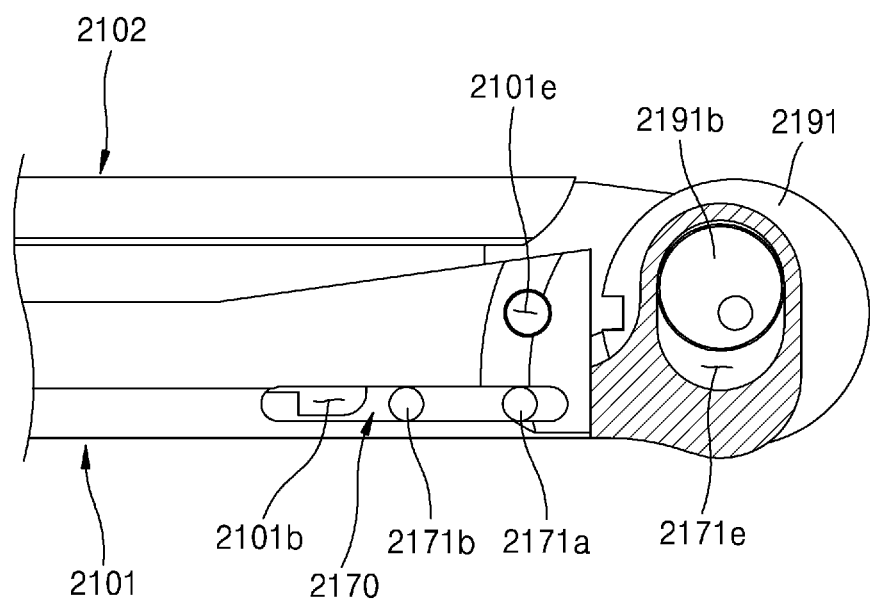
Figure 23:
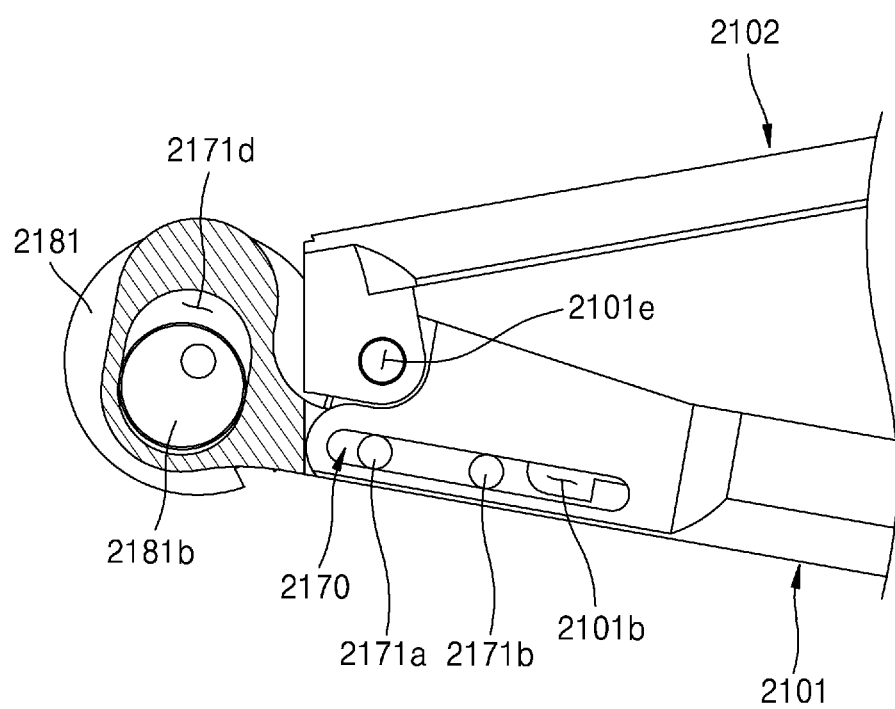
Figure 24:
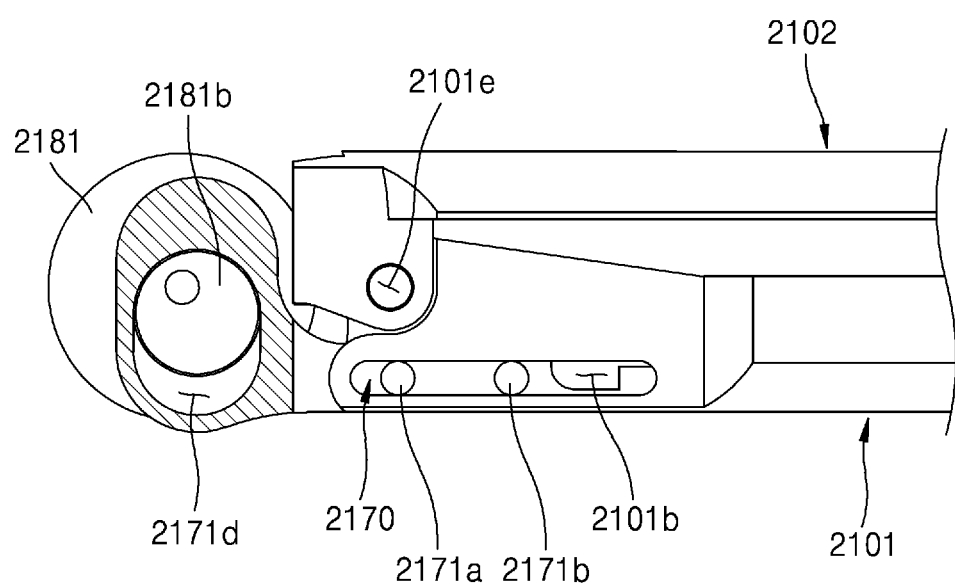

FIG. 13 is a plan view illustrating a first jaw of the surgical instrument of FIG. 2, and FIG. 14 is a plan view illustrating a second jaw of the surgical instrument of FIG. 2. FIGS. 21 and 22 are plan views illustrating opening and closing motions of the first jaw and the second jaw of the surgical instrument of FIG. 2. FIGS. 23 and 24 are plan views illustrating opening and closing motions of the first jaw and the second jaw of the surgical instrument of FIG. 2. FIGS. 25 and 26 are perspective views illustrating opening and closing motions of the end tool of the surgical instrument of FIG. 2.

Referring to FIGS. 9 to 26 and the like, the first jaw 2101 includes a cartridge accommodation portion 2101*a*, the guide groove 2101*b*, a movable-coupling hole 2101*c*, a jaw pulley coupling hole 2101*d*, and a shaft pass-through part 2101*e*.

The first jaw 2101 is formed entirely in the shape of an elongated bar, the cartridge 500 is accommodated in the side of the distal end 2101*f*, and the pulley 2111 is coupled to the proximal end 2101*g*, such that the first jaw 2101 is formed to be rotatable around the rotation shaft 2141. In other words, the first jaw 2101 may be formed entirely in the form of a hollow box whose one surface (upper surface) is removed, such that the cartridge accommodation portion 2101*a* capable of accommodating the cartridge 500 may be formed inside the first jaw 2101. That is, the first jaw 2101 may be formed in an approximately 'U' shape in cross section.

The guide groove 2101*b* to guide the movement of the staple link assembly 2170 to be described below may be formed on one side of the cartridge accommodation portion 2101*a* of the first jaw 2101, for example, on the side of the proximal end 2101*g*. The guide groove 2101*b* may be formed in the shape of a groove formed along a moving path of the staple link assembly 2170. In addition, as the first protrusion 2171*a* and the second protrusion 2171*b* move along the guide groove 2101*b* in a state in which the first protrusion 2171*a* and the second protrusion 2171*b* of the link member 2171 formed in a protruding shape are fitted into the groove-shaped guide groove 2101*b*, the staple link assembly 2170 moves with respect to the first jaw 2101 (and the cartridge 500 therein). That is, the staple link assembly 2170 may move along the guide groove 2101*b* of the first jaw 2101.

Meanwhile, the movable-coupling hole 2101*c*, the jaw pulley coupling hole 2101*d*, and the shaft pass-through part 2101*e* may be formed on the side of the proximal end of the first jaw 2101.

Here, the movable-coupling hole 2101*c* may be formed to have a predetermined curvature, and may be formed in an approximately elliptical shape. A shaft coupling portion 2111*a* of the pulley 2111 to be described below may be fitted into the movable-coupling hole 2101*c*. Here, a short radius of the movable-coupling hole 2101*c* may be substantially equal to or slightly greater than a radius of the shaft coupling portion 2111*a*. Meanwhile, a long radius of the movable-coupling hole 2101*c* may be greater than the radius of the shaft coupling portion 2111*a*. Thus, the shaft coupling portion 2111*a* is formed to be movable to a certain extent within the movable-coupling hole 2101*c* in a state in which the shaft coupling portion 2111*a* of the pulley 2111 is fitted into the movable-coupling hole 2101*c* of the first jaw 2101. This will be described in more detail below.

Meanwhile, the jaw pulley coupling hole 2101*d* is formed in the form of a cylindrical hole, and a jaw coupling portion 2111*b* of the pulley 2111 to be described below may be fitted into the jaw pulley coupling hole 2101*d*. Here, a radius of the jaw pulley coupling hole 2101*d* may be substantially equal to or slightly greater than a radius of the jaw coupling portion 2111*b*. Thus, the jaw coupling portion 2111*b* of the pulley 2111 may be formed to be rotatably coupled to the jaw pulley coupling hole 2101*d* of the first jaw 2101. This will be described in more detail below.

The shaft pass-through part 2101*e* may be formed closer to the distal end 2101*f* of the first jaw 2101 compared to the movable-coupling hole 2101*c* and the jaw pulley coupling hole 2101*d*. The shaft pass-through part 2101*e* may be formed in the form of a hole, and the rotation shaft 2145, which is a jaw rotation shaft, may be inserted through the shaft pass-through part 2101*e*.

The second jaw 2102 includes an anvil 2102*a*, a movable-coupling hole 2102*c*, a jaw pulley coupling hole 2102*d*, and a shaft pass-through part 2102*e*.

The second jaw 2102 is formed entirely in the shape of an elongated bar, the anvil 2102*a* is formed on the side of a distal end 2102*f*, and the pulley 2112 is coupled to a proximal end 2102*g*, such that the second jaw 2102 is formed to be rotatable around the rotation shaft 2141.

In detail, the anvil 2102*a* is formed in the form of a flat plane, shapes corresponding to the shapes of staples 530 to be described below may be formed on one surface of the anvil 2102*a*. The anvil 2102*a* may serve as a support for supporting the staple 530 on the opposite side of the operation member 540 when the operation member 540 pushes and raises the staple 530 during a stapling motion, such that the staple 530 is bent.

Meanwhile, the movable-coupling hole 2102*c*, the jaw pulley coupling hole 2102*d*, and the shaft pass-through part 2102*e* may be formed on the side of the proximal end of the second jaw 2102.

Here, the movable-coupling hole 2102*c* may be formed to have a predetermined curvature, and may be formed in an approximately elliptical shape. A shaft coupling portion 2121*a* of the pulley 2121 to be described below may be fitted into the movable-coupling hole 2102*c*. Here, a short radius of the movable-coupling hole 2102*c* may be substantially equal to or slightly greater than a radius of the shaft coupling portion 2121*a*. Meanwhile, a long radius of the movable-coupling hole 2102*c* may be greater than the radius of the shaft coupling portion 2121*a*. Thus, the shaft coupling portion 2121*a* is formed to be movable to a certain extent within the movable-coupling hole 2102c in a state in which the shaft coupling portion 2121a of the pulley 2121 is fitted into the movable-coupling hole 2102c of the second jaw 2102. This will be described in more detail below.

Meanwhile, the jaw pulley coupling hole 2102d is formed in the form of a cylindrical hole, and a jaw coupling portion 2121b of the pulley 2121 to be described below may be fitted into the jaw pulley coupling hole 2102d. Here, a radius of the jaw pulley coupling hole 2102d may be substantially equal to or slightly greater than a radius of the jaw coupling portion 2121b. Thus, the jaw coupling portion 2121b of the pulley 2121 may be formed to be rotatably coupled to the jaw pulley coupling hole 2102d of the second jaw 2102. This will be described in more detail below.

Meanwhile, the shaft pass-through part 2102e may be formed on the side of the distal end 2102g of the second jaw 2102 compared to the movable-coupling hole 2102c and the jaw pulley coupling hole 2102d. The shaft pass-through part 2102e may be formed in the form of a hole, and the rotation shaft 2145, which is a jaw rotation shaft, may be inserted through the shaft pass-through part 2102e.

The pulley 2111, which is a first jaw pulley, may include the shaft coupling portion 2111a and the jaw coupling portion 2111b. The pulley 2111 is formed entirely in the form of a rotatable disk, and the shaft coupling portion 2111a and the jaw coupling portion 2111b may be formed to protrude to a certain extent from one surface of the pulley 2111. As described above, the shaft coupling portion 2111a of the pulley 2111 may be fitted into the movable-coupling hole 2101c of the first jaw 2101, and the jaw coupling portion 2111b of the pulley 2111 may be fitted into the jaw pulley coupling hole 2101d of the first jaw 2101. The pulley 2111 may be formed to be rotatable around the center of the rotation shaft 2141, which is an end tool jaw pulley rotation shaft.

Meanwhile, the pulley 2121, which is a second jaw pulley, may include the shaft coupling portion 2121a and the jaw coupling portion 2121b. The pulley 2121 is formed entirely in the form of a rotatable disk, and the shaft coupling portion 2121a and the jaw coupling portion 2121b may be formed to protrude to a certain extent from one surface of the pulley 2121. As described above, the shaft coupling portion 2112a of the pulley 2112 may be fitted into the movable-coupling hole 2102c of the second jaw 2102, and the jaw coupling portion 2112b of the pulley 2112 may be fitted into the jaw pulley coupling hole 2102d of the second jaw 2102. The pulley 2121 may be formed to be rotatable around the center of the rotation shaft 2141, which is an end tool jaw pulley rotation shaft.

The coupling relationship between the components described above is as follows.

The rotation shaft 2141, which is an end tool jaw pulley rotation shaft, is sequentially inserted through the shaft coupling portion 2111a of the pulley 2111, the movable-coupling hole 2101c of the first jaw 2101, the shaft pass-through part 2181c of the first staple pulley 2181, the movable-coupling hole 2102c of the second jaw 2102, and the shaft coupling portion 2121a of the pulley 2121.

The rotation shaft 2145, which is a jaw rotation shaft, is sequentially inserted through the shaft pass-through part 2101e of the first jaw 2101 and the shaft pass-through part 2102e of the second jaw 2102.

The shaft coupling portion 2111a of the pulley 2111 is fitted into the movable-coupling hole 2101c of the first jaw 2101, and the jaw coupling portion 2111b of the pulley 2111 is fitted into the jaw pulley coupling hole 2101d of the first jaw 2101.

Here, the jaw pulley coupling hole 2101d of the first jaw 2101 and the jaw coupling portion 2111b of the pulley 2111 are axially coupled to each other to be rotatable, and the movable-coupling hole 2101c of the first jaw 2101 and the shaft coupling portion 2111a of the pulley 2111 are movably coupled to each other.

The shaft coupling portion 2121a of the pulley 2121 is fitted into the movable-coupling hole 2102c of the second jaw 2102, and the jaw coupling portion 2121b of the pulley 2121 is fitted into the jaw pulley coupling hole 2102d of the second jaw 2102.

Here, the jaw pulley coupling hole 2102d of the second jaw 2101 and the jaw coupling portion 2121b of the pulley 2121 are axially coupled to each other to be rotatable, and the movable-coupling hole 2102c of the second jaw 2102 and the shaft coupling portion 2121a of the pulley 2121 are movably coupled to each other.

Here, the pulley 2111 and the pulley 2121 rotate around the rotation shaft 2141, which is an end tool jaw pulley rotation shaft. The first jaw 2101 and the second jaw 2102 rotate around the rotation shaft 2145, which is a jaw rotation shaft. That is, the pulley 2111 and the first jaw 2101 differ from each other in rotation shaft. Similarly, the pulley 2121 and the second jaw 2102 differ from each other in rotation shaft.

That is, the rotation angle of the first jaw 2101 is limited to a certain extent by the movable-coupling hole 2101c, but is basically rotate around the rotation shaft 2145, which is a jaw rotation shaft. Similarly, the rotation angle of the second jaw 2102 is limited to a certain extent by the movable-coupling hole 2102c, but is basically rotate around the rotation shaft 2145, which is a jaw rotation shaft.

Amplification of grip force due to the coupling relationship between the above-described components will be described.

In the surgical instrument 2000 according to an embodiment of the present disclosure, the coupling structure of the first jaw 2101 and the second jaw 2102 forms an X-shaped structure, and thus, when the first jaw 2101 and the second jaw 2102 rotate in directions in which they approach to each other close (i.e., when the first jaw 2101 and the second jaw 2102 are closed), the grip force becomes stronger in a direction in which the first jaw 2101 and the second jaw 2102 are closed. This will be described in more detail as follows.

As described above, in motions of opening and closing the first jaw 2101 and the second jaw 2102, there are two shafts that are the center of rotation of the jaws. That is, the first jaw 2101 and the second jaw 2102 perform opening and closing motions around two shafts, which are the rotation shaft 2141 and the rotation shaft 2145. Here, the center of rotation of the first jaw 2101 and the second jaw 2102 is the rotation shaft 2145, and the center of rotation of the pulley 2111 and the pulley 2121 is the rotation shaft 2141. Here, the rotation shaft 2141 is a shaft whose position is relatively fixed, and the rotation shaft 2145 is a shaft whose position linearly moves. In other words, when the pulley 2111 and the pulley 2121 rotate in a state in which the position of the rotation shaft 2141 is fixed, the first jaw 2101 and the second jaw 2102 are opened/closed as the rotation shaft 2145, which is the rotation shaft of the first jaw 2101 and the second jaw 2102, moves backward and forward.

With this configuration, the grip force becomes stronger when the first jaw 2101 and the second jaw 2102 are closed, thereby enabling a surgical operator to perform the actuation motion powerfully even with a weak force.

(Cartridge)

Hereinafter, the cartridge 500 of the surgical instrument 2000 of FIG. 2 will be described in more detail.

FIG. 27 is a perspective view illustrating the first jaw and a cartridge of the surgical instrument of FIG. 2. FIG. 28 is an exploded perspective view illustrating the cartridge of FIG. 27. FIG. 29 is a combined perspective view illustrating the cartridge of FIG. 27. FIG. 30 is a side view illustrating the cartridge of FIG. 27. FIG. 31 is a perspective cross-sectional view illustrating the cartridge of FIG. 27. FIG. 32 is a side cross-sectional view illustrating the cartridge of FIG. 27. FIGS. 33 and 34 are perspective views illustrating an operation member of the cartridge of FIG. 27. FIG. 35 is a side cross-sectional view illustrating a stapling-related structure of the end tool of the surgical instrument of FIG. 2. FIGS. 36 and 37 are perspective cross-sectional views illustrating a stapling structure of the end tool of the surgical instrument of FIG. 2. FIGS. 38 to 41 are perspective views illustrating a ratchet drive operation of the end tool of FIG. 30. FIGS. 42 and 43 are plan views illustrating a ratchet drive operation of the end tool of FIG. 36. FIG. 44 is a perspective view illustrating an entire ratchet drive operation of the end tool of FIG. 36. FIGS. 45 and 46 are perspective views illustrating an entire stapling motion of the end tool of FIG. 36.

Referring to FIGS. 27 to 46 and the like, the cartridge 500 is formed to be mountable to and dismountable from the first jaw 2101, and includes a plurality of staples 530 and a blade 542 therein to perform suturing and cutting of tissue. Here, the cartridge 500 may include a cover 510, a housing 520, the staples 530, withdrawal members 535, the operation member 540, and the reciprocating assembly 550.

The housing 520 forms an outer shape of the cartridge 500, and may be formed entirely in the form of a hollow box with one surface (upper surface) thereof is removed to accommodate the reciprocating assembly 550, the operation member 540, and the staple 530 therein. Here, the housing 520 may be formed in an approximately "U" shape in cross section.

The cover 510 is formed to cover an upper portion of the housing 520. Staple holes 511 through which the plurality of staples 530 may be ejected to the outside may be formed in the cover 510. As the staples 530, which are accommodated inside the housing 520 before a stapling operation, are pushed and raised upward by the operation member 540 during a stapling motion, and pass through the staple holes 511 of the cover 510 to be withdrawn to the outside of the cartridge 500, stapling is performed.

Meanwhile, a slit 512 may be formed in the cover 510 along a length direction of the cover 510. The blade 542 of the operation member 540 may protrude out of the cartridge 500 through the slit 512. As the blade 542 of the operation member 540 passes along the slit 512, staple-completed tissue may be cut.

The plurality of staples 530 may be disposed inside the housing 520. As the operation member 540, which will be described later, is linearly moved in one direction, the plurality of staples 530 are sequentially pushed and raised from the inside of the housing 520 to the outside, thereby performing sealing, that is, stapling. Here, the staples 530 may be made of a material that may include titanium, stainless steel, or the like.

Meanwhile, the withdrawal member 535 may be further disposed between the housing 520 and the staple 530. In other words, it may be said that the staple 530 is disposed above the withdrawal member 535. In this case, the operation member 540 is linearly moved in one direction to push and raise the withdrawal member 535, and the withdrawal member 535 may push and raise the staple 530.

As such, the operation member 540 may be described as pushing and raising the staples 530 in both the case in which the operation member 540 directly pushes and raises the staples 530 and the case in which the operation member 540 pushes and raises the withdrawal members 535 and the withdrawal members 535 pushes and raises the staples 530 (i.e., the operation member 540 indirectly pushes and raises the staples 530).

The reciprocating assembly 550 may be disposed at an inner lower side of the housing 520. The reciprocating assembly 550 may include one or more reciprocating members 551. In the present embodiment, it is illustrated that one reciprocating member 551 is provided, but in embodiments to be described later, a plurality of reciprocating members 551 may be provided.

In the present embodiment, the reciprocating member 551 may be a rack. The reciprocating member 551 may include recesses 551b and the coupling part 551a. In detail, the reciprocating member 551 may be formed in the form of an elongated bar, and a plurality of recesses 551b having a sawtooth shape may be formed on one surface thereof. The recess 551b may be formed to be in contact with the operation member 540 to be described later, in particular, a ratchet member 543 of the operation member 540. In other words, the reciprocating member 551 may include the plurality of recesses 551b shaped to engage with ratchets 543a of the ratchet member 543.

Meanwhile, although not shown in the drawings, in addition to a rack shape, the reciprocating member 551 may be provided as various shapes of members, which are directly or indirectly connected to the staple pulley assembly 2160 and may perform a linear reciprocating motion according to a rotational motion of the staple pulley assembly 2160. For example, the reciprocating member 551 may be in the form of a clutch in which recesses are not present.

Here, the reciprocating member 551 is not fixedly coupled to the other components of the cartridge 500, and may be formed to be movable relatively to the other components of the cartridge 500. That is, the reciprocating member 551 may perform a reciprocating linear motion with respect to the housing 520 and the cover 510 coupled to the housing 520.

Meanwhile, in the reciprocating member 551, the coupling part 551a may be formed at the proximal end 501 side adjacent to the pulley 2111, and the coupling part 551a may be fastened and coupled to the staple link assembly 2170 of the end tool 2100. Thus, when the staple link assembly 2170 performs a reciprocating linear motion in the extension direction (i.e., the Y-axis direction) of the connection part 400, the reciprocating member 551 coupled thereto may also perform a reciprocating linear motion in the extension direction (i.e., the Y-axis direction) of the connection part 400. This will be described in more detail later.

The operation member 540 may be disposed inside the housing 520. The operation member 540 is formed to be in contact with the reciprocating member 551, and may be formed to linearly move in one direction according to the reciprocating linear motion of the reciprocating member 551. In other words, the operation member 540 interacts with the reciprocating member 551 to perform stapling and cutting motions while moving in the extension direction of the connection part 400.

The operation member 540 may include a wedge 541, the blade 542, the ratchet member 543, an elastic member 544, and a body 545.

The body 545 may be formed in the shape of an elongated square column, and forms a base of the operation member 540.

The wedge 541 is formed on at least one side of the body 545, and may be formed to have a predetermined inclined surface. That is, the wedge 541 may be formed to be inclined to a certain extent in the extension direction of the connection part 400. In other words, the wedge 541 may be formed to have a greater height at a proximal end 501 side of the cartridge 500 than a distal end 502 side of the cartridge 500. In the drawing, it is illustrated that two wedges 541 are formed on each side of the body 545, but the concept of the present disclosure is not limited thereto, and the wedge 541 may be formed in various numbers and shapes depending on the shape of the staple 530 or the withdrawal member 535 that is in contact with the wedge 541.

Figure 40:
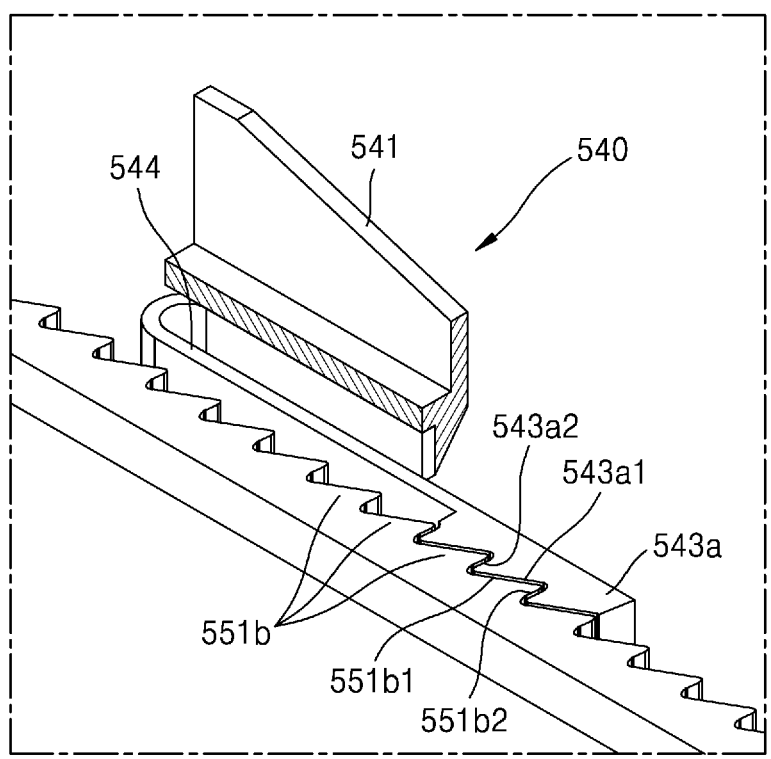

The wedge 541 may be formed to be in contact with the withdrawal members 535 or the plurality of staples 530 in turn and may serve to sequentially push and raise the staples 530. As shown in FIG. 40 to be described later and elsewhere herein, the operation member 540 may serve to withdraw the staples 530 to the outside of the cartridge 500 by sequentially pushing and raising the staples 530 while moving toward the distal end 502

The blade 542 may be formed on one side of the wedge 541, more specifically, on one side of the wedge 541 at the proximal end 501 side. An edge 542a formed to be sharp to cut tissue is formed in one region of the blade 542. As at least a portion of the edge 542a is withdrawn to the outside of the first jaw 2101 and the cartridge 500, tissue disposed between the first jaw 2101 and the second jaw 2102 may be cut. The edge 542a of the blade 542 may be always withdrawn to the outside of the first jaw 2101. Alternatively, the edge 542a of the blade 542 may normally be accommodated inside the first jaw 2101 or inside the cartridge 500, and may be withdrawn to the outside of the first jaw 2101 only when the operation member 540 is moved in a length direction.

The ratchet member 543 is formed on one side of the wedge 541, more specifically, below wedge 541, and may be formed to face the reciprocating member 551 to be described later. The ratchet member 543 may be formed in the form of a bar and may include a plurality of ratchets 543a on one surface. The operation member 540 is moved only in one direction (i.e., toward the distal end) with respect to the reciprocating member 551 by the ratchet member 543. The ratchets 543a of the ratchet member 543 may be formed to be in contact with the recess 551b of the reciprocating member 551 described above.

The elastic member 544 is formed on one side of the body 545 or the wedge 541 and serves to apply a predetermined elastic force to the ratchet member 543. In an example, one region of the elastic member 544 may be connected to the wedge 541 or the body 545, and another region of the elastic member 544 may be connected to the ratchet member 543, so that the elastic member 544 may connect the wedge 541 or the body 545 to the ratchet member 543. Here, the elastic member 544 may apply an elastic force in a direction in which the ratchet member 543 comes into close contact with the reciprocating member 551. To this end, the elastic member 544 may be formed in the form of a leaf spring, and may be provided in various forms capable of providing a predetermined elastic force to the ratchet member 543, such as a coil spring, a dish spring, and the like.

Here, the ratchet 543a of the ratchet member 543 may be formed such that a first surface 543a1 (specifically, at the distal end 502 side) is formed to have a gentle slope with a predetermined angle, and a second surface 543a2 (specifically, at the proximal end 501 side) is formed to be vertical or near vertical.

In addition, in order to be engaged with the ratchet 543a of the ratchet member 543, the recess 551b of the reciprocating member 551 may also be formed such that a first surface 551b1 (specifically, at the distal end 502 side) is formed to have a gentle slope with a predetermined angle, and a second surface 551b2 (specifically, at the proximal end 501 side) is formed to be vertical or near vertical.

In a state in which the reciprocating member 551 and the ratchet member 543 are coupled to each other (or engaged or in close contact with each other), the inclined first surface 543a1 of the ratchet 543a and the inclined first surface 551b1 of the recess 551b may be formed to face each other (that is, in contact with each other). In addition, the vertically formed second surface 543a2 of the ratchet 543a and the vertically formed second surface 551b2 of the recess 551b may be disposed to face each other (i.e., in contact with each other).

With this configuration, in a state in which the ratchet 543a and the recess 551b are coupled to (or engaged with) each other, the ratchet 543a and the recess 551b may be allowed to move only in one direction, acting as a kind of ratchet.

In an example, when it is assumed that the reciprocating member 551 is in a fixed state, the operation member 540 is movable in a direction in which the second surface 543a2 and the second surface 551b2, which are vertically formed, are away from each other, but when the second surface 543a2 and the second surface 551b2 are in contact with each other, the operation member 540 is not movable in a direction in which the second surface 543a2 and the second surface 551b2 are closer to each other.

In other words, when the reciprocating member 551 is moved toward the distal end 502 in a state in which the reciprocating member 551 and the ratchet member 543 are coupled to each other (or engaged or in close contact with each other), the ratchet member 543 is moved together toward the distal end 502 by the reciprocating member 551. That is, the vertically formed second surface 551b2 of the reciprocating member 551 pushes the vertically formed second surface 543a2 of the operation member 540 such that the ratchet member 543 is moved together toward the distal end 502 by the reciprocating member 551.

In contrast, when the reciprocating member 551 is moved toward the proximal end 501 in a state in which the reciprocating member 551 and the ratchet member 543 are coupled to each other (or engaged or in close contact with each other), only the reciprocating member 551 is moved alone toward the proximal end 501 while the ratchet member 543 a fixed. That is, the inclined first surface 551b1 of the reciprocating member 551 is moved along the inclined first surface 543a1 of the operation member 540 in a state in which the operation member 540 is fixed, so that only the reciprocating member 551 is moved alone toward the proximal end 501.

Referring to FIGS. 34 to 37, when the reciprocating member 551 is moved toward (in the direction of an arrow K1 of FIGS. 35 and 37) of the proximal end 501 in the state of FIGS. 34 and 36, as the inclined first surface 551b1 of the reciprocating member 551 is moved along the inclined first surface 543a1 of the operation member 540, the ratchet member 543 is pushed as a whole in the direction of an arrow K2 of FIG. 35. In addition, at this time, the elastic member 544 is elastically deformed to a certain extent.

In this state, when the reciprocating member 551 is further moved toward the proximal end 501, and the inclined first surface 551*b*1 of the reciprocating member 551 is moved beyond an end of the inclined first surface 543*a*l of the operation member 540, the recess 551*b* of the reciprocating member 551 meets the next ratchet 543*a* of the ratchet member 543. In this case, since the elastic member 544 applies an elastic force in a direction in which the ratchet member 543 comes into close contact with the reciprocating member 551, front surfaces of the reciprocating member 551 and the ratchet member 543 are brought into close contact with each other again.

As a result, the cartridge 500 is accommodated in the cartridge accommodation part 2101*a* of the first jaw 2101, and in this case, the reciprocating member 551 of the cartridge 500 is coupled to the staple link assembly 2170 of the end tool 2100. Accordingly, the rotational motion of the first staple pulley 2181 of the end tool 100 is converted into a linear motion of the reciprocating member 551 through the staple link assembly 2170.

In this case, when the coupling part 551*a* of the reciprocating member 551 is connected to the staple pulley assembly 2160 through the staple link assembly 2170, and the first staple pulley 2181 and the second staple pulley 2191 of the staple pulley assembly 2160 is rotated alternately in the clockwise/counterclockwise directions, the reciprocating member 551 may be repeatedly moved forward and backward. In addition, when the reciprocating member 551 is moved forward, the operation member 540 may be moved forward together with the reciprocating member 551, and when the reciprocating member 551 is moved backward, only the reciprocating member 551 may be moved backward and the operation member 540 may remain stationary in place. As the operation member 540 is moved forward while repeating this process, the staple 530 may be stapled by the wedge 541 while the blade 542 cuts stapled tissue.

This will be described in more detail as follows.
(Stapling and Cutting Motions)

Referring to FIG. 44, a method of driving a surgical instrument according to an embodiment of the present disclosure is described as follows.

First, when the first staple pulley 2181 rotates in the clockwise direction and the second staple pulley 2191 rotates in the counterclockwise direction, the staple link assembly 2170 connected to the staple pulley assembly 2160 and the reciprocating assembly 550 of the cartridge 500 connected to the staple link assembly 2170 move toward a distal end 502 of the cartridge 500. In addition, when the reciprocating assembly 550 moves toward the distal end 502 of the cartridge 500, the operation member 540 in contact with the reciprocating assembly 550 moves toward the distal end 502 of the cartridge 500 together with the reciprocating assembly 550.

In addition, as the operation member 540 moves toward the distal end 502 of the cartridge 500, the blade 542 of the operation member 540 moves toward the distal end 502 of the cartridge 500 while the operation member 540 ejects the staples 530 out of the cartridge 500.

Meanwhile, when the first staple pulley 2181 rotates in the counterclockwise direction and the second staple pulley 2191 rotates in the clockwise direction, the staple link assembly 2170 connected to the staple pulley assembly 2160 and the reciprocating assembly 550 of the cartridge 500 connected to the staple link assembly 2170 move toward a proximal end 501 of the cartridge 500, and at this time, the operation member 540 remains stationary.

In addition, as the above operations are repeatedly performed, a stapling motion by the wedge 541 and a cutting motion by the blade 542 are simultaneously performed.

This will be described in more detail as follows.

First, in the state illustrated in (a) of FIG. 44, when the first staple pulley 2181 rotates in the direction of an arrow A1 (i.e., the clockwise direction), and the second staple pulley 2191 rotates in the direction of an arrow B1 (i.e., the counterclockwise direction) as illustrated in (b) of FIG. 44, the staple link assembly 2170 connected thereto and the reciprocating member 551 coupled to the staple link assembly 2170 move in the direction of an arrow C1 (i.e., toward the distal end). In this state, the reciprocating member 551 and the operation member 540 are in close contact with each other by the elastic member (see 544 of FIG. 43), and thus, when the reciprocating member 551 moves in the direction of the arrow C1, the operation member 540 also moves in the direction of the arrow C1 together with the reciprocating member 551.

Meanwhile, when the first staple pulley 2181 rotates in the direction of an arrow A2 (i.e., the counterclockwise direction), and the second staple pulley 2191 rotates in the direction of an arrow B2 (i.e., the clockwise direction) as illustrated in (c) of FIG. 44, the staple link assembly 2170 connected thereto and the reciprocating member 551 coupled to the staple link assembly 2170 move in the direction of an arrow C2 (i.e., toward the proximal end). In this state, due to the coupling structure of the ratchet member 543 and the reciprocating member 551, even when the reciprocating member 551 moves in the direction of the arrow C2, only the ratchet member 543 is repeatedly spaced apart from and in contact with the reciprocating member 551 to a certain extent as the elastic member 544 is repeatedly elastically deformed and restored in a state in which the overall position of the operation member 540 remains unchanged (see FIGS. 41 and 43). That is, even when the reciprocating member 551 moves in the direction of the arrow C2, the operation member 540 remains stationary in place when viewed in the X-axis direction.

When the first staple pulley 2181 further rotates in the direction of an arrow A3 and the second staple pulley 2191 further rotates in the direction of an arrow B3 as illustrated in (d) of FIG. 44, only the staple link assembly 2170 and the reciprocating member 551 connected thereto further move in the direction of an arrow C3.

In this state, when the first staple pulley 2181 stops rotating, as illustrated in (a) of FIG. 44, the staple link assembly 2170, the reciprocating member 551, and the operation member 540 also stop moving.

When the first staple pulley 2181 and the second staple pulley 2191 alternately rotate in the clockwise/counterclockwise directions while repeating the above process, the reciprocating member 551 repeatedly moves forward and backward, and the operation member 540 repeatedly moves forward and stops, and as a result, the operation member 540 moves toward the distal end 502. In addition, as the operation member 540 moves toward the distal end 502, a stapling motion by the wedge 541 and a cutting motion by the blade 542 are simultaneously performed.

Hereinafter, a stapling motion of the surgical instrument according to an embodiment of the present disclosure will be described.

FIG. 45 is a perspective view illustrating a stapling motion of the end tool of FIG. 36 for each section, and FIG. 46 is a perspective view illustrating an entire stapling motion of the end tool of FIG. 36.

Referring to FIGS. 45 and 46, in the state illustrated in (a) of FIG. 45, as the operation member 540 moves in the direction of an arrow A1 of (b) of FIG. 45, the wedge 541 of the operation member 540 pushes and raises the withdrawal member 535, and the withdrawal member 535 pushes and raises one side of a lower portion of the staple 530. In addition, accordingly, the staple 530 is ejected to the outside of the first jaw 2101 and the cartridge 500.

In this state, when the operation member 540 further moves in the direction of an arrow A2 of (c) of FIG. 45, the ejected staple 530 is continuously pushed and raised by the operation member 540 while being in contact with the anvil 2102a of the second jaw 2102, such that stapling is performed while both ends of the staple 530 are bent.

As such motions are continuously performed, stapling is sequentially performed from the staple 530 on the side of the proximal end 501 to the staple 530 on the side of the distal end 502 among the plurality of staples 530, as illustrated in FIG. 46.

(Manipulation Part)

FIGS. 47 and 48 are perspective views illustrating the manipulation part of the surgical instrument of FIG. 2. FIG. 49 is a view schematically illustrating only a configuration of pulleys and wires constituting joints of the surgical instrument illustrated in FIG. 2.

Figure 41:
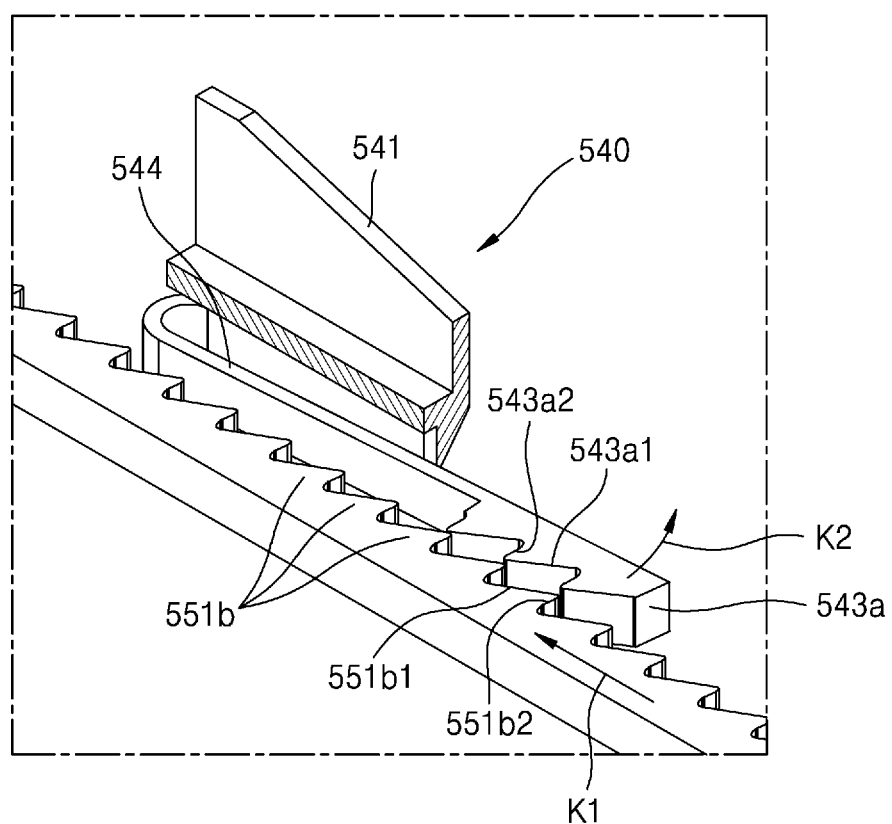

Referring to FIGS. 2 to 49, the manipulation part 200 of the surgical instrument 2000 according to the first embodiment of the present disclosure includes a first handle 204 that a user can grip, the actuation manipulation part 203 configured to control an actuation motion of the end tool 2100, the yaw manipulation part 202 configured to control a yaw motion of the end tool 2100, and the pitch manipulation part 201 configured to control a pitch motion of the end tool 2100. Here, it is understood that only the components related to the pitch/yaw/actuation motions of the surgical instrument 2000 are illustrated in FIGS. 41 and 42.

In addition, the manipulation part 200 of the surgical instrument 2000 may further include a staple manipulation part 260 configured to control the motion of the staple pulley assembly 160 of the end tool 2100 to perform stapling and cutting motions.

The manipulation part 200 may include the pulley 210, a pulley 211, a pulley 212, a pulley 213, a pulley 214, a pulley 215, a pulley 216, a pulley 217, and a pulley 218 that are related to a rotational motion of the first jaw 2101. In addition, the manipulation part 200 may include the pulley 220, a pulley 221, a pulley 222, a pulley 223, a pulley 224, a pulley 225, a pulley 226, a pulley 227, and a pulley 228 that are related to a rotational motion of the second jaw 2102. In addition, the manipulation part 200 may include the pulley 231, the pulley 232, a pulley 233, and a pulley 234 that are related to a pitch motion thereof. In addition, the manipulation part 200 may include a pulley 235, which is a relay pulley disposed at some places along the bent part 402 of the connection part 400.

Here, the pulleys facing each other are illustrated in the drawings as being formed parallel to each other, but the concept of the present disclosure is not limited thereto, and each of the pulleys may be variously formed with a position and a size suitable for the configuration of the manipulation part.

Further, the manipulation part 200 of the first embodiment of the present disclosure may include a rotation shaft 241, a rotation shaft 242, the rotation shaft 243, a rotation shaft 244, a rotation shaft 245, and the rotation shaft 246. Here, the rotation shaft 241 may function as a manipulation part first jaw actuation rotation shaft, and the rotation shaft 242 may function as a manipulation part second jaw actuation rotation shaft. In addition, the rotation shaft 243 may function as a manipulation part yaw main rotation shaft, and the rotation shaft 244 may function as a manipulation part yaw sub-rotation shaft. In addition, the rotation shaft 245 may function as a manipulation part pitch sub-rotation shaft, and the rotation shaft 246 may function as a manipulation part pitch main rotation shaft.

The rotation shaft 241/rotation shaft 242, the rotation shaft 243, the rotation shaft 244, the rotation shaft 245, and the rotation shaft 246 may be sequentially disposed from a distal end 205 of the manipulation part 200 toward a proximal end 206.

Each of the rotation shafts 241, 242, 243, 244, 245, and 246 may be fitted into one or more pulleys, which will be described in detail later.

The pulley 210 functions as a manipulation part first jaw actuation pulley, the pulley 220 functions as a manipulation part second jaw actuation pulley, and these components may also be collectively referred to as a manipulation part actuation pulley.

The pulley 211 and the pulley 212 function as manipulation part first jaw yaw main pulleys, the pulley 221 and the pulley 222 function as manipulation part second jaw yaw main pulleys, and these components may also be collectively referred to as a manipulation part yaw main pulley.

The pulley 213 and the pulley 214 function as manipulation part first jaw yaw sub-pulleys, the pulley 223 and the pulley 224 function as manipulation part second jaw yaw sub-pulleys, and these components may also be collectively referred to as a manipulation part yaw sub-pulley.

The pulley 215 and the pulley 216 function as manipulation part first jaw pitch sub-pulleys, the pulley 225 and the pulley 226 function as manipulation part second jaw pitch sub-pulleys, and these components may also be collectively referred to as a manipulation part pitch sub-pulley.

The pulley 217 and the pulley 218 function as manipulation part first jaw pitch main pulleys, and the pulley 227 and the pulley 228 function as manipulation part second jaw pitch main pulleys, and these components may also be collectively referred to as the manipulation part pitch main pulley.

The pulley 231 and the pulley 232 function as manipulation part pitch wire main pulleys, and the pulley 233 and the pulley 234 function as manipulation part pitch wire sub-pulleys.

The above components are categorized from the perspective of the manipulation part for each motion (pitch/yaw/actuation) as follows.

The pitch manipulation part 201 configured to control a pitch motion of the end tool 2100 may include the pulley 215, the pulley 216, the pulley 217, the pulley 218, the pulley 225, the pulley 226, the pulley 227, the pulley 228, the pulley 231, the pulley 232, and the pulley 234. In addition, the pitch manipulation part 201 may include the rotation shaft 245 and the rotation shaft 246. In addition, the pitch manipulation part 201 may further include a pitch frame 208.

The yaw manipulation part 202 configured to control a yaw motion of the end tool 2100 may include the pulley 211, the pulley 212, the pulley 213, the pulley 214, the pulley 221, the pulley 222, the pulley 223, and the pulley 224. In addition, the yaw manipulation part 202 may include the rotation shaft 243 and the rotation shaft 244. In addition, the yaw manipulation part 202 may further include a yaw frame 207.

The actuation manipulation part 203 configured to control an actuation motion of the end tool 2100 may include the pulley 210, the pulley 220, the rotation shaft 241, and the rotation shaft 242. In addition, the actuation manipulation part 203 may further include the first actuation manipulation part 251 and the second actuation manipulation part 256.

Hereinafter, each component of the manipulation part 200 will be described in more detail.

The first handle 204 may be formed to be gripped by a user with the hand, and in particular, may be formed to be grasped by the user by wrapping the first handle 204 with his/her palm. In addition, the actuation manipulation part 203 and the yaw manipulation part 202 are formed on the first handle 204, and the pitch manipulation part 201 is formed on one side of the yaw manipulation part 202. In addition, the other end portion of the pitch manipulation part 201 is connected to the bent part 402 of the connection part 400.

The actuation manipulation part 203 includes the first actuation manipulation part 251 and the second actuation manipulation part 256. The first actuation manipulation part 251 includes the rotation shaft 241, the pulley 210, the first actuation extension part 252, and a first actuation gear 253. The second actuation manipulation part 256 includes the rotation shaft 242, the pulley 220, the second actuation extension part 257, and a second actuation gear 258. Here, end portions of the first actuation extension part 252 and the second actuation extension part 257 are formed in the shape of a hand ring, which may act as a second handle.

Here, the rotation shaft 241 and the rotation shaft 242, which are actuation rotation axes, may be formed to form a predetermined angle with an XY plane on which the connection part 400 is formed. For example, the rotation shaft 241 and the rotation shaft 242 may be formed in a direction parallel to the Z-axis, and in this state, when the pitch manipulation part 201 or the yaw manipulation part 202 is rotated, the coordinate system of the actuation manipulation part 203 may change relatively. Of course, the concept of the present disclosure is not limited thereto, and the rotation shaft 241 and the rotation shaft 242 may be formed in various directions so as to be suitable for a structure of the hand of the user gripping the actuation manipulation part 203 according to an ergonomic design.

Meanwhile, the pulley 210, the first actuation extension part 252, and the first actuation gear 253 are fixedly coupled to each other to be rotatable together around the rotation shaft 241. Here, the pulley 210 may be configured to be a single pulley or two pulleys fixedly coupled to each other.

Similarly, the pulley 220, the second actuation extension part 257, and the second actuation gear 258 are fixedly coupled to each other to be rotatable together around the rotation shaft 242. Here, the pulley 220 may be configured to be a single pulley or two pulleys fixedly coupled to each other.

Here, the first actuation gear 253 and the second actuation gear 258 are formed to be engaged with each other such that, when any one gear is rotated in one direction, the other gear is rotated together in a direction opposite to the one direction.

The yaw manipulation part 202 may include the rotation shaft 243, the pulleys 211 and 212, which are manipulation part first jaw yaw main pulleys, the pulleys 221 and 222, which are manipulation part second jaw yaw main pulleys, and the yaw frame 207. In addition, the yaw manipulation part 202 may further include the pulleys 213 and 214, which are manipulation part first jaw yaw sub-pulleys formed on one side of the pulleys 211 and 212, and the pulleys 223 and 224 that are manipulation part second jaw yaw sub-pulleys formed on one side of the pulleys 221 and 222. Here, the pulleys 213 and 214 and the pulleys 223 and 224 may be coupled to the pitch frame 208 to be described later.

Here, it is illustrated in the drawings that the yaw manipulation part 202 includes the pulleys 211 and 212 and the pulleys 221 and 222, wherein the pulleys 211 and 212 and the pulleys 221 and 222 are each provided with two pulleys formed to face each other and independently rotatable, but the concept of the present disclosure is not limited thereto. That is, one or more pulleys having the same diameter or different diameters may be provided according to the configuration of the yaw manipulation part 202.

In detail, the rotation shaft 243, which is a manipulation part yaw main rotation shaft, is formed on one side of the actuation manipulation part 203 on the first handle 204. At this time, the first handle 204 is formed to be rotatable around the rotation shaft 243.

Here, the rotation shaft 243 may be formed to form a predetermined angle with the XY plane on which the connection part 400 is formed. For example, the rotation shaft 243 may be formed in a direction parallel to the Z-axis, and in this state, when the pitch manipulation part 201 is rotated, the coordinate system of the rotation shaft 243 may change relatively as described above. Of course, the concept of the present disclosure is not limited thereto, and the rotation shaft 243 may be formed in various directions so as to be suitable for a structure of the hand of the user gripping the manipulation part 200 according to an ergonomic design.

Meanwhile, the pulleys 211 and 212 and the pulleys 221 and 222 are coupled to the rotation shaft 243 so as to be rotatable around the rotation shaft 243. In addition, the wire 301 or the wire 305, which is a first jaw wire, is wound around the pulleys 211 and 212, and the wire 302 or the wire 306, which is a second jaw wire, may be wound around the pulleys 221 and 222. In this case, the pulleys 211 and 212 and the pulleys 221 and 222 may each be configured as two pulleys formed to face each other and independently rotatable. Accordingly, a wire being wound and a wire being released may be wound around respective separate pulleys so that the wires may perform motions without interference with each other.

The yaw frame 207 rigidly connects the first handle 204, the rotation shaft 241, the rotation shaft 242, and the rotation shaft 243, so that the first handle 204, the yaw manipulation part 202, and the actuation manipulation part 203 are integrally yaw-rotated around the rotation shaft 243.

The pitch manipulation part 201 may include the rotation shaft 246, the pulley 217 and the pulley 218, which are manipulation part first jaw pitch main pulleys, the pulleys 227 and 228, which are manipulation part second jaw pitch main pulleys, and the pitch frame 208. In addition, the pitch manipulation part 201 may further include the rotation shaft 245, the pulleys 215 and 216, which are manipulation part first jaw pitch sub-pulleys formed on one side of the pulley 217 and the pulley 218, and the pulleys 225 and 226, which are manipulation part second jaw pitch sub-pulleys formed on one side of the pulley 227 and the pulley 228. The pitch manipulation part 201 may be connected to the bent part 402 of the connection part 400 through the rotation shaft 246.

In detail, the pitch frame 208 is a base frame of the pitch manipulation part 201, and the rotation shaft 243 is rotatably coupled to one end portion thereof. That is, the yaw frame 207 is formed to be rotatable around the rotation shaft 243 with respect to the pitch frame 208.

As described above, since the yaw frame 207 connects the first handle 204, the rotation shaft 243, the rotation shaft 241, and the rotation shaft 242, and the yaw frame 207 is also axially coupled to the pitch frame 208, when the pitch frame 208 is pitch-rotated around the rotation shaft 246, the yaw frame 207 connected to the pitch frame 208, the first handle 204, the rotation shaft 241, the rotation shaft 242, and the rotation shaft 243 are pitch-rotated together. That is, when the pitch manipulation part 201 is rotated around the rotation shaft 246, the actuation manipulation part 203 and the yaw manipulation part 202 are rotated together with the pitch manipulation part 201. In other words, when a user pitch-rotates the first handle 204 around the rotation shaft 246, the actuation manipulation part 203, the yaw manipulation part 202, and the pitch manipulation part 201 are moved together.

The pulleys 217 and 218 and the pulleys 227 and 228 are coupled to the rotation shaft 246 so as to be rotatable around the rotation shaft 246 of the pitch frame 208.

Here, the pulley 217 and the pulley 218 may be formed to face each other so as to be independently rotatable. Accordingly, a wire being wound and a wire being released may be wound around respective separate pulleys so that the wires may perform motions without interference with each other. Similarly, the pulley 227 and the pulley 228 may also be formed to face each other so as to be independently rotatable. Accordingly, a wire being wound and a wire being released may be wound around respective separate pulleys so that the wires may perform motions without interference with each other.

Next, a motion of each of the wires 303 and 304, which are pitch wires, is described as follows.

The pulley 2131, which is an end tool pitch pulley, is fixedly coupled to the end tool hub 2106 in the end tool 2100, and the pulley 231 and the pulley 232, which are manipulation part pitch pulleys, are fixedly coupled to the pitch frame 208 in the manipulation part 200. In addition, these pulleys are connected to each other by the wires 303 and 304, which are pitch wires, so that a pitch motion of the end tool 2100 may be performed more easily according to the pitch manipulation of the manipulation part 200. Here, the wire 303 is fixedly coupled to the pitch frame 208 via the pulley 231 and the pulley 233, and the wire 304 is fixedly coupled to the pitch frame 208 via the pulley 232 and the pulley 234. That is, the pitch frame 208 and the pulleys 231 and 232 are rotated together around the rotation shaft 246 by the pitch rotation of the manipulation part 200, and as a result, the wires 303 and 304 are also moved, and thus, a driving force of additional pitch rotation may be transmitted separately from the pitch motion of the end tool by the wire 301, the wire 302, the wire 305, and the wire 306, which are jaw wires.

A connection relationship of each of the first handle 204, the pitch manipulation part 201, the yaw manipulation part 202, and the actuation manipulation part 203 is summarized as follows. The rotation shafts 241 and 242, the rotation shaft 243, the rotation shaft 244, the rotation shaft 245, and the rotation shaft 246 may be formed on the first handle 204. In this case, since the rotation shafts 241 and 242 are directly formed on the first handle 204, the first handle 204 and the actuation manipulation part 203 may be directly connected to each other. Meanwhile, since the rotation shaft 243 is directly formed on the first handle 204, the first handle 204 and the yaw manipulation part 202 may be directly connected to each other. On the other hand, since the pitch manipulation part 201 is formed on one side of the yaw manipulation part 202 so as to be connected to the yaw manipulation part 202, the pitch manipulation part 201 is not directly connected to the first handle 204, and the pitch manipulation part 201 and the first handle 204 may be formed to be indirectly connected to each other via the yaw manipulation part 202.

Continuing to refer to the drawings, in the surgical instrument 2000 according to the first embodiment of the present disclosure, the pitch manipulation part 201 and the end tool 2100 may be formed on the same or parallel axis (X-axis). That is, the rotation shaft 246 of the pitch manipulation part 201 is formed at one end portion of the bent part 402 of the connection part 400, and the end tool 2100 is formed at the other end portion of the connection part 400.

In addition, one or more relay pulleys 235 configured to change or guide paths of the wires may be disposed at some places along the connection part 400, particularly in the bent part 402. As at least some of the wires are wound around the relay pulleys 235 to guide the paths of the wires, these wires may be disposed along a bent shape of the bent part 402.

Here, in the drawings, it is illustrated that the connection part 400 is formed to be curved with a predetermined curvature by having the bent part 402, but the concept of the present disclosure is not limited thereto, and the connection part 400 may be formed linearly or to be bent one or more times as necessary, and even in this case, it may be said that the pitch manipulation part 201 and the end tool 2100 are formed on substantially the same axis or parallel axes. In addition, although FIG. 3 illustrates that each of the pitch manipulation part 201 and the end tool 2100 is formed on an axis parallel to the X-axis, the concept of the present disclosure is not limited thereto, and the pitch manipulation part 201 and the end tool 2100 may be formed on different axes.

The staple manipulation part 260 is connected to the first staple pulley 2181 of the end tool 2100 by the wires 307 and 308, which are first staple wires, and serves to alternately rotate the first staple pulley 2181 in the clockwise or counterclockwise direction. The staple manipulation part 260 is connected to the second staple pulley 2191 of the end tool 2100 by the wires 309 and 310, which are second staple wires, and serves to alternately rotate the second staple pulley 2191 in the counterclockwise or clockwise direction.

To this end, although not shown in the drawings, the staple manipulation part 260 may include a motor (not shown). That is, the motor (not shown) is driven while the user presses the staple manipulation part 260 formed in the form of a button to alternately rotate the manipulation part staple pulley (see 269 of FIG. 47) in the clockwise or counterclockwise direction. In addition, due thereto, the first staple pulley 2181 and the second staple pulley 2191 of the end tool 2100 may be alternately rotated in the clockwise or counterclockwise direction.

(Actuation, Yaw, and Pitch Motions)

Actuation, yaw, and pitch motions in the present embodiment will be described as follows.

First, the actuation motion will be described below.

In a state in which a user inserts his/her index finger in the hand ring formed on the first actuation extension part 252 and his/her thumb in the hand ring formed on the second actuation extension part 257, when the user rotates the actuation rotation parts 252 and 257 using one or both of his/her index finger and thumb, the pulley 210 and the first actuation gear 253 fixedly coupled to the first actuation extension part 252 are rotated around the rotation shaft 241, and the pulley 220 and the second actuation gear 258 fixedly coupled to the second actuation extension part 257 are rotated around the rotation shaft 242. At this time, the pulley 210 and the pulley 220 are rotated in opposite directions, and thus the wires 301 and 305 fixedly coupled to the pulley 210 at one end portion thereof and the wires 302 and 306 fixedly coupled to the pulley 220 at one end portion thereof are also moved in opposite directions. In addition, a rotating force is transmitted to the end tool 2100 through the power transmission part 300, and two jaws 2103 of the end tool 2100 perform an actuation motion.

Here, as described above, the actuation motion refers to a motion in which the two jaws 2101 and 2102 are splayed or closed while being rotated in opposite directions. That is, when the actuation rotation parts 252 and 257 of the actuation manipulation part 203 are rotated in directions close to each other, the first jaw 2101 is rotated in the counterclockwise direction, and the second jaw 2102 is rotated in the clockwise direction, thereby closing the end tool 2100. That is, when the actuation rotation parts 252 and 257 of the actuation manipulation part 203 are rotated in directions away from each other, the first jaw 121 is rotated in the counterclockwise direction, and the second jaw 122 is rotated in the clockwise direction, thereby opening the end tool 2100.

In the present embodiment, for the actuation manipulation described above, the first actuation extension part 252 and the second actuation extension part 257 are provided to configure the second handle and manipulated by gripping the second handle with two fingers. However, for the actuation manipulation in which the two jaws of the end tool 2100 are opened or closed, the actuation manipulation part 203 may be configured in a manner different from the above-described manner, such as configuring the two actuation pulleys (the pulley 210 and the pulley 220) to act in opposition to each other with an actuation rotation part.

Next, the yaw motion will be described below.

When a user rotates the first handle 204 around the rotation shaft 243 while holding the first handle 204, the actuation manipulation part 203 and the yaw manipulation part 202 are yaw-rotated around the rotation shaft 243. That is, when the pulley 210 of the first actuation manipulation part 251 to which the wires 301 and 305 are fixedly coupled is rotated around the rotation shaft 243, the wires 301 and 305 wound around the pulleys 211 and 212 are moved. Similarly, when the pulley 220 of the second actuation manipulation part 256, to which the wires 302 and 306 are fixedly coupled, is rotated around the rotation shaft 243, the wires 302 and 306 wound around the pulleys 221 and 222 are moved. At this time, the wires 301 and 305 connected to the first jaw 2101 and the wires 302 and 306 connected to the second jaw 2102 are wound around the pulleys 211 and 212 and the pulleys 221 and 222, so that the first jaw 2101 and the second jaw 2102 are rotated in the same direction during yaw rotation. In addition, a rotating force is transmitted to the end tool 2100 through the power transmission part 300, and thus a yaw motion in which two jaws 2103 of the end tool 2100 are rotated in the same direction is performed.

At this time, since the yaw frame 207 connects the first handle 204, the rotation shaft 241, the rotation shaft 242, and the rotation shaft 243, the first handle 204, the yaw manipulation part 202, and the actuation manipulation part 203 are rotated together around the rotation shaft 243.

Next, the pitch motion will be described below.

When a user rotates the first handle 204 around the rotation shaft 246 while holding the first handle 204, the actuation manipulation part 203, the yaw manipulation part 202, and the pitch manipulation part 201 are pitch-rotated around the rotation shaft 246. That is, when the pulley 210 of the first actuation manipulation part 251 to which the wires 301 and 305 are fixedly coupled is rotated around the rotation shaft 246, the wires 301 and 305 wound around the pulley 217 and the pulley 218 are moved. Similarly, when the pulley 220 of the second actuation manipulation part 256, to which the wires 302 and 306 are fixedly coupled, is rotated around the rotation shaft 246, the wires 302 and 306 wound around the pulley 227 and the pulley 228 are moved. At this time, as described with reference to FIG. 5, in order to allow the first jaw 2101 and the second jaw 2102 to pitch-rotate, the wires 301 and 305, which are first jaw wires, are moved in the same direction and respectively wound around the pulley 217 and the pulley 218, which are manipulation part pitch main pulleys, and the wires 302 and 306, which are second jaw wires, are moved in the same direction and respectively wound around the pulley 227 and the pulley 228, which are manipulation part pitch main pulleys. In addition, a rotating force is transmitted to the end tool 2100 through the power transmission part 300, and two jaws 103 of the end tool 2100 perform a pitch motion.

At this time, since the pitch frame 208 is connected to the yaw frame 207, and the yaw frame 207 connects the first handle 204, the rotation shaft 241, the rotation shaft 242, and the rotation shaft 243, when the pitch frame 208 is rotated around the rotation shaft 246, the yaw frame 207, the first handle 204, the rotation shaft 241, the rotation shaft 242, and the rotation shaft 243 connected to the pitch frame 208 are rotated together. That is, when the pitch manipulation part 201 is rotated around the rotation shaft 246, the actuation manipulation part 203 and the yaw manipulation part 202 are rotated together with the pitch manipulation part 201.

In summary, in the surgical instrument 2000 according to an embodiment of the present disclosure, the pulleys are formed on respective joint points (an actuation joint, a yaw joint, and a pitch joint), the wires (the first jaw wire or the second jaw wire) are wound around the pulleys, the rotational manipulations (actuation rotation, yaw rotation, and pitch rotation) of the manipulation part cause the movement of each wire, which in turn induces the desired motion of the end tool 2100. Furthermore, the auxiliary pulley may be formed on one side of each of the pulleys, and the wire may not be wound several times around one pulley due to the auxiliary pulley.

FIG. 49 is a view schematically illustrating only a configuration of pulleys and wires constituting joints of the surgical instrument 2000 according to an embodiment of the present disclosure illustrated in FIG. 2. In FIG. 49, the relay pulleys for changing paths of the wires and not related to the operation of joints are omitted.

Referring to FIG. 49, the manipulation part 200 may include the pulley 210, the pulley 211, the pulley 212, the pulley 213, the pulley 214, the pulley 215, the pulley 216, the pulley 217, and the pulley 218 that are related to a rotational motion of the first jaw 2101.

In addition, the manipulation part 200 may include the pulley 220, the pulley 221, the pulley 222, the pulley 223, the pulley 224, the pulley 225, the pulley 226, the pulley 227, and the pulley 228 that are related to a rotational motion of the second jaw 2102 (the arrangement and structure of each of the pulleys of the manipulation part 200 are the same in principle as the arrangement and structure of each of the pulleys of the end tool 2100, and thus specific designations of some reference numerals are omitted in the drawings).

The pulleys 211 and 212 and the pulleys 221 and 222 may be formed to be rotatable independently of each other around the same shaft, that is the rotation shaft 243. In this case, the pulleys 211 and 212 and the pulleys 221 and 222 may each be formed as two pulleys formed to face each other and formed to be independently rotatable.

The pulleys 213 and 214 and the pulleys 223 and 224 may be formed to be rotatable independently of each other around the same shaft, that is the rotation shaft 244. Here, the pulleys 213 and 214 may be formed as two pulleys formed to face each other and formed to be independently rotatable, and in this case, the two pulleys may be formed to have different diameters. Similarly, the pulleys 223 and 224 may be formed as two pulleys formed to face each other and formed to be independently rotatable, and in this case, the two pulleys may be formed to have different diameters.

The pulleys 215 and 216 and the pulleys 225 and 226 may be formed to be rotatable independently of each other around the same shaft, that is the rotation shaft 245. In this case, the pulleys 215 and 216 may be formed to have different diameters. In addition, the pulleys 225 and 226 may be formed to have different diameters.

The pulleys 217 and 218 and the pulleys 227 and 228 may be formed to be rotatable independently of each other around the same shaft, that is the rotation shaft 246.

The wire 301 is wound around the pulley 210 after sequentially passing through the pulley 217, the pulley 215, the pulley 213, and the pulley 211 of the manipulation part 200, and then is coupled to the pulley 210 by the coupling member 324. Meanwhile, the wire 305 sequentially passes through the pulley 218, the pulley 216, the pulley 214, and the pulley 212 of the manipulation part 200 and is coupled to the pulley 210 by the coupling member 324. Thus, when the pulley 210 is rotated, the wires 301 and 305 are wound around or released from the pulley 210, and accordingly, the first jaw 2101 is rotated.

The wire 306 is wound around the pulley 220 after sequentially passing through the pulley 227, the pulley 225, the pulley 223, and the pulley 221 of the manipulation part 200, and then is coupled to the pulley 220 by the coupling member 327. Meanwhile, the wire 302 sequentially passes through the pulley 228, the pulley 226, the pulley 224, and the pulley 222 of the manipulation part 200 and is coupled to the pulley 220 by the coupling member 327. Thus, when the pulley 220 is rotated, the wire 302 and the wire 306 are wound around or released from the pulley 220, and accordingly, the second jaw 2102 is rotated.

(Conceptual Diagram of Pulleys and Wires)

FIGS. 51 and 52 are diagrams illustrating a configuration of pulleys and wires, which are related to an actuation motion and a yaw motion of the surgical instrument 2000 according to an embodiment of the present disclosure illustrated in FIG. 2, in detail for each of the first jaw and the second jaw. FIG. 51 is a diagram illustrating only pulleys and wires related to the second jaw, and FIG. 52 is a diagram illustrating only pulleys and wires related to the first jaw. In addition, FIG. 50 is a perspective view illustrating a yaw motion of the surgical instrument of FIG. 2. Here, in FIG. 50, components related to stapling and cutting motions are omitted.

First, a wire motion of the actuation motion will be described.

Referring to FIG. 52, when the first actuation extension part 252 is rotated around the rotation shaft 241 in the direction of an arrow OPA 1, the pulley 210 connected to the first actuation extension part 252 is rotated, and the wire 301 and the wire 305 wound around the pulley 210 are moved in directions W1a and W1b, respectively, and as a result, the first jaw 2101 of the end tool 2100 is rotated in the direction of an arrow EPA1.

Referring to FIG. 51, when the second actuation extension part 257 is rotated around the rotation shaft 242 in the direction of an arrow OPA 2, the pulley 220 connected to the second actuation extension part 257 is rotated, and thus both strands of the wires 302 and 306 wound around the pulley 220 are moved in directions W2a and W2b, respectively, and as a result, the second jaw 2102 of the end tool 2100 is rotated in the direction of an arrow EPA2. Accordingly, when a user manipulates the first actuation extension part 252 and the second actuation extension part 257 in directions close to each other, a motion of the first jaw 2101 and the second jaw 2102 of the end tool being close to each other is performed.

Next, a wire motion of the yaw motion will be described.

First, since the rotation shaft 243 is connected to the rotation shafts 241 and 242 by the yaw frame (see 207 of FIG. 30), the rotation shaft 243 and the rotation shafts 241 and 242 are integrally rotated together.

Referring to FIG. 52, when the first handle 204 is rotated around the rotation shaft 243 in the direction of an arrow OPY1, the pulley 210 and the pulleys 211 and 212 and the wires 301 and 305 wound therearound are rotated as a whole around the rotation shaft 243, and as a result, the wires 301 and 305 wound around the pulleys 211 and 212 are moved in the directions W1a and W1b, respectively, which in turn causes the first jaw 2101 of the end tool 2100 to rotate in the direction of an arrow EPY1.

Referring to FIG. 51, when the first handle 204 is rotated around the rotation shaft 243 in the direction of an arrow OPY2, the pulley 220 and the pulleys 221 and 222 and the wires 302 and 306 wound therearound are rotated as a whole around the rotation shaft 243, and as a result, the wires 302 and 306 wound around the pulleys 221 and 222 are respectively moved in a direction opposite to a direction W1a and a direction opposite to a direction W1b, which in turn causes the first jaw 2101 of the end tool 2100 to rotate in the direction of an arrow EPY2.

FIGS. 53 to 55B are diagrams illustrating a configuration of pulleys and wires, which are related to stapling and cutting motions of the surgical instrument 2000 according to an embodiment of the present disclosure illustrated in FIG. 2, in detail for each of the first jaw and the second jaw. Here, FIGS. 47 to 49 are drawings mainly illustrating pulleys and wires related to the second jaw.

Figure 53:
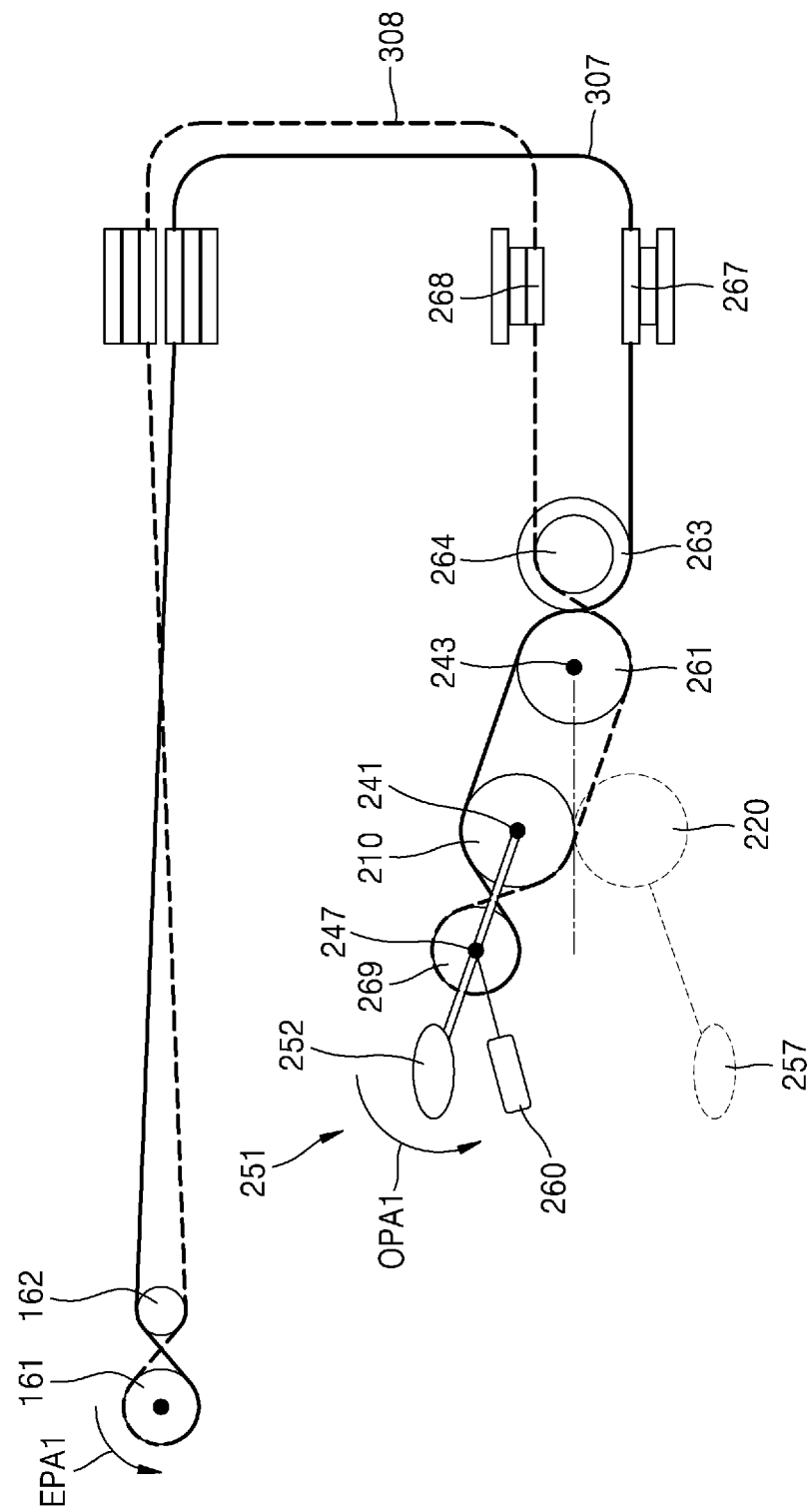
Figure 54:
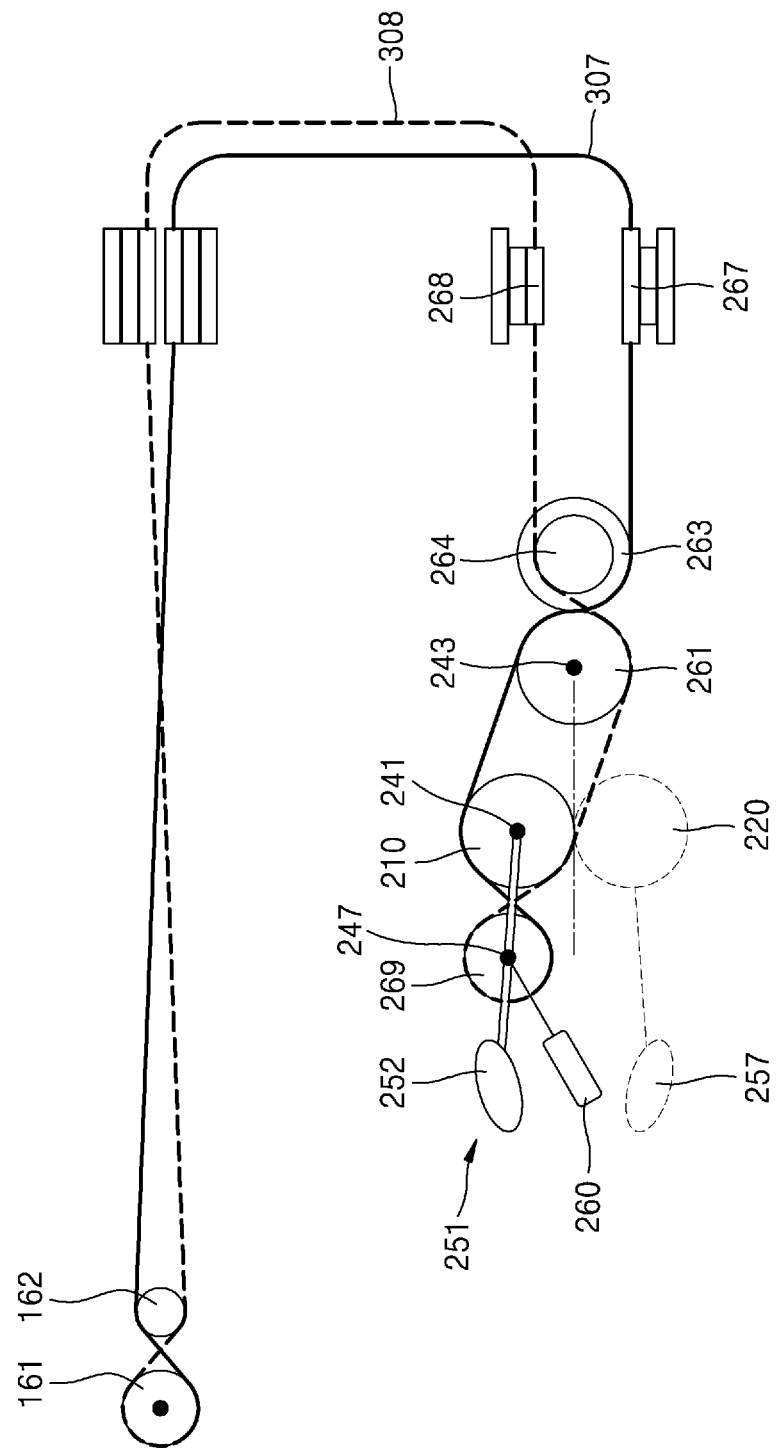

Here, FIGS. 53 and 54 illustrate the process of actuation motion of closing two jaws, and FIGS. 54 and 55 illustrate the process of motion of stapling and cutting of tissue interposed between two jaws.

First, a wire motion of the actuation motion will be described.

Referring to FIGS. 53 and 54, when the first actuation extension part 252 of the first actuation manipulation part 251 is rotated in the direction of an arrow OPA 1 around the rotation shaft 241, the pulley 210 connected to the first actuation extension part 252 is rotated, and each of the wire (see 301 of FIG. 49) and the wire (see 305 of FIG. 49) wound around the pulley 210 is moved, which in turn causes the first jaw 2101 of the end tool 2100 to rotate in the direction of an arrow EPA1.

At this time, the manipulation part staple pulley 269 of the staple manipulation part 260 is formed to be rotatable around the rotation shaft 241 together with the first actuation manipulation part 251. Thus, when the first actuation extension part 252 is rotated around the rotation shaft 241, the staple manipulation part 260 is also rotated around the rotation shaft 241 together with the first actuation manipulation part 251.

As a result, in the actuation motion, when the pulley 2111 is rotated in the end tool 2100, the first staple pulley 2181 is also rotated together with the pulley 2111.

Next, a wire operation of the stapling and cutting motions will be described.

Figure 55A:
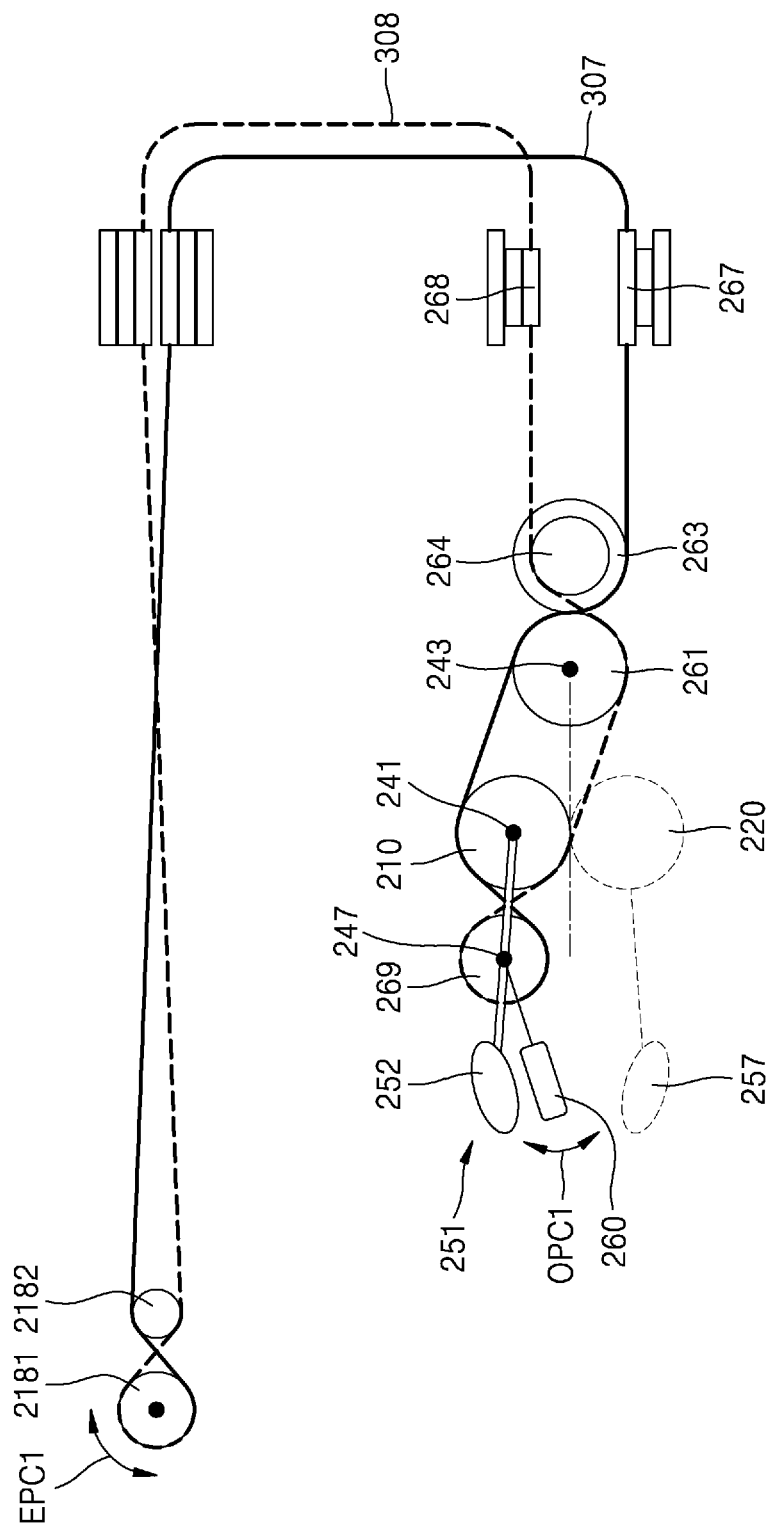

Referring to FIG. 55A, when the staple manipulation portion 260 is rotated in the direction of an arrow OPC1 around a rotation shaft 247, which is a manipulation portion cutting rotation shaft, the manipulation portion staple pulley 269, and the wire 307 and the wire 308, which are staple wires wound around the manipulation portion staple pulley 269, rotate around the rotation shaft 247, and as a result, each of the wire 307 and the wire 308 wound around the manipulation portion staple pulley 269 moves, which in turn causes the first staple pulley 2181 of the end tool 2100 to rotate in the direction of an arrow EPC1.

Figure 55B:
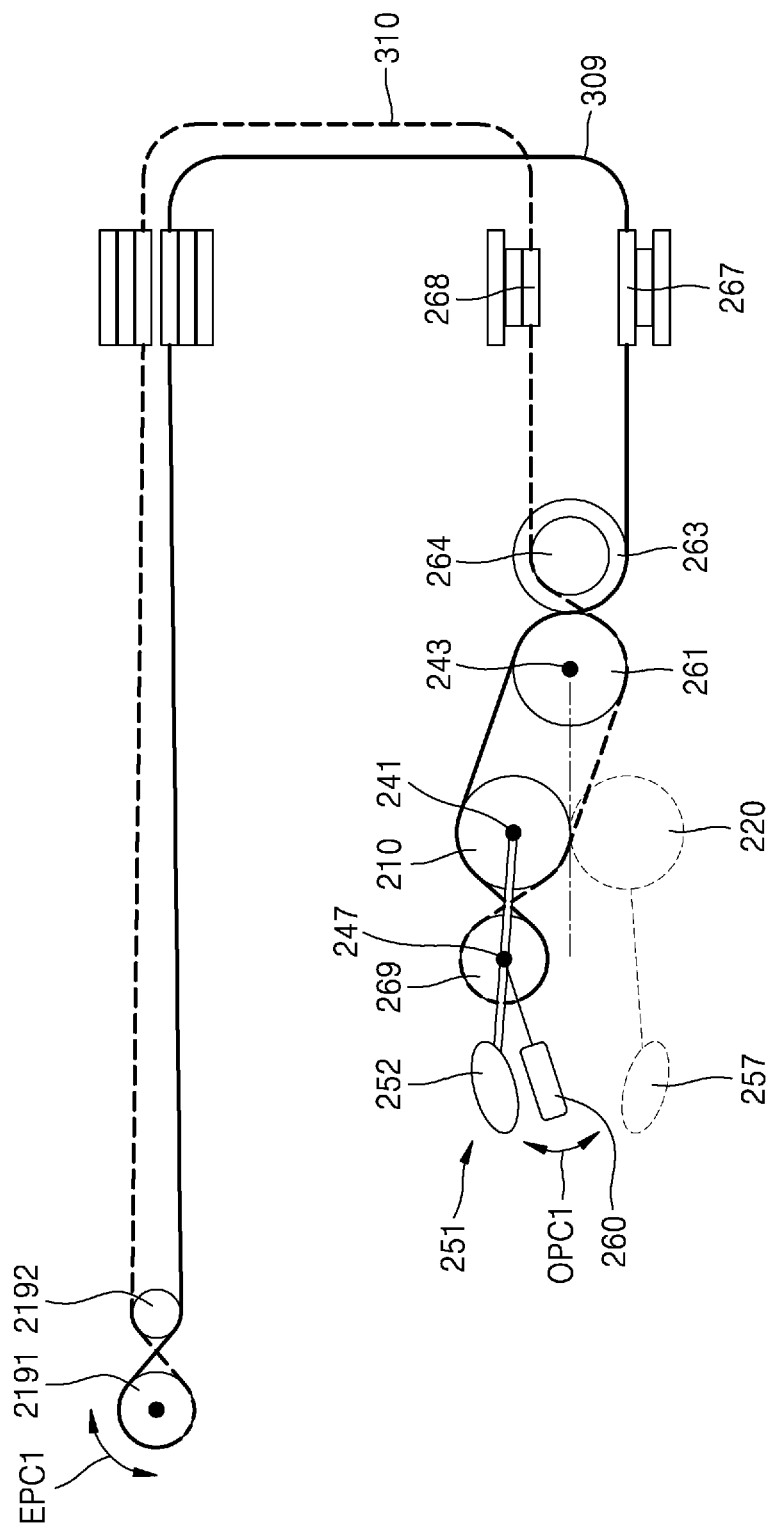

Referring to FIG. 55B, when the staple manipulation portion 260 is rotated in the direction of an arrow OPC1 around the rotation shaft 247, which is a manipulation portion cutting rotation shaft, the manipulation portion staple pulley 269, and the wire 309 and the wire 310, which are staple wires wound around the manipulation portion staple pulley 269, rotate around the rotation shaft 247, and as a result, each of the wire 309 and the wire 310 wound around the manipulation portion staple pulley 269 moves, which in turn causes the second staple pulley 2191 of the end tool 2100 to rotate in the direction of an arrow EPC1.

Meanwhile, when the staple manipulation portion 260 rotates, the manipulation portion staple pulley 269 rotates around the rotation shaft 247, and at this time, the rotation of the staple manipulation portion 260 does not affect the first actuation manipulation portion 251.

As a result, when the manipulation portion staple pulley 269 rotates, the first staple pulley 2181 and the second staple pulley 2191 of the end tool 2100 rotate independently of the first jaw 2101. In addition, when the first staple pulley 2181 and the second staple pulley 2191 rotate alternately in the clockwise/counterclockwise directions, the staple link assembly 2170 connected to the first staple pulley 2181 and the second staple pulley 2191, and the reciprocating assembly 550 of the cartridge 500 connected thereto perform a reciprocating linear motion, and accordingly, as the operation member 540 of the cartridge 500 moves toward the distal end 502, stapling and cutting motions are performed.

Here, as described above, the first staple pulley 2181 and the second staple pulley 2191 may rotate in opposite directions. For example, when the staple manipulation portion 260 rotates in any one direction, the first staple pulley 2181 rotates in the clockwise direction and the second staple pulley 2191 rotates in the counterclockwise direction, such that the staple link assembly 2170 may move toward the distal end 2104 of the end tool 2100. On the contrary, when the staple manipulation portion 260 rotates in the opposite direction, the first staple pulley 2181 rotates in the counterclockwise direction and the second staple pulley 2191 rotates in the clockwise direction, such that the staple link assembly 2170 may move toward the proximal end 2105 of the end tool 2100.

Here, although the drawings illustrate that the staple manipulation portion 260 is formed in a bar shape and a user manually rotates the staple manipulation portion 260, but the technical concepts of the present disclosure is not limited thereto. That is, as described above, the staple manipulation portion 260 may include a motor (not shown), and while the user presses the staple manipulation portion 260 formed in a button shape, the motor (not shown) may be driven to alternately rotate the manipulation portion staple pulley 269 in the clockwise or counterclockwise direction. In addition, accordingly, the first staple pulley 2181 of the end tool 2100 may alternately rotate in the clockwise or counterclockwise direction.

FIGS. 57 to 59 are diagrams illustrating a configuration of pulleys and wires, which are related to a pitch motion of the surgical instrument 2000 according to an embodiment of the present disclosure illustrated in FIG. 2, in detail for each of the first jaw and the second jaw. FIG. 57 is a diagram illustrating only pulleys and wires related to the second jaw, and FIG. 58 is a diagram illustrating only pulleys and wires related to the first jaw. FIG. 59 is a diagram illustrating only pulleys and wires related to the staple pulley. As shown in FIG. 9 and elsewhere herein, there are two pulleys related to the pitch motion, and both strands of each wire are wound in the same path, which is illustrated with one line in FIGS. 57 and 59. In addition, FIG. 56 is a perspective view illustrating a pitch motion of the surgical instrument of FIG. 2. Here, in FIG. 56, components related to stapling and cutting motions are omitted.

Referring to FIG. 57, when the first handle 204 is rotated around the rotation shaft 246 in the direction of an arrow OPP1, the pulley 210, the pulley 215, the pulley 217, and the like, and the wire 301 and the like wound therearound are rotated as a whole around the rotation shaft 246. At this time, since the wires 301 and 305, which are first jaw wires, are wound around upper portions of the pulley 217 and the pulley 218 as shown in FIG. 57, the wires 301 and 305 are moved in the direction of an arrow W1. As a result, as described with reference to FIG. 5, the first jaw 2101 of the end tool 2100 is rotated in the direction of an arrow EPP1.

Referring to FIG. 58, when the first handle 204 is rotated around the rotation shaft 246 in the direction of an arrow OPP2, the pulley 220, the pulley 225, the pulley 227, and the like, and the wire 302 and the like wound therearound are rotated as a whole around the rotation shaft 246. At this time, since the wires 302 and 306, which are second jaw wires, are wound around lower portions of the pulley 227 and the pulley 228 as shown in FIG. 58, the wires 302 and 306 are moved in the direction of an arrow W2. As a result, as described with reference to FIG. 5, the second jaw 2102 of the end tool 2100 is rotated in the direction of an arrow EPP2.

Referring to FIG. 59, when the first handle 204 is rotated around the rotation shaft 246 in the direction of an arrow OPC1, the manipulation part staple pulley 269, a pulley 265, a pulley 267, and the like, and the wires 307 and 308 and the like wound therearound are rotated as a whole around the rotation shaft 246. At this time, since the wires 307 and 308, which are first staple wires, are wound around lower portions of the pulley 267 and a pulley 268, the wires 307 and 308 are moved in the direction of an arrow W3. As a result, as described with reference to FIG. 5, the first staple pulley 2181 of the end tool 2100 is rotated in the direction of an arrow EPC1.

As a result, in the pitch motion, when the pulley 2111 is rotated around the rotation shaft 2143 in the end tool 2100, the first staple pulley 2181 is also rotated around the rotation shaft 2143 together with the pulley 2111.

Thus, the actuation, yaw, and pitch manipulations are manipulatable independent of each other.

Figure 1:
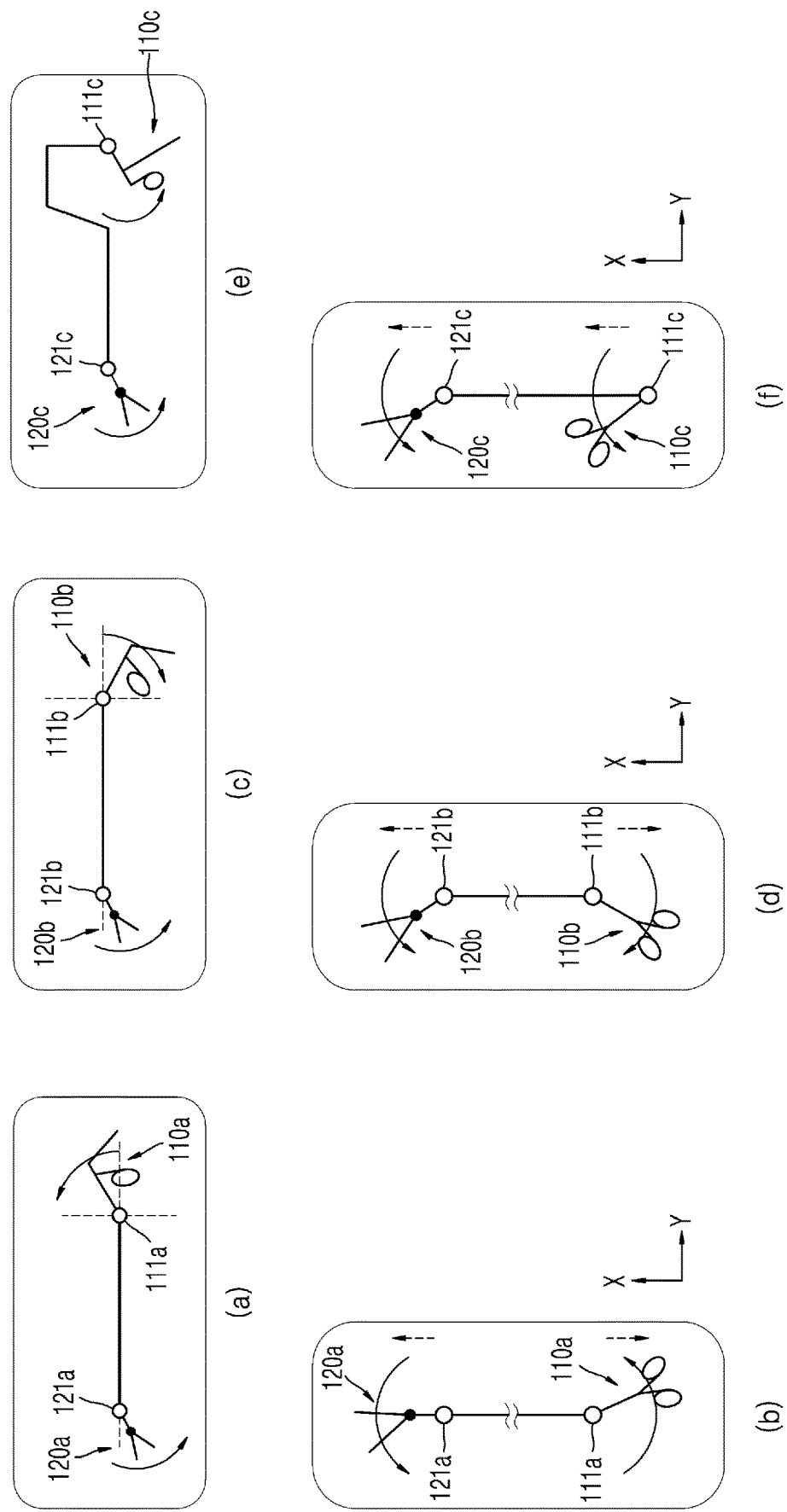

As described with reference to FIG. 1, the actuation manipulation part 203, the yaw manipulation part 202, and the pitch manipulation part 201 are configured such that the respective rotation shafts are located at the rear thereof to be identical to the joint configuration of the end tool, so that a user may intuitively perform matching manipulations.

In particular, in the surgical instrument 2000 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation part cause the movement of each wire, which in turn induces the desired motion of the end tool 2100. Furthermore, the auxiliary pulleys may be formed on one side of the respective pulleys, and these auxiliary pulleys may prevent the wire from being wound on one pulley multiple times, so that the wires wound on the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation part 202 and the actuation manipulation part 203 are directly formed on the first handle 204. Thus, when the first handle 204 is rotated around the rotation shaft 246, the yaw manipulation part 202 and the actuation manipulation part 203 are also rotated together with the first handle 204. Accordingly, the coordinate systems of the yaw manipulation part 202 and the actuation manipulation part 203 are not fixed, but are continuously changed relative to the rotation of the first handle 204. That is, in FIG. 2 or the like, the yaw manipulation part 202 and the actuation manipulation part 203 are illustrated as being parallel to the z-axis. However, when the first handle 204 is rotated, the yaw manipulation part 202 and the actuation manipulation part 203 are not parallel to the Z-axis any longer. That is, the coordinate systems of the yaw manipulation part 202 and the actuation manipulation part 203 are changed according to the rotation of the first handle 204. However, in the present specification, for convenience of description, unless described otherwise, the coordinate systems of the yaw manipulation part 202 and the actuation manipulation part 203 are described on the basis of a state in which the first handle 204 is located perpendicular to the connection part 400 as illustrated in FIG. 2.

(Correlation Between Stapling and Cutting Motions and Other Motions)

Hereinafter, a correlation between stapling and cutting motions and other motions (pitch, yaw, and actuation motions) will be described.

First, when the end tool 2100 performs a pitch motion, the first staple pulley 2181 and the second staple pulley 2191 also perform a pitch motion. That is, when the pulley 2111 and the pulley 2121 perform a pitch motion of rotating in the same direction around the rotation shaft 2143, the first staple pulley 2181 and the second staple pulley 2191 need to rotate in the same direction together with the pulley 2111 and the pulley 2121. If the first staple pulley 2181 and the second staple pulley 2191 do not rotate together when the pulley 2111 and the pulley 2121 rotate around the rotation shaft 2143, there is a risk that the cartridge 500 connected to the first staple pulley 2181 and the second staple pulley 2191 moves relative to the first jaw 2101 and is separated from the first jaw 2101. In addition, rotation of the first staple pulley 2181 and the second staple pulley 2191 that is not synchronized with the pulley 2111 may cause the reciprocating member 551 to unintentionally move forward, which in turn may cause an unintended stapling motion.

Next, when the end tool 2100 performs a yaw motion, the first staple pulley 2181 and the second staple pulley 2191 also perform a yaw motion. That is, when the pulley 2111 and the pulley 2121 perform a yaw motion of rotating in the same direction around the rotation shaft 2141, the first staple pulley 2181 and the second staple pulley 2191 need to rotate in the same direction together with the pulley 2111 and the pulley 2121. If the first staple pulley 2181 and the second staple pulley 2191 do not rotate together when the pulley 2111 and the pulley 2121 rotate around the rotation shaft 2141, there is a risk that the cartridge 500 connected to the first staple pulley 2181 and the second staple pulley 2191 moves relative to the first jaw 2101 and is separated from the first jaw 2101. In addition, rotation of the first staple pulley 2181 and the second staple pulley 2191 that is not synchronized with the pulley 2111 may cause the reciprocating member 551 to unintentionally move forward, which in turn may cause an unintended stapling motion.

Next, when the end tool 2100 performs an actuation motion, the first staple pulley 2181 and the second staple pulley 2191 rotate together with the pulley 2111. That is, when the pulley 2111 and the pulley 2121 perform an actuation motion of rotating in opposite directions around the rotation shaft 2141, the first staple pulley 2181 and the second staple pulley 2191 need to rotate together with the pulley 2111. If the first staple pulley 2181 and the second staple pulley 2191 do not rotate together with the pulley 2111 when the pulley 2111 rotates around the rotation shaft 2143, there is a risk that the cartridge 500 connected to the first staple pulley 2181 and the second staple pulley 2191 moves relative to the first jaw 2101 and is separated from the first jaw 2101. In addition, rotation of the first staple pulley 2181 and the second staple pulley 2191 that is not synchronized with the pulley 2111 may cause the reciprocating member 551 to unintentionally move forward, which in turn may cause an unintended stapling motion.

Meanwhile, when the end tool 2100 performs stapling and cutting motions, the pulley 2111 and the pulley 2121 do not rotate. That is, when the first staple pulley 2181 and the second staple pulley 2191 rotate around the rotation shaft 2141, and the link member 2171 and the reciprocating member 551 of the cartridge 500 connected thereto perform a linear reciprocating motion, the pulley 2111 and the pulley 2121 need not to rotate. Otherwise, the first jaw 2101 or the second jaw 2102 rotate during the stapling and cutting motions, and thus, the stapling and cutting motions will not be performed normally.

As a result, when the pulley 2111, which is a first jaw pulley, rotates, the first staple pulley 2181 and the second staple pulley 2191 accommodated in the first jaw 2101 need to rotate together with the pulley 2111. On the contrary, when the first staple pulley 2181 and the second staple pulley 2191 rotate for stapling and cutting, the pulley 2111 and the pulley 2121 need to maintain their positions without rotating. As such, the correlation between the stapling and cutting motions and other motions (the yaw and actuation motions) are discussed above.

In other words, it may be said that the pulley 2111 and the pulley 2121 are independent of the rotation of the first staple pulley 2181 and the second staple pulley 2191. That is, even when the first staple pulley 2181 and the second staple pulley 2191 rotate by staple wires, the pulley 2111 and the pulley 2121 may not rotate. On the contrary, it may be said that the first staple pulley 2181 and the second staple pulley 2191 are dependent on rotation of the pulley 2111. That is, when the pulley 2111 rotates by a jaw wire, the first staple pulley 2181 and the second staple pulley 2191 may also rotate together with the pulley 2111.

Figure 60:
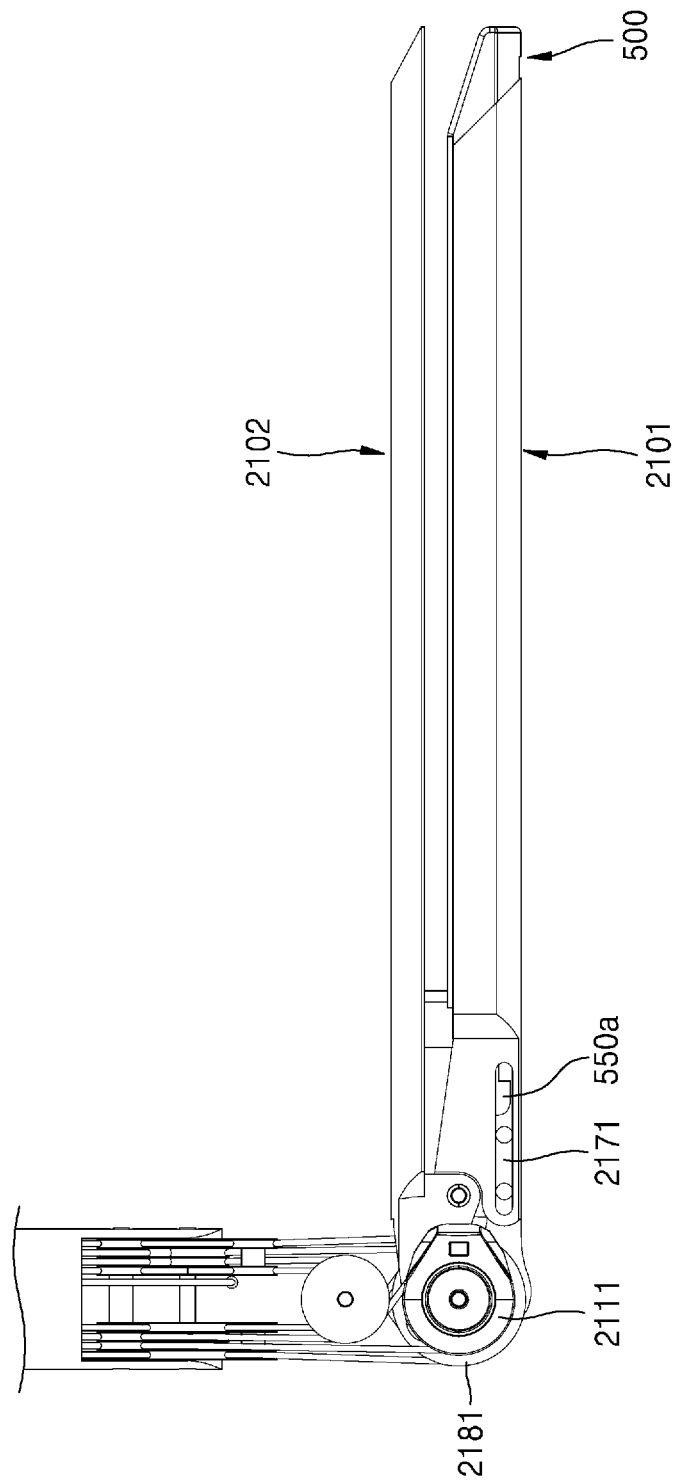
Figure 61:
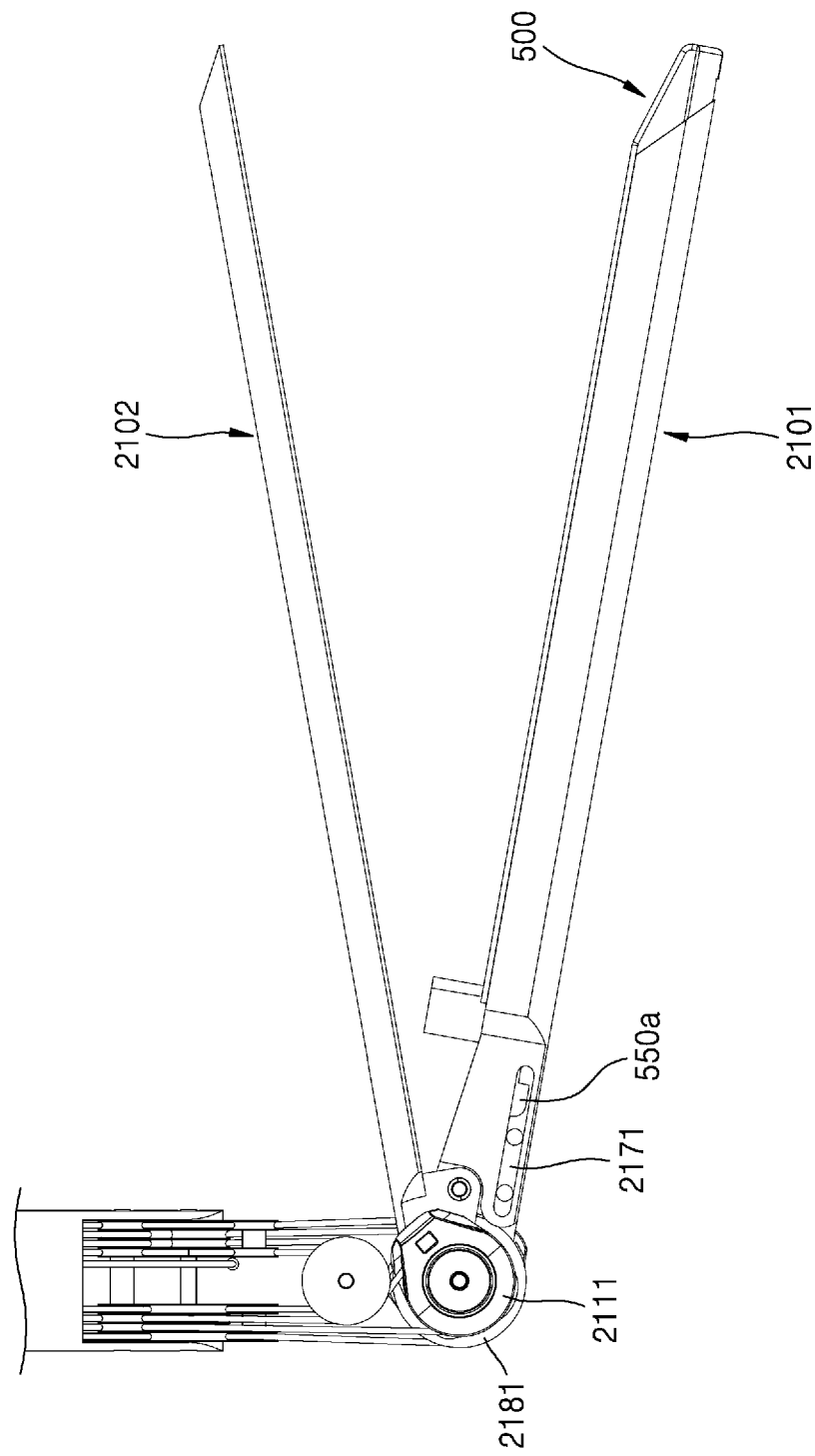
Figure 62:
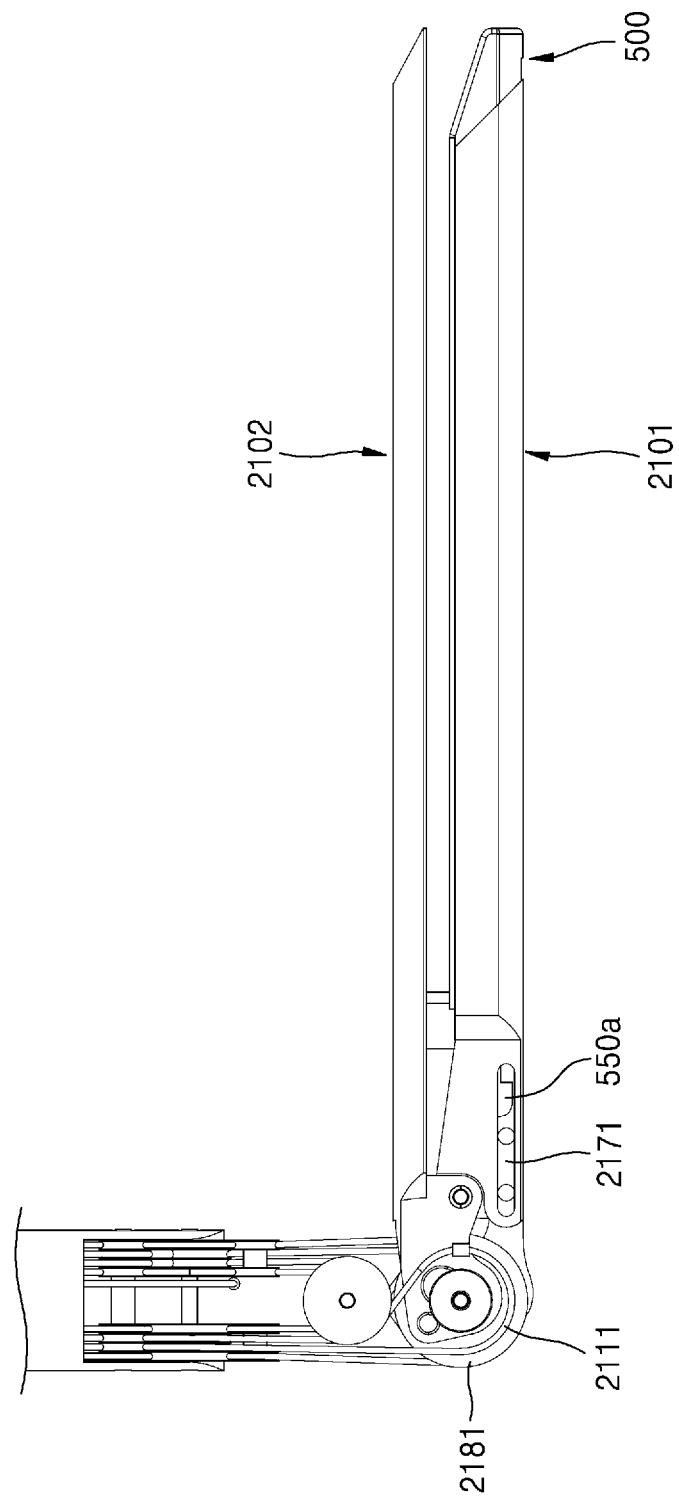
Figure 63:
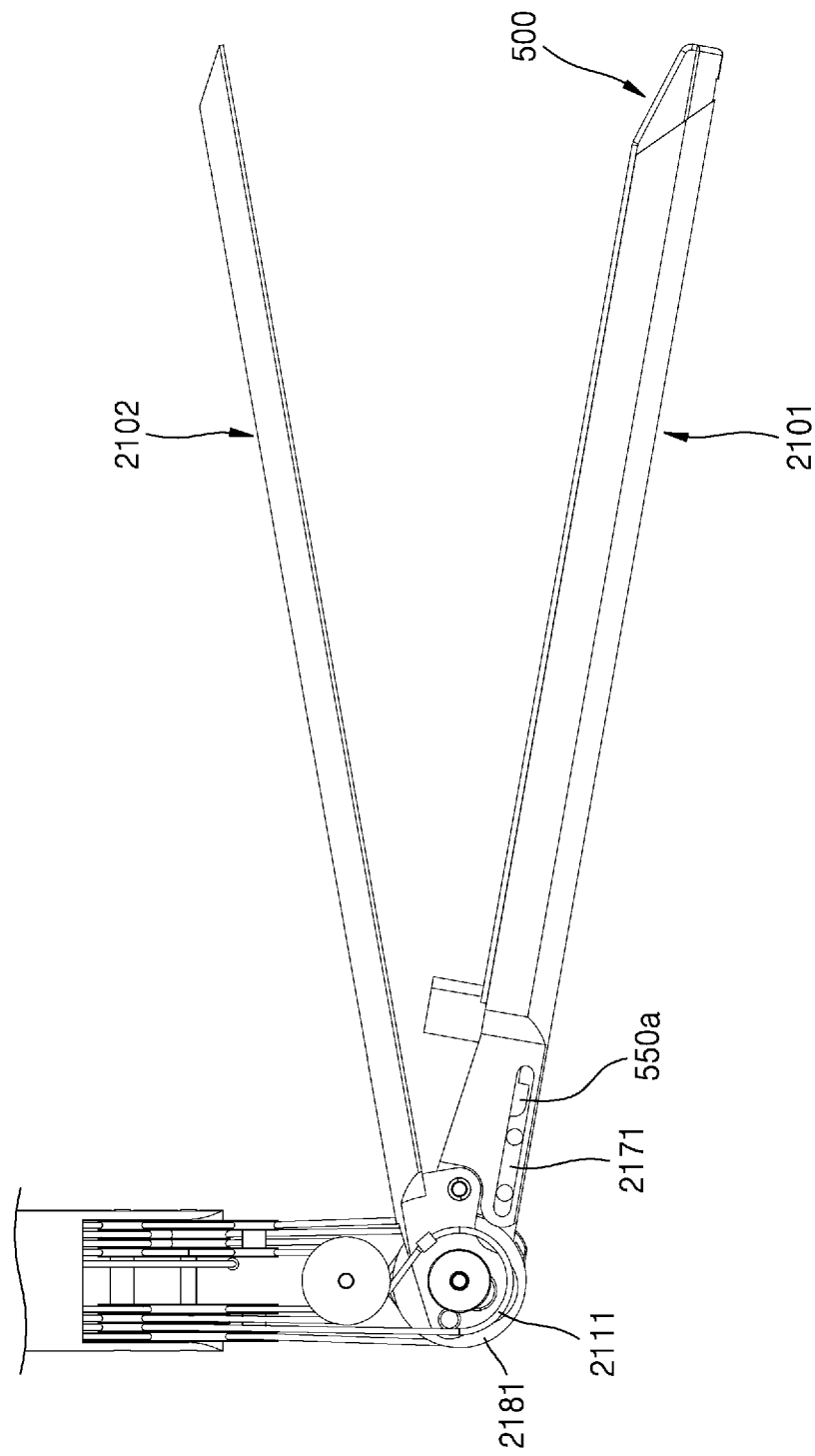

FIGS. 60 and 62 are diagrams illustrating a state in which jaws are yaw-rotated by −90°, and FIGS. 61 and 63 are diagrams illustrating a process of performing an actuation motion in a state in which jaws are yaw-rotated by −90°. Here, FIGS. 60 and 61 are diagrams in which the pulley 2111 is illustrated, and FIGS. 62 and 63 are diagrams in which the pulley 2111 is omitted.

Figure 64:
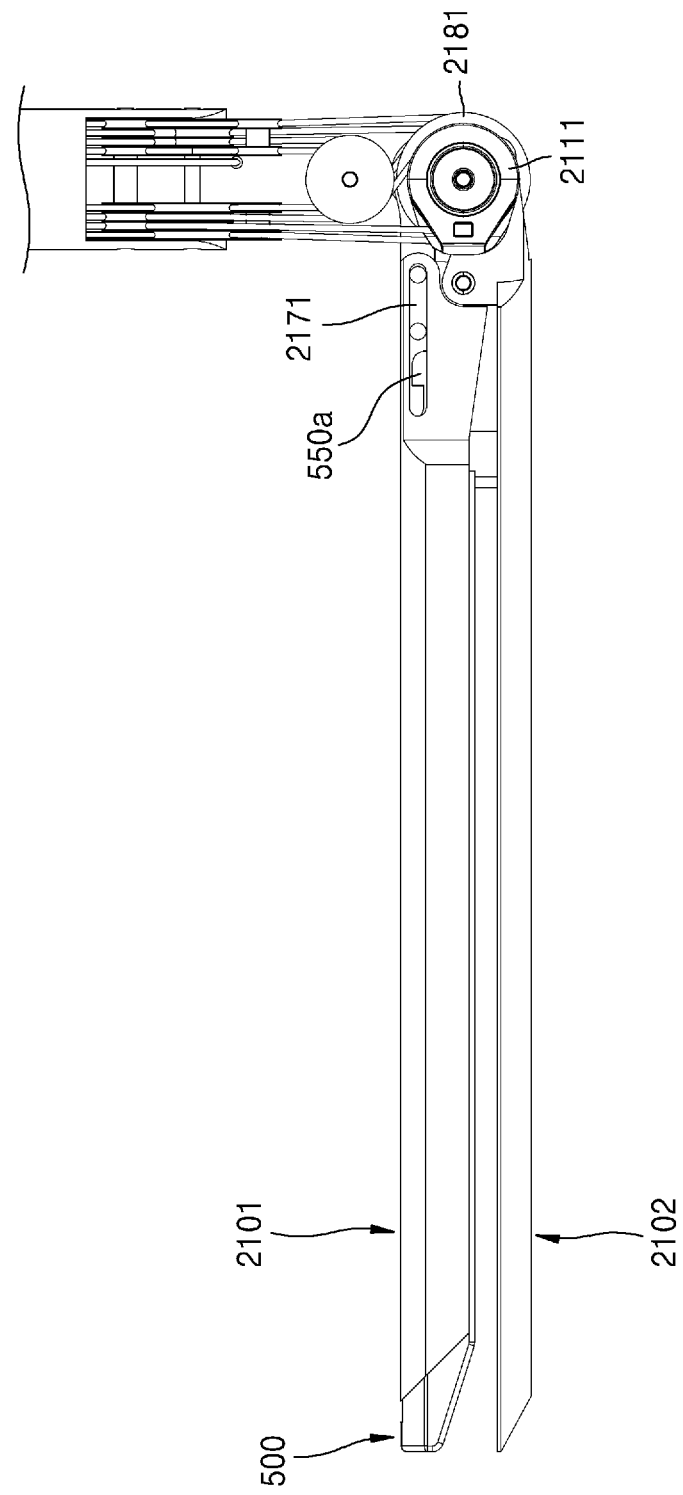
Figure 65:
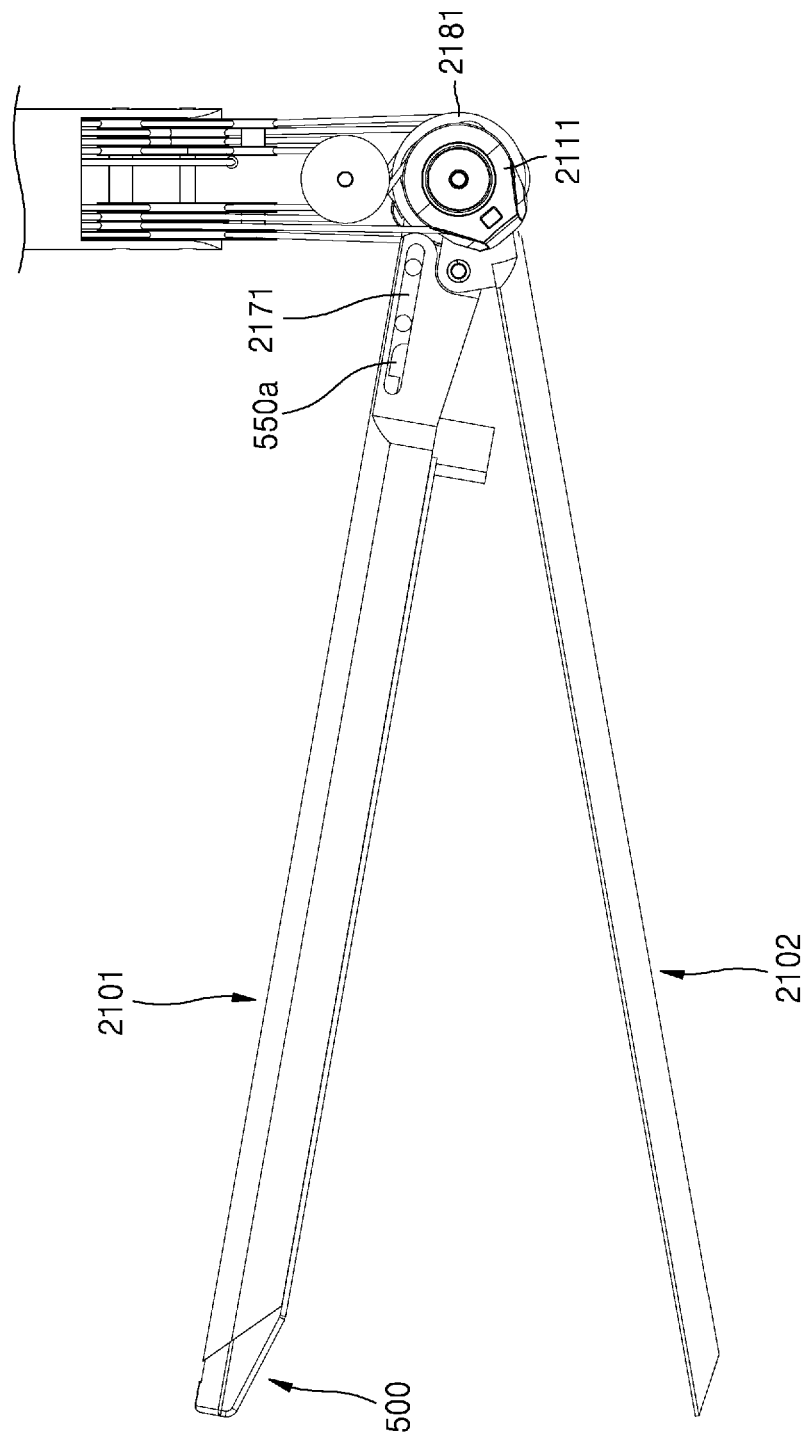
Figure 66:
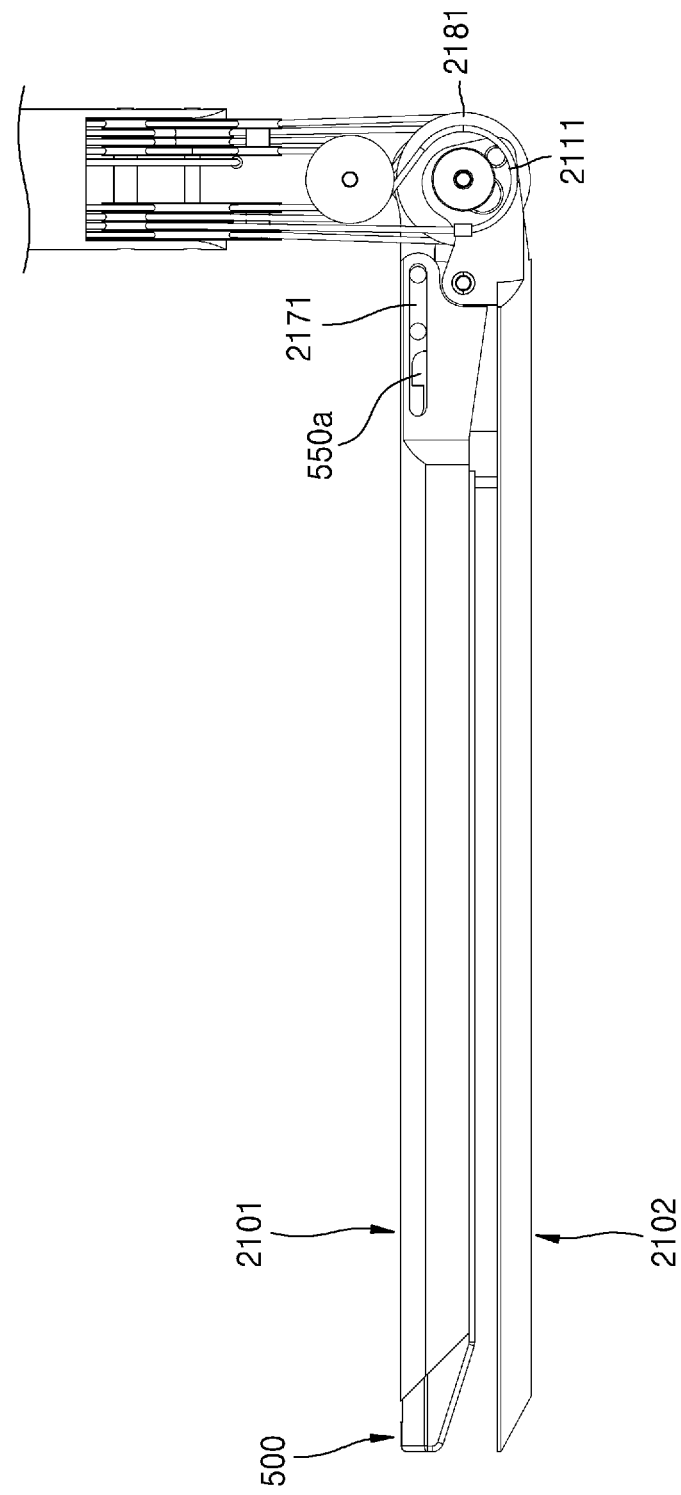
Figure 67:
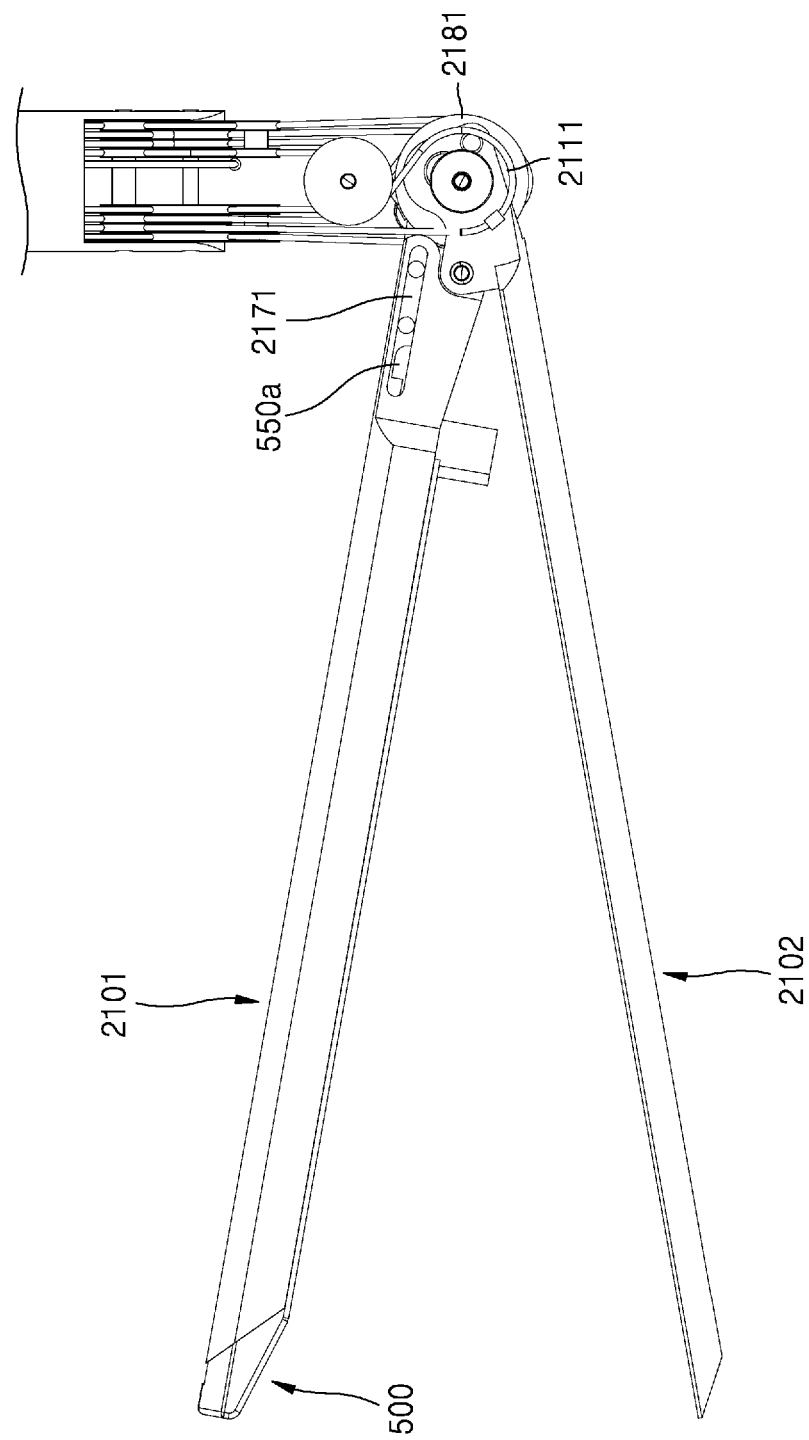

FIGS. 64 and 66 are diagrams illustrating a state in which jaws are yaw-rotated by −90°, and FIGS. 65 and 67 are diagrams illustrating a process of performing an actuation motion in a state in which jaws are yaw-rotated by −90°. Here, FIGS. 64 and 65 are diagrams in which the pulley 2111 is illustrated, and FIGS. 66 and 67 are diagrams in which the pulley 2111 is omitted.

As illustrated in FIGS. 60 to 67, the end tool of the surgical instrument according to the first embodiment of the present disclosure is formed to be able to normally perform an actuation motion even when the jaws are yaw-rotated by +90° or −90°.

FIGS. 68 and 69 are plan views illustrating stapling and cutting motions of the end tool of the surgical instrument of FIG. 2, and illustrating a process of performing the stapling and cutting motions in a state in which jaws are yaw-rotated by +90°. As illustrated in FIG. 68, the end tool of the surgical instrument according to the first embodiment of the present disclosure is formed to be able to normally perform the stapling and cutting motions even when the jaws are yaw-rotated by +90°.

In detail, in a state in which the pulley 2111, the pulley 2121, and the first staple pulley 2181 rotate by +90° around the rotation shaft 2141, when the first staple pulley 2181 rotates alternately in the clockwise/counterclockwise directions, the link member 2171 and the reciprocating member 551 connected thereto repeatedly move forward and backward. In addition, when the reciprocating member 551 moves forward, the operation member 540 moves forward together with the reciprocating member 551, and when the reciprocating member 551 moves backward, only the reciprocating member 551 moves backward and the operation member 540 remains stationary in place. By repeating this process, the stapling and cutting motions are performed as the operation member 540 moves toward the distal end 502.

FIGS. 70 and 71 are plan views illustrating stapling and cutting motions of the end tool of the surgical instrument of FIG. 2, and illustrating a process of performing the stapling and cutting motions in a state in which jaws are yaw-rotated by −90°. As illustrated in FIG. 70, the end tool of the surgical instrument according to the first embodiment of the present disclosure is formed to be able to normally perform the stapling and cutting motions even when the jaws are yaw-rotated by −90°.

In detail, in a state in which the pulley 2111, the pulley 2121, and the first staple pulley 2181 rotate by −90° around the rotation shaft 2141, when the first staple pulley 2181 rotates alternately in the clockwise/counterclockwise directions, the link member 2171 and the reciprocating member 551 connected thereto repeatedly move forward and backward. In addition, when the reciprocating member 551 moves forward, the operation member 540 moves forward together with the reciprocating member 551, and when the reciprocating member 551 moves backward, only the reciprocating member 551 moves backward and the operation member 540 remains stationary in place. By repeating this process, the stapling and cutting motions are performed as the operation member 540 moves toward the distal end 502.

Figure 72:
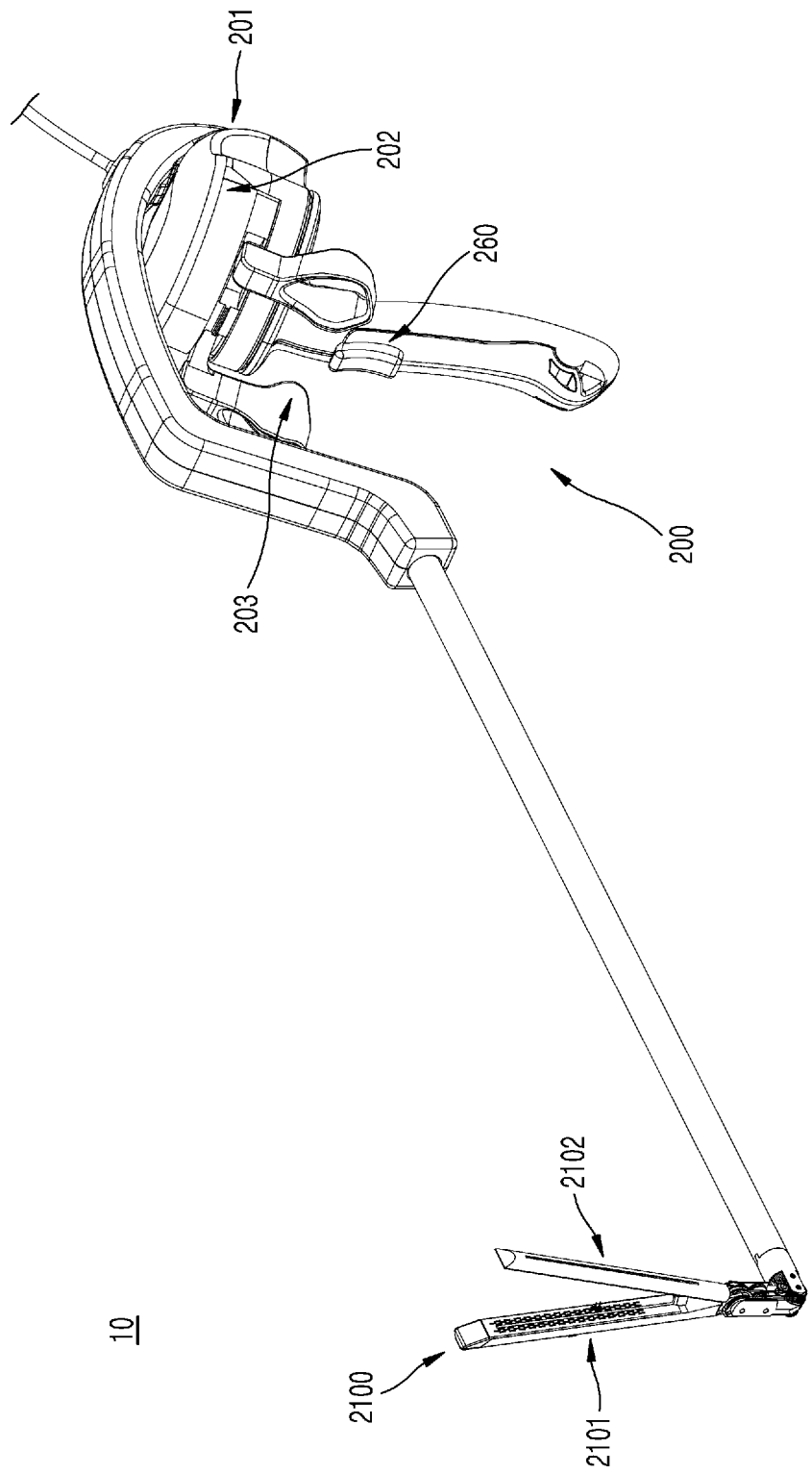
Figure 73:
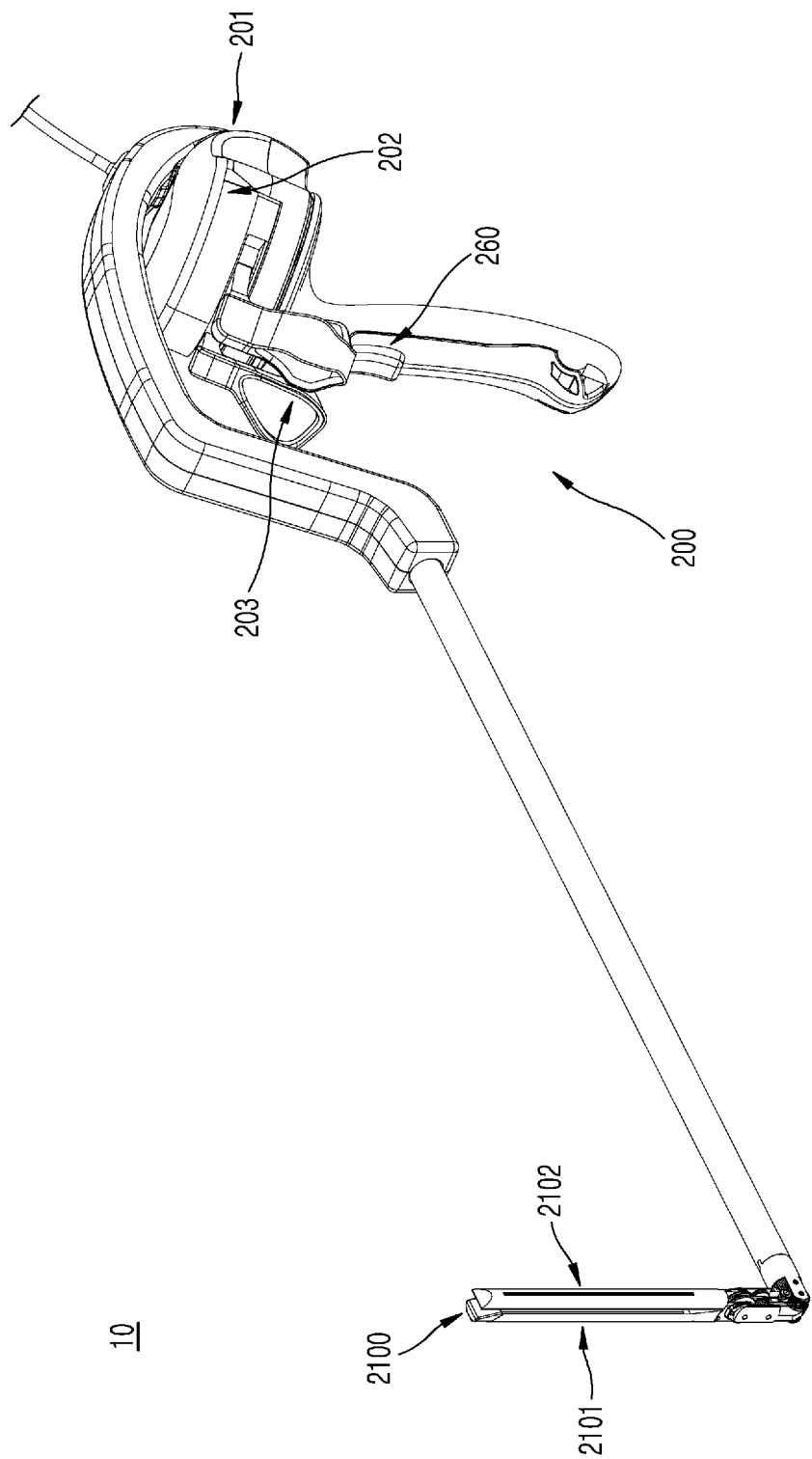
Figure 74:
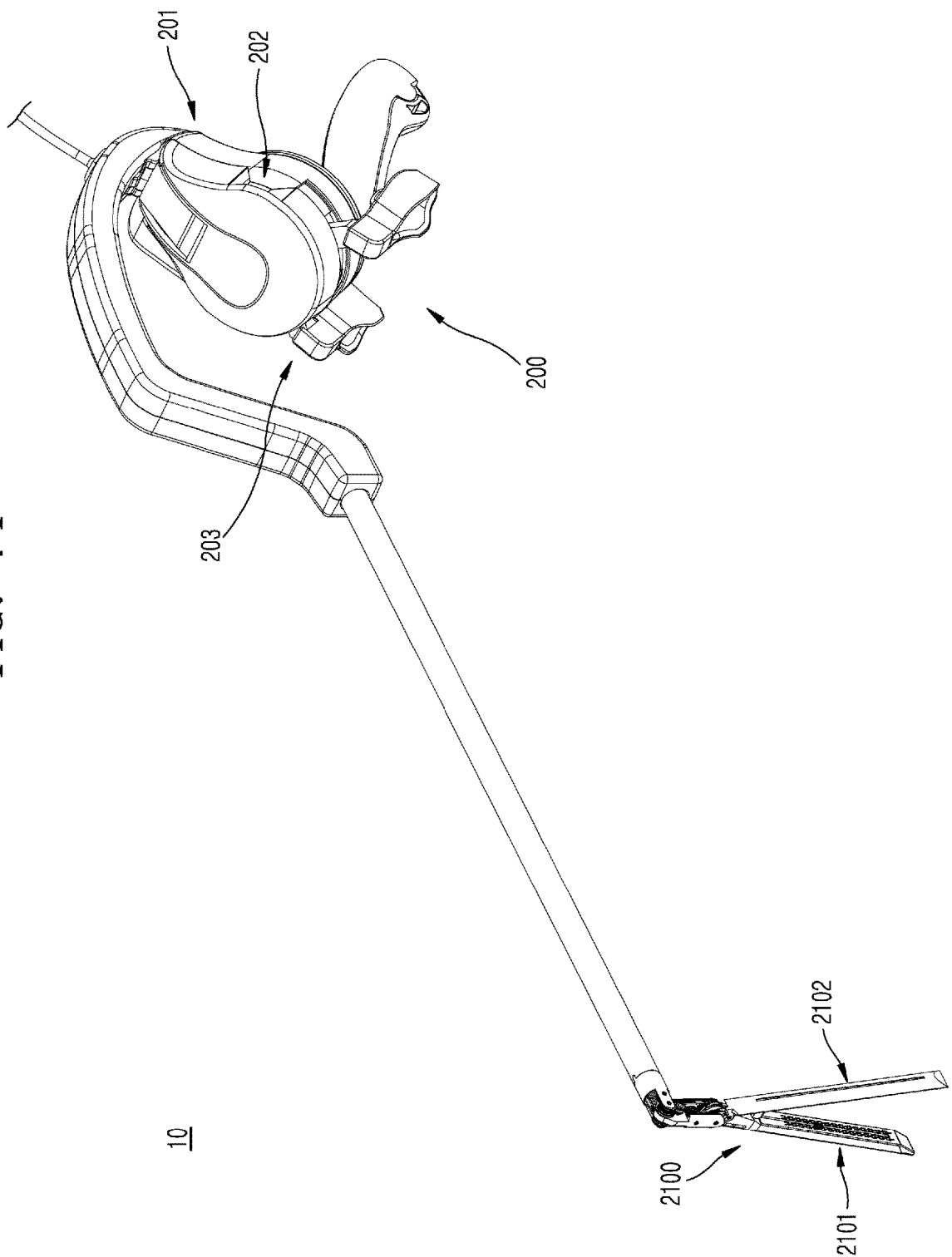
Figure 75:
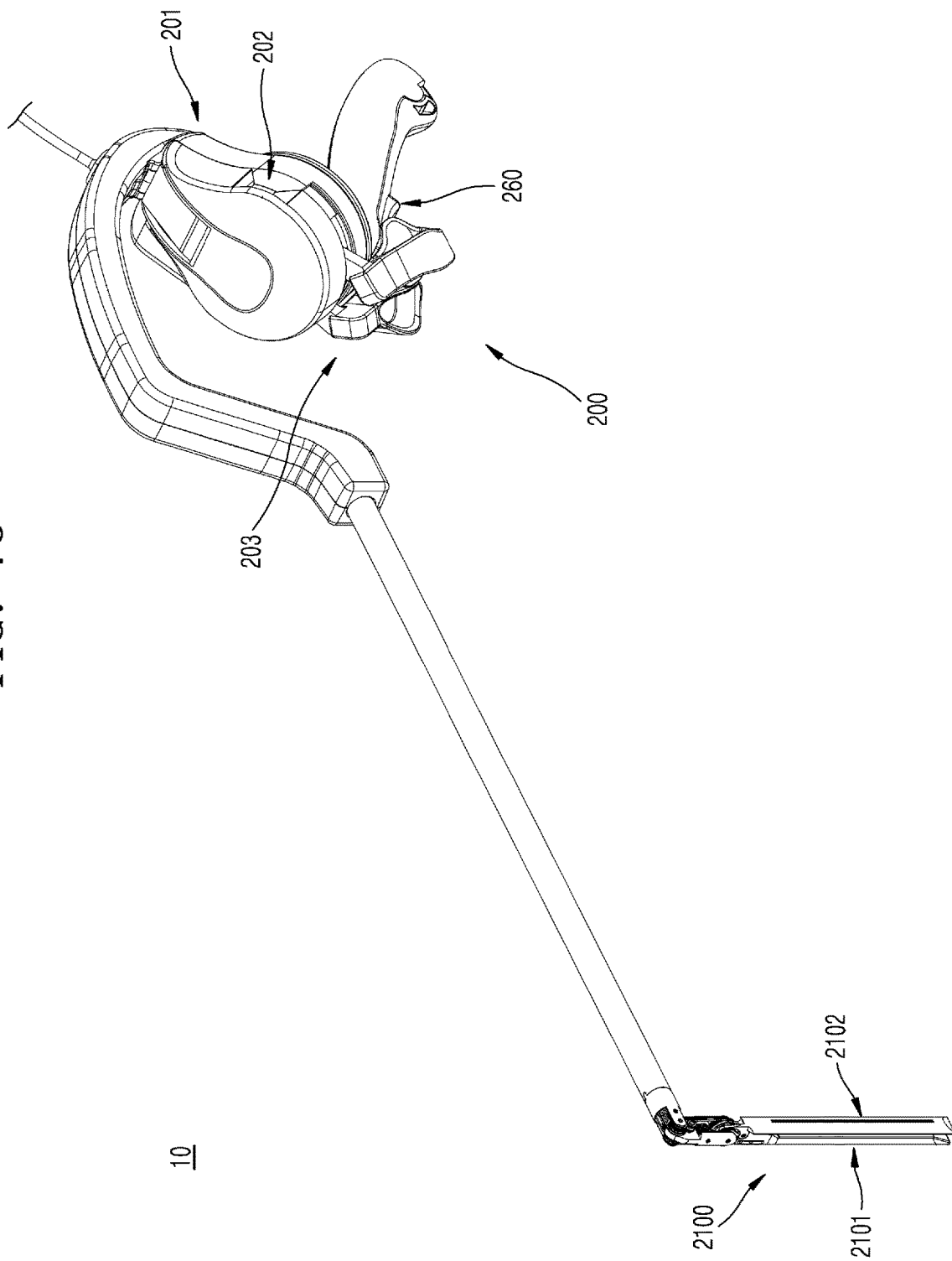

FIG. 72 is a diagram illustrating a state in which jaws are pitch-rotated by −90°, and FIG. 73 is a diagram illustrating a process of performing an actuation motion in a state in which jaws are pitch-rotated by −90°. FIG. 74 is a diagram illustrating a state in which jaws are pitch-rotated by +90°, and FIG. 75 is a diagram illustrating a process of performing an actuation motion in a state in which jaws are pitch-rotated by +90°.

Referring to FIGS. 72 to 75, it may be seen that, in performing a pitch motion, the motions of the manipulation portion 200 and the end tool 2100 are intuitively matched. That is, when the manipulation portion 200 rotates in a positive (+) direction with respect to the pitch rotation shaft (Y-axis), the end tool 2100 also rotates in the positive (+) direction with respect to the pitch rotation shaft (Y-axis). In addition, when the manipulation portion 200 is rotated in a negative (−) direction with respect to the pitch rotation shaft (Y-axis), the end tool 2100 also rotates in the negative (−) direction with respect to the pitch rotation shaft (Y-axis). Here, the rotation angle of the manipulation portion 200 and the rotation angle of the end tool 2100 may be variously set according to the proportions of the pulleys.

Figure 76:
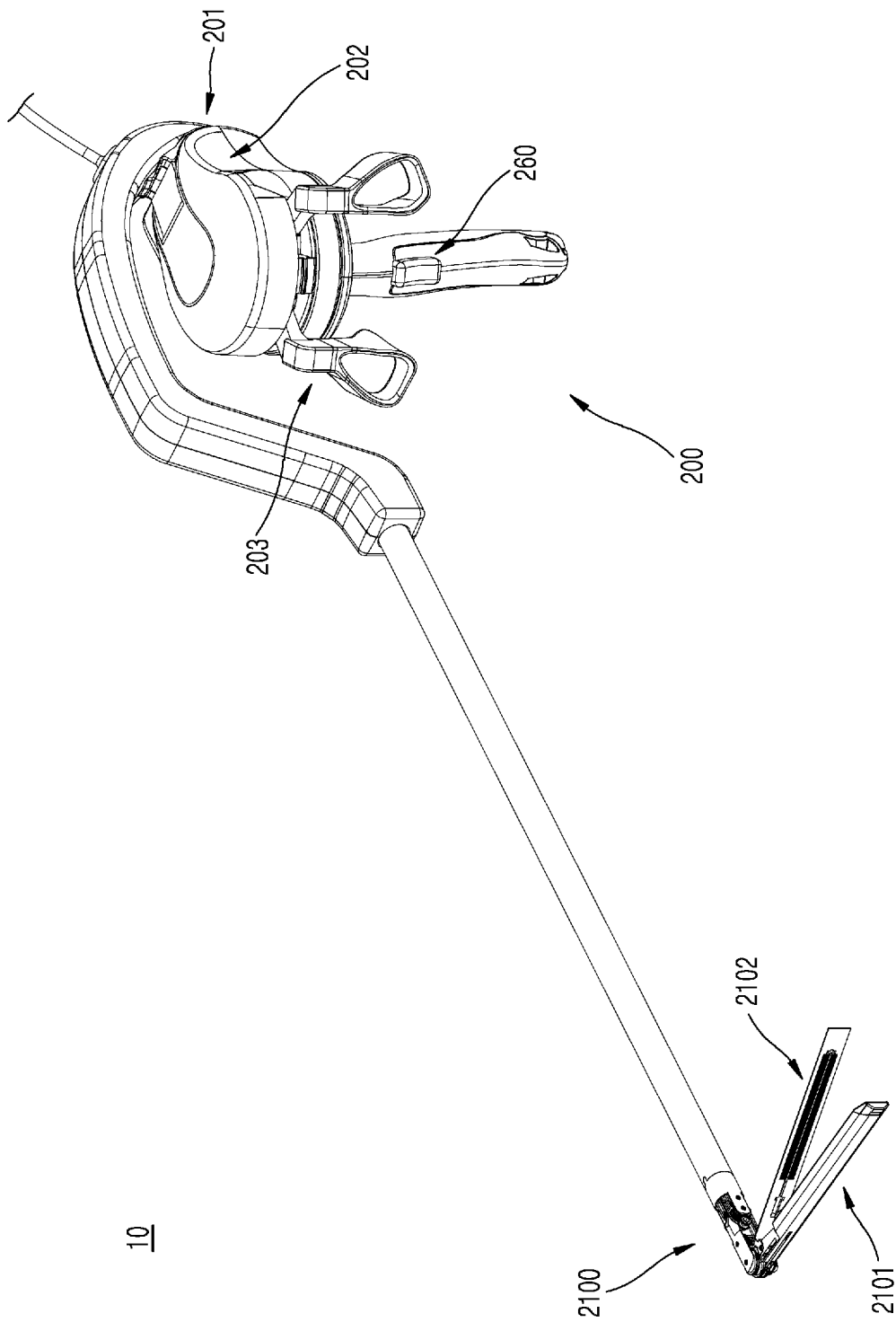
Figure 77:
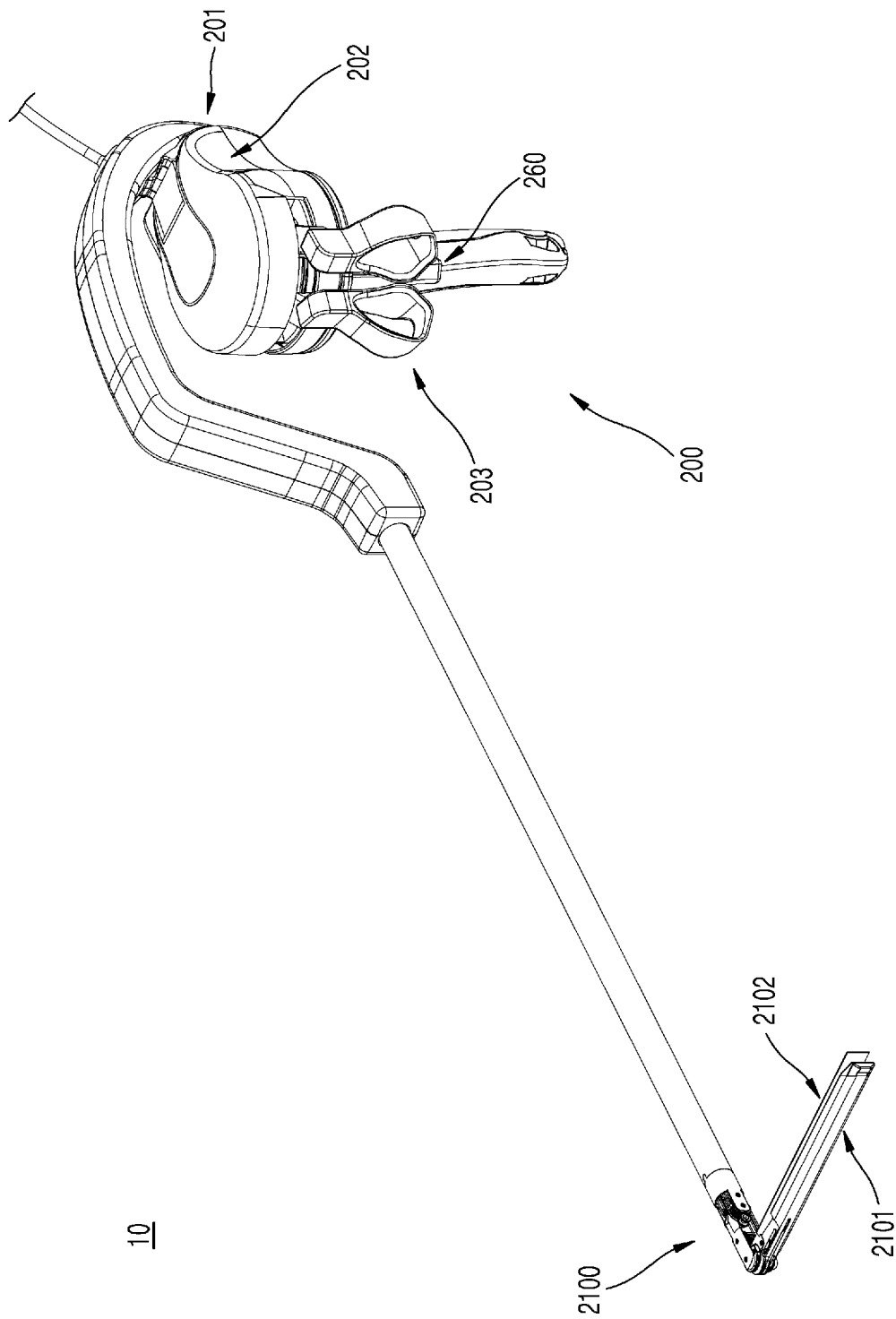
Figure 78:
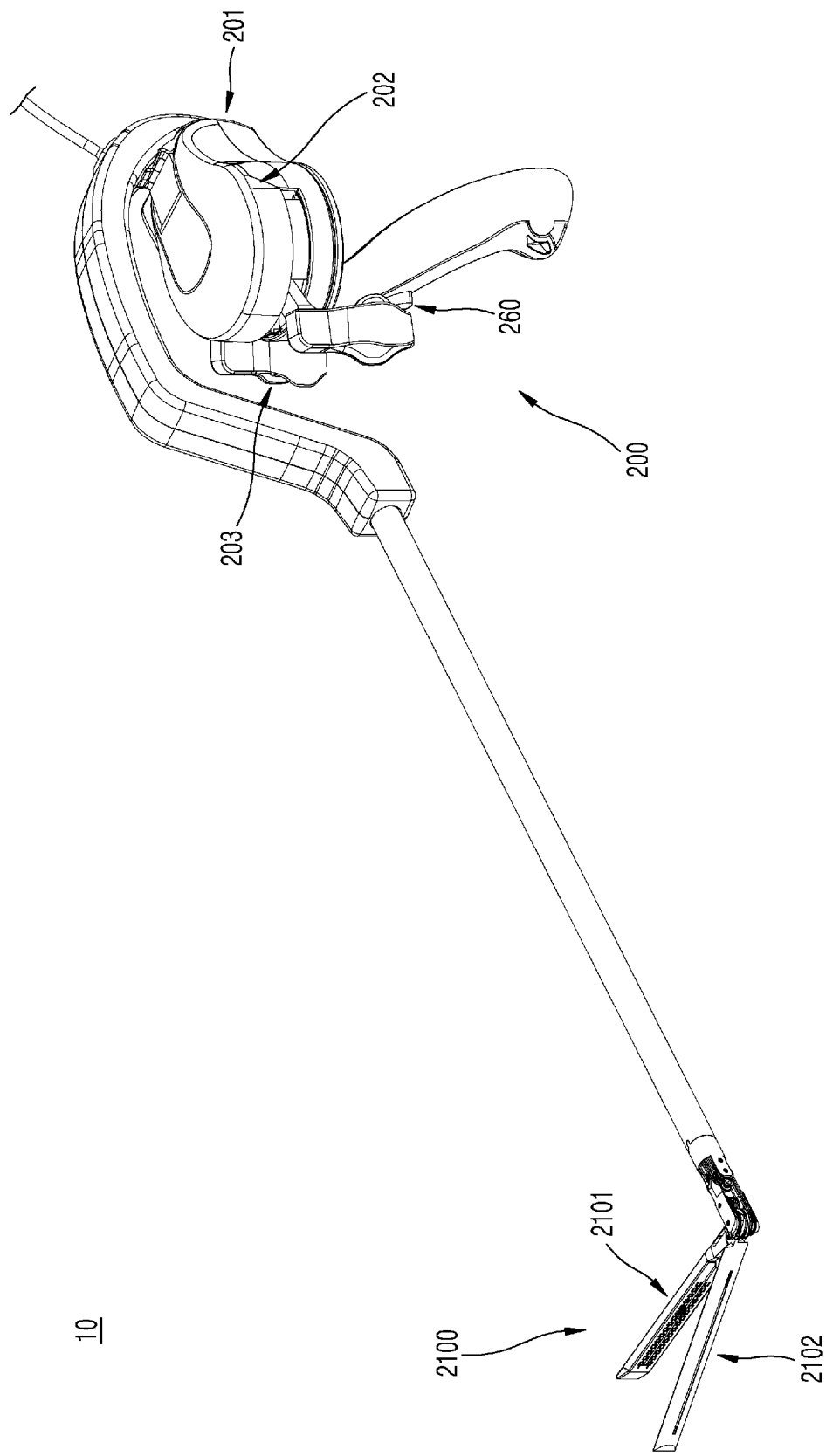
Figure 79:
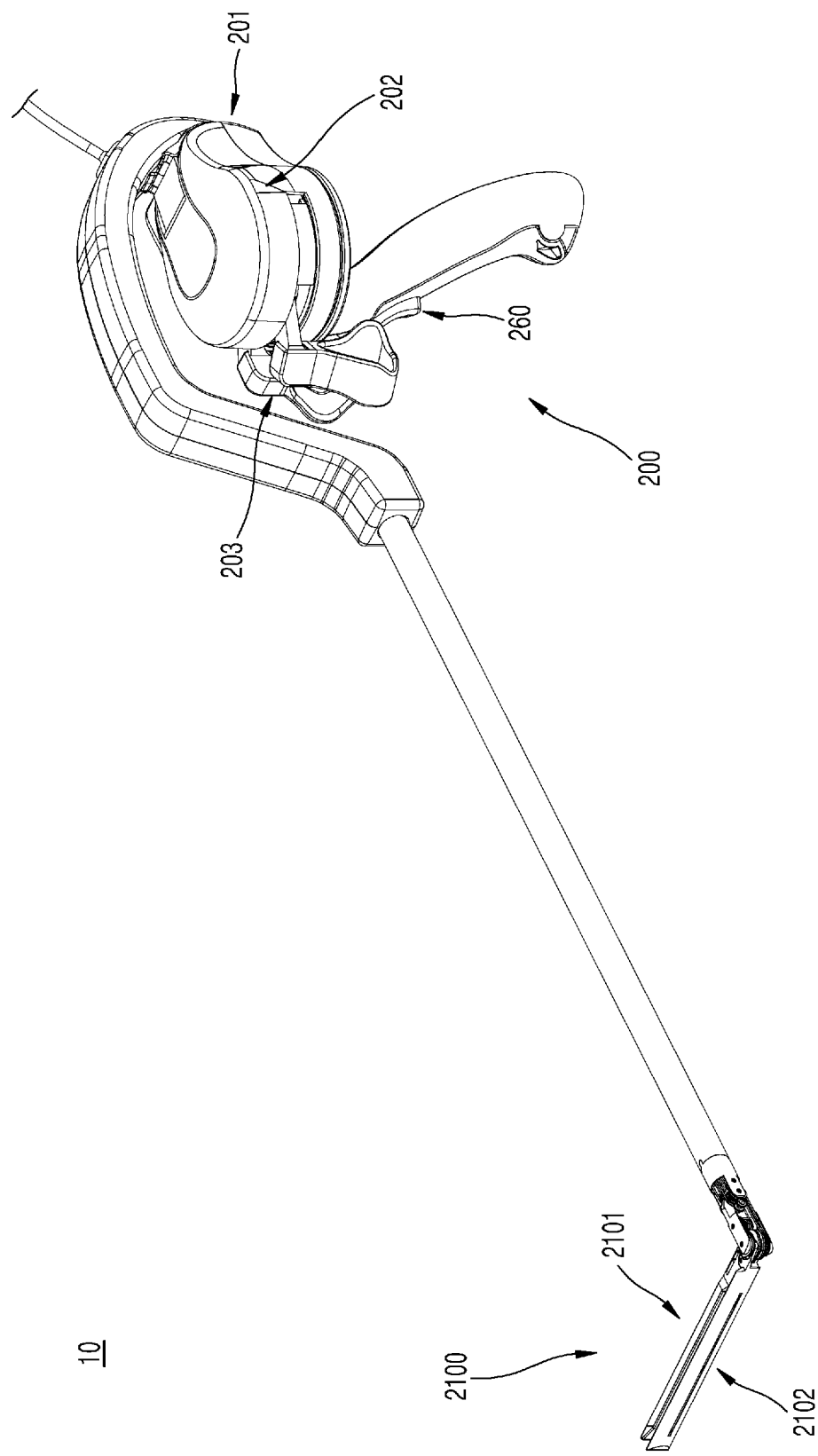

FIG. 76 is a diagram illustrating a state in which jaws are yaw-rotated by +90°, and FIG. 77 is a diagram illustrating a process of performing an actuation motion in a state in which jaws are yaw-rotated by +90°. FIG. 78 is a diagram illustrating a state in which jaws are yaw-rotated by −90°, and FIG. 79 is a diagram illustrating a process of performing an actuation motion in a state in which jaws are yaw-rotated by −90°.

Referring to FIGS. 76 to 79, it may be seen that, in performing a yaw motion, the motions of the manipulation portion 200 and the end tool 2100 are intuitively matched. That is, when the manipulation portion 200 rotates in a positive (+) direction with respect to the yaw rotation shaft (Z-axis), the end tool 2100 also rotates in the positive (+) direction with respect to the yaw rotation shaft (Z-axis). In addition, when the manipulation portion 200 rotates in a negative (−) direction with respect to the yaw rotation shaft (Z-axis), the end tool 2100 also rotates in the negative (−) direction with respect to the yaw rotation shaft (Z-axis). Here, the rotation angle of the manipulation portion 200 and the rotation angle of the end tool 2100 may be variously set according to the proportions of the pulleys.

Figure 80:
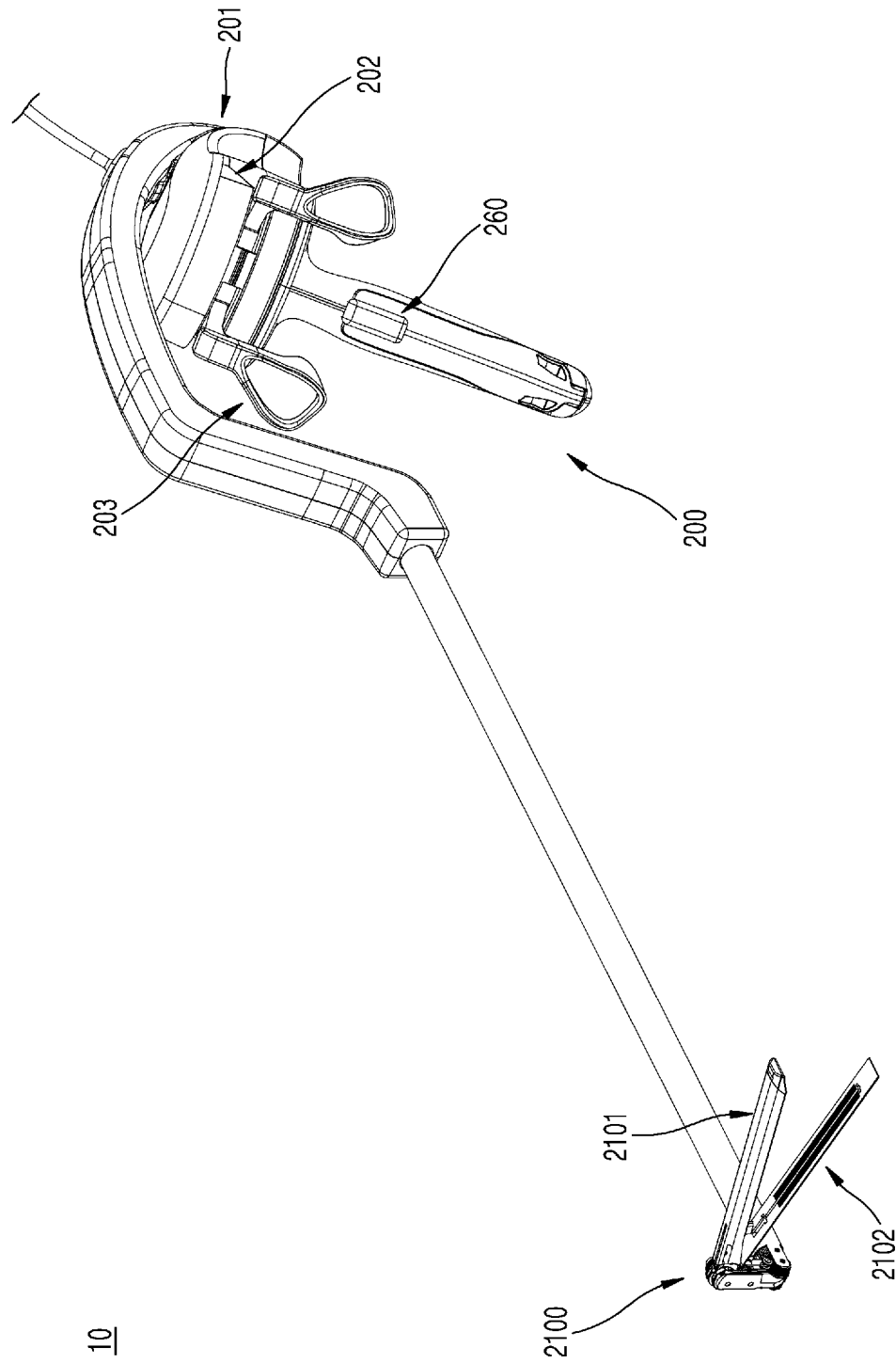
Figure 81:
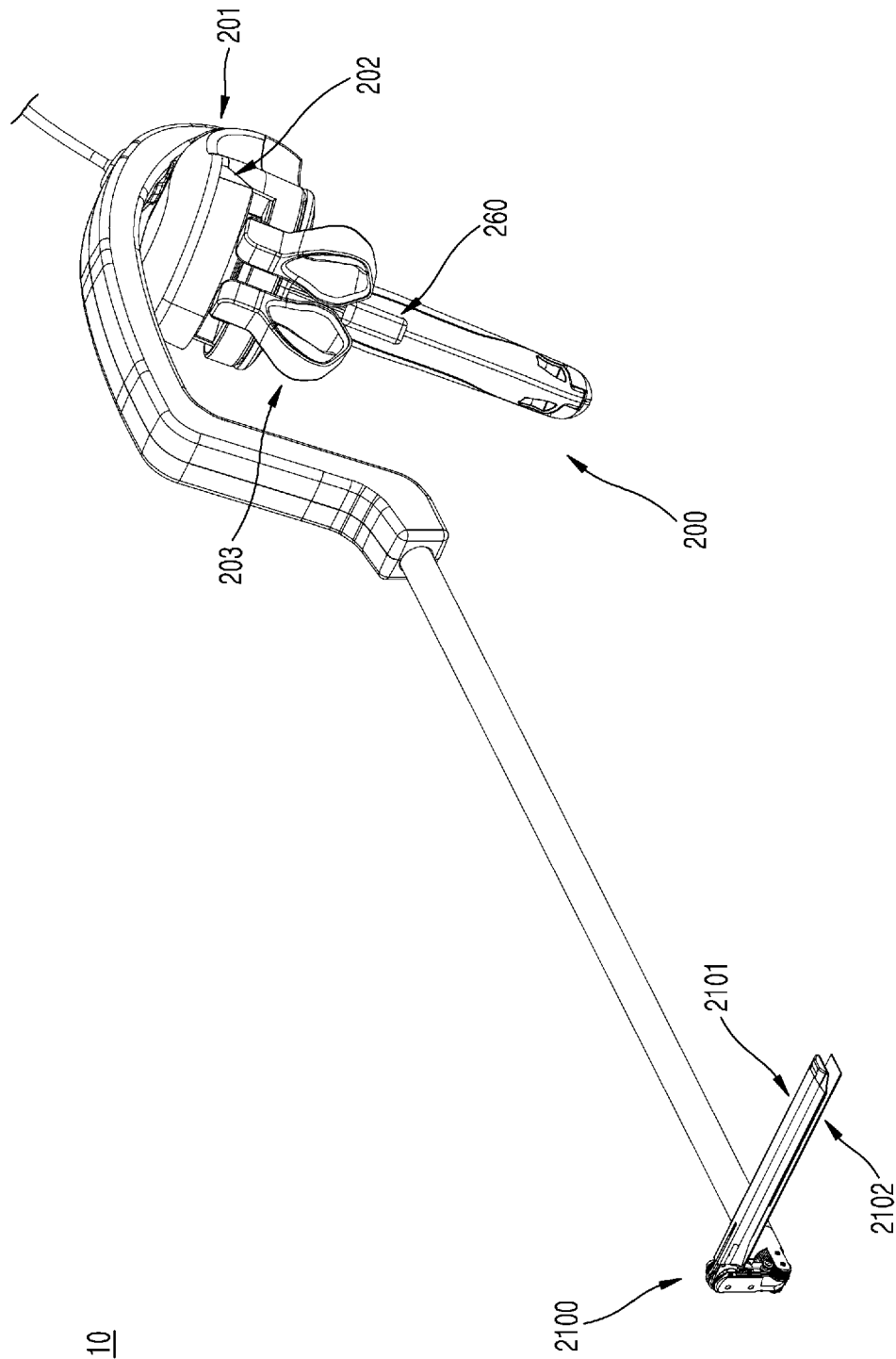
Figure 82:
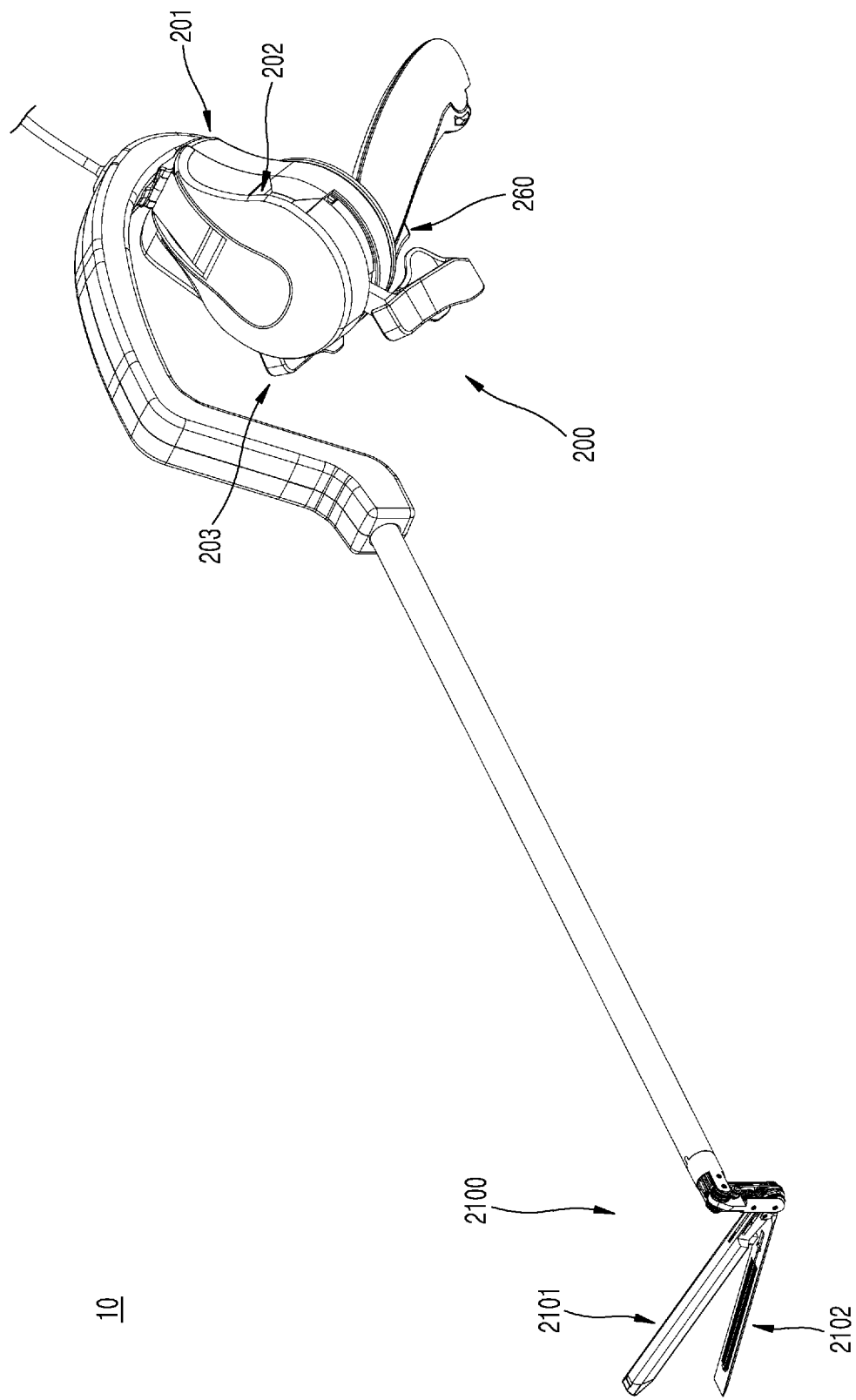
Figure 83:
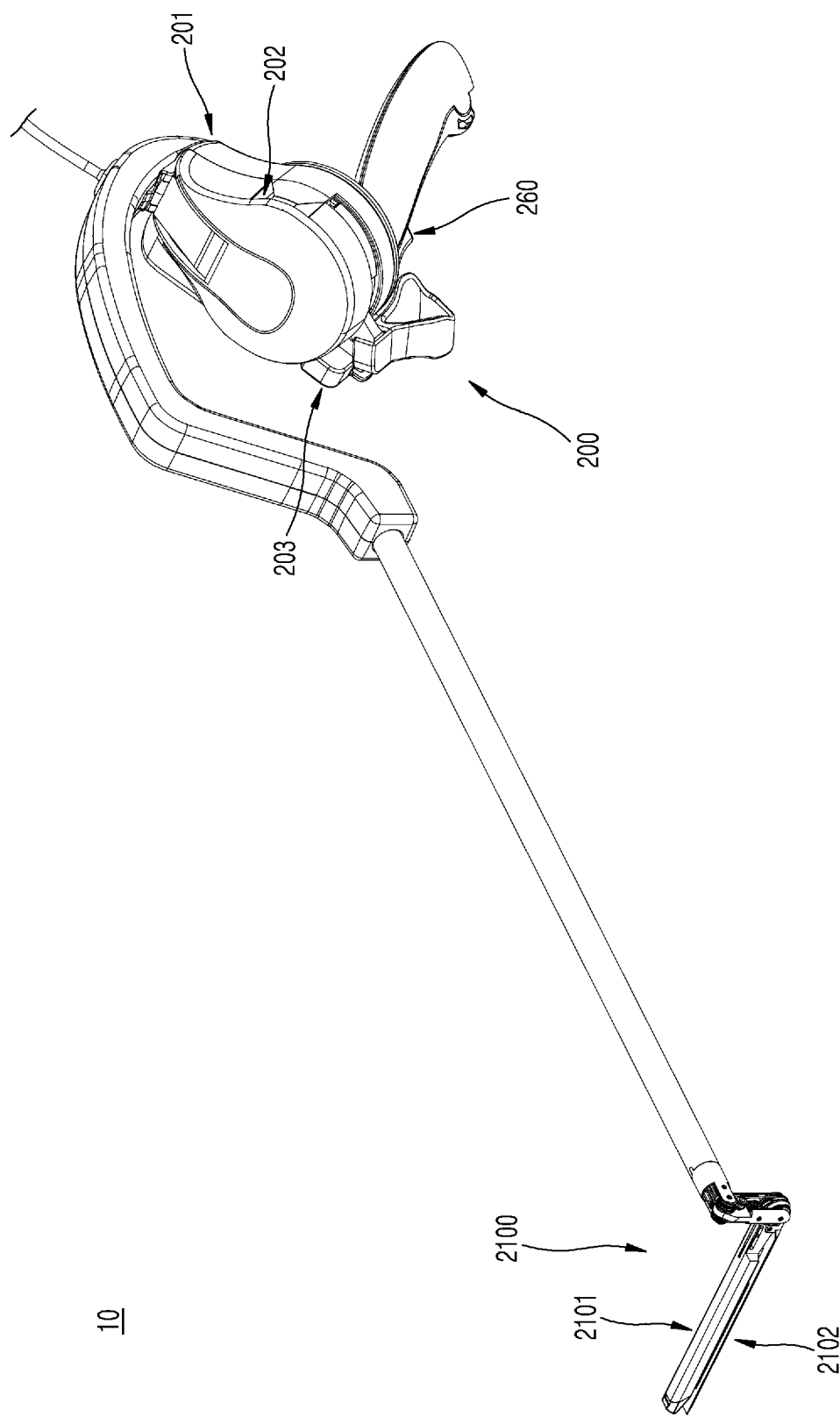

FIG. 80 is a diagram illustrating a state in which jaws are pitch-rotated by −90° and simultaneously yaw-rotated by +90°, and FIG. 81 is a diagram illustrating a process of performing an actuation motion in the state in which jaws are pitch-rotated by −90° and simultaneously yaw-rotated by +90°. FIG. 82 is a diagram illustrating a state in which jaws are pitch-rotated by +90° and simultaneously yaw-rotated by −90°, and FIG. 83 is a diagram illustrating a process of performing an actuation motion in the state in which jaws are pitch-rotated by +90° and simultaneously yaw-rotated by −90°.

Referring to FIGS. 80 to 83, it may be seen that the motions of the manipulation portion 200 and the end tool 2100 are intuitively matched, even when performing the pitch and yaw motions simultaneously.

<Embodiment—Pin/Slot Type>

Hereinafter, an end tool 2200 of a surgical instrument according to a modified example of the present disclosure will be described. Here, the end tool 2200 of the surgical instrument according to a modified example of the present disclosure is different from the end tool (see 100 of FIG. 2 or the like) of the surgical instrument according to the first embodiment of the present disclosure described above in that a configuration of a staple pulley assembly 2260 and a staple link assembly 2270 is different. Hereinafter, the configuration that is different from that of the first embodiment will be described in detail.

FIGS. 84 and 85 are perspective views illustrating an end tool of a surgical instrument according to a modified example of the present disclosure. FIGS. 86 and 87 are exploded perspective views of the tool end of the surgical instrument of FIG. 84. FIGS. 88 and 89 are exploded perspective views illustrating a staple pulley assembly and a staple link assembly of the surgical instrument of FIG. 84.

FIGS. 90 and 91 are side views illustrating operating states of a staple pulley in the end tool of the surgical instrument of FIG. 84. FIGS. 92 and 93 are perspective views illustrating operating states of the staple pulley in the end tool of the surgical instrument of FIG. 84. Here, FIG. 85 illustrates a state in which the end tool hub is removed.

Referring to FIGS. 84 to 93, the end tool 2200 of a modified example of the present disclosure includes a pair of jaws 2203 for performing a grip motion, that is, a first jaw 2201 and a second jaw 2202. Here, each of the first jaw 2201 and the second jaw 2202, or a component encompassing the first jaw 2201 and the second jaw 2202 may be referred to as a jaw.

Meanwhile, the end tool 2200 includes a plurality of pulleys including a pulley 2211 and a pulley 2212 that are associated with a rotational motion of the first jaw 2201. The pulleys associated with the rotational motion of the first jaw 2201 described in the present embodiment are substantially the same as the pulley 111, the pulley 112, the pulley 113, the pulley 114, the pulley 115, and the pulley 116 of the first embodiment described above with reference to FIG. 8 and the like, and thus, detailed descriptions thereof will be omitted.

Meanwhile, the end tool 2200 includes a plurality of pulleys including a pulley 2221 and a pulley 2222 that are associated with a rotational motion of the second jaw 2202. The pulleys associated with the rotational motion of the second jaw 2202 described in the present embodiment are substantially the same as the pulley 121, the pulley 122, the pulley 123, the pulley 124, the pulley 125, and the pulley 126 of the first embodiment described above with reference to FIG. 8 and the like, and thus, detailed descriptions thereof will be omitted.

In addition, the end tool 2200 of a modified example of the present disclosure may include a rotation shaft 2241, a rotation shaft 2242, a rotation shaft 2243, and a rotation shaft 2244. Here, the rotation shaft 2241 and the rotation shaft 2242 may be inserted through an end tool hub 2206, and the rotation shaft 2243 and the rotation shaft 2244 may be inserted through a pitch hub 2207. The rotation shaft 2241, the rotation shaft 2242, the rotation shaft 2243, and the rotation shaft 2244 may be arranged sequentially from a distal end 2204 of the end tool 2200 toward a proximal end 2205.

In addition, the end tool 2200 of a modified example of the present disclosure may include an end tool hub 22802206 and a pitch hub 2207.

The rotation shaft 2241 and the rotation shaft 2242 may be inserted through the end tool hub 2280, and the pulley 2211 and the pulley 2221 axially coupled to the rotation shaft 2241 and at least portions of the first jaw 2201 and the second jaw 2202 coupled to the pulley 2211 and the pulley 2221 may be accommodated in the end tool hub 2280.

The rotation shaft 2243 and the rotation shaft 2244 may be inserted through the pitch hub 2207, and the pitch hub 2207 may be axially coupled to the end tool hub 2280 by the rotation shaft 2243. Thus, the end tool hub 2280 may be formed to be pitch-rotatable around the rotation shaft 2243 with respect to the pitch hub 2207.

Meanwhile, the end tool 2200 of a modified example of the present disclosure may further include components, such as the staple drive assembly (see 150 of FIG. 15) including the staple pulley assembly 2260 and the staple link assembly 2270, to perform stapling and cutting motions.

The staple pulley assembly 2260 may be formed between the pulley 2211 and the pulley 2221 to be adjacent to the pulley 2211 and the pulley 2221. In the present embodiment, it is assumed that the staple pulley assembly 2260 includes a first staple pulley 2281 and a second staple pulley 2291.

In a modified example of the present disclosure, by arranging the staple pulley assembly 2260 between the pulley 2211, which is a first jaw pulley, and the pulley 2221, which is a second jaw pulley, the end tool 2200 is allowed to perform pitch and yaw motions as well as stapling and cutting motions using a cartridge 2210.

Hereinafter, the staple pulley assembly 2260, the staple link assembly 2270, and a reciprocating assembly 2250 of the end tool 2200 of the surgical instrument according to a modified example of the present disclosure will be described in more detail.

In the end tool 2200 of the surgical instrument according to a modified example of the present disclosure, the staple pulley assembly 2260 and the staple link assembly 2270 form a pin/slot structure. In addition, with such a structure, a force for moving the reciprocating assembly 550 forward may be amplified.

Referring to FIGS. 84 to 93, the staple pulley assembly 2260 may include the first staple pulley 2281 and the second staple pulley 2291.

The first staple pulley 2281 may include a body 2281a, a protruding member 2281b, and a shaft pass-through part 2281c.

The body 2281a is formed in a disk shape.

The shaft pass-through part 2281c may be formed in a central portion of the body 2281a. The shaft pass-through part 2281c may be formed in the form of a hole, and the rotation shaft 2241, which is an end tool jaw pulley rotation shaft, may be inserted through the shaft pass-through part 2281c.

In addition, the protruding member 2281b may be formed on the body part 2281a of the first staple pulley 2281. The protruding member 2281b may be coupled to a link member 2271 of the staple link assembly 2270. Here, the protruding member 2261b is formed in the form of a pin, and may be fitted into a first slot 2272d of the link member 2271 to be described below.

Meanwhile, the second staple pulley 2291 may include a body 2291a, a protruding member 2291b, and a shaft pass-through part 2291c.

The body 2291a is formed in a disk shape.

The shaft pass-through part 2291c may be formed in a central portion of the body 2291a. The shaft pass-through part 2291c may be formed in the form of a hole, and the rotation shaft 2241, which is an end tool jaw pulley rotation shaft, may be inserted through the shaft pass-through part 2291c.

In addition, the protruding member 2291b may be formed on the body 2291a of the second staple pulley 2291. The protruding member 2291b may be coupled to the link member 2271 of the staple link assembly 2270. Here, the protruding member 2261b is formed in the form of a pin, and may be fitted into a second slot 2272e of the link member 2271 to be described below.

Meanwhile, the end tool 2200 of a modified example of the present disclosure may further include the staple link assembly 2270 connected to the staple pulley assembly 2260, and the staple link assembly 2270 may include the link member 2271. Here, the staple link assembly 2270 may serve to connect the staple pulley assembly 2260 to the reciprocating assembly (see 550 of FIG. 28) of the cartridge (see 500 of FIG. 28).

In the present embodiment, the staple link assembly 2270 includes one link member 2271, and the link member 2271 includes only one link. That is, by coupling the staple pulley assembly 2260 to the staple link assembly 2270 by a pin/slot structure, it is possible to convert a rotational motion of the staple pulley assembly 2260 into a linear motion of the staple link assembly 2270 even when the staple link assembly 2270 includes only one link.

In detail, the link member 2271 may be formed as a single link.

The link member 2271 is formed in a shape of a combination of an elongated bar with an elliptical flat plate, and may be formed in an approximately 'L' shape. Here, the link member 2271 may include a first protrusion 2272a, a second protrusion 2272b, a fastening portion 2272c, the first slot 2272d, and the second slot 2272e.

the first protrusion 2272a and the second protrusion 2272b may be formed in one region of a central portion of the link member 2271. The first protrusion 2272a and the second protrusion 2272b may be fitted into a guide groove 2201b of the first jaw 2201.

As such, as the first protrusion 2272a and the second protrusion 2272b move along the guide groove 2201b in a state in which the first protrusion 2272a and the second protrusion 2272b of the link member 2271 formed in a protruding shape are fitted into the groove-shaped guide groove 2201b, the link member 2271 moves with respect to the first jaw 2201 (and the cartridge 500 therein). This will be described in more detail below.

Meanwhile, the fastening portion 2272c may be formed at one end of the link member 2271. The fastening portion 2272c may be coupled to the fastening portion (see 551a of FIG. 28) of the reciprocating member (see 551 of FIG. 28) of the cartridge (see 500 of FIG. 28).

Meanwhile, the first slot 2171d and the second slot 2171e may be formed at an end opposite to the end of the link member 2171 at which the fastening portion 2171c is formed.

In detail, the first slot 2171d may be formed on a surface of the link member 2171 facing the first staple pulley 2181. Here, the first slot 2171d may be formed in the shape of an elongated hole, and the protruding member 2181b of the first staple pulley 2181 may be inserted into the first slot 2171d. The first slot 2171d may be formed to have a predetermined curvature, and may be formed in an approximately elliptical shape. Here, a short radius of the first slot 2272d may be substantially equal to or slightly greater than a radius of the protruding member 2281b. Meanwhile, a long radius the first slot 2272d may be greater than a radius of the protruding member 2281b. Accordingly, the protruding member 2281b is formed to be movable to a certain extent in the first slot 2272d in a state in which the protruding member 2281b of the first staple pulley 2281 is fitted into the first slot 2272d of the link member 2271.

Here, the first slot 2272d may be formed obliquely rather than concentrically. Accordingly, when the first staple pulley 2281 rotates, the protruding member 2281b in contact with the first slot 2272d may push the first slot 2272d to move the link member 2271. That is, when the first staple pulley 2281 rotates, the protruding member 2281b may move while being in contact with the first slot 2272d within the first slot 2272d, and accordingly, the link member 2271 may linearly move along the guide groove 2201b of the first jaw 2201.

Here, the first slot 2271d may be formed not to pass through the entire thickness of the link member 2271, but to pass through about half of the entire thickness of the link member 2271. In other words, the first slot 2271d may be formed to have substantially the same thickness as the thickness of the protruding member 2281b of the first staple pulley 2281.

Meanwhile, the second slot 2271e may be formed in the link member 2271. In detail, the second slot 2271e may be formed on a surface of the link member 2271 facing the second staple pulley 2291. Here, the second slot 2271e may be formed in the shape of an elongated hole, and the protruding member 2291b of the second staple pulley 2291 may be inserted into the second slot 2271e. The second slot 2271e may be formed to have a predetermined curvature, and may be formed in an approximately elliptical shape.

Here, a short radius of the second slot 2272e may be substantially equal to or slightly greater than a radius of the protruding member 2291b. Meanwhile, a long radius the second slot 2272e may be greater than a radius of the protruding member 2291b. Accordingly, the protruding member 2291b is formed to be movable to a certain extent in the second slot 2272e in a state in which the protruding member 2291b of the second staple pulley 2291 is fitted into the second slot 2272e of the link member 2271.

As described above, the second slot 2272e may be formed obliquely rather than concentrically. Accordingly, when the second staple pulley 2291 rotates, the protruding member 2291b in contact with the second slot 2272e may push the second slot 2272e to move the link member 2271. That is, when the second staple pulley 2291 rotates, the protruding member 2291b may move while being in contact with the second slot 2272e within the second slot 2272e, and accordingly, the link member 2271 may linearly move along the guide groove 2201b of the first jaw 2201.

Here, the second slot 2271e may be formed not to pass through the entire thickness of the link member 2271, but to pass through about half of the entire thickness of the link member 2271. In other words, the second slot 2271e may be formed to have substantially the same thickness as the thickness of the protruding member 2291b of the second staple pulley 2291.

Here, the first slot 2271d and the second slot 2271e may be formed to at least partially overlap each other. In addition, the sum of the thicknesses of the first slot 2271d and the second slot 2271e in the Y-axis direction may be substantially equal to the thickness of the link member 2271 in the Y-axis direction.

Here, the first slot 2271d and the second slot 2271e may be formed to be vertically symmetrical with respect to the rotation shaft 2241. As such, as the first slot 2271d and the second slot 2271e are vertically symmetrical with respect to the rotation shaft 2241, the protruding member 2281b of the first staple pulley 2281 and the protruding member 2291b of the second staple pulley 2291, which are coupled to the link member 2271, may be arranged to be symmetrical with each other. This will be described in more detail below.

(Displacement and Operation of Staple Link Assembly According to Rotation of Staple Pulley)

Hereinafter, displacement of the staple link assembly 2270 according to rotation of the first staple pulley 2281 and the second staple pulley 2291 will be described.

Referring to FIG. 88, in a modified example of the present disclosure, the first staple pulley 2281 and the staple link assembly 2270 are coupled to each other in a pin/slot form. That is, the pin-shaped protruding member 2281b formed in the first staple pulley 2281 is coupled to the first slot 2271d formed in the link member 2271. Thus, when the first staple pulley 2281 rotates in the direction of an arrow A, the displacement of the protruding member 2281b of the first staple pulley 2281 in the X-axis direction becomes B. In addition, the displacement of the staple link assembly 2270 in the X-axis direction becomes C.

Similarly, referring to FIG. 89, in the first embodiment of the present disclosure, the second staple pulley 2291 and the staple link assembly 2270 are coupled to each other in a pin/slot form. That is, the pin-shaped protruding member 2291*b* formed in the second staple pulley 2291 is coupled to the second slot 2271*e* formed in the link member 2271. Thus, when the second staple pulley 2291 rotates in the direction of an arrow D, the displacement of the protruding member 2291*b* of the second staple pulley 2291 in the X-axis direction becomes E. In addition, the displacement of the staple link assembly 2270 in the X-axis direction becomes F.

In comparison with the above case, when a staple pulley and a staple link assembly are coupled to each other in a link-shaft manner rather than the pin/slot manner, the displacement of the staple link assembly in the X-axis direction becomes much longer than that in a modified example of the present disclosure.

In other words, compared to when the staple pulley and the staple link assembly are axially coupled to each other, when the staple pulley and the staple link assembly are coupled to each other in the pin/slot manner as in the present embodiment, the displacement of the staple link assembly displacement in the X-axis direction decreases even when the staple pulley rotates by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in a modified example of the present disclosure, because the first staple pulley 2281 and the second staple pulley 2291 are each coupled to the staple link assembly 2270 in the pin/slot form, and the displacement of the staple link assembly 2270 in the X-axis direction due to the rotation of the first staple pulley 2281 and the second staple pulley 2291 is relatively reduced compared to other embodiments, the force received by the staple link assembly 2270 in the X-axis direction relatively increases compared to a simple link structure.

According to a modified example of the present disclosure described above, a force for moving forward the staple link assembly 2270 and the reciprocating assembly 550 connected thereto is amplified, and thus, a stapling motion may be performed more robustly.

In particular, in a modified example of the present disclosure, because two staple pulleys (i.e., the first staple pulley 2281 and the second staple pulley 2291) symmetrical to each other are provided, the force with which the staple pulley assembly 2260 pushes the staple link assembly 2270 may be amplified by approximately two times compared to a case in which only one staple pulley is provided. In addition, because the first staple pulley 2281 and the second staple pulley 2291 are arranged to be horizontally symmetrical with each other with respect to an XZ plane, the horizontal balance is achieved in performing a stapling motion, such that the end tool 2200 may stably perform the motion without shaking left and right.

Hereinafter, rotation directions of the first staple pulley 2281 and the second staple pulley 2291 will be described.

Referring to FIGS. 90, 91, 92, 93, and the like, the first staple pulley 2281 moves forward the staple link assembly 2270 when rotating in the direction of an arrow A of FIG. 93 (i.e., the clockwise direction), and the second staple pulley 2291 moves forward the staple link assembly 2270 when rotating in the direction of an arrow D of FIG. 93 (i.e., the counterclockwise direction).

On the contrary, the first staple pulley 2281 moves backward the staple link assembly 2270 when rotating in the counterclockwise direction, and the second staple pulley 2291 moves backward the staple link assembly 2270 when rotating in the clockwise direction.

Accordingly, when the first staple pulley 2281 and the second staple pulley 2291 rotate in opposite directions, the staple link assembly 2270 is moved (forward or backward). On the contrary, when the first staple pulley 2281 and the second staple pulley 2291 rotate in the same direction, the rotation of the two pulleys is offset, and thus, the staple link assembly 2270 is not moved.

Accordingly, in a state illustrated in FIG. 92, when the first staple pulley 2281 rotates in the clockwise direction and the second staple pulley 2291 rotates in the counterclockwise direction at the same time, the link member 2271 connected to the first staple pulley 2281 and the second staple pulley 2291 may move toward the distal end (see 2101*f* of FIG. 13) of the first jaw 2201.

On the contrary, when the first staple pulley 2281 rotates in the counterclockwise direction and the second staple pulley 2291 rotates in the clockwise direction at the same time, the link member 2271 connected to the first staple pulley 2281 and the second staple pulley 2291 may move toward the proximal end (see 2101*g* of FIG. 13) of the first jaw 2201.

Thus, a bidirectional rotational motion of the staple pulley assembly 2260 causes a reciprocating linear motion of the reciprocating assembly (see 550 of FIG. 28) of the cartridge (see 500 of FIG. 28) through the staple link assembly 2270.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to an end tool of a surgical instrument and a surgical instrument including the same, and more particularly, may be used to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

The invention claimed is:
1. A surgical instrument comprising:
 an end tool comprising:
  a first jaw;
  a second jaw formed to face the first jaw;
  a first jaw pulley coupled to the first jaw and formed to be rotatable around a first shaft;
  a second jaw pulley coupled to the second jaw, formed to be rotatable around a shaft that is substantially the same as or parallel to the first shaft, and formed to be spaced apart from the first jaw pulley by a certain extent; and a staple drive assembly comprising a first staple pulley and a second staple pulley formed adjacent to the first jaw pulley or the second jaw pulley; and a cartridge comprising:
- a reciprocating assembly that is connected to the staple drive assembly, and is linearly moved when the first staple pulley and the second staple pulley are rotationally moved; and
- an operation member that is brought into contact with the reciprocating assembly, and is moved in one direction by the reciprocating assembly when the reciprocating assembly is moved in the one direction.

2. The surgical instrument of claim 1, wherein, when the first staple pulley or the second staple pulley is rotated, the reciprocating assembly connected to the staple drive assembly is moved toward a distal end or a proximal end of the cartridge.

3. The surgical instrument of claim 2, wherein, when the first staple pulley or the second staple pulley is rotated alternately in a clockwise direction and a counterclockwise direction, the reciprocating assembly connected to the staple drive assembly is moved alternately toward the distal end and the proximal end of the cartridge.

4. The surgical instrument of claim 3, wherein, when the reciprocating assembly is moved toward the distal end of the cartridge, the operation member is moved toward the distal end of the cartridge by the reciprocating assembly.

5. The surgical instrument of claim 1, wherein a bidirectional rotational motion of the first staple pulley or the second staple pulley is converted, by the staple drive assembly, into a reciprocating linear motion of the reciprocating assembly connected to the staple drive assembly.

6. The surgical instrument of claim 1, wherein as the operation member is moved in the one direction, a wedge of the operation member sequentially pushes and raises a plurality of staples in the cartridge to perform a stapling motion, and simultaneously a blade formed on one side of the wedge of the operation member is moved in the one direction to perform a cutting motion.

7. The surgical instrument of claim 1, wherein the staple drive assembly further comprises a link member connecting the first staple pulley and the second staple pulley to the reciprocating assembly.

8. The surgical instrument of claim 7, wherein the operation member comprises a ratchet member having a ratchet formed on at least one surface thereof, and
the ratchet of the ratchet member is formed to be able to be in contact with the reciprocating assembly.

9. The surgical instrument of claim 8, wherein the operation member is moved toward a distal end of the cartridge together with the reciprocating assembly only when the reciprocating assembly is moved toward the distal end of the cartridge.

10. The surgical instrument of claim 8, wherein, when the first staple pulley is rotated in a first direction among a clockwise direction and a counterclockwise direction, and the second staple pulley is rotated in a direction opposite to the first direction among the clockwise direction and the counterclockwise direction, the link member connected to the first staple pulley and the second staple pulley, the reciprocating assembly connected to the link member, and the operation member in contact with the reciprocating assembly are moved toward a distal end of the cartridge.

11. The surgical instrument of claim 10, wherein, when the first staple pulley is rotated in the direction opposite to the first direction among the clockwise direction and the counterclockwise direction, and the second staple pulley is rotated in the first direction among the clockwise direction and the counterclockwise direction, the link member connected to the staple pulleys, and the reciprocating assembly connected to the link member are moved toward a proximal end of the end tool, and the operation member remains stationary with respect to the one direction.

12. The surgical instrument of claim 7, wherein a first protruding member is formed in the first staple pulley,
a second protruding member is formed in the second staple pulley,
a first slot is formed on a surface of the link member facing the first staple pulley, and
a second slot is formed on one surface of the link member facing the second staple pulley.

13. The surgical instrument of claim 12, wherein the first protruding member and the second protruding member are formed in a form of a cam, and
the link member is moved, as the first protruding member presses the first slot of the link member while rotating, and the second protruding member presses the second slot of the link member while rotating.

14. The surgical instrument of claim 12, wherein a center of the first protruding member does not coincide with a center of the first staple pulley,
the first protruding member is formed to be eccentric to a certain extent with respect to the first staple pulley,
a center of the second protruding member does not coincide with a center of the second staple pulley, and
the second protruding member is formed to be eccentric to a certain extent with respect to the second staple pulley.

15. The surgical instrument of claim 12, wherein, when the first staple pulley and the second staple pulley are rotated in directions opposite to each other, the link member is moved in one direction, and
when the first staple pulley and the second staple pulley are rotated in the same direction, the link member remains stationary with respect to the one direction.

16. The surgical instrument of claim 1, further comprising:
a first staple wire coupled to the first staple pulley to rotate the first staple pulley; and
a second staple wire coupled to the second staple pulley to rotate the second staple pulley.

17. The surgical instrument of claim 1, further comprising:
a pair of end tool first jaw pitch main pulleys formed on one side of the first jaw pulley, and formed to be rotatable around a second shaft forming a predetermined angle with the first shaft; and
a pair of end tool second jaw pitch main pulleys formed on one side of the second jaw pulley, and formed to be rotatable around a shaft that is substantially the same as or parallel to the second shaft.

18. The surgical instrument of claim 17, wherein the end tool is formed to be yaw-rotatable around the first shaft and simultaneously pitch-rotatable around the second shaft.

19. The surgical instrument of claim 1, wherein the first jaw pulley, the first staple pulley, the second staple pulley, and the second jaw pulley are sequentially stacked.

20. The surgical instrument of claim 1, wherein the staple drive assembly is formed between the first jaw pulley and the second jaw pulley.

* * * * *